US010034872B2

(12) United States Patent
Thakurta et al.

(10) Patent No.: US 10,034,872 B2
(45) Date of Patent: Jul. 31, 2018

(54) METHODS OF TREATING MULTIPLE MYELOMA WITH IMMUNOMODULATORY COMPOUNDS IN COMBINATION WITH ANTIBODIES

(71) Applicant: Celgene Corporation, Summit, NJ (US)

(72) Inventors: Anjan Thakurta, Basking Ridge, NJ (US); Mohamed Hussein, Odessa, FL (US); Christian Jacques, Hamburg, NJ (US)

(73) Assignee: Celgene Corporation, Summit, NJ (US)

(*) Notice: Subject to any disclaimer, the term of this patent is extended or adjusted under 35 U.S.C. 154(b) by 0 days.

(21) Appl. No.: 14/831,616

(22) Filed: Aug. 20, 2015

(65) Prior Publication Data
US 2016/0051530 A1 Feb. 25, 2016

Related U.S. Application Data

(60) Provisional application No. 62/040,918, filed on Aug. 22, 2014.

(51) Int. Cl.
| A61K 31/454 | (2006.01) |
| A61K 31/5377 | (2006.01) |
| A61K 31/573 | (2006.01) |
| A61K 31/69 | (2006.01) |
| C07K 16/28 | (2006.01) |
| A61K 39/00 | (2006.01) |
| A61K 35/28 | (2015.01) |

(52) U.S. Cl.
CPC ........ *A61K 31/454* (2013.01); *A61K 31/5377* (2013.01); *A61K 31/573* (2013.01); *A61K 31/69* (2013.01); *C07K 16/2803* (2013.01); *A61K 35/28* (2013.01); *A61K 2039/545* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,551,177 A | 11/1985 | Trubiano et al. |
| 4,810,643 A | 3/1989 | Souza |
| 4,994,443 A | 2/1991 | Folkman et al. |
| 4,999,291 A | 3/1991 | Souza |
| 5,001,116 A | 3/1991 | Folkman et al. |
| 5,059,595 A | 10/1991 | Le Grazie |
| 5,073,543 A | 12/1991 | Marshall et al. |
| 5,120,548 A | 6/1992 | McClelland et al. |
| 5,134,127 A | 7/1992 | Stella et al. |
| 5,229,496 A | 7/1993 | Deeley et al. |
| 5,354,556 A | 10/1994 | Sparks et al. |
| 5,385,901 A | 1/1995 | Kaplan et al. |
| 5,387,421 A | 2/1995 | Amidon et al. |
| 5,391,485 A | 2/1995 | Deeley et al. |
| 5,393,870 A | 2/1995 | Deeley et al. |
| 5,528,823 A | 6/1996 | Rudy, Jr. et al. |
| 5,580,755 A | 12/1996 | Souza |
| 5,591,767 A | 1/1997 | Mohr et al. |
| 5,593,696 A | 1/1997 | McNally et al. |
| 5,593,990 A | 1/1997 | D'Amato |
| 5,594,637 A | 1/1997 | Eisenberg et al. |
| 5,619,991 A | 4/1997 | Sloane |
| 5,629,327 A | 5/1997 | D'Amato |
| 5,635,517 A | 6/1997 | Muller et al. |
| 5,639,476 A | 6/1997 | Oshlack et al. |
| 5,641,758 A | 6/1997 | Kluge et al. |
| 5,643,915 A | 7/1997 | Andrulis et al. |
| 5,674,533 A | 10/1997 | Santus et al. |
| 5,698,579 A | 12/1997 | Muller |
| 5,712,291 A | 1/1998 | D'Amato |
| 5,731,325 A | 3/1998 | Andrulis, Jr. et al. |
| 5,733,566 A | 3/1998 | Lewis |
| 5,798,368 A | 8/1998 | Muller et al. |
| 5,832,449 A | 11/1998 | Cunningham |
| 5,874,448 A | 2/1999 | Muller et al. |
| 5,877,200 A | 3/1999 | Muller |
| 5,882,656 A | 3/1999 | Bechard et al. |
| 5,929,117 A | 7/1999 | Muller et al. |

(Continued)

FOREIGN PATENT DOCUMENTS

| JP | 11-286455 | 10/1999 |
| JP | 2002-513391 | 5/2002 |

(Continued)

OTHER PUBLICATIONS

Paiva et al. (Blood Jan. 19, 2012 119 (3): 687-691).*
Rawstron et al. (Blood Jan. 19, 2012 119 (3): 687-691).*
Induction Therapy (NCI Dictionary of Cancer Terms, https://www.cancer.gov/publications/dictionaries/cancer-terms?cdrid=45736, downloaded Nov. 8, 2016).*
Carstensen, Drug Stability: Principles & Practices, Second Edition, Marcel Dekker, New York, NY, pp. 379-380 (1995).
Corral et al., "Immunomodulation by thalidomide and thalidomide analogues," Ann. Rheum. Dis., 58:(Suppl 1)1107-1113 (1999).
Emens et al., "Chemotherapy: friend of foe to cancer vaccines," Curr. Opin. Mol. Ther., 3(1):77-84 (2001).
Folkman et al., "Angiogenesis inhibition and tumor regression caused by heparin or a heparin fragment in the presence of cortisone," Science, 221:719-725 (1983).

(Continued)

Primary Examiner — Peter J Reddig
(74) Attorney, Agent, or Firm — Jones Day

(57) ABSTRACT

Methods of treating, preventing and/or managing multiple myeloma are disclosed. Specific methods encompass the administration of an immunomodulatory compound, e.g., lenalidomide or pomalidomide with an anti-CS1 antibody, e.g., elotuzumab in patients who have received autologous stem cell transplantation.

35 Claims, No Drawings

(56) References Cited

U.S. PATENT DOCUMENTS

| | | |
|---|---|---|
| 5,955,476 A | 9/1999 | Muller et al. |
| 5,974,203 A | 10/1999 | Tadokoro et al. |
| 6,011,050 A | 1/2000 | Muller et al. |
| 6,020,358 A | 2/2000 | Muller et al. |
| 6,045,501 A | 4/2000 | Elsayed et al. |
| 6,055,507 A | 4/2000 | Cunningham |
| 6,063,026 A | 5/2000 | Schauss et al. |
| 6,071,948 A | 6/2000 | D'Amato |
| 6,096,757 A | 8/2000 | Bishop et al. |
| 6,114,355 A | 9/2000 | D'Amato |
| 6,131,090 A | 10/2000 | Basso et al. |
| 6,140,346 A | 10/2000 | Andrulis, Jr. et al. |
| 6,202,923 B1 | 3/2001 | Boyer et al. |
| 6,228,879 B1 | 5/2001 | Green et al. |
| 6,235,756 B1 | 5/2001 | D'Amato |
| 6,281,230 B1 | 8/2001 | Muller et al. |
| 6,315,720 B1 | 11/2001 | Williams et al. |
| 6,316,471 B1 | 11/2001 | Muller et al. |
| 6,326,388 B1 | 12/2001 | Man et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,420,414 B1 | 7/2002 | D'Amato |
| 6,432,924 B1 | 8/2002 | Nyce |
| 6,458,810 B1 | 10/2002 | Muller et al. |
| 6,469,045 B1 | 10/2002 | D'Amato |
| 6,476,052 B1 | 11/2002 | Muller et al. |
| 6,518,298 B2 | 2/2003 | Green et al. |
| 6,555,554 B2 | 4/2003 | Muller et al. |
| 6,561,976 B2 | 5/2003 | Elsayed et al. |
| 6,561,977 B2 | 5/2003 | Williams et al. |
| 6,673,828 B1 | 1/2004 | Green et al. |
| 6,755,784 B2 | 6/2004 | Williams et al. |
| 6,878,733 B1 | 4/2005 | Shenoy et al. |
| 6,887,855 B2 | 5/2005 | Ionescu et al. |
| 6,890,547 B1 | 5/2005 | Takada et al. |
| 6,896,399 B2 | 5/2005 | Nomura et al. |
| 6,908,432 B2 | 6/2005 | Elsayed et al. |
| 6,943,249 B2 | 9/2005 | Ionescu et al. |
| 7,078,518 B2 | 7/2006 | Ionescu et al. |
| 7,091,353 B2 | 8/2006 | Robarge et al. |
| 7,112,602 B2 | 9/2006 | D'Amato et al. |
| 7,119,106 B2 | 10/2006 | Muller et al. |
| 7,182,953 B2 | 2/2007 | Zeldis |
| 7,189,740 B2 | 3/2007 | Zeldis |
| 7,323,479 B2 | 1/2008 | Zeldis |
| 7,393,862 B2 | 7/2008 | Zeldis |
| 7,435,726 B2 | 10/2008 | Zeldis et al. |
| 7,435,745 B2 | 10/2008 | D'Amato |
| 7,465,800 B2 | 12/2008 | Jaworsky et al. |
| 7,468,363 B2 | 12/2008 | Zeldis |
| 7,498,171 B2 | 3/2009 | Hariri et al. |
| 7,563,810 B2 | 7/2009 | Zeldis |
| 7,635,700 B2 | 12/2009 | Muller et al. |
| 7,855,217 B2 | 12/2010 | Jaworski et al. |
| 7,959,566 B2 | 6/2011 | Williams et al. |
| 7,968,569 B2 | 6/2011 | Zeldis et al. |
| 8,158,653 B2 | 4/2012 | Muller et al. |
| 8,188,118 B2 * | 5/2012 | Zeldis .................... A61K 31/00 514/321 |
| 8,198,262 B2 | 6/2012 | Zeldis et al. |
| 8,198,306 B2 * | 6/2012 | Zeldis .................... A61K 31/00 514/321 |
| 8,204,763 B2 | 6/2012 | Elsayed et al. |
| 8,207,200 B2 * | 6/2012 | Zeldis .................... A61K 31/00 514/321 |
| 8,315,886 B2 | 11/2012 | Williams et al. |
| 8,410,136 B2 | 4/2013 | Zeldis |
| 8,440,194 B2 | 5/2013 | Zeldis |
| 8,492,406 B2 | 7/2013 | Zeldis |
| 8,530,498 B1 * | 9/2013 | Zeldis .................... A61K 31/00 514/320 |
| 8,589,188 B2 | 11/2013 | Elsayed et al. |
| 8,623,384 B2 | 1/2014 | Zeldis |
| 8,626,531 B2 | 1/2014 | Williams et al. |
| 8,628,927 B2 | 1/2014 | Faham et al. |
| 8,632,787 B2 | 1/2014 | Zeldis |
| 8,648,095 B2 * | 2/2014 | Zeldis .................... A61K 31/00 514/321 |
| 8,673,939 B2 | 3/2014 | Zeldis |
| 8,722,705 B2 | 5/2014 | Zeldis |
| 8,735,428 B2 | 5/2014 | Zeldis |
| 8,759,375 B2 | 6/2014 | Zeldis |
| 8,828,427 B2 | 9/2014 | Tutino et al. |
| 9,050,324 B2 | 6/2015 | Zeldis |
| 9,056,103 B2 | 6/2015 | Zeldis |
| 9,101,621 B2 * | 8/2015 | Zeldis .................... A61K 31/00 |
| 9,101,622 B2 * | 8/2015 | Zeldis .................... A61K 31/00 |
| 9,155,730 B2 | 10/2015 | Zeldis |
| 9,393,238 B2 | 7/2016 | Zeldis |
| 9,498,472 B2 | 11/2016 | Zeldis |
| 2001/0018445 A1 | 8/2001 | Huang et al. |
| 2001/0021380 A1 | 9/2001 | Pluenneke |
| 2001/0026807 A1 | 10/2001 | Watts |
| 2001/0056114 A1 | 12/2001 | D'Amato |
| 2002/0035090 A1 | 3/2002 | Zeldis et al. |
| 2002/0045643 A1 | 4/2002 | Muller et al. |
| 2002/0051820 A1 | 5/2002 | Shell et al. |
| 2002/0052398 A1 | 5/2002 | D'Amato |
| 2002/0054899 A1 | 5/2002 | Zeldis et al. |
| 2002/0061923 A1 | 5/2002 | D'Amato |
| 2002/0128228 A1 | 9/2002 | Hwu |
| 2002/0161023 A1 | 10/2002 | D'Amato |
| 2002/0173658 A1 | 11/2002 | Muller et al. |
| 2002/0183360 A1 | 12/2002 | Muller et al. |
| 2003/0013739 A1 | 1/2003 | Masferrer et al. |
| 2003/0028028 A1 | 2/2003 | Man et al. |
| 2003/0039688 A1 | 2/2003 | Shell et al. |
| 2003/0045552 A1 | 3/2003 | Robarge et al. |
| 2003/0049311 A1 | 3/2003 | McAllister et al. |
| 2003/0069428 A1 | 4/2003 | Muller et al. |
| 2003/0096841 A1 | 5/2003 | Robarge et al. |
| 2003/0104053 A1 | 6/2003 | Gusler et al. |
| 2003/0104062 A1 | 6/2003 | Berner et al. |
| 2003/0139451 A1 | 7/2003 | Shah et al. |
| 2003/0144325 A1 | 7/2003 | Muller et al. |
| 2003/0181428 A1 | 9/2003 | Green et al. |
| 2003/0187024 A1 | 10/2003 | D'Amato |
| 2003/0191098 A1 | 10/2003 | D'Amato |
| 2003/0220254 A1 | 11/2003 | Khan et al. |
| 2003/0235909 A1 | 12/2003 | Harris et al. |
| 2004/0029832 A1 | 2/2004 | Zeldis |
| 2004/0077685 A1 | 4/2004 | Figg et al. |
| 2004/0077686 A1 | 4/2004 | Dannenberg et al. |
| 2004/0087546 A1 | 5/2004 | Zeldis |
| 2004/0091455 A1 | 5/2004 | Zeldis |
| 2004/0122052 A1 | 6/2004 | Muller et al. |
| 2004/0152632 A1 | 8/2004 | Feingold |
| 2004/0162263 A1 | 8/2004 | Sands et al. |
| 2004/0266809 A1 | 12/2004 | Emanuel et al. |
| 2005/0272675 A1 | 12/2005 | Ionescu et al. |
| 2006/0247189 A1 | 11/2006 | Ionescu et al. |
| 2007/0155791 A1 | 7/2007 | Zeldis et al. |
| 2007/0270374 A1 | 11/2007 | Gallop |
| 2008/0057086 A1 | 3/2008 | Etter |
| 2009/0010877 A1 | 1/2009 | Zeldis |
| 2009/0093504 A1 | 4/2009 | Muller et al. |
| 2009/0123416 A1 | 5/2009 | Zeldis |
| 2009/0286752 A1 | 11/2009 | Etter et al. |
| 2010/0093683 A1 * | 4/2010 | Zeldis .................... A61K 31/00 514/171 |
| 2010/0196369 A1 | 8/2010 | Zeldis |
| 2010/0278779 A1 | 11/2010 | Zeldis |
| 2011/0172273 A1 | 7/2011 | Zeldis |
| 2012/0035145 A1 | 2/2012 | Zeldis |
| 2012/0230983 A1 | 9/2012 | Muller et al. |
| 2013/0183381 A1 | 7/2013 | Zeldis |
| 2014/0186404 A1 | 7/2014 | Zeldis |

FOREIGN PATENT DOCUMENTS

| | | |
|---|---|---|
| WO | WO 92/06712 | 4/1992 |
| WO | WO 92/14455 | 9/1992 |

(56) References Cited

FOREIGN PATENT DOCUMENTS

| WO | WO 94/20085 | 9/1994 |
|---|---|---|
| WO | WO 96/13790 | 5/1996 |
| WO | WO 98/03502 | 1/1998 |
| WO | WO 98/54170 | 3/1998 |
| WO | WO 98/13783 | 4/1998 |
| WO | WO 98/19649 | 5/1998 |
| WO | WO 99/10829 | 3/1999 |
| WO | WO 2000/051053 | 8/2000 |
| WO | WO 2001/070275 | 9/2001 |
| WO | WO 2001/087306 | 11/2001 |
| WO | WO 2001/087307 | 11/2001 |
| WO | WO 2002/015926 | 2/2002 |
| WO | WO 02/059106 | 8/2002 |
| WO | WO 2002/064083 | 8/2002 |
| WO | WO 2003/086373 | 10/2003 |
| WO | WO 2003/097040 | 11/2003 |
| WO | WO 2003/097052 | 11/2003 |
| WO | WO 2004/035064 | 4/2004 |
| WO | WO 2005/110085 | 11/2005 |
| WO | WO 2005/110408 | 11/2005 |
| WO | WO 2006/063111 | 6/2006 |
| WO | WO 2008/019378 | 2/2008 |
| WO | WO 2008/027049 | 3/2008 |
| WO | WO 2008/028193 | 3/2008 |
| WO | WO 2009/052287 | 4/2009 |
| WO | WO 2009/058394 | 5/2009 |

OTHER PUBLICATIONS

Foster, "Deuterium isotope effects in the metabolism of drugs and xenobiotics: implications for drug design," Adv. Drug Res., 14:1-40 (1985).
Galustian et al., "Lenalidomide: a novel anticancer drug with multiple modalities," Expert Opin. Pharmacother., 10(1):125-133 (2009).
Gatley et al., "Deuterioglucose: alteration of biodistribution by an isotope effect," J. Nucl. Med., 27(3):388-394 (1986).
Gordon et al., "The metabolism of the abortifacient terpene, (R)-(+)-pulegone, to a proximate toxin, menthofuran," Drug Metab. Dispos., 15(5):589-594 (1987).
Hiroyuki et al., "A Comparison Between Next-Generation Seqencing and ASO-qPCR for Minimal Residual Disease Detection in Multiple Myeloma: The Clinical Value in ASCT Setting," Database accession No. PREV201400360880 (2013).
Kushner et al., "Pharmacological uses and perspectives of heavy water and deuterated compounds," Can. J. Physiol. Pharmacol, 77(2):79-88 (1999).
Lijinsky et al., "Dose-response studies in carcinogenesis by nitroso-N-methyl-N-(2-phenyl)ethylamine in rats and the effects of deuterium substitution," Food Chem. Toxicol., 20(4);393-399 (1982).
Lijinsky et al., "Dose-response studies with nitrosoheptamethyleneimine and its alpha-deuterium-labeled derivative in F344 rats," J. Natl. Cancer Instit., 69(5):1127-1133 (1982).
Mangold et al., "Effects of deuterium labeling on azido amino acid mutagenicity in *Salmonella typhimurium*," Mutat. Res., 308(1):33-42 (1994).
Marriott et al "Immunotherapeutic and antitumor potential of thalidomide analogues," Expert Opin. Biol. Ther., 1(4):1-8 (2001).
McCarthy, Philip, "Lenalidomide after Stem-Cell Transplantation for Multiple Myeloma," The New England Journal of Medicine, 366(19):1770-1781 (2012).
Muller et al., "Structural modifications of thalidomide produce analogs with enhanced tumor necrosis factor inhibitory activity," J. Med. Chem., 39(17):3238-3240 (1996).
Muller et al., "Thalidomide analogs and PDE4 inhibition," Bioorg. & Med. Chem. Lett., 8:2669-2674 (1998).
Munshi et al., "Minimal Residual Disease in Multiple Myeloma," Journal of Clinical Oncology, 31(20):2523-2526 (2013).

Penichet et al., "Antibody-cytokine fusion proteins for the therapy of cancer," J. Immunol. Methods, 284:91-101 (2001).
Physicians' Desk Reference, 56th Edition, Medical Economics Company, Inc., Motvale, NJ, pp. 1755-1760 (2002).
Rawstron et al., Blood. 2015;125(12):1932-1935 (2015).
Roitt et al., Immunology, Third Edition, Mosby, St. Louis, MO, 17.1-17.12 (1993).
Taylor et al., "Protamine is an inhibitor of angiogenesis," Nature, 297:307-312 (1982).
Van De Donk, Niels, "New developments in the management and treatment of newly diagnosed and relapsed/refractory multiple myeloma patients," Expert Opinion on Pharmacotherapy, 14(12):1569-1573 (2013).
Wade, "Deuterium isotope effects on noncovalent interactions between molecules," Chem. Biol. Interact., 117:191-217 (1999).
Wilen et al., "Strategies in optical resolutions," Tetrahedron, 33:2725-2736 (1977).
Wilen, Tables of Resolving Agents and Optical Resolutions, (E.L. Eliel, Ed.), University of Notre Dame Press, Notre Dame, IN, p. 268 (1972).
Wolff ed., Burger's Medicinal Chemistry and Drug Discovery, 5th Edition, John Wiley & Sons, Inc., pp. 172-178, 949-982 (1995).
Zello et al., "Plasma and urine enrichments following infusion of L-[1-13C]phenylalanine and L[ring-2H5]phenylalanine in humans: evidence for an isotope effect in renal tubular reabsorption," Metabolism, 43(4):487-491 (1994).
"CDC meeting: Mar. 26, 1997 minutes and agenda regarding thalidomide."
"Center for drug evaluation and research approval package for: Application No. 18-662/S-038."
"Center for drug evaluation and research approval package for: Application No. NDA 20-785 approval letter(s)," Sep. 19, 1997 and Jul. 16, 1998.
NCT00480363: "Quiredex: Revlimid (lenalidomide) and dexamethasone (ReDex) treatment versus observation in patients with smoldering multiple myeloma with high risk of progression (Quiredex)."
Adams et al., "Proteasome inhibitors: A novel class of potent and effective antitumor agents," *Cancer Res.* 59:2615-2622 (1999).
Alder et al., "The return of thaliomide—A shunned compound makes a scientific comeback," *Science News* 146:424-425 (1994).
Alexanian et al., "High-dose glucocorticoid treatment of resistant myeloma," *Ann. Intern. Med.* 105:8-11 (1986).
Alexanian et al., "Consolidation therapy of multiple myeloma with thalidomide-dexamethasone after intensive chemotherapy," *Ann Oncol.* 13:1116-9 (2002).
Anderson et al., "Multiple myeloma: New insights and therapeutic approaches," *Hematology Am. Soc. Hematol. Educ. Program* 2000:147-165 (2000).
Barlogie et al., "Effective treatment of advanced multiple myeloma refractory to alkylating agents," *N. Engl. J. Med.* 310:1353-1356 (1984).
Bjorkstrand et al., "Prognostic factors in autologous stem cell transplantation for multiple myeloma: an EBMT registry study," *Leuk. Lymphoma* 15:265-272 (1994).
Bor, J., "Thalidomide shows that it can heal, too from deformer of babies to force for good," *Baltimore Sun* Apr. 2, 1995.
Broder et al., "Dideoxycytidine: Current clinical experience and future prospects. A summary," *Am. J. Med.*, 88:31S-33S (1990).
Cairo, "Dose reductions and delays: Limitations of myelosuppressive chemotherapy," *Cancer Network* Sep. 1, 2000.
Canal et al., "Benefits of pharmacological knowledge in the design and monitoring of cancer chemotherapy," *Pathology Oncol. Res.* 4:171-178 (1998).
Celgene Press Release, "Initial phase I solid tumor data on Celgene's lead IMiD™, Revimid™," Jun. 2001.
Celgene News Release, "Positive interim results presented at the VIIIth international myeloma workshop on Celgene Corporation's lead IMiD™ (REV/MID™)," May 8, 2001.
Celgene Corporation Awarded Additional Patent Protection for Lead IMiD(™), REVIMID(™); Comprehensive Patent Protection

(56) References Cited

OTHER PUBLICATIONS for REVIMID Includes Coverage of the Active Ingredient, Pharmaceutical Compositions, and Therapeutic Uses PR Newswire; Aug. 28, 2001.
Chu et al., "Principles of cancer management: Chemotherapy." In *Cancer: Principles and Practice of Oncology*, 6th Ed.; De Vita, Jr., Hellman, and Rosenberg Ed.; Lippincott Williams & Wilkins, Philadelphia, pp. 289-306 (2001).
Corral et al., "Differential cytokine modulation and T cell activation by two distinct classes of thalidomide analogues that are potent inhibitors of TNF-alpha," *J. Immunol.* 163:380-386 (1999).
D'Amato et al., "Mechanism of action of thalidomide and 3-aminothalidomide in multiple myeloma," *Semin. Oncol.* 28:597-601 (2001).
D'Amato et al., "Thalidomide is an inhibitor of angiogenesis," *Proc. Natl. Acad. Sci. USA* 91:4082-4085 (1994).
Dancey et al., "Neutrophil kinetics in man," *J. Clin. Invest.* 58:705-715 (1976).
Davies et al., "Thalidomide and immunomodulatory derivatives augment natural killer cell cytotoxicity in multiple myeloma," *Blood* 98:210-216 (2001).
Devita et al., eds., "Plasma cell neoplasm." In *Cancer Principles & Practice of Oncology*, 5th Ed.; Lippincott-Raven Publishers, pp. 2344-2379 (1997).
Dimopoulos et al., "Thalidomide and dexamethasone combination for refractory multiple myeloma," *Ann. Oncol.* 12:991-995 (2001).
Dimopoulos et al., "Thalidomide and dexamethasone combination for multiple myeloma refractory to dexamethasone-based reginens," *Blood*, 96(Supp):286b (2000).
Dishman et al., "Pharmacists'ranscript role in clozapine therapy at a veterans affairs medical center," *Am. J. Hosp. Pharm.* 51:899-901 (1994).
Durie and Stepan, "Efficacy of low dose thalidomide in multiple myeloma," *Eur. J. Oncol.* 1:1-8 (2000).
Edwards, D., "Thalidomide: Is there a silver lining?" *Science News* 131:198 (1987).
Elliot et al., "The proteasome: a new target for novel drug therapies," *Am. J. Chn. Pathol.* 116:637-646 (2001).
"EntreMed moves towards commercialization with production of thalidomide analogs; Next generation drug candidates to be manufactured in preparation for clinical studies," *PR Newswire* Aug. 7, 2001.
Figg et al., "Pharmacokinetics of thalidomide in an elderly prostate cancer population," *J. Pharm. Sci.* 88:121-125 (1999).
Filella et al., "Cytokines (IL-6, TNF-alpha, IL-1 alpha) and soluble interleukin-2 receptor as serum tumor markers in multiple myeloma," *Cancer Detect. Prev.* 20:52-56 (1996).
Foerster et al., "Effects of thalidomide and EM12 on the synthesis of TNF-α in coclutures of human monocytes and lymphocytes," Abstract 517 (1995).
Gahrton et al., "Progress in haematopoietic stem cell transplantation for multiple myeloma," *J. Intern. Med* 248:185-201 (2000).
Gardner et al., "Assessing the effectiveness of a computerized pharmacy system." In *Decision Support Systems in Critical Care*; Shabot et al., eds.; pp. 174-183 (1994).
Glasmacher et al., "Oral idarubicin, dexamethasone and vincristine (VID) in the treatment of multiple myeloma," *Leukemia* 11:S22-S26 (1997).
Gupta et al., "Adherence of multiple myeloma cells to bone marrow stromal cells upregulates vascular endothelial growth factor secretion: therapeutic applications," *Leukemia* 15:1950-1961 (2001).
Hamera et al., "Alcohol, cannabis, nicotine, and caffeine use and symptom distress in Schizophrenia," *J. Nerv. Ment. Dis.* 183:559-565 (1995).
Kibbe ed., *Handbook of Pharmaceutical Excipients*, 3rd Ed.; pp. 160-162 (2000).
He et al., "Synthesis of thalidomide analogs and their biological potential for treatment of graft versus host disease," 206th ACS National Meeting 0-8412-2620-2, American Chemical Society, Chicago, IL, Abstract 216 (1993).

Hideshima et al., "Novel therapies targeting the myeloma cell and its bone marrow microenvironment," *Semin. Oncol.* 28:607-612 (2001).
Hideshima et al., "The proteasome inhibitor PS-341 inhibits growth, induces apoptosis, and overcomes drug resistance in human multiple myeloma cells," *Cancer Res.* 61:3071-3076 (2001).
Hideshima et al., "Thalidomide (Thal) and its analogs overcome drug resistance of human multiple myeloma (MM) cells to conventional therapy," Abstract 1313, American Society of Hematology, Dec. 1-5, 2000.
Hideshima et al., "Thalidomide and its analogs overcome drug resistance of human multiple myeloma cells to conventional therapy," *Blood* 96:2943-2950 (2000).
Hochster et al., "Activity and pharmacodynamics of 21-Day topotecan infusion in patients with ovarian cancer previously treated with platinum-based chemotherapy. New York Gynecologic Oncology Group," *J. Clin. Oncol.* 17:2553-2561 (1999).
Hus et al., "Thalidomide treatment of resistant or relapsed multiple myeloma patients," *Haematologica* 86:404-408 (2001).
Jagannath et al., "Pomalidomide (POM) with or without low-dose dexamethasone (LoDEX) in patients (Pts) with relapsed and refractory multiple myeloma (RRMM): MM-002 phase II age subgroup analysis," *J. Clin. Oncol.* 31, Abstrct # 8532, (2013).
Jönsson, "Chemical structure and teratogenic properties. 3. A review of available data on structure-activity relationships and mechanism of action of thalidomide analogues," *Acta Pharm. Suec.* 9:521-542 (1972).
Jourdan et al., "Tumor necrosis factor is a survival and proliferation factor for human myeloma cells," *Eur. Cytokine Netw.* 10:65-70 (1999).
Keravich et al., "Challenges of thalidomide distribution in a hospital setting," *Am. J. Health Syst. Pharm.* 56:1721-1725 (1999).
Knight, "Cancer patients ahead of FDA on thalidomide use," *Washington Post* Jun. 25, 2001.
Kosten et al., "Substance abuse and Schizophrenia: Editors' Introduction," *Schizophrenia Bulletin* 23:181-186 (1997).
Kyle et al., "Therapeutic application of thalidomide in multiple myeloma," *Semin. Oncol.* 28:583-587 (2001).
Lacy et al., "Pomalidomide (CC4047) plus low-dose dexamethasone as therapy for relapsed multiple myeloma," *J. Clin. Oncol.* 27:5008-5014 (2009).
Lacy et al., "Pomalidomide plus low-dose dexamethasone in myeloma refractory to both bortezomib and lenalidomide: Comparison of 2 dosing strategies in dual-refractory disease," *Blood* 118:2970-2975 (2011).
Lentzsch et al., "S-3-amino-phthalimido-glutarimide inhibits angiogenesis and growth of B-cell neoplasias in mice," *Cancer Res.* 62:2300-2305 (2002).
Linnarsson, "Decision support for drug prescription integrated with computer-based patient records in primary care," *Med. Inform.* 18:131-142 (1993).
Lipkin, "Deriving new drugs from thalidomide," *Science News* 148:171 (1995).
Mann et al., "Passage of chemicals into human and animal semen: mechanisms and significance," *Crit. Rev. Toxicol.* 11:1-14 (1982).
"Celgene's Revlimid an orphan chug, says FDA," *Marketletter* Oct. 15, 2001.
Marwick, "Thalidomide back—under strict control," *JAMA* 278:1135-1137 (1997).
Menill, "Substance Abuse and Women on Welfare," *National Center on Addiction and Substance Abuse at Columbia University*, Jun. 1994.
Mitchell et al., "A pregnancy-prevention program in women of childbearing age receiving isotretinoin," *N. Engl. J. Med.* 333:101-106 (1995).
Mitsiades et al., "Concepts in the use of TRAIL/Apo2L: An emerging biotherapy for myeloma and other neoplasias," *Expert Opin. Investig. Drugs* 10:1521-1530 (2001).
Mitsiades et al., "Apoptic signaling induced by immunomodulatory thalidomide analogs in human multiple myeloma cells: therapeutic implications," *Blood* 99:4525-4530 (2002).
Montero et al., "Economic study of neutropenia induced by myelotoxic chemotherapy," *Pharm. World Sci.* 16(:187-192 (1994).

(56) References Cited

OTHER PUBLICATIONS

Morgan et al., "Lenalidomide (Revlimid), in combination with cyclophosphamide and dexamethasone (RCD), is an effective and tolerated regimen for myeloma patients," *Br. J. Haematol.* 137:268-269 (2007).
Muller et al., "Amino-substituted thalidomide analogs: potent inhibitors of TNF-α production," *Bioorg. Med. Chem. Lett.* 9:1625-1630 (1999).
Heger et al., "Embryotoxic effects of thalidomide derivatives in the non-human primate callithrixjacchus. IV teratogenicity of µg/kg doses of the EMJ 2 enantiomers," *Teratogenesis, Carcinogenesis, and Mutagenenesis* 4:115-122 (1994).
Muller, "Thalidomide: From tragedy to new drug discovery," *Chemtech* 27:21-25 (1997).
Mundt, "Interactive voice response systems in clinical research and treatment," *Psychiatr. Serv.* 48:611-612, 623 (1997).
National Cancer Institute, Common Toxicity Criteria Manual, Ver. 2.0, Jun. 1, 1999.
Noguelra et al., "Effect of thalidomide and some derivatives on the adhesion of lymphocytes to endothelial cells," Abstract 518 (1995).
Olson et al., "Thalidomide (N-phthaloylglutamimide) in the treatment of advanced cancer," *Clinical Pharmacology and Therapeutics* 6:292-297 (1965).
Palumbo et al., "Low-dose thalidomide plus dexamethasone is an effective salvage therapy for advanced myeloma," *Haematologica* 86:399-403 (2001).
Pastuszak et al., "Use of the retinoid pregnancy prevention program in Canada: Patterns of contraception use in women treated with isotretinoin and etretinate," *Reprod. Toxicol.* 8:63-68 (1994).
Pestotnik et al., "Therapeutic antibiotic monitoring: Surveillance using a computerized expert system," *Am. J. Med.* 88:43-48 (1990).
Piper et al., "Anti-inflammatory immunosuppressive thalidomide analogs. Screening," *Int. J. Leprosy* 49:511-512 (1981).
Powell et al., "Guideline for the clinical use and dispensing of thalidomide," *Postgrad. Med. J.* 70:901-904 (1994).
Bwire et al., "Managing the teratogenic risk of thalidomide and lenalidomide: An industry perspective," *Expert Opin. Drug Saf*, 10:3-8 (2011).
Raje et al., "Thalidomide—a revival story," *N. Engl. J. Med.* 341:1606-1609 (1999).
Rajkumar et al., "Thalidomide in the treatment of plasma cell malignancies," *J. Clin. Oncol.* 19:3593-3595 (2001).
Rajkumar et al., "Lenalidomide plus high-dose dexamethasone versus lenalidomide plus low-dose dexamethasone as initial therapy for newly diagnosed multiple myeloma: an open-label randomised controlled trial," *Lancet* 11:29-37 (2010).
Rajkumar et al., "Phase III trial of lenalidomide plus highdose dexamethasone versus lenalidomide plus low-dose dexamethasone in newly diagnosed multiple myeloma (E4A03): A trial coordinated by the Eastern Cooperative Oncology Group," *J. Clin. Oncol.* 25:18S (2007).
Rajkumar et al "Thalidomide plus dexamethasone (Thal/Dex) and thalidomide alone (Thal) as first line therapy for newly diagnosed myeloma (MM)," *Blood* 96(Supp.):167 (2000).
Rajkumar et al., "Combination therapy with lenalidomide plus dexamethasone (Rev/Dex) for newly diagnosed myeloma," *Blood* 106:4050-4053 (2005).
Rajkumar, "Thalidomide in multiplem myeloma," *Oncology* 14:11-16 (2000).
Ratain, "Pharmacology of Cancer Chemotherapy." In *Cancer: Principles & Practice of Oncology*, pp. 335-459 (2001).
Reiman et al., "Meeting synopsis, VIII International Myeloma Workshop, Banff Springs Hotel, Banff, Alberta, Canada, May 4-8, 2001," *Eur. J. Haematol.* 67:199-202 (2001).
Richardson et al., "A randomized phase 2 study of lenalidomide therapy for patients with relapsed or relapsed and refractory multiple myeloma," *Blood* 108:3458-3464 (2006).
Richardson et al., "Thalidomide in multiple Myeloma," *Biomed. Pharmacother.* 56:115-128 (2002).
Richardson et al., "Thalidomide: Emerging role in cancer medicine," *Ann. Rev. Med.* 53:629-657 (2002).
Richardson et al., "Immunomodulatory drug CC-5013 overcomes drug resistance and is well tolerated in patients with relapsed multiple myeloma," *Blood* 100:3063-3067 (2002).
Richardson et al., "A phase 1/2 multi-center, randomized, open label dose escalation study to determine the maximum tolerated dose (MTD), safety, and efficacy of pomalidomide (POM) alone or in combination with low-dose dexamethasone (DEX) in patients (PTS) with relapsed and refractory multiple myeloma (RRMM) who have received prior treatment (TX) that includes lenalidomide (LEN) and bortezomib (BORT)," *Haematologica*, 96:S31 (2001).
Robert et al., "Phase I and pharmacologic study of 7- and 21-day continuous etoposide infusion in patients with advanced cancer," *Cancer Chemother. Pharmacol.* 38:459-465 (1996).
Samlowski et al., "Evaluation of gemcitabine in patients with recurrent or metastatic squamous cell carcinoma of the head and neck: A southwest oncology group phase II study," *Invest. New Drugs* 19:311-315 (2001).
Sampaio et al., "Thalidomide selectively inhibits tumor necrosis factor alpha production by stimulated human monocytes," *J. Exp. Med.* 173:699-703 (1991).
Schey et al., "Phase I study of an immunomodulatory thalidomide analog, CC-4047, in relapsed or refractory multiple myeloma," *J. Clin. Oncol.* 22:3269-3276 (2004).
Schey et al., "Pomalidomide therapy for myeloma," *Expert Opin. Invest. Drugs* 20:691-700 (2011).
Schey et al., "A phase I study of an immunomodulatory thalidomide analogue (CC4047) in relapse/refractory multiple myeloma," *International Society for Experimental Hematology*, 31st Annual Meeting, Jul. 6-9, Montreal, Canada, 2002; Abstract #248.
Schey, "Thalidomide in the management of multiple myeloma," *Hematology* 7:291-299 (2002).
Schlossman et al., "Bone marrow transplatation in multiple myeloma," *Curr. Opin. Oncol.* 11:102-108 (1999).
Seppa, "Thalidomide combats myeloma blood cancer," *Science News* 156:326 (1999).
Shinn et al., "Development of a computerized drug interaction database (Medicom) for use in a patient specific environment," *Drug Inf. J.* 17:205-210 (1983).
Siegel et al., "Long-term safety and efficacy of pomalidomide (POM) with or without low-dose dexamethasone (LoDEX) in relapsed and refractory multiple myeloma (RRMM) patients enrolled in the MM-002 phase II trial," *J. Clin. Oncol.* 31, 2013 (Abstract No. 8588).
Singhal et al., "Antitumor activity of thalidomide in refractory multiple myeloma," *N. Engl. J. Med.* 341:1565-1571 (1999).
Smith et al., "Studies on the relationship between the chemical structure and embryotoxic activity of thalidomide and related compounds," in *A Symposium on Embryopathic Activity of Drugs*, J. & A. Churchill Ltd., 1965, Session 6, pp. 194-209.
Sorbera et al., "CC-5013. Treatment of multiple myeloma. Treatment of Melanoma. Treatment of myelodysplastic syndrome. Angiogenesis inhibitor. TNF-α production inhibitor," *Drugs of the Future* 28:425-431 (2003).
Soyka et al., "Prevalence of alcohol and drug abuse in schizophrenic inpatients," *Eur. Arch. Psychiatry Clin. Neurosci.* 242:362-372 (1993).
Steiner et al., "The assessment of refill compliance using pharmacy records: methods, validity, and applications," *J. Clin. Epidemiol.* 50:105-116 (1997).
Stirling et al., "Thalidomide. A surprising recovery," *J. Am. Pharm. Assoc.* NS37:306-313 (1997).
Stirling, "Thalidomide: A novel template for anticancer drugs," *Seminars Oncology* 28:602-606 (2001).
Szelényi et al., "Cyclophosphamide, adriamycin and dexamethasone (CAD) is a highly effective therapy for patients with advanced multiple myeloma," *Ann. Oncol.* 12:105-108 (2001).
THALOMID™ (thalidomide) Capsules Revised Package Insert (Jul. 15, 1998).
Perry ed., "The chemotherapy source book" (1992).

(56) References Cited

OTHER PUBLICATIONS

The Comprehensive Guide to Banff, Understanding the VIIIth International Myeloma Workshop was published by the International Myeloma Foundation in Jul. 2001.
Transcript of the Forty-Seventh Meeting of the Dermatologic and Ophthalmic Drugs Advisory Committee (Sep. 4, 1997).
Transcript of the Forty-Seventh Meeting of the Dermatologic and Ophthalmic Drugs Advisory Committee (Sep. 5, 1997).
Tseng et al., "Rediscovering thalidomide: a review of its mechanism of action, side effects, and potential uses," J. Am. Acad. Dermatol. 35(6):969-979 (1996).
Vij et al., "Pomalidomie (POM) with Low-Dose Dexamethasone (LoDex) in Patients with Relapsed and Refractory Multiple Myeloma (RRMM): Outcomes Based on Prior Treatment Exposure," presented at 54th ASH Annual Meeting and Exposition, Atlanta, Georgia, Dec. 8-11, 2012, Abstract #4070.
Vogelsang et al., "Thalidomide for the treatment of chronic graft-versus-host disease," N. Engl. J. Med. 326(16):1055-1058 (1992).
Weber et al., "Thalidomide alone or with dexamethasone for multiple myeloma," Blood 94:604 (1999).
Weber et al., "Thalidomide with dexamethasone of resistant multiple myeloma," Blood 96:167 (2000).
Welte et al., "Influence of socially desirable responding in a study of stress and substance abuse," Alcohol Clin. Exp. Res. 17:758-761 (1993).
Yuen et al., "Phase I study of an antisense oligonucleotide to protein kinase C-α (ISIS 3521/CGP 64128A) in patients with cancer," Clin. Cancer Res. 5:3357-3363 (1999).
Zangari et al., "Increased risk of deep-vein thrombosis in patients with multiple myeloma receiving thalidomide chemotherapy," Blood 98:1614 (2001).
Zangari et al., "Thrombogenic activity of doxorubicin in myeloma patients receiving thalidomide: Implications for therapy," Blood 100:1168-1171 (2002).
Zeldis et al., "S.T.E.P.S.: A comprehensive program for controlling and monitoring access to thalidomide," Clin. Ther. 21:319-330 (1999).
U.S. Appl. No. 09/287,377, filed Apr. 7, 1999 (62 pages).
U.S. Appl. No. 60/372,348, filed Apr. 12, 2002 (85 pages).
U.S. Appl. No. 60/499,723, filed Sep. 4, 2003 (55 pages).
Anderson et al., "Novel biologically based therapies for myeloma," VIII the International Myeloma Workshop, Banff, Alberta, Canada, May 4-8, 2001; Abstract #S27.
Celgene Corporation, Form 424B4 (2000).
Cheson, "New drug development in non-Hodgkin lymphomas," Curr. Oncol. Rep. 3:250-259 (2001).
Crane et al., "Immunomodulatory drugs," Cancer Invest. 23:625-634 (2005).
Damaj et al., "Thalidomide therapy induces response in relapsed mantle cell lymphoma," Leukemia 17:1914-1915 (2003).
Drach et al., "Treatment of mantle cell lymphoma: Targeting the microenvironment," Expert Rev. Anticancer Ther. 5:477-485 (2005).
Lentzsch et al., "Immunomodulatory derivatives (IMiDs) of thalidomide (Thal) inhibit the proliferation of multiple myeloma (MM) cell lines and block VEGF-induced activation of the MAPK-pathway," Blood 96:579 (Abstract# 2486) (2000).
Pro et al., "Phase II study of thalidomide in patients with recurrent Hodgkin's disease (HD) and non-Hodgkin's lymphoma (NHL)," Blood 98:246b (Abstract# 4712) (2001).
Querfeld et al., "Preliminary results of a phase II study of CC-5013 (lenalidomide, revlimid®) in patients with cutaneous T-cell lymphoma," Blood 106:936a-937a (2005).
Ribatti et al., "Angiogenesis spectrum in the stroma of B-cell non-Hodgkin's lymphomas. An immunohistochemical and ultrastructural study," Eur. J. Haematol. 56:45-53 (1996).
Richardson et al., "A phase 1 study of oral CC5013, an immunomodulatory thalidomide (Thal) derivative, in patients iwth relapsed and refractory multiple myeloma (MM)," Blood 98:775a (2001).
Richardson et al., "A Phase I study of oral CC5013, an immunomodulatory thalidomide (Thal) derivative, in patients with relapsed and refractory multiple myeloma (MM)," Blood, 98(11), Abstract# 3225 (2001).
Richardson et al., "A phase I study of the safety and efficacy of CC5013 treatment for patients with relapsed multiple myeloma: Preliminary results," VIII the International Myeloma Workshop, Banff, Alberta, Canada, May 4-8, 2001; Abstract #P230.
Srkalovic et al., "Use of melphalan, thalidomide, and dexamethasone in treatment of refractory and relapsed multiple myeloma," Med. Oncol. 19:219-226 (2002).
Thomas et al., "Current role of thalidomide in cancer treatment," Curr. Opin. Oncol. 12:564-573 (2000).
Vacca et al., "Angiogenesis in B cell lymphoproliferative diseases. Biological and clinical studies," Leuk. Lymphoma 20:27-38 (1995).
Wilson et al., "Response to thalidomide in chemotherapy-resistant mantle cell lymphoma: a case report," Br. J. Haematol. 119:128-130 (2002).
Zangari et al., Results of phase I study of CC-5013 for the treatment of multiple myeloma (MM) patients who relapse after high dose chemotherapy (HDT), Blood 98(11), Abstract# 3226 (2001).

* cited by examiner

METHODS OF TREATING MULTIPLE MYELOMA WITH IMMUNOMODULATORY COMPOUNDS IN COMBINATION WITH ANTIBODIES

1. FIELD OF THE INVENTION

This invention relates to methods of treating, preventing and/or managing multiple myeloma, by the administration of one or more immunomodulatory compounds in combination with one or more antibodies. Specifically, this invention relates to methods of treating multiple myeloma in patients who have received autologous stem cell transplantation, with the immunomodulatory compound lenalidomide in combination with an anti-CS1 antibody such as elotuzumab. The invention also relates to pharmaceutical compositions and dosing regimens.

2. BACKGROUND OF THE INVENTION 2.1 Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples includes cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, bFGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, fibrosis, arthritis and autoimmune diseases. Examples of such diseases and conditions include, but are not limited to: diabetic retinopathy; retinopathy of prematurity; corneal graft rejection; neovascular glaucoma; retrolental fibroplasia; and proliferative vitreoretinopathy.

Accordingly, compounds that can control and/or inhibit unwanted angiogenesis or inhibit the production of certain cytokines, including TNF-α, may be useful in the treatment and prevention of various diseases and conditions.

Multiple myeloma is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin. M-protein, short for monoclonal protein, also known as paraprotein, is a particularly abnormal protein produced by the myeloma plasma cells and can be found in the blood or urine of almost all patients with multiple myeloma.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Bone marrow stromal cells are well known to support multiple myeloma disease progression and resistance to chemotherapy. Disrupting the interactions between multiple myeloma cells and stromal cells is an additional target of multiple myeloma chemotherapy.

In the last decade, novel therapeutic agents, in particular immunomodulatory drugs such as lenalidomide and pomalidomide, significantly increased the response rates and prolonged progression free survival (PFS) and overall survival (OS) in multiple myeloma patients. However, persistent levels of residual disease that are below the sensitivity of bone marrow (BM) morphology, protein electrophoresis with immunofixation, and light chain quantitation exists in many patients with multiple myeloma, even after these patients have achieved complete response (CR), and will eventually cause relapse of the disease. Minimal residual disease (MRD) in myeloma is an independent predictor of progression-free survival (PFS) and is under consideration as a surrogate trial endpoint to improve the identification of effective treatments, particularly for frontline trials, which now require 5 to 10 years of follow-up to identify survival differences. Monitoring minimal residual disease (MRD) in patients with multiple myeloma thus provides prognostic value in predicting PFS and OS and making treatment decisions. The detection of minimal residual disease (MRD) in myeloma can use a 0.01% threshold ($10^{-4}$) after treatment, i.e., having $10^{-4}$ cells or fewer is considered MRD-negative, and having $10^{-4}$ cells or higher MRD-positive. The $10^{-4}$ MRD threshold was originally based on technical capability, but quantitative MRD detection is now possible at $10^{-5}$ by flow cytometry and $10^{-6}$ by high-throughput sequencing. Rawstron et al., Blood. 2015; 125(12):1932-1935 (2015). Methods for measuring MRD include polymerase chain reaction (PCR) and multiparameter flow cytometry (MPF). Assays for MRD, e.g., based on clonotype profile measurement are also described in U.S. Pat. No. 8,628,927, to Faham et al., which is incorporated herein by reference.

2.2 Methods of Treating Cancer

Current cancer therapy may involve surgery, chemotherapy, hormonal therapy and/or radiation treatment to eradicate neoplastic cells in a patient (see, for example, Stockdale, 1998, Medicine, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443. Thalidomide and certain derivatives of it have also been proposed for the treatment of such diseases and conditions. U.S. Pat. Nos. 5,593,990, 5,629,327, 5,712,291, 6,071,948 and 6,114,355 to D'Amato.

Still, there is a significant need for safe and effective methods of treating, preventing and managing cancer (e.g., multiple myeloma) and other diseases and conditions associated with, or characterized by, undesired angiogenesis, while reducing or avoiding the toxicities and/or side effects associated with the conventional therapies.

2.3 Immunomodulatory Drug(s)

A number of studies have been conducted with the aim of providing compounds that can safely and effectively be used to treat diseases associated with abnormal production of TNF-α. See, e.g., Marriott, J. B., et al., *Expert Opin. Biol. Ther.* 1(4):1-8 (2001); G. W. Muller, et al., Journal of Medicinal Chemistry 39(17): 3238-3240 (1996); and G. W. Muller, et al., Bioorganic & Medicinal Chemistry Letters 8: 2669-2674 (1998). Some studies have focused on a group of compounds selected for their capacity to potently inhibit TNF-α production by LPS stimulated PBMC. L. G. Corral, et al., Ann. Rheum. Dis. 58:(Suppl I) 1107-1113 (1999). These compounds, which are referred to as immunomodulatory drug(s) (Celgene Corporation), show not only potent inhibition of TNF-α but also marked inhibition of LPS induced monocyte IL1β and IL12 production. LPS induced IL6 is also inhibited by immunomodulatory compounds, albeit partially. These compounds are potent stimulators of LPS induced IL10. Id. Particular examples of immunomodulatory drug(s) include, but are not limited to, the substituted 2-(2,6-dioxopiperidin-3-yl) phthalimides and substituted 2-(2,6-dioxopiperidin-3-yl)-1-oxoisoindoles described in U.S. Pat. Nos. 6,281,230 and 6,316,471, both to G. W. Muller, et al.

Compounds for the methods provided herein include, but are not limited to, the substituted 2-(2,6-dioxopiperidin-3-yl) phthalimides and substituted 2-(2,6-dioxopiperidin-3-yl)-1-oxoisoindoles described in U.S. Pat. Nos. 6,281,230 and 6,316,471, both to G. W. Muller, et al. Still other specific compounds disclosed herein belong to a class of isoindole-imides disclosed in U.S. Pat. Nos. 6,395,754, 6,555,554, 7,091,353, U.S. Publication No. 2004/0029832, and International Publication No. WO 98/54170, each of which is incorporated herein by reference.

Thalidomide and immunomodulatory drugs such as lenalidomide and pomalidomide have shown remarkable responses in patients with multiple myeloma, lymphoma and other hematological diseases such as myelodysplastic syndrome. See Galustian C, et al., *Expert Opin Pharmacother.*, 2009, 10:125-133. These drugs display a broad spectrum of activity, including anti-angiogenic properties, modulation of pro-inflammatory cytokines, co-stimulation of T cells, increased NK cell toxicity, direct anti-tumor effects and modulation of stem cell differentiation.

For example, thalidomide, lenalidomide and pomalidomide have emerged as important options for the treatment of multiple myeloma in newly diagnosed patients, in patients with advanced disease who have failed chemotherapy or transplantation, and in patients with relapsed or refractory multiple myeloma. Lenalidomide in combination with dexamethasone has been approved for the treatment of patients with multiple myeloma who have received at least one prior therapy. Pomalidomide has also been approved for the treatment of patients with multiple myeloma who have received at least two prior therapies including lenalidomide and bortezomib and have demonstrated disease progression on or within 60 days of completion of the last therapy. Phase 3 clinical trials have confirmed the efficacy of pomalidomide in combination with dexamethasone to treat relapsed and/or refractory multiple myeloma after prior therapy. U.S. Pat.

Nos. 7,968,569 and 8,198,262, the disclosures of which are hereby incorporated in its entirety, disclose the treatment of multiple myeloma.

3. SUMMARY OF THE INVENTION

One aspect of the invention encompasses methods of treating, managing and preventing multiple myeloma, in a patient that has received prior stem cell transplantation. The methods comprise administering to a patient in need of such treatment, management, or prevention a therapeutically or prophylactically effective amount of an immunomodulatory compound, or a pharmaceutically acceptable salt, solvate, hydrate, stereoisomer, clathrate, or prodrug thereof, in combination with a therapeutically effective amount of an antibody.

In certain embodiments, the immunomodulatory compound has the formula of

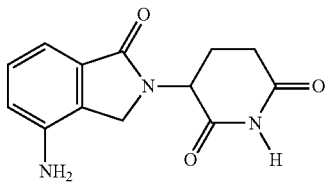 [SMILES: Nc1cccc2c1CN(C1CCC(=O)NC1=O)C2=O]

(i.e., lenalidomide),
or a pharmaceutically acceptable salt, solvate or stereoisomer thereof. In some embodiments, the compound is the free base. In other embodiments, the compound is a pharmaceutically acceptable salt or a pharmaceutically acceptable solvate. In a preferred embodiment, the compound is a hydrate.

In certain embodiments, the immunomodulatory compound has the formula of

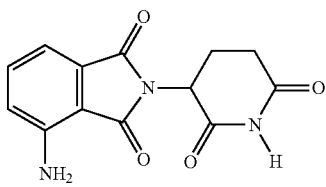 [SMILES: Nc1cccc2c1C(=O)N(C1CCC(=O)NC1=O)C2=O]

(i.e., pomalidomide), or a pharmaceutically acceptable salt, solvate or stereoisomer thereof. In some embodiments, the compound is the free base. In other embodiments, the compound is a pharmaceutically acceptable salt or a pharmaceutically acceptable solvate. In a preferred embodiment, the compound is the free base. In a preferred embodiment, the compound is lenalidomide.

In certain embodiments, the multiple myeloma is newly diagnosed multiple myeloma. In other embodiments, the multiple myeloma is relapsed, refractory, or relapsed and refractory multiple myeloma.

In certain embodiments, the method comprises cyclic administration of the compound. In a preferred embodiment, the compound is administered for 21 days followed by seven days of rest in a 28 day cycle.

In certain embodiments, the compound is administered in an amount of from 1 to about 50 mg per day. In certain embodiments, the compound is administered in an amount of from 1 to about 50 mg per day, in combination with the antibody, preferably with elotuzumab. In some embodiments, the compound is administered in an amount of 2.5 mg, 5 mg, 10 mg, 15 mg, 20 mg or 25 mg per day. In some embodiments, the compound is administered in an amount of 2.5 mg, 5 mg, 10 mg, 15 mg, 20 mg or 25 mg per day, in combination with with the antibody, preferably with elotuzumab. In a preferred embodiment, the compound is administered in an amount of about 25 mg per day. In a preferred embodiment, the compound is administered in an amount of about 25 mg per day, in combination with the antibody, preferably with elotuzumab. In a preferred embodiment, the compound is administered in an amount of about 20 mg per day. In a preferred embodiment, the compound is administered in an amount of about 20 mg per day, in combination with the antibody, preferably with elotuzumab. In a preferred embodiment, the compound is administered in an amount of about 15 mg per day. In a preferred embodiment, the compound is administered in an amount of about 15 mg per day, in combination with the antibody, preferably with elotuzumab. In another preferred embodiment, the compound is administered in an amount of about 10 mg per day. In another preferred embodiment, the compound is administered in an amount of about 10 mg per day; in combination with the antibody, preferably with elotuzumab. In a preferred embodiment, the compound is administered in an amount of about 5 mg per day. In a preferred embodiment, the compound is administered in an amount of about 5 mg per day, in combination with the antibody, preferably with elotuzumab. In a preferred embodiment, the compound is administered in an amount of about 2.5 mg per day. In a preferred embodiment, the compound is administered in an amount of about 2.5 mg per day, in combination with the antibody, preferably with elotuzumab.

In certain embodiments, the compound is administered orally. In certain embodiments, the compound is administered orally, whereas the antibody during combination therapy is not administered orally. In some embodiments, the compound is administered in the form of a capsule or tablet. The capsule may comprise about 2.5 mg, 5 mg, 10 mg, 15 mg, 20 mg or 25 mg of the compound. The tablet may comprise about 2.5 mg, 5 mg, 10 mg, 15 mg, 20 mg or 25 mg of the compound. The capsule may comprise about 2.5 mg of the compound. The tablet may comprise about 2.5 mg of the compound. The capsule may comprise about 5 mg. The tablet may comprise about 5 mg of the compound. The capsule may comprise about 10 mg of the compound. The tablet may comprise about 10 mg of the compound. The capsule may comprise about 15 mg of the compound. The tablet may comprise about 15 mg of the compound. The capsule may comprise about 20 mg of the compound. The tablet may comprise about 20 mg of the compound. The capsule may comprise about 25 mg of the compound. The tablet may comprise about 25 mg of the compound. In certain embodiments, the capsule comprises lactose anhydrous, microcrystalline cellulose, croscarmellose sodium and magnesium stearate in addition to the compound.

In certain embodiments, the antibody administered with the compound is an anti-CS1 antibody. In some embodiments, the anti-CS1 antibody is a monoclonal antibody. In some embodiments, the anti-CS1 antibody administered with the compound is a monoclonal antibody, the compound is preferably lenalidomide or pomalidomide. In some embodiments, the anti-CS antibody is a humanized monoclonal antibody. In some embodiments, the anti-CS antibody administered with the compound is a humanized monoclonal antibody, the compound is preferably lenalidomide or pomalidomide. In a preferred embodiment, the anti-CS1 antibody is elotuzumab. In a preferred embodiment, the anti-CS1 antibody administered with the compound is elotuzumab, the compound is preferably lenalidomide or pomalidomide.

In certain embodiments, the antibody administered with the compound is an anti-CD20 antibody. In some embodiments, the anti-CD20 antibody is a monoclonal antibody. In some embodiments, the anti-CD20 antibody administered with the compound is a monoclonal antibody. In a specific embodiment, the anti-CD20 antibody is obinutuzumab (Gazyva®). In a specific embodiment, the anti-CD20 antibody administered with the compound is obinutuzumab (Gazyva®). In another specific embodiment, the anti-CD20 antibody is rituximab (e.g., Rituxa e). In another specific embodiment, the anti-CD20 antibody administered with the compound is rituximab (e.g., Rituxan®). In another specific embodiment, the anti-CD20 antibody is ibritumomab tiuxetan (Zevalin®). In another specific embodiment, the anti-CD20 antibody administered with the compound is ibritumomab tiuxetan (Zevalin®). In another specific embodiment, the anti-CD20 antibody is tositumomab (Bexxar®). In another specific embodiment, the anti-CD20 antibody administered with the compound is tositumomab (Bexxar®). In another specific embodiment, the anti-CD20 antibody is ofatumumab (Arzerra®). In another specific embodiment, the anti-CD20 antibody administered with the compound is ofatumumab (Arzerra®). In another specific embodiment, the anti-CD20 antibody is AME-133v (ocaratuzumab). In another specific embodiment, the anti-CD20 antibody administered with the compound is AME-133v (ocaratuzumab). In another specific embodiment, the anti-CD20 antibody is ocrelizumab. In another specific embodiment, the anti-CD20 antibody administered with the compound is ocrelizumab. In another specific embodiment, the anti-CD20 antibody is TRU-015. In another specific embodiment, the anti-CD20 antibody administered with the compound is TRU-015. In another specific embodiment, the anti-CD20 antibody is IMMU-106 (veltuzumab). In another specific embodiment, the anti-CD20 antibody administered with the compound is IMMU-106 (veltuzumab). The compound administered in combination with the anti-CD20 antibody is lenalidomide or pomalidomide.

In certain embodiments, the antibody administered with the compound is an anti-PD-1 or anti-PD-L1 antibody. In some embodiments, the anti-PD-1 or anti-PD-L1 antibody is a monoclonal antibody. In some embodiments, the anti-PD-1 or anti-PD-L1 antibody administered with the compound is a monoclonal antibody. In a specific embodiment, the anti-PD-1 or anti-PD-L1 antibody is lambrolizumab (MK-3475). In a specific embodiment, the anti-PD-1 or anti-PD-L1 antibody administered with the compound is lambrolizumab (MK-3475). In another specific embodiment, the anti-PD-1 or anti-PD-L1 antibody is BMS-936559. In another specific embodiment, the anti-PD-1 or anti-PD-L1 antibody administered with the compound is BMS-936559. In another specific embodiment, the anti-PD-1 or anti-PD-L1 antibody is atezolizumab (MPDL3280A). In another specific embodiment, the anti-PD-1 or anti-PD-L1 antibody administered with the compound is atezolizumab (MPDL3280A). In another specific embodiment, the anti-PD-1 or anti-PD-L1 antibody is pidilizumab (CT-011). In another specific embodiment, the anti-PD-1 or anti-PD-L1 antibody administered with the compound is pidilizumab (CT-011). In another specific embodiment, the anti-PD-1 or anti-PD-L1 antibody is pembrolizumab (Keytruda®). In another specific embodiment, the anti-PD-1 or anti-PD-L1 antibody administered with the compound is pembrolizumab (Keytruda®). In another specific embodiment, the anti-PD-1 or anti-PD-L1 antibody is Medi7436. In another specific embodiment, the anti-PD-1 or anti-PD-L1 antibody administered with the compound is Medi7436. In another specific embodiment, the anti-PD-1 or anti-PD-L1 antibody is nivolumab (OPDIVO®; BMS-936558). In another specific embodiment, the anti-PD-1 or anti-PD-L1 antibody administered with the compound is nivolumab (OPDIVO®; BMS-936558). In another specific embodiment, the anti-PD-1 or anti-PD-L1 antibody is MDX-1106. In another specific embodiment, the anti-PD-1 or anti-PD-L1 antibody administered with the compound is MDX-1106. In another specific embodiment, the anti-PD-1 or anti-PD-L1 antibody is ONO-4538. In another specific embodiment, the anti-PD-1 or anti-PD-L1 antibody administered with the compound is ONO-4538. The compound administered in combination with the anti-PD-1 or anti-PD-L1 antibody is preferably lenalidomide or pomalidomide.

In certain embodiments, the antibody administered with the compound is an anti-KIR antibody. In some embodiments, the anti-KIR antibody is a monoclonal antibody. In a specific embodiment, the anti-KIR antibody is IPH2101. The compound administered in combination with the anti-KIR antibody is preferably lenalidomide or pomalidomide.

In certain embodiments, the antibody administered with the compound is an anti-CD40 antibody. In some embodiments, the anti-CD40 antibody is a monoclonal antibody. In a specific embodiment, the anti-CD40 antibody is SGN-40 (dacetuzumab). In another specific embodiment, the anti-CD40 antibody is HCD122 (lucatumumab). The compound administered in combination with the anti-CD40 antibody is preferably lenalidomide or pomalidomide.

In certain embodiments, the antibody administered with the compound is an anti-IGF1-R antibody. In some embodiments, the anti-IGF1-R antibody is a monoclonal antibody. In a specific embodiment, the anti-IGF1-R antibody is CP751,871 (figitumumab). The compound administered in combination with the anti-IGF1-R antibody is preferably lenalidomide or pomalidomide.

In certain embodiments, the antibody administered with the compound is an anti-DKK-1 antibody. In some embodiments, the anti-DKK-1 antibody is a monoclonal antibody. In a specific embodiment, the anti-DKK-1 antibody is BHQ880. The compound administered in combination with the anti-DKK-1 antibody is preferably lenalidomide or pomalidomide.

In certain embodiments, the antibody administered with the compound is an anti-FGFR3 antibody. In some embodiments, the anti-FGFR3 antibody is a monoclonal antibody. In a specific embodiment, the anti-FGFR3 antibody is PRO-001. The compound administered in combination with the anti-FGFR3 antibody is preferably lenalidomide or pomalidomide.

In certain embodiments, the antibody administered with the compound is an anti-CD56 antibody. In some embodiments, the anti-CD56 antibody is a monoclonal antibody. In a specific embodiment, the anti-CD56 antibody is IMGN901 (lorvotuzumab). The compound administered in combination with the anti-CD56 antibody is preferably lenalidomide or pomalidomide.

In certain embodiments, the antibody administered with the compound is an anti-RANKL antibody. In some embodiments, the anti-RANKL antibody is a monoclonal antibody. In a specific embodiment, the anti-RANKL antibody is denosumab. The compound administered in combination with the anti-RANKL antibody is preferably lenalidomide or pomalidomide.

In certain embodiments, the antibody administered with the compound is an anti-IL-6 antibody. In some embodiments, the anti-IL-6 antibody is a monoclonal antibody. In a specific embodiment, the anti-IL-6 antibody is siltuximab. The compound administered in combination with the anti-IL-6 antibody is preferably lenalidomide or pomalidomide.

In certain embodiments, the antibody administered with the compound is an anti-CD138 antibody. In some embodiments, the anti-CD138 antibody is a monoclonal antibody. In a specific embodiment, the anti-CD138 antibody is BT062 (indatuximab). The compound administered in combination with the anti-CD138 antibody is preferably lenalidomide or pomalidomide.

In certain embodiments, the antibody administered with the compound is an anti-CD38 antibody. In some embodiments, the anti-CD38 antibody is a monoclonal antibody. In a specific embodiment, the anti-CD38 antibody is daratumumab. The compound administered in combination with the anti-CD38 antibody is preferably lenalidomide or pomalidomide.

In certain embodiments, the antibody is administered intravenously in an amount of from about 1 to about 1000 mg weekly or every other week. In a preferred embodiment, elotuzumab is administered as a 10 mg/kg IV solution. In another preferred embodiment, elotuzumab is administered weekly on days 1, 8, 15, 22 in a 28-day cycle (cycles 1 & 2), and days 1 and 15 in a 28-day cycle (cycles 3-onward).

In certain embodiments, the stem cell transplantation is autologous stem cell transplantation. In other embodiments, the stem cell transplantation is hematopoietic stem cell transplantation or peripheral blood stem cell transplantation. In other embodiments, the stem cell transplantation is hematopoietic stem cell transplantation. In other embodiments, the stem cell transplantation is peripheral blood stem cell transplantation.

In certain embodiments, the patient has received treatment with the compound, a proteasome inhibitor, or both, prior to receiving the stem cell transplantation. In a specific embodiment, the proteasome inhibitor is bortezomib or carfilzomib. In a specific embodiment, the proteasome inhibitor is bortezomib. In a specific embodiment, the proteasome inhibitor is carfilzomib.

In certain embodiments, the patient is identified as minimal residual disease positive (MRD(+)) prior to administering the compound. In other embodiments, the patient is identified as MRD negative (MRD(−)) prior to administering the compound.

In yet other embodiments, the immunomodulatory compound is administered in further combination with a second active agent or therapy conventionally used to treat, prevent or manage cancer. Examples of such second active agents are described in section 4.2. Specific examples include, but are not limited to, proteasome inhibitors such as ixazomib and marizomib, immunomodulators such as cyclophosphamide, vaccines such as Prevnar, checkpoint inhibitors such as PD-L1 inhibitors, and epigenetic modifiers such as azacitidine. Examples of such conventional therapies include, but are not limited to, surgery, chemotherapy, radiation therapy, hormonal therapy, biological therapy and immunotherapy. Specific examples include, but are not limited to, cell therapy such as CAR T-cell immunotherapy.

Another aspect of this invention encompasses pharmaceutical compositions, single unit dosage forms, dosing regimens and kits which comprise an immunomodulatory compound, or a pharmaceutically acceptable salt, solvate, hydrate, stereoisomer, clathrate, or prodrug thereof, and an antibody.

4. DETAILED DESCRIPTION OF THE INVENTION

An embodiment of the invention encompasses methods of treating, managing, or preventing multiple myeloma which comprises administering to a patient in need of such treatment or prevention a therapeutically or prophylactically effective amount of an immunomodulatory compound described in section 4.1, or a pharmaceutically acceptable salt, solvate, hydrate, stereoisomer, clathrate, or prodrug thereof, in combination with a therapeutically or prophylactically effective amount of an antibody. The term "in combination with" or "administered with" within the meaning of the invention includes administration as a mixture, simultaneous administration using separate formulations, and consecutive administration in any order.

Antibodies that can be used in combination with compounds of the invention include monoclonal and polyclonal antibodies. Examples of such antibodies include, but are not limited to, trastuzumab (Herceptin®), bevacizumab (Avastin™), pertuzumab (Omnitarg™), edrecolomab (Panorex®), and G250. The immunomodulatory compounds can also be combined with, or used in combination with, anti-TNF-α antibodies.

The antibody is preferably an anti-CS1 antibody, and, more preferably, a humanized monoclonal anti-CS1 antibody. In a particular embodiment, the anti-CS1 antibody is elotuzumab.

The antibody is also preferably an anti-CD20 antibody, such as obinutuzumab (Gazyva®), rituximab (e.g., Rituxan®), ibritumomab tiuxetan (Zevalin®), tositumomab (Bexxar®), ofatumumab (Arzerra®), AME-133v (ocaratuzumab), ocrelizumab, TRU-015, or IMMU-106 (veltuzumab).

The antibody is also preferably an anti-PD-L1 antibody, such as lambrolizumab (MK-3475), BMS-936559, atezolizumab (MPDL3280A), pidilizumab (CT-011), pembrolizumab (Keytruda®), Medi7436, nivolumab (OPDIVO®; BMS-936558), MDX-1106, or ONO-4538.

The antibody may also be an anti-KIR antibody such as IPH2101; an anti-CD40 antibody such as SGN-40 (dacetuzumab), HCD122 (lucatumumab); an anti-IGF1-R antibody such as CP751,871 (figitumumab); an anti-DKK-1 antibody such as BHQ880; an anti-FGFR3 antibody such as PRO-001; an anti-CD56 antibody such as IMGN901 (lorvotuzumab); an anti-RANKL antibody such as denosumab; an anti-IL-6 antibody such as siltuximab; an anti-CD138 antibody such as BT062 (indatuximab), or an anti-CD38 antibody such as daratumumab.

In particular methods encompassed by this embodiment, the immunomodulatory compound is administered in combination with elotuzumab in patients having multiple myeloma who have received autologous stem cell transplantation. In more particular methods, the patients have received treatment with the immunomodulatory compound, a proteasome inhibitor (e.g., bortezomib or carfilzomib), or both in induction therapy prior to the autologous stem cell transplantation.

Methods encompassed by the present invention may comprise administering a therapeutically or prophylactically effective amount of one or more additional active agents (i.e., second active agent) or other method of treating, managing, or preventing multiple myeloma. Second active agents include small molecules and large molecules (e.g., proteins), examples of which are provided herein, as well as stem cells. Methods or therapies that can be used in combination with the administration of the immunomodulatory compound and the antibody include, but are not limited to, surgery, blood transfusions, immunotherapy, biological therapy, radiation therapy, and other non-drug based therapies presently used to treat, prevent or manage cancer or disease and conditions associated with, or characterized by, undesired angiogenesis.

The invention also encompasses pharmaceutical compositions (e.g., single unit dosage forms) or kits that can be used in methods disclosed herein. Particular pharmaceutical compositions or kits comprise an immunomodulatory compound, or a pharmaceutically acceptable salt, solvate, hydrate, stereoisomer, clathrate, or prodrug thereof, and an antibody.

4.1 Immunomodulatory Compounds

Compounds used in the invention include immunomodulatory compounds that are racemic, stereomerically enriched or stereomerically pure, and pharmaceutically acceptable salts, solvates, hydrates, stereoisomers, clathrates, and prodrugs thereof. Preferred compounds used in the invention are small organic molecules having a molecular weight less than about 1,000 g/mol, and are not proteins, peptides, oligonucleotides, oligosaccharides or other macromolecules.

As used herein and unless otherwise indicated, the terms "immunomodulatory compounds" (Celgene Corporation) encompass small organic molecules that markedly inhibit TNF-α, LPS induced monocyte IL1β and IL12, and partially inhibit IL6 production. Specific immunomodulatory compounds are discussed below.

TNF-α is an inflammatory cytokine produced by macrophages and monocytes during acute inflammation. TNF-α is responsible for a diverse range of signaling events within cells. TNF-α may play a pathological role in cancer. Without being limited by theory, one of the biological effects exerted by the immunomodulatory compounds of the invention is the reduction of synthesis of TNF-α. Immunomodulatory compounds of the invention enhance the degradation of TNF-α mRNA.

Further, without being limited by theory, immunomodulatory compounds used in the invention may also be potent co-stimulators of T cells and increase cell proliferation dramatically in a dose dependent manner. Immunomodulatory compounds of the invention may also have a greater co-stimulatory effect on the CD8+ T cell subset than on the CD4+ T cell subset. In addition, the compounds preferably have anti-inflammatory properties, and efficiently co-stimulate T cells.

Specific examples of immunomodulatory compounds of the invention, include, but are not limited to, cyano and carboxy derivatives of substituted styrenes such as those disclosed in U.S. Pat. No. 5,929,117; 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. No. 5,874,448; the tetra substituted 2-(2,6-dioxopiperdin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide and EM-12), including, but not limited to, those disclosed in U.S. Pat. No. 5,635,517; and a class of non-polypeptide cyclic amides disclosed in U.S. Pat. Nos. 5,698,579 and 5,877,200; analogs and derivatives of thalidomide, including hydrolysis products, metabolites, derivatives and precursors of thalidomide, such as those described in U.S. Pat. Nos. 5,593,990, 5,629,327, and 6,071,948 to D'Amato; aminothalidomide, as well as analogs, hydrolysis products, metabolites, derivatives and precursors of aminothalidomide, and substituted 2-(2,6-dioxopiperidin-3-yl) phthalimides and substituted 2-(2,6-dioxopiperidin-3-yl)-1-oxoisoindoles such as those described in U.S. Pat. Nos. 6,281,230 and 6,316,471; isoindole-imide compounds such as those described in U.S. patent application Ser. No. 09/972,487 filed on Oct. 5, 2001, U.S. patent application Ser. No. 10/032,286 filed on Dec. 21, 2001, and International Application No. PCT/US01/50401 (International Publication No. WO 02/059106). The entireties of each of the patents and patent applications identified herein are incorporated herein by reference. Immunomodulatory compounds of the invention do not include thalidomide.

Other specific immunomodulatory compounds of the invention include, but are not limited to, 1-oxo- and 1,3 dioxo-2-(2,6-dioxopiperidin-3-yl) isoindolines substituted with amino in the benzo ring as described in U.S. Pat. No. 5,635,517 which is incorporated herein by reference. These compounds have the structure I:

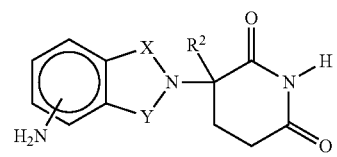

in which one of X and Y is C=O, the other of X and Y is C=O or CH$_2$, and R$^2$ is hydrogen or lower alkyl, in particular methyl. Specific immunomodulatory compounds include, but are not limited to:

1-oxo-2-(2,6-dioxopiperidin-3-yl)-4-aminoisoindoline;

1-oxo-2-(2,6-dioxopiperidin-3-yl)-5-aminoisoindoline;

1-oxo-2-(2,6-dioxopiperidin-3-yl)-6-aminoisoindoline;

1-oxo-2-(2,6-dioxopiperidin-3-yl)-7-aminoisoindoline;

1,3-dioxo-2-(2,6-dioxopiperidin-3-yl)-4-aminoisoindoline; and 1,3-dioxo-2-(2,6-dioxopiperidin-3-yl)-5-aminoisoindoline.

Other specific immunomodulatory compounds of the invention belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Compounds representative of this class are of the formulas:

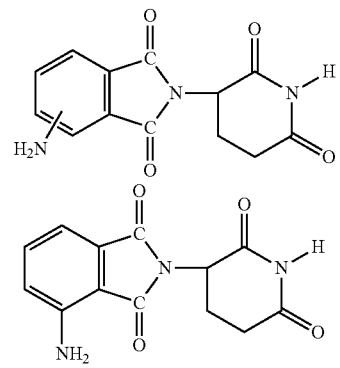

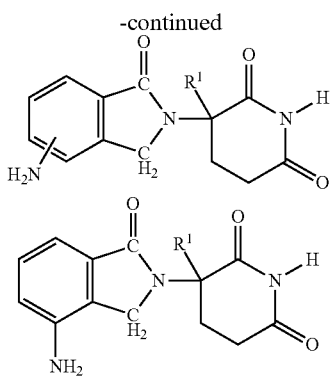

wherein $R^1$ is hydrogen or methyl. In a separate embodiment, the invention encompasses the use of enantiomerically pure forms (e.g. optically pure (R) or (S) enantiomers) of these compounds.

Still other specific immunomodulatory compounds of the invention belong to a class of isoindole-imides disclosed in U.S. patent application Ser. Nos. 10/032,286 and 09/972,487, and International Application No. PCT/US01/50401 (International Publication No. WO 02/059106), each of which are incorporated herein by reference. Representative compounds are of formula II:

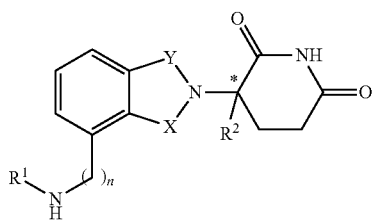

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^{3'}$, $C(S)NR^3R^{3'}$ or $(C_1-C_8)$alkyl-$O(CO)R^5$;

$R^2$ is H, F, benzyl, $(C_1-C_8)$alkyl, $(C_2-C_8)$alkenyl, or $(C_2-C_8)$alkynyl;

$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;

$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O$—$R^5$ or the $R^6$ groups can join to form a heterocycloalkyl group;

n is 0 or 1; and

* represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$;

$R^2$ is H or $(C_1-C_8)$alkyl; and $R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_5-C_8)$alkyl-$N(R^6)_2$; $(C_0-C_8)$alkyl-NH—$C(O)O$—$R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.

In other specific compounds of formula II, $R^2$ is H or $(C_1-C_4)$alkyl.

In other specific compounds of formula II, $R^1$ is $(C_1-C_8)$alkyl or benzyl.

In other specific compounds of formula II, $R^1$ is H, $(C_1-C_8)$alkyl, benzyl, $CH_2OCH_3$, $CH_2CH_2OCH_3$, or

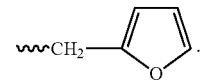

In another embodiment of the compounds of formula II, $R^1$ is

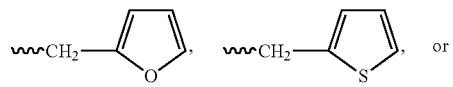

wherein Q is O or S, and each occurrence of $R^7$ is independently H, $(C_1-C_8)$alkyl, benzyl, $CH_2OCH_3$, or $CH_2CH_2OCH_3$.

In other specific compounds of formula II, $R^1$ is $C(O)R^3$.

In other specific compounds of formula II, $R^3$ is $(C_0-C_4)$alkyl-$(C_2-C_5)$heteroaryl, $(C_1-C_8)$alkyl, aryl, or $(C_0-C_4)$alkyl-$OR^5$.

In other specific compounds of formula II, heteroaryl is pyridyl, furyl, or thienyl.

In other specific compounds of formula II, $R^1$ is $C(O)OR^4$.

In other specific compounds of formula II, the H of C(O)NHC(O) can be replaced with $(C_1-C_4)$alkyl, aryl, or benzyl.

Still other specific immunomodulatory compounds of the invention belong to a class of isoindole-imides disclosed in U.S. patent application Ser. No. 09/781,179, International Publication No. WO 98/54170, and U.S. Pat. No. 6,395,754, each of which are incorporated herein by reference. Representative compounds are of formula III:

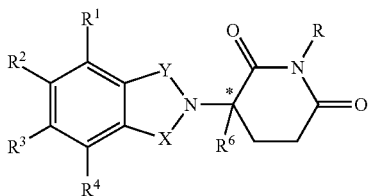

(III)

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;
R is H or $CH_2OCOR'$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;
$R^5$ is hydrogen or alkyl of 1 to 8 carbons;
$R^6$ hydrogen, alkyl of 1 to 8 carbon atoms, benzo, chloro, or fluoro;
$R'$ is $R^7$—$CHR^{10}$—$N(R^8R^9)$;
$R^7$ is m-phenylene or p-phenylene or —$(C_nH_{2n})$— in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2[X]X_1CH_2CH_2$— in which $[X]X_1$ is —O—, —S—, or —NH—;
$R^{10}$ is hydrogen, alkyl of to 8 carbon atoms, or phenyl; and
* represents a chiral-carbon center.

The compounds to be used in the methods and compositions provided herein are collectively referred to herein as "5-Substituted Quinazolinone Compound(s)." Specific 5-Substituted Quinazolinone Compounds provided herein include, but are not limited to, compounds such as those described in U.S. Pat. No. 7,635,700 and U.S. Patent Publication No. 2012/0230983, published Sep. 13, 2012, each of which is incorporated herein by reference in its entirety. In one embodiment, representative 5-Substituted Quinazolinone Compounds are of the formula (I):

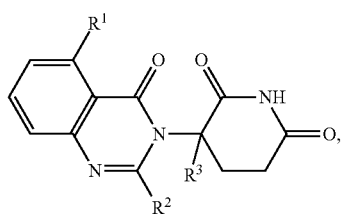

(I)

and pharmaceutically acceptable salts, solvates, and stereoisomers thereof, wherein:
$R^1$ is: hydrogen; halo; —$(CH_2)_nOH$; $(C_1-C_6)$alkyl, optionally substituted with one or more halo; $(C_1-C_6)$alkoxy, optionally substituted with one or more halo; or —$(CH_2)_nNHR^a$, wherein
$R^a$ is: hydrogen; $(C_1-C_6)$alkyl, optionally substituted with one or more halo; —$(CH_2)_n$-(6 to 10 membered aryl); —C(O)—$(CH_2)_n$-(6 to 10 membered aryl) or —C(O)—$(CH_2)_n$-(6 to 10 membered heteroaryl), wherein the aryl or heteroaryl is optionally substituted with one or more of: halo; —$SCF_3$; $(C_1-C_6)$alkyl, itself optionally substituted with one or more halo; or $(C_1-C_6)$alkoxy, itself optionally substituted with one or more halo; —C(O)—$(C_1-C_8)$alkyl, wherein the alkyl is optionally substituted with one or more halo; —C(O)—$(CH_2)_n$—$(C_3-C_{10}$-cycloalkyl); —C(O)—$(CH_2)_n$—$NR^bR^c$, wherein $R^b$ and $R^c$ are each independently: hydrogen; $(C_1-C_6)$alkyl, optionally substituted with one or more halo; $(C_1-C_6)$alkoxy, optionally substituted with one or more halo; or 6 to 10 membered aryl, optionally substituted with one or more of: halo; $(C_1-C_6)$alkyl, itself optionally substituted with one or more halo; or $(C_1-C_6)$alkoxy, itself optionally substituted with one or more halo; —C(O)—$(CH_2)_n$—O—$(C_1-C_6)$alkyl; or —C(O)—$(CH_2)_n$—O—$(CH_2)_n$-(6 to 10 membered aryl);
$R^2$ is: hydrogen; —$(CH_2)_nOH$; phenyl; —O—$(C_1-C_6)$alkyl; or $(C_1-C_6)$alkyl, optionally substituted with one or more halo;
$R^3$ is: hydrogen; or $(C_1-C_6)$alkyl, optionally substituted with one or more halo; and
n is 0, 1, or 2.

In one embodiment, representative 5-Substituted Quinazolinone Compounds are of the formula (II):

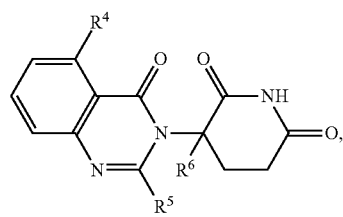

(II)

and pharmaceutically acceptable salts, solvates, and stereoisomers thereof, wherein:
$R^4$ is: hydrogen; halo; —$(CH_2)_nOH$; $(C_1-C_6)$alkyl, optionally substituted with one or more halo; or $(C_1-C_6)$alkoxy, optionally substituted with one or more halo;
$R^5$ is: hydrogen; —$(CH_2)_nOH$; phenyl; —O—$(C_1-C_6)$alkyl; or $(C_1-C_6)$alkyl, optionally substituted with one or more halo;
$R^6$ is: hydrogen; or $(C_1-C_6)$alkyl, optionally substituted with one or more halo; and
n is 0, 1, or 2.

In one embodiment, $R^4$ is hydrogen. In another embodiment, $R^4$ is halo. In another embodiment, $R^4$ is $(C_1-C_6)$alkyl, optionally substituted with one or more halo. In another embodiment, $R^4$ is —$(CH_2)_nOH$ or hydroxyl. In another embodiment, $R^4$ is $(C_1-C_6)$alkoxy, optionally substituted with one or more halo.

In one embodiment, $R^5$ is hydrogen. In another embodiment, $R^5$ is —$(CH_2)_nOH$ or hydroxyl. In another embodiment, $R^5$ is phenyl. In another embodiment, $R^5$ is —O—$(C_1-C_6)$alkyl, optionally substituted with one or more halo. In another embodiment, $R^5$ is $(C_1-C_6)$alkyl, optionally substituted with one or more halo.

In one embodiment, $R^6$ is hydrogen. In another embodiment, $R^6$ is $(C_1-C_6)$alkyl, optionally substituted with one or more halo.

In one embodiment, n is 0. In another embodiment, n is 1. In another embodiment, n is 2.

Compounds provided herein encompass any of the combinations of $R^4$, $R^5$, $R^6$ and n described above.

In one specific embodiment, $R^4$ is methyl. In another embodiment, $R^4$ is methoxy. In another embodiment, $R^4$ is —CF3. In another embodiment, $R^4$ is F or Cl.

In another specific embodiment, $R^5$ is methyl. In another embodiment, $R^5$ is —CF3.

Specific examples of 5-Substituted Quinazolinone Compounds include, but are not limited to those from Table A:

TABLE A

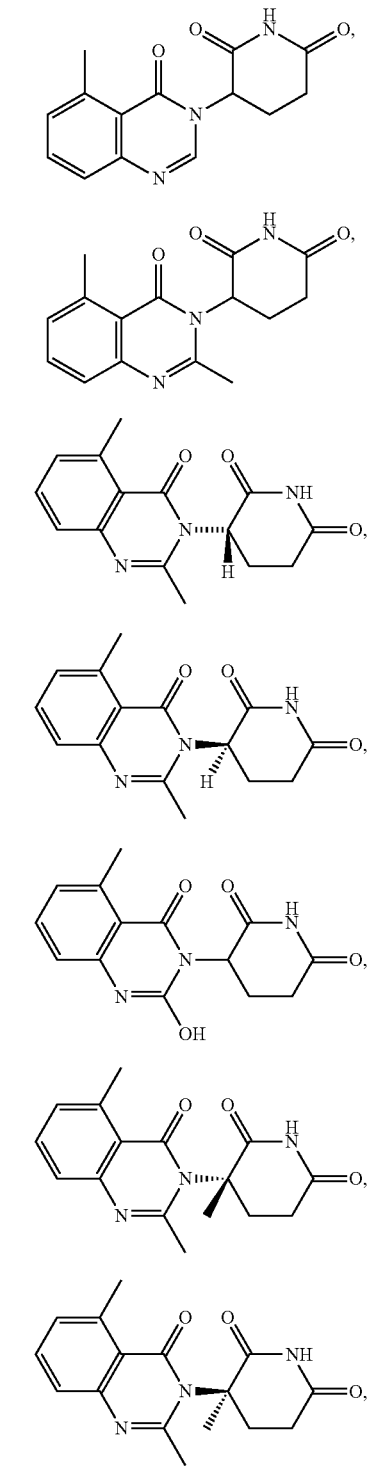

TABLE A-continued

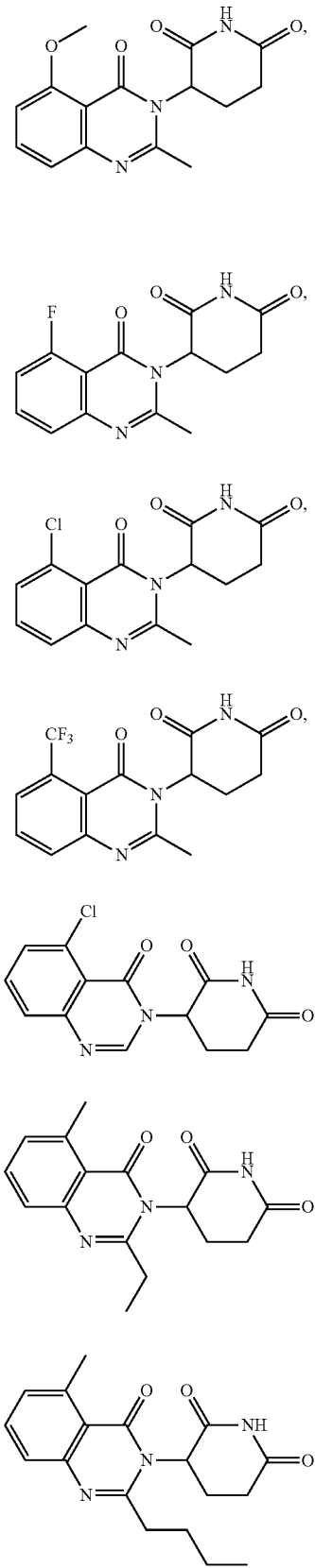

TABLE A-continued

[Chemical structure: 5-methyl quinazolinone with trifluoromethyl substituent linked to piperidine-2,6-dione], or.

[Chemical structure: 5-methyl-2-phenyl quinazolinone linked to piperidine-2,6-dione].

In another embodiment, representative 5-Substituted Quinazolinone Compounds are of the formula (III):

$$\text{(III)}$$

[Chemical structure of formula (III) with $(CH_2)_n$—$NHR^d$ at 5-position, $R^8$ substituent, and $R^7$ at 2-position]

and pharmaceutically acceptable salts, solvates, and stereoisomers thereof, wherein:
$R^d$ is:
 hydrogen;
 $(C_1\text{-}C_6)$alkyl, optionally substituted with one or more halo;
 —C(O)~$(C_1\text{-}C_8)$alkyl, wherein the alkyl is optionally substituted with one or more halo;
 —C(O)—$(CH_2)_n$—$(C_3\text{-}C_{10}\text{-cycloalkyl})$;
 —C(O)—$(CH_2)_n$—$NR^eR^f$, wherein $R^e$ and $R^f$ are each independently:
  hydrogen;
  $(C_1\text{-}C_6)$alkyl, optionally substituted with one or more halo; or
  $(C_1\text{-}C_6)$alkoxy, optionally substituted with one or more halo; or
 —C(O)—$(CH_2)_n$—O—$(C_1\text{-}C_6)$alkyl.
$R^7$ is: hydrogen; —$(CH_2)_n$OH; phenyl; —O—$(C_1\text{-}C_6)$alkyl; or $(C_1\text{-}C_6)$alkyl, optionally substituted with one or more halo;
$R^8$ is: hydrogen; or $(C_1\text{-}C_6)$alkyl, optionally substituted with one or more halo; and
n is 0, 1, or 2.

In one embodiment, $R^d$ is hydrogen. In another embodiment, $R^d$ is $(C_1\text{-}C_6)$alkyl, optionally substituted with one or more halo. In another embodiment, $R^d$ is —C(O)—$(C_1\text{-}C_8)$alkyl. In another embodiment, $R^d$ is —C(O)—$(CH_2)_n$—$(C_3\text{-}C_{10}\text{-cycloalkyl})$. In another embodiment, $R^d$ is —C(O)—$(CH_2)_n$—$NR^eR^f$, wherein $R^e$ and $R^f$ are as described herein above. In another embodiment, $R^d$ is —C(O)—$(CH_2)_n$—O—$(CH_2)_n$—$(C_1\text{-}C_6)$alkyl.

In one embodiment, $R^7$ is hydrogen. In another embodiment, $R^7$ is —$(CH_2)_n$OH or hydroxyl. In another embodiment, $R^7$ is phenyl. In another embodiment, $R^7$ is —O—$(C_1\text{-}C_6)$alkyl, optionally substituted with one or more halo. In another embodiment, $R^7$ is $(C_1\text{-}C_6)$alkyl, optionally substituted with one or more halo.

In one embodiment, $R^8$ is hydrogen. In another embodiment, $R^8$ is $(C_1\text{-}C_6)$alkyl, optionally substituted with one or more halo.

In one embodiment, n is 0. In another embodiment, n is 1. In another embodiment, n is 2.

5-Substituted Quinazolinone Compounds provided herein encompass any of the combinations of $R^d$, $R^7$, $R^8$ and n described above.

In one specific embodiment, $R^7$ is methyl. In another embodiment, $R^d$ is —C(O)~$(C_1\text{-}C_6)$alkyl. In another embodiment, $R^d$ is $NH_2$. In another embodiment, $R^d$ is —C(O)—$CH_2$—O—$(C_1\text{-}C_6)$alkyl.

Specific examples of 5-Substituted Quinazolinone Compounds include, but are not limited to those from Table B:

TABLE B

[Chemical structure: 5-amino-2-methyl quinazolinone linked to piperidine-2,6-dione],

[Chemical structure: 5-amino-2-methyl quinazolinone linked to piperidine-2,6-dione with (S)-stereochemistry at piperidine],

[Chemical structure: 5-amino-2-methyl quinazolinone linked to piperidine-2,6-dione with (R)-stereochemistry at piperidine],

[Chemical structure: 5-amino-2-methyl quinazolinone linked to 3-methyl-piperidine-2,6-dione],

[Chemical structure: 5-amino-2-methyl quinazolinone linked to 3-methyl-piperidine-2,6-dione with defined stereochemistry], TABLE B-continued
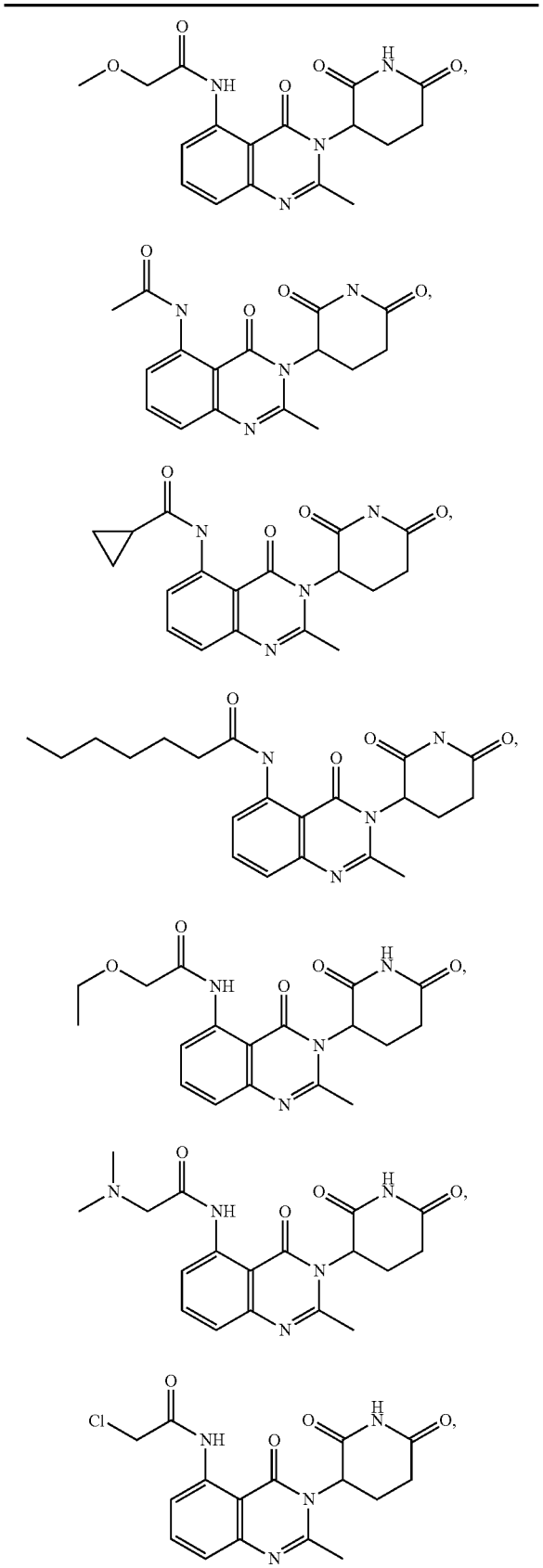
TABLE B-continued
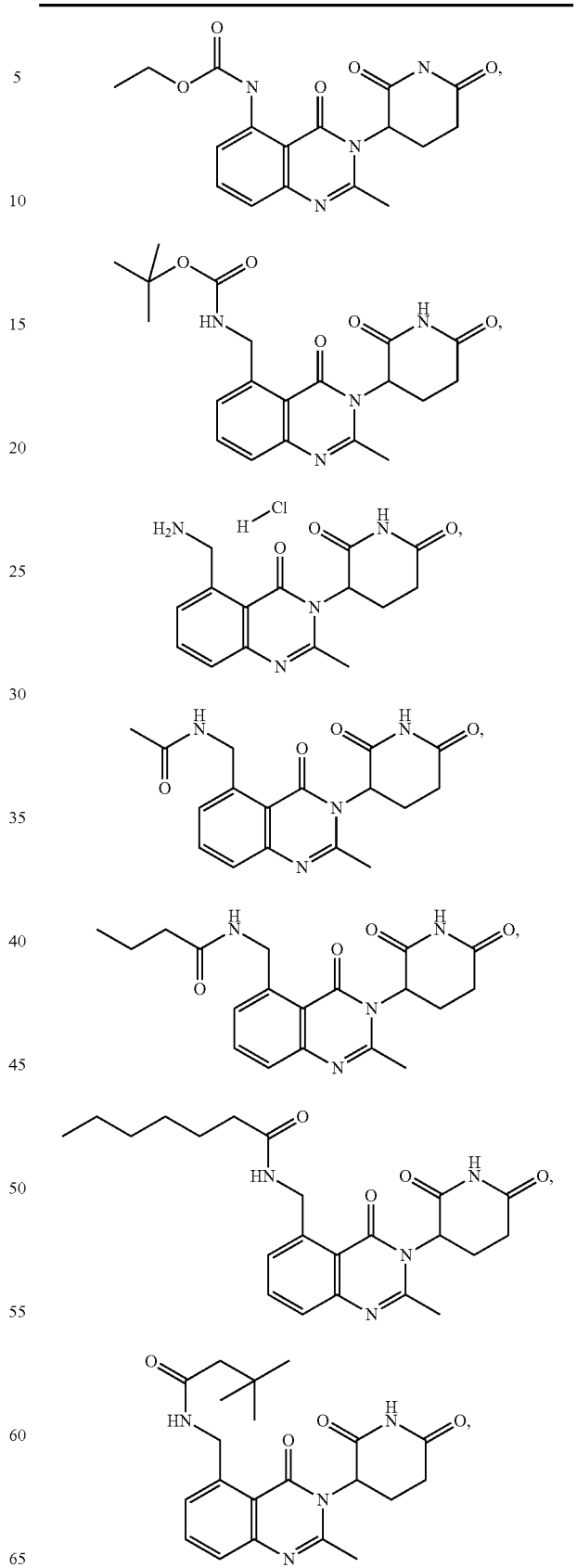

TABLE B-continued

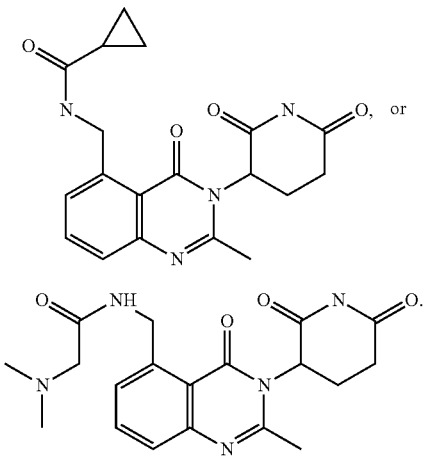

In one embodiment, the 5-Substituted Quinazolinone Compound is:

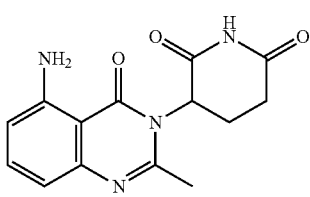 [SMILES: Cc1nc2cccc(N)c2c(=O)n1C1CCC(=O)NC1=O]

or a pharmaceutically acceptable salt, solvate, prodrug, or stereoisomer thereof.

In one embodiment, the 5-Substituted Quinazolinone Compound is 3-(5-Amino-2-methyl-4-oxoquinazolin-3 (4H)-yl)-piperidine-2,6-dione hydrochloride.

In one embodiment, the 5-Substituted Quinazolinone Compound is:

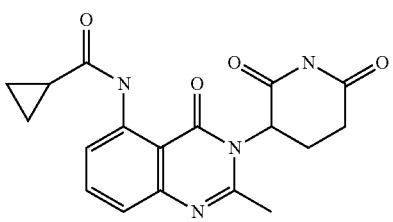 [SMILES: Cc1nc2cccc(NC(=O)C3CC3)c2c(=O)n1C1CCC(=O)NC1=O]

or a pharmaceutically acceptable salt, solvate, prodrug, or stereoisomer thereof.

In one embodiment, the 5-Substituted Quinazolinone Compound is:

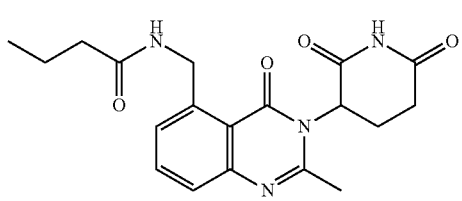 [SMILES: CCCC(=O)NCc1cccc2nc(C)n(C3CCC(=O)NC3=O)c(=O)c12]

or a pharmaceutically acceptable salt, solvate, prodrug, or stereoisomer thereof.

In one embodiment, the 5-Substituted Quinazolinone Compound is:

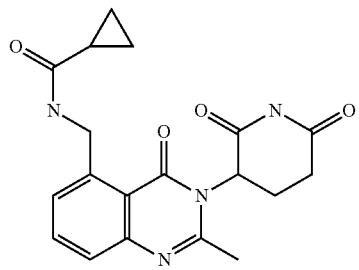 [SMILES: Cc1nc2cccc(CNC(=O)C3CC3)c2c(=O)n1C1CCC(=O)NC1=O]

or a pharmaceutically acceptable salt, solvate, prodrug, or stereoisomer thereof.

In another embodiment, representative 5-Substituted Quinazolinone Compounds are of the formula (IV):

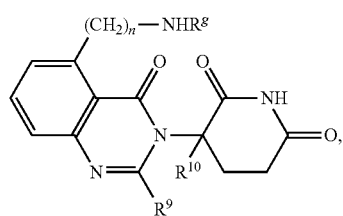

(IV)

and pharmaceutically acceptable salts, solvates, and stereoisomers thereof, wherein:

$R^g$ is:
- —$(CH_2)_n$-(6 to 10 membered aryl);
- —C(O)—$(CH_2)_n$-(6 to 10 membered aryl) or —C(O)—$(CH_2)_n$-(6 to 10 membered heteroaryl), wherein the aryl or heteroaryl is optionally substituted with one or more of: halo; —$SCF_3$; ($C_1$-$C_6$)alkyl, itself optionally substituted with one or more halo; or ($C_1$-$C_6$)alkoxy, itself optionally substituted with one or more halo;
- —C(O)—$(CH_2)_n$—$NHR^h$, wherein $R^h$ is:
  6 to 10 membered aryl, optionally substituted with one or more of: halo;
  ($C_1$-$C_6$)alkyl, itself optionally substituted with one or more halo; or
  ($C_1$-$C_6$)alkoxy, itself optionally substituted with one or more halo; or
- —C(O)—$(CH_2)_n$—O—$(CH_2)_n$-(6 to 10 membered aryl);

$R^9$ is: hydrogen; —$(CH_2)_n$OH; phenyl; —O—($C_1$-$C_6$)alkyl; or ($C_1$-$C_6$)alkyl, optionally substituted with one or more halo;

$R^{10}$ is: hydrogen; or ($C_1$-$C_6$)alkyl, optionally substituted with one or more halo; and n is 0, 1, or 2.

In one embodiment, $R^g$ is —$(CH_2)_n$-(6 to 10 membered aryl). In another embodiment, $R^g$ is —C(O)—$(CH_2)_n$-(6 to 10 membered aryl) or —C(O)—$(CH_2)_n$-(6 to 10 membered heteroaryl), wherein the aryl or heteroaryl is optionally substituted as described above. In another embodiment, $R^g$ is —C(O)—$(CH_2)_n$—$NHR^h$, wherein $R^h$ is 6 to 10 membered aryl, optionally substituted as described above. In another embodiment, $R^g$ is —C(O)—$(CH_2)_n$—O—$(CH_2)_n$-(6 to 10 membered aryl).

In one embodiment, $R^9$ is hydrogen. In another embodiment, $R^9$ is —$(CH_2)_n$OH or hydroxyl. In another embodiment, R⁹ is phenyl. In another embodiment, R⁹ is —O—(C₁-C₆)alkyl, optionally substituted with one or more halo. In another embodiment, R⁹ is (C₁-C₆)alkyl, optionally substituted with one or more halo.

In one embodiment, $R^{10}$ is hydrogen. In another embodiment, $R^{10}$ is (C₁-C₆)alkyl, optionally substituted with one or more halo.

In one embodiment, n is 0. In another embodiment, n is 1. In another embodiment, n is 2.

5-Substituted Quinazolinone Compounds provided herein encompass any of the combinations of $R^g$, $R^9$, $R^{10}$ and n described above.

In one specific embodiment, $R^9$ is methyl. In another embodiment, $R^g$ is —C(O)-phenyl or —C(O)—CH₂-phenyl, wherein the phenyl is optionally substituted with methyl, —CF₃, and/or halo. In another embodiment, $R^g$ is —C(O)—NH-phenyl, wherein the phenyl is optionally substituted with methyl, —CF₃, and/or halo.

Specific 5-Substituted Quinazolinone Compounds include, but are not limited to those from Table C:

TABLE C

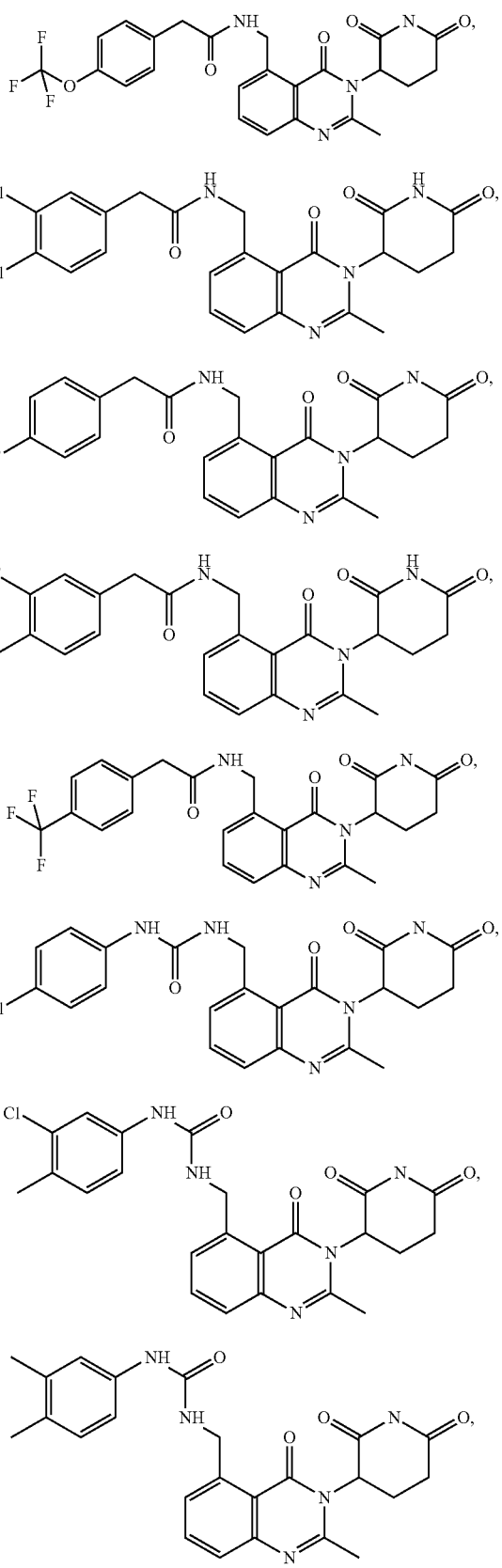

TABLE C-continued
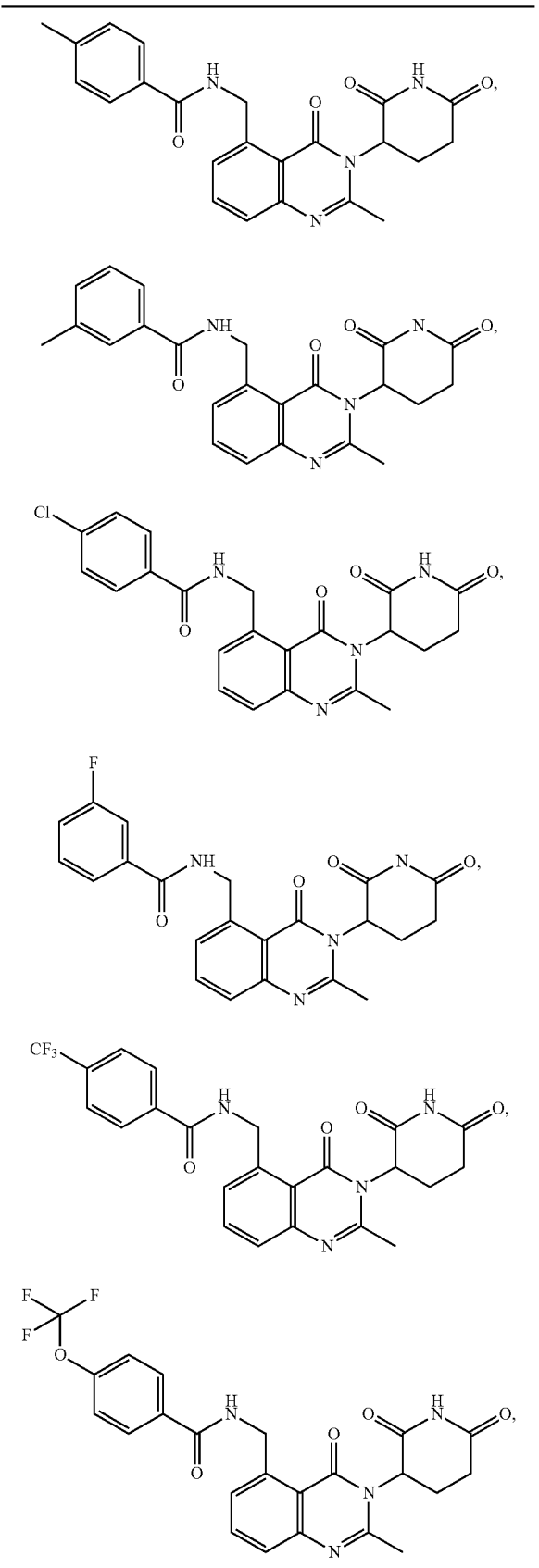
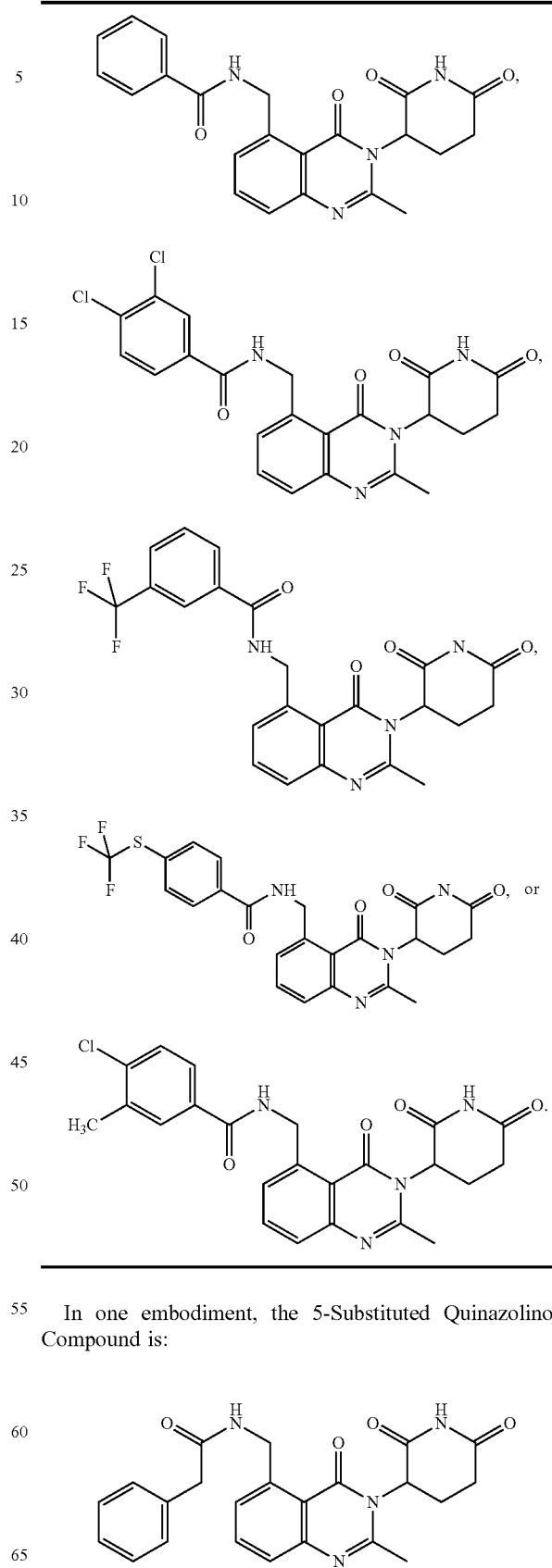
In one embodiment, the 5-Substituted Quinazolinone Compound is:
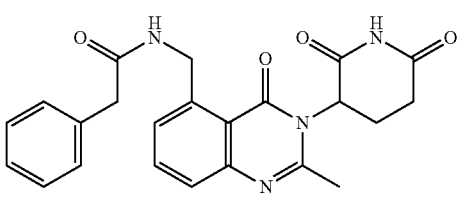 [SMILES: Cc1nc2cccc(CNC(=O)Cc3ccccc3)c2c(=O)n1C1CCC(=O)NC1=O]

or a pharmaceutically acceptable salt, solvate, prodrug, or stereoisomer thereof.

In one embodiment, the 5-Substituted Quinazolinone Compound is:

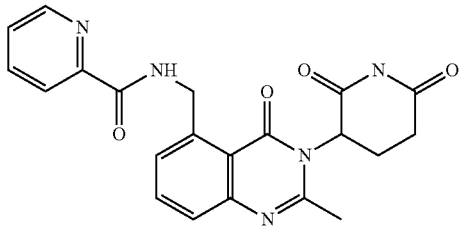 [SMILES: Cc1nc2cccc(CNC(=O)c3ccccn3)c2c(=O)n1C1CCC(=O)NC1=O]

or a pharmaceutically acceptable salt, solvate, prodrug, or stereoisomer thereof.

In one embodiment, the 5-Substituted Quinazolinone Compound is:

or a pharmaceutically acceptable salt, solvate, prodrug, or stereoisomer thereof.

In one embodiment, the 5-Substituted Quinazolinone Compound is:

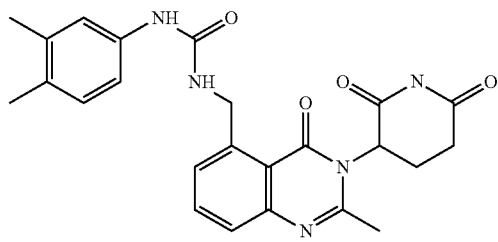 [SMILES: Cc1ccc(NC(=O)NCc2cccc3nc(C)n(C4CCC(=O)NC4=O)c(=O)c23)cc1C]

or a pharmaceutically acceptable salt, solvate, prodrug, or stereoisomer thereof.

In one embodiment, the 5-Substituted Quinazolinone Compound is:

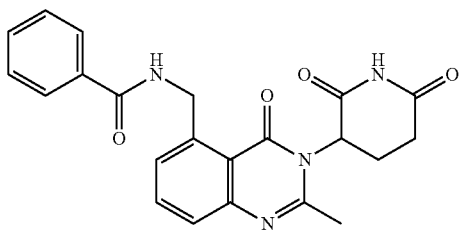 [SMILES: Cc1nc2cccc(CNC(=O)c3ccccc3)c2c(=O)n1C1CCC(=O)NC1=O]

or a pharmaceutically acceptable salt, solvate, prodrug, or stereoisomer thereof.

Specific 5-Substituted Quinazolinone Compounds provided herein include, but are not limited to, 6-, 7-, or 8-substituted quinazolinone compounds such as those described in U.S. Patent Application Publication No. US 2009/0093504, the entirety of which is incorporated herein by reference. In one embodiment, representative 5-Substituted Quinazolinone Compounds are of the formula (V):

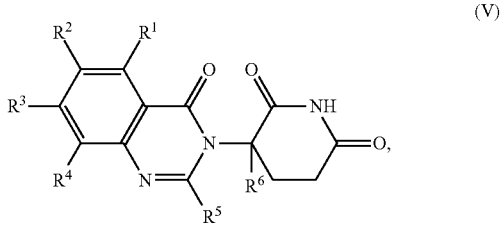

and pharmaceutically acceptable salts, solvates, and stereoisomers thereof, wherein:

$R^1$ is hydrogen;

each of $R^2$, $R^3$, and $R^4$ is independently: hydrogen; halo; —$(CH_2)_n$OH; $(C_1-C_6)$alkyl, optionally substituted with one or more halo; $(C_1-C_6)$alkoxy, optionally substituted with one or more halo; or —$(CH_2)_n$NHR$^a$, wherein R$^a$ is: hydrogen; $(C_1-C_6)$alkyl, optionally substituted with one or more halo; —$(CH_2)_n$-(6 to 10 membered aryl); —C(O)—$(CH_2)_n$-(6 to 10 membered aryl) or —C(O)—$(CH_2)_n$-(6 to 10 membered heteroaryl), wherein the aryl or heteroaryl is optionally substituted with one or more of: halo; —SCF$_3$; $(C_1-C_6)$alkyl, said alkyl itself optionally substituted with one or more halo; or $(C_1-C_6)$alkoxy, said alkoxy itself optionally substituted with one or more halo; —C(O)—$(C_1-C_8)$alkyl, wherein the alkyl is optionally substituted with one or more halo; —C(O)—$(CH_2)_n$—$(C_3-C_{10}$-cycloalkyl); —C(O)—$(CH_2)_n$—NR$^b$R$^c$, wherein R$^b$ and R$^c$ are each independently: hydrogen; $(C_1-C_6)$alkyl, optionally substituted with one or more halo; $(C_1-C_6)$alkoxy, optionally substituted with one or more halo; 6 to 10 membered aryl, optionally substituted with one or more of: halo; $(C_1-C_6)$alkyl, itself optionally substituted with one or more halo; or $(C_1-C_6)$alkoxy, itself optionally substituted with one or more halo; —C(O)—$(CH_2)_n$—O—$(C_1-C_6)$alkyl; or —C(O)—$(CH_2)_n$—O—$(CH_2)_n$-(6 to 10 membered aryl); or two of $R^1$-$R^4$ together can form a 5 or 6 membered ring, optionally substituted with one or more of: halo; $(C_1-C_6)$alkyl, optionally substituted with one or more halo; and $(C_1-C_6)$alkoxy, optionally substituted with one or more halo;

$R^5$ is: hydrogen; —$(CH_2)_n$OH; phenyl; —O—$(C_1-C_6)$alkyl; or $(C_1-C_6)$alkyl, optionally substituted with one or more halo;

$R^6$ is: hydrogen; or $(C_1-C_6)$alkyl, optionally substituted with one or more halo; and n is 0, 1, or 2.

In another embodiment, representative 5-Substituted Quinazolinone Compounds are of formula (VI):

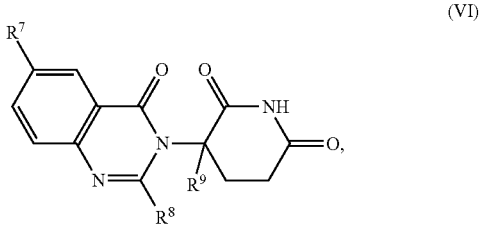

and pharmaceutically acceptable salts, solvates, and stereoisomers thereof, wherein:

$R^7$ is: hydrogen; halo; —$(CH_2)_n$OH; $(C_1-C_6)$alkyl, optionally substituted with one or more halo; $(C_1-C_6)$alkoxy, optionally substituted with one or more halo; or —$(CH_2)_n$NHR$^d$, wherein R$^d$ is:
hydrogen;
$(C_1-C_6)$alkyl, optionally substituted with one or more halo;
—$(CH_2)_n$-(6 to 10 membered aryl);
—C(O)—$(CH_2)_n$-(6 to 10 membered aryl) or —C(O)—$(CH_2)_n$-(6 to 10 membered heteroaryl), wherein the aryl or heteroaryl is optionally substituted with one or more of: halo; —SCF$_3$; $(C_1-C_6)$alkyl, itself optionally substituted with one or more halo; or $(C_1-C_6)$alkoxy, itself optionally substituted with one or more halo;
—C(O)—$(C_1-C_8)$alkyl, wherein the alkyl is optionally substituted with one or more halo;
—C(O)—$(CH_2)_n$—$(C_3-C_{10}$-cycloalkyl);
—C(O)—$(CH_2)_n$—NR$^e$R$^f$, wherein R$^e$ and R$^f$ are each independently:
hydrogen;
$(C_1-C_6)$alkyl, optionally substituted with one or more halo;
$(C_1-C_6)$alkoxy, optionally substituted with one or more halo; or
6 to 10 membered aryl, optionally substituted with one or more of: halo; $(C_1-C_6)$alkyl, itself optionally substituted with one or more halo; or $(C_1-C_6)$alkoxy, itself optionally substituted with one or more halo;
—C(O)—$(CH_2)_n$—O—$(C_1-C_6)$alkyl; or
—C(O)—$(CH_2)_n$—O—$(CH_2)_n$-(6 to 10 membered aryl);

$R^8$ is: hydrogen; —$(CH_2)_n$OH; phenyl; —O—$(C_1-C_6)$alkyl; or $(C_1-C_6)$alkyl, optionally substituted with one or more halo;

$R^9$ is: hydrogen; or $(C_1-C_6)$alkyl, optionally substituted with one or more halo; and n is 0, 1, or 2.

In another embodiment, representative 5-Substituted Quinazolinone Compounds are of formula (VII):

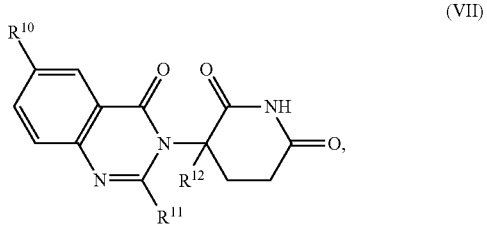

(VII)

and pharmaceutically acceptable salts, solvates, and stereoisomers thereof, wherein:

$R^{10}$ is: hydrogen; halo; —$(CH_2)_n$OH; $(C_1-C_6)$alkyl, optionally substituted with one or more halo; or $(C_1-C_6)$alkoxy, optionally substituted with one or more halo;

$R^{11}$ is: hydrogen; —$(CH_2)_n$OH; phenyl; —O—$(C_1-C_6)$alkyl; or $(C_1-C_6)$alkyl, optionally substituted with one or more halo;

$R^{12}$ is: hydrogen; or $(C_1-C_6)$alkyl, optionally substituted with one or more halo; and n is 0, 1, or 2.

In one embodiment, $R^{10}$ is hydrogen. In another embodiment, $R^{10}$ is halo. In another embodiment, $R^{10}$ is $(C_1-C_6)$alkyl, optionally substituted with one or more halo. In another embodiment, $R^{10}$ is —$(CH_2)_n$OH or hydroxyl. In another embodiment, $R^{10}$ is $(C_1-C_6)$alkoxy, optionally substituted with one or more halo.

In one embodiment, $R^{11}$ is hydrogen. In another embodiment, $R^{11}$ is —$(CH_2)_n$OH or hydroxyl. In another embodiment, $R^{11}$ is phenyl. In another embodiment, $R^{11}$ is —O—$(C_1-C_6)$alkyl, optionally substituted with one or more halo. In another embodiment, $R^{11}$ is $(C_1-C_6)$alkyl, optionally substituted with one or more halo.

In one embodiment, $R^{12}$ is hydrogen. In another embodiment, $R^{12}$ is $(C_1-C_6)$alkyl, optionally substituted with one or more halo.

In one embodiment, n is 0. In another embodiment, n is 1. In another embodiment, n is 2.

5-Substituted Quinazolinone Compounds provided herein encompass any of the combinations of $R^{10}$, $R^{11}$, $R^{12}$ and n described above.

In one specific embodiment, $R^{10}$ is halo. In another embodiment, $R^{10}$ is hydroxyl. In another embodiment, $R^{10}$ is methyl.

In another specific embodiment, $R^{11}$ is hydrogen. In another embodiment, $R^{11}$ is methyl.

In another specific embodiment, $R^{12}$ is hydrogen. In another embodiment, $R^{12}$ is methyl.

Specific 5-Substituted Quinazolinone Compounds include, but are not limited to those from Table D:

TABLE D

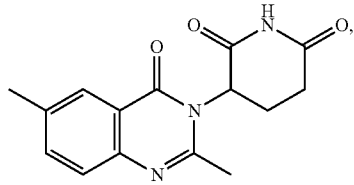 [SMILES: Cc1ccc2nc(C)n(C3CCC(=O)NC3=O)c(=O)c2c1]

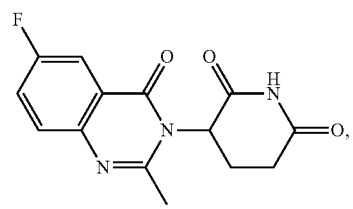 [SMILES: Cc1nc2ccc(F)cc2c(=O)n1C1CCC(=O)NC1=O]

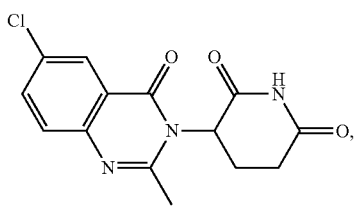 [SMILES: Cc1nc2ccc(Cl)cc2c(=O)n1C1CCC(=O)NC1=O]

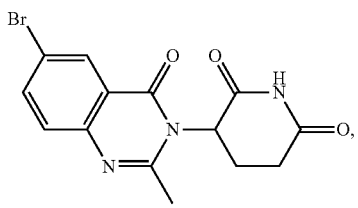 [SMILES: Cc1nc2ccc(Br)cc2c(=O)n1C1CCC(=O)NC1=O]

TABLE D-continued

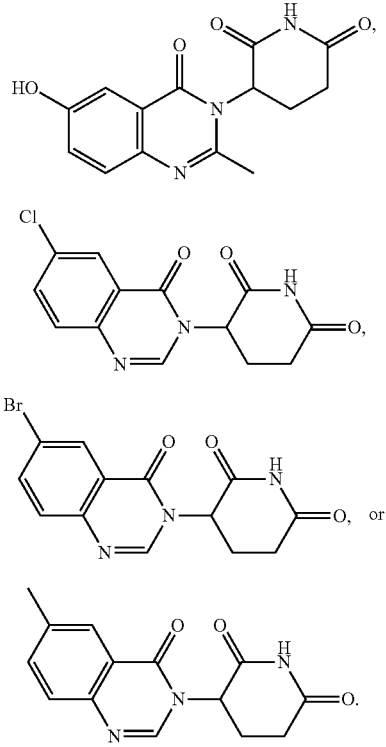

In another embodiment, provided herein are 5-Substituted Quinazolinone Compounds of formula (VIII):

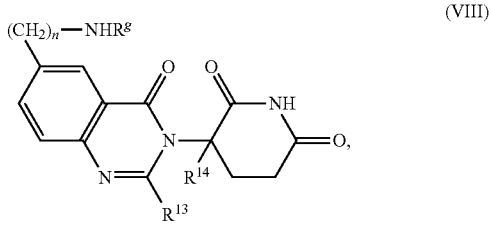

and pharmaceutically acceptable salts, solvates, and stereoisomers thereof, wherein:

$R^g$ is:
hydrogen;
$(C_1-C_6)$alkyl, optionally substituted with one or more halo;
—$(CH_2)_n$-(6 to 10 membered aryl);
—$C(O)$—$(CH_2)_n$-(6 to 10 membered aryl) or —$C(O)$—$(CH_2)_n$-(6 to 10 membered heteroaryl), wherein the aryl or heteroaryl is optionally substituted with one or more of: halo; —$SCF_3$; $(C_1-C_6)$alkyl, itself optionally substituted with one or more halo; or $(C_1-C_6)$alkoxy, itself optionally substituted with one or more halo;
—$C(O)$–$(C_1-C_8)$alkyl, wherein the alkyl is optionally substituted with one or more halo;
—$C(O)$—$(CH_2)_n$—$(C_3-C_{10}$-cycloalkyl);
—$C(O)$—$(CH_2)_n$—$NR^hR^i$, wherein $R^h$ and $R^i$ are each independently:
hydrogen;
$(C_1-C_6)$alkyl, optionally substituted with one or more halo;

$(C_1-C_6)$alkoxy, optionally substituted with one or more halo; or
6 to 10 membered aryl, optionally substituted with one or more of: halo;
$(C_1-C_6)$alkyl, itself optionally substituted with one or more halo; or
$(C_1-C_6)$alkoxy, itself optionally substituted with one or more halo;
—$C(O)$—$(CH_2)_n$—$O$—$(C_1-C_6)$alkyl; or
—$C(O)$—$(CH_2)_n$—$O$—$(CH_2)_n$-(6 to 10 membered aryl);
$R^{13}$ is: hydrogen; —$(CH_2)_n$OH; phenyl; —$O$—$(C_1-C_6)$alkyl; or $(C_1-C_6)$alkyl, optionally substituted with one or more halo;
$R^{14}$ is: hydrogen; or $(C_1-C_6)$alkyl, optionally substituted with one or more halo; and
n is 0, 1, or 2.

In one embodiment, $R^g$ is hydrogen. In another embodiment, $R^g$ is $(C_1-C_6)$alkyl, optionally substituted with one or more halo. In another embodiment, $R^g$ is —$(CH_2)_n$-(6 to 10 membered aryl). In another embodiment, $R^g$ is —$C(O)$—$(CH_2)_n$-(6 to 10 membered aryl) or —$C(O)$—$(CH_2)_n$-(6 to 10 membered heteroaryl), wherein the aryl or heteroaryl is optionally substituted as described above. In another embodiment, $R^g$ is —$C(O)$—$(C_1-C_8)$alkyl, wherein the alkyl is optionally substituted with one or more halo. In another embodiment, $R^g$ is —$C(O)$—$(CH_2)_n$—$(C_3-C_{11}$-cycloalkyl). In another embodiment, $R^g$ is —$C(O)$—$(CH_2)_n$—$NR^hR^i$, wherein $R^h$ and $R^i$ are as described above. In another embodiment, $R^g$ is —$C(O)$—$(CH_2)_n$—$O$—$(C_1-C_6)$alkyl. In another embodiment, $R^g$ is —$C(O)$—$(CH_2)_n$—$O$—$(CH_2)_n$-(6 to 10 membered aryl).

In one embodiment, $R^{13}$ is hydrogen. In another embodiment, $R^{13}$ is —$(CH_2)_n$OH or hydroxyl. In another embodiment, $R^{13}$ is phenyl. In another embodiment, $R^{13}$ is —$O$—$(C_1-C_6)$alkyl, optionally substituted with one or more halo. In another embodiment, $R^{13}$ is $(C_1-C_6)$alkyl, optionally substituted with one or more halo.

In one embodiment, $R^{14}$ is hydrogen. In another embodiment, $R^{14}$ is $(C_1-C_6)$alkyl, optionally substituted with one or more halo.

In one embodiment, n is 0. In another embodiment, n is 1. In another embodiment, n is 2.

5-Substituted Quinazolinone Compounds provided herein encompass any of the combinations of $R^g$, $R^{13}$, $R^{14}$ and n described above.

In one specific embodiment, $R^g$ is hydrogen, and n is 0 or 1. In another embodiment, $R^g$ is —$C(O)$–$(C_1-C_6)$alkyl. In another embodiment, $R^g$ is —$C(O)$-phenyl, optionally substituted with one or more methyl, halo, and/or $(C_1-C_6)$alkoxy.

In another specific embodiment, $R^{13}$ is methyl. In another embodiment, $R^{14}$ is hydrogen.

Specific 5-Substituted Quinazolinone Compounds include, but are not limited to those from Table E:

TABLE E

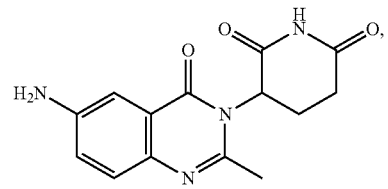 [SMILES: Cc1nc2ccc(N)cc2c(=O)n1C1CCC(=O)NC1=O]

TABLE E-continued
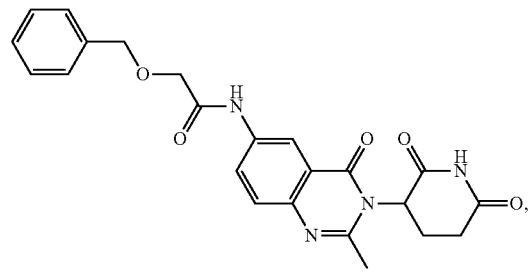 [SMILES: Cc1nc2ccc(NC(=O)COCc3ccccc3)cc2c(=O)n1C1CCC(=O)NC1=O]
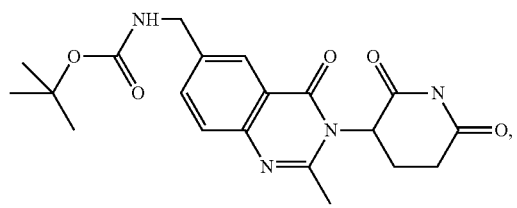 [SMILES: Cc1nc2ccc(CNC(=O)OC(C)(C)C)cc2c(=O)n1C1CCC(=O)NC1=O]
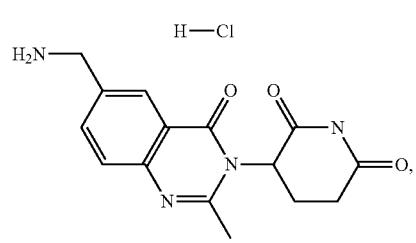 [SMILES: Cl ; Cc1nc2ccc(CN)cc2c(=O)n1C1CCC(=O)NC1=O]
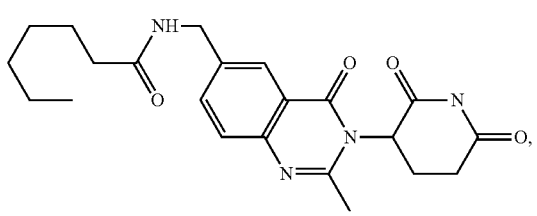 [SMILES: CCCCCCC(=O)NCc1ccc2nc(C)n(C3CCC(=O)NC3=O)c(=O)c2c1]
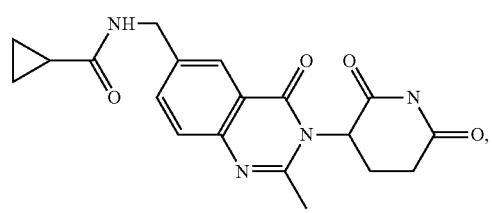 [SMILES: Cc1nc2ccc(CNC(=O)C3CC3)cc2c(=O)n1C1CCC(=O)NC1=O]
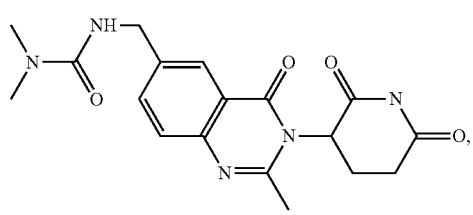 [SMILES: Cc1nc2ccc(CNC(=O)N(C)C)cc2c(=O)n1C1CCC(=O)NC1=O]
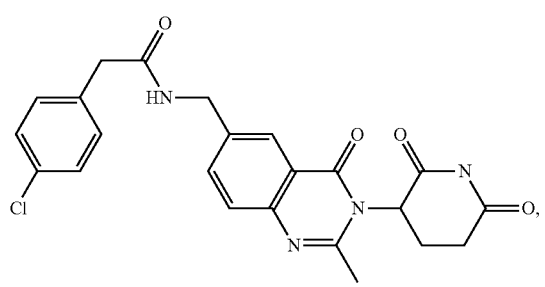 [SMILES: Cc1nc2ccc(CNC(=O)Cc3ccc(Cl)cc3)cc2c(=O)n1C1CCC(=O)NC1=O]
TABLE E-continued
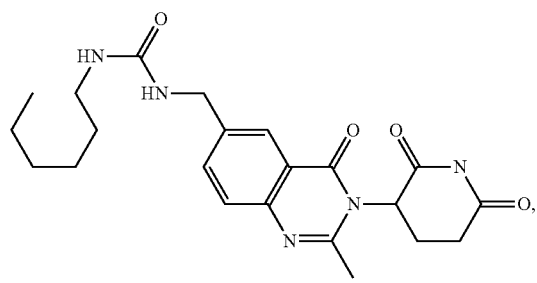 [SMILES: CCCCCCNC(=O)NCc1ccc2nc(C)n(C3CCC(=O)NC3=O)c(=O)c2c1]
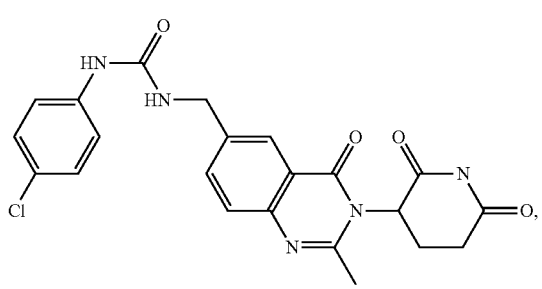 [SMILES: Cc1nc2ccc(CNC(=O)Nc3ccc(Cl)cc3)cc2c(=O)n1C1CCC(=O)NC1=O]
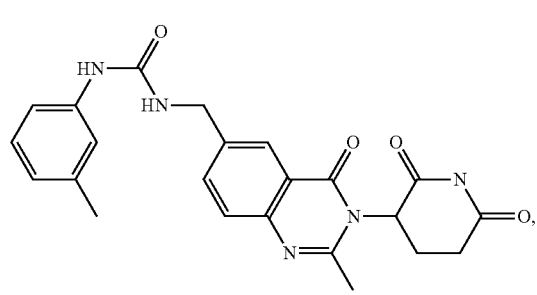 [SMILES: Cc1cccc(NC(=O)NCc2ccc3nc(C)n(C4CCC(=O)NC4=O)c(=O)c3c2)c1]
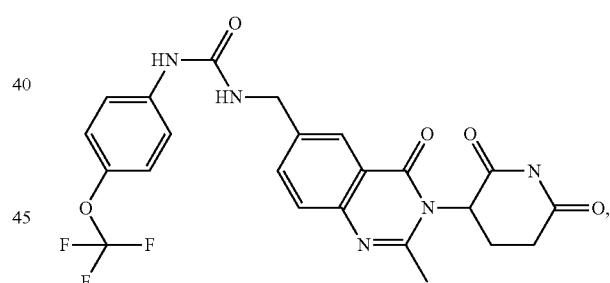
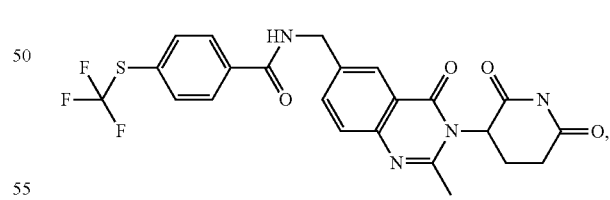
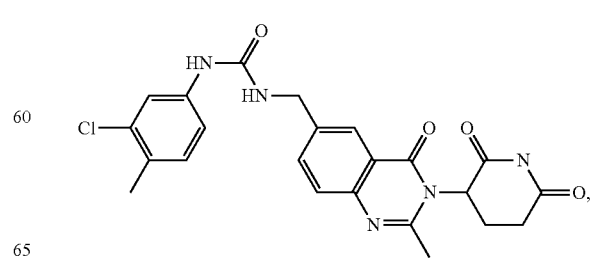

TABLE E-continued

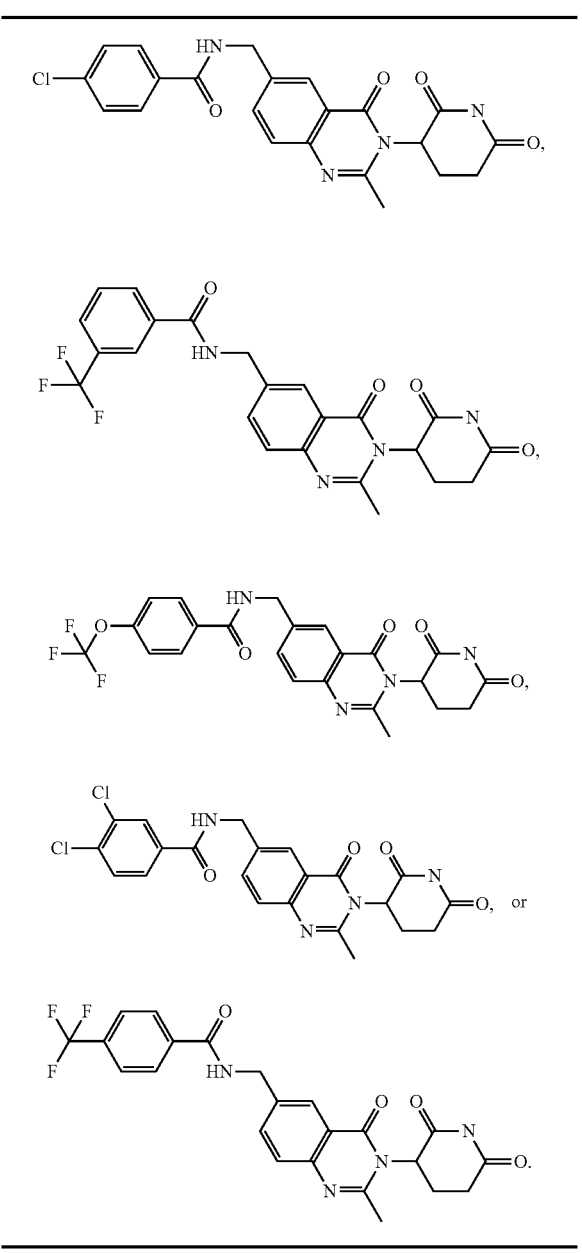

In one embodiment, the 5-Substituted Quinazolinone Compound is:

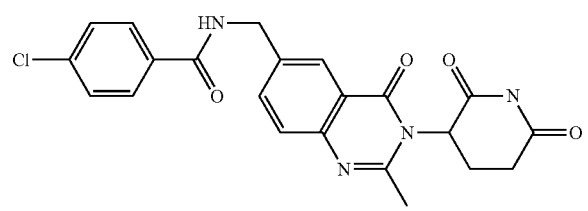 [SMILES: Cc1nc2ccc(CNC(=O)c3ccc(Cl)cc3)cc2c(=O)n1C1CCC(=O)NC1=O]

or a pharmaceutically acceptable salt, solvate, prodrug, or stereoisomer thereof.

In one embodiment, the 5-Substituted Quinazolinone Compound is:

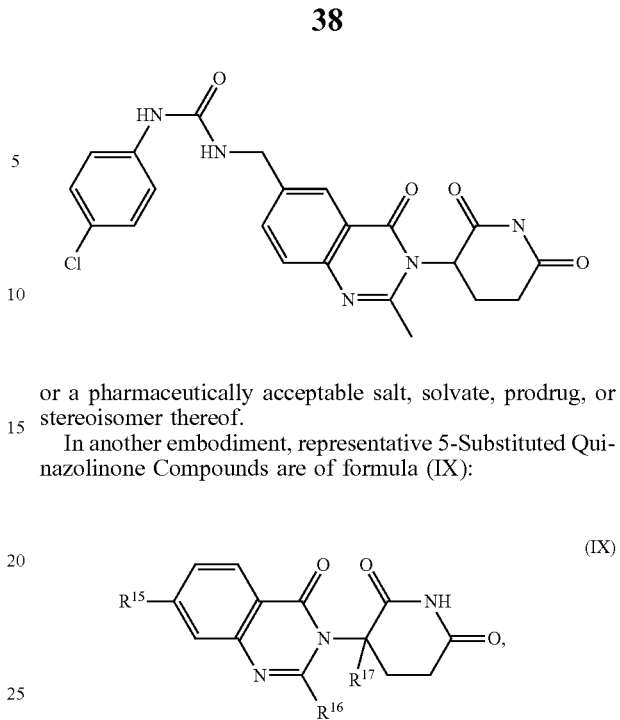

or a pharmaceutically acceptable salt, solvate, prodrug, or stereoisomer thereof.

In another embodiment, representative 5-Substituted Quinazolinone Compounds are of formula (IX):

$$\text{(IX)}$$

and pharmaceutically acceptable salts, solvates, and stereoisomers thereof, wherein:

$R^{15}$ is: hydrogen; halo; —$(CH_2)_n$OH; $(C_1-C_6)$alkyl, optionally substituted with one or more halo; $(C_1-C_6)$alkoxy, optionally substituted with one or more halo; or —$(CH_2)_n$NHR$^j$, wherein R$^j$ is:
  hydrogen;
  $(C_1-C_6)$alkyl, optionally substituted with one or more halo;
  —$(CH_2)_n$-(6 to 10 membered aryl);
  —C(O)—$(CH_2)_n$-(6 to 10 membered aryl) or —C(O)—$(CH_2)_n$-(6 to 10 membered heteroaryl), wherein the aryl or heteroaryl is optionally substituted with one or more of: halo; —SCF$_3$; $(C_1-C_6)$alkyl, itself optionally substituted with one or more halo; or $(C_1-C_6)$alkoxy, itself optionally substituted with one or more halo;
  —C(O)~$(C_1-C_8)$alkyl, wherein the alkyl is optionally substituted with one or more halo;
  —C(O)—$(CH_2)_n$—$(C_3-C_{10}$-cycloalkyl);
  —C(O)—$(CH_2)_n$—NR$^k$R$^l$, wherein R$^k$ and R$^l$ are each independently:
  hydrogen;
  $(C_1-C_6)$alkyl, optionally substituted with one or more halo;
  $(C_1-C_6)$alkoxy, optionally substituted with one or more halo; or
  6 to 10 membered aryl, optionally substituted with one or more of: halo;
  $(C_1-C_6)$alkyl, itself optionally substituted with one or more halo; or
  $(C_1-C_6)$alkoxy, itself optionally substituted with one or more halo;
  —C(O)—$(CH_2)_n$—O—$(C_1-C_6)$alkyl; or
  —C(O)—$(CH_2)_n$—O—$(CH_2)_n$-(6 to 10 membered aryl);
$R^{16}$ is: hydrogen; —$(CH_2)_n$OH; phenyl; —O—$(C_1-C_6)$alkyl; or $(C_1-C_6)$alkyl, optionally substituted with one or more halo;
$R^{17}$ is: hydrogen; or $(C_1-C_6)$alkyl, optionally substituted with one or more halo; and
n is 0, 1, or 2.

In one embodiment, $R^5$ is hydrogen. In another embodiment, $R^5$ is halo. In another embodiment, $R^{15}$ is $(C_1-C_6)$alkyl, optionally substituted with one or more halo. In another embodiment, $R^{15}$ is $—(CH_2)_n OH$ or hydroxyl. In another embodiment, $R^{15}$ is $(C_1-C_6)$alkoxy, optionally substituted with one or more halo.

In one embodiment, $R^5$ is $—(CH_2)_n NHR^j$. In one embodiment, wherein $R^{15}$ is $—(CH_2)_n NHR^j$, $R^j$ is hydrogen. In another embodiment, $R^j$ is $(C_1-C_6)$alkyl, optionally substituted with one or more halo. In another embodiment, $R^j$ is $—(CH_2)_n$-(6 to 10 membered aryl). In another embodiment, $R^j$ is $—C(O)—(CH_2)_n$-(6 to 10 membered aryl) or $—C(O)—(CH_2)_n$-(6 to 10 membered heteroaryl), wherein the aryl or heteroaryl is optionally substituted as described above. In another embodiment, $R^j$ is $—C(O)—(C_1-C_8)$alkyl, wherein the alkyl is optionally substituted with one or more halo. In another embodiment, $R^j$ is $—C(O)—(CH_2)_n—(C_3-C_{10}$-cycloalkyl). In another embodiment, $R^j$ is $—C(O)—(CH_2)_n—NR^k R^l$, wherein $R^k$ and $R^l$ are as described above. In another embodiment, $R^j$ is $—C(O)—(CH_2)_n—O—(C_1-C_6)$alkyl. In another embodiment, $R^j$ is $—C(O)—(CH_2)_n—O—(CH_2)_n$-(6 to 10 membered aryl).

In one embodiment, $R^{16}$ is hydrogen. In another embodiment, $R^{16}$ is $—(CH_2)_n OH$ or hydroxyl. In another embodiment, $R^{16}$ is phenyl. In another embodiment, $R^{16}$ is $—O—(C_1-C_6)$alkyl, optionally substituted with one or more halo. In another embodiment, $R^{16}$ is $(C_1-C_6)$alkyl, optionally substituted with one or more halo.

In one embodiment, $R^{17}$ is hydrogen. In another embodiment, $R^{17}$ is $(C_1-C_6)$alkyl, optionally substituted with one or more halo.

In one embodiment, n is 0. In another embodiment, n is 1. In another embodiment, n is 2.

5-Substituted Quinazolinone Compounds provided herein encompass any of the combinations of $R^{15}$, $R^{16}$, $R^{17}$ and n described above.

In one specific embodiment, $R^{15}$ is methyl. In another embodiment, $R^{15}$ is halo. In another embodiment, $R^{15}$ is $—CF_3$. In another embodiment, $R^{15}$ is $—(CH_2)_n NHR^j$.

In one specific embodiment wherein $R^{15}$ is $—(CH_2)_n NHR^j$, $R^j$ is hydrogen, and n is 0 or 1. In another embodiment wherein $R^{15}$ is $—(CH_2)_n NHR^j$, $R^j$ is $—C(O)—(O)—(C_1-C_6)$alkyl.

In one specific embodiment, $R^{16}$ is hydrogen. In another embodiment, $R^{16}$ is methyl. In another specific embodiment, $R^{17}$ is hydrogen or methyl.

Specific 5-Substituted Quinazolinone Compounds include, but are not limited to those from Table F:

TABLE F

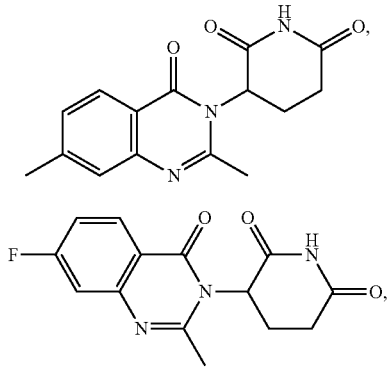

TABLE F-continued

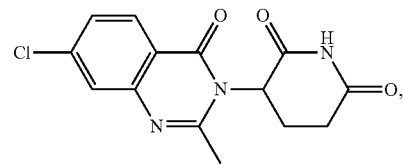 [SMILES: Cc1nc2cc(Cl)ccc2c(=O)n1C1CCC(=O)NC1=O]

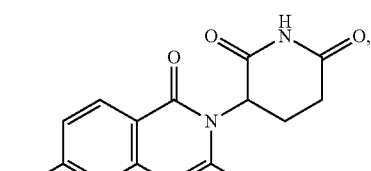

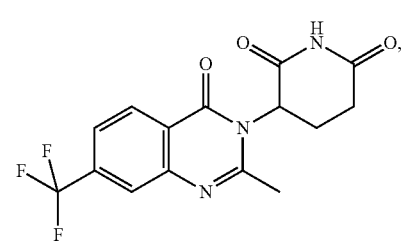 [SMILES: Cc1nc2cc(C(F)(F)F)ccc2c(=O)n1C1CCC(=O)NC1=O]

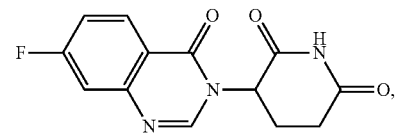

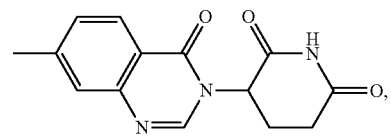 [SMILES: Cc1ccc2c(=O)n(C3CCC(=O)NC3=O)cnc2c1]

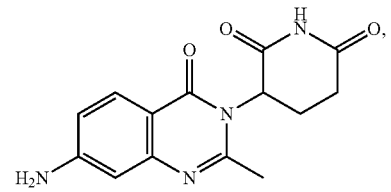

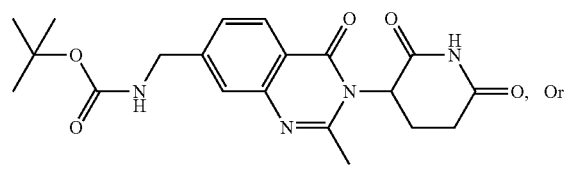

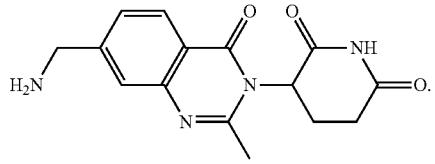

In one embodiment, the 5-Substituted Quinazolinone Compound is:

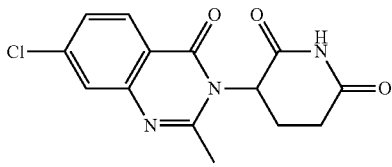 [SMILES: Cc1nc2cc(Cl)ccc2c(=O)n1C1CCC(=O)NC1=O]

or a pharmaceutically acceptable salt, solvate, prodrug, or stereoisomer thereof.

In one embodiment, the 5-Substituted Quinazolinone Compound is:

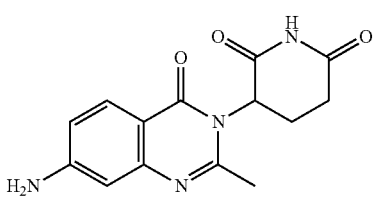 [SMILES: Cc1nc2cc(N)ccc2c(=O)n1C1CCC(=O)NC1=O]

or a pharmaceutically acceptable salt, solvate, prodrug, or stereoisomer thereof.

In another embodiment, representative 5-Substituted Quinazolinone Compounds are of formula (X):

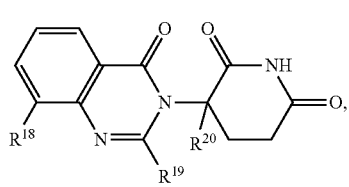

and pharmaceutically acceptable salts, solvates, and stereoisomers thereof, wherein:

$R^{18}$ is: hydrogen; halo; —$(CH_2)_n$OH; $(C_1$-$C_6)$alkyl, optionally substituted with one or more halo; $(C_1$-$C_6)$alkoxy, optionally substituted with one or more halo; or
—$(CH_2)_n$NHR$^m$, wherein R$^m$ is:
hydrogen;
$(C_1$-$C_6)$alkyl, optionally substituted with one or more halo;
—$(CH_2)_n$-(6 to 10 membered aryl);
—C(O)—$(CH_2)_n$-(6 to 10 membered aryl) or —C(O)—$(CH_2)_n$-(6 to 10 membered heteroaryl), wherein the aryl or heteroaryl is optionally substituted with one or more of: halo; —SCF$_3$; $(C_1$-$C_6)$alkyl, itself optionally substituted with one or more halo; or $(C_1$-$C_6)$alkoxy, itself optionally substituted with one or more halo;
—C(O)~$(C_1$-$C_8)$alkyl, wherein the alkyl is optionally substituted with one or more halo;
—C(O)—$(CH_2)_n$—$(C_3$-$C_{10}$-cycloalkyl);
—C(O)—$(CH_2)_n$—NR″R°, wherein R″ and R° are each independently:
hydrogen;
$(C_1$-$C_6)$alkyl, optionally substituted with one or more halo;
$(C_1$-$C_6)$alkoxy, optionally substituted with one or more halo; or
6 to 10 membered aryl, optionally substituted with one or more of: halo;
$(C_1$-$C_6)$alkyl, itself optionally substituted with one or more halo; or
$(C_1$-$C_6)$alkoxy, itself optionally substituted with one or more halo;
—C(O)—$(CH_2)_n$—O—$(C_1$-$C_6)$alkyl; or
—C(O)—$(CH_2)_n$—O—$(CH_2)_n$-(6 to 10 membered aryl);
$R^{19}$ is: hydrogen; —$(CH_2)_n$OH; phenyl; —O—$(C_1$-$C_6)$ alkyl; or $(C_1$-$C_6)$alkyl, optionally substituted with one or more halo;
$R^{20}$ is: hydrogen; or $(C_1$-$C_6)$alkyl, optionally substituted with one or more halo; and
n is 0, 1, or 2.

In one embodiment, $R^{18}$ is hydrogen. In another embodiment, $R^{18}$ is halo. In another embodiment, $R^{18}$ is $(C_1$-$C_6)$ alkyl, optionally substituted with one or more halo. In another embodiment, $R^{18}$ is —$(CH_2)_n$OH or hydroxyl. In another embodiment, $R^{18}$ is $(C_1$-$C_6)$alkoxy, optionally substituted with one or more halo.

In one embodiment, $R^{18}$ is —$(CH_2)_n$NHR$^m$. In one embodiment, wherein $R^{28}$ is —$(CH_2)_n$NHR$^s$, R$^s$ is hydrogen. In another embodiment, R$^m$ is $(C_1$-$C_6)$alkyl, optionally substituted with one or more halo. In another embodiment, R$^m$ is —$(CH_2)_n$-(6 to 10 membered aryl). In another embodiment, R$^m$ is —C(O)—$(CH_2)_n$-(6 to 10 membered aryl) or —C(O)—$(CH_2)_n$-(6 to 10 membered heteroaryl), wherein the aryl or heteroaryl is optionally substituted as described above. In another embodiment, R$^s$ is —C(O)~$(C_1$-$C_8)$alkyl, wherein the alkyl is optionally substituted with one or more halo. In another embodiment, R$^m$ is —C(O)—$(CH_2)_n$—$(C_3$-$C_{10}$-cycloalkyl). In another embodiment, R$^m$ is —C(O)—$(CH_2)_n$—NR″R°, wherein R″ and R° are as described above. In another embodiment, R$^m$ is —C(O)—$(CH_2)_n$—O—$(C_1$-$C_6)$alkyl. In another embodiment, R$^m$ is —C(O)—$(CH_2)_n$—O—$(CH_2)_n$-(6 to 10 membered aryl).

In one embodiment, $R^{19}$ is hydrogen. In another embodiment, $R^{19}$ is —$(CH_2)_n$OH or hydroxyl. In another embodiment, $R^{19}$ is phenyl. In another embodiment, $R^{19}$ is —O—$(C_1$-$C_6)$alkyl, optionally substituted with one or more halo. In another embodiment, $R^{19}$ is $(C_1$-$C_6)$alkyl, optionally substituted with one or more halo.

In one embodiment, $R^{20}$ is hydrogen. In another embodiment, $R^{20}$ is $(C_1$-$C_6)$alkyl, optionally substituted with one or more halo.

In one embodiment, n is 0. In another embodiment, n is 1. In another embodiment, n is 2.

5-Substituted Quinazolinone Compounds provided herein encompass any of the combinations of $R^{18}$, $R^{19}$, $R^{20}$ and n described above.

In one specific embodiment, $R^{18}$ is methyl. In another embodiment, $R^{18}$ is halo. In another embodiment, $R^{18}$ is hydroxyl. In another embodiment, $R^{18}$ is —CF$_3$.

In one specific embodiment, $R^{19}$ is hydrogen. In another embodiment, $R^{19}$ is methyl. In another specific embodiment, $R^{20}$ is hydrogen.

Specific 5-Substituted Quinazolinone Compounds include, but are not limited to those from Table G:

TABLE G

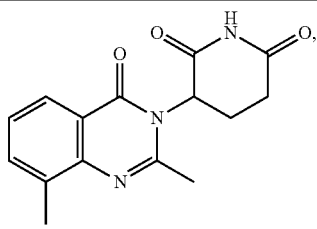

TABLE G-continued

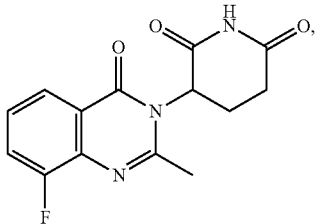 [SMILES: Cc1nc2c(F)cccc2c(=O)n1C1CCC(=O)NC1=O]

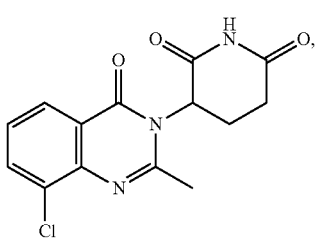 [SMILES: Cc1nc2c(Cl)cccc2c(=O)n1C1CCC(=O)NC1=O]

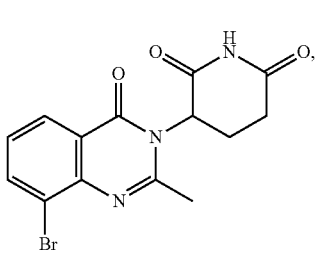 [SMILES: Cc1nc2c(Br)cccc2c(=O)n1C1CCC(=O)NC1=O]

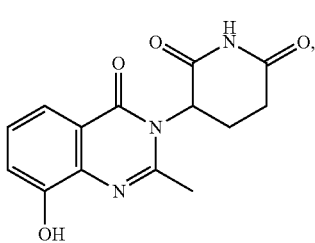 [SMILES: Cc1nc2c(O)cccc2c(=O)n1C1CCC(=O)NC1=O]

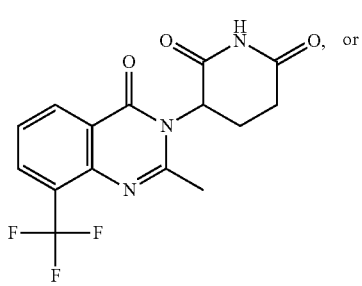 [SMILES: Cc1nc2c(C(F)(F)F)cccc2c(=O)n1C1CCC(=O)NC1=O ; "or"]

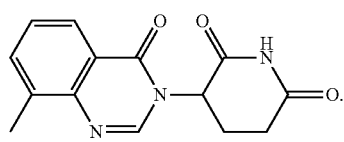 [SMILES: Cc1cccc2c(=O)n(C3CCC(=O)NC3=O)cnc12]

In one embodiment, the 5-Substituted Quinazolinone Compound is:

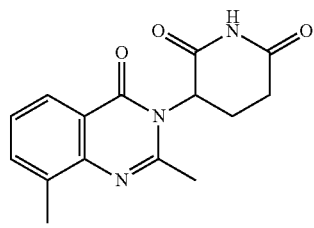 [SMILES: Cc1cccc2c(=O)n(C3CCC(=O)NC3=O)c(C)nc12]

or a pharmaceutically acceptable salt, solvate, prodrug, or stereoisomer thereof.

In one embodiment, the 5-Substituted Quinazolinone Compound is:

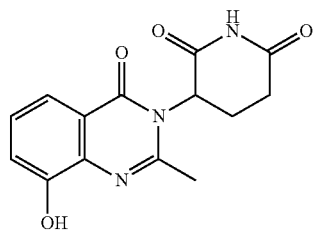 [SMILES: Cc1nc2c(O)cccc2c(=O)n1C1CCC(=O)NC1=O]

or a pharmaceutically acceptable salt, solvate, prodrug, or stereoisomer thereof.

In another embodiment, representative 5-Substituted Quinazolinone Compounds are of formula (XI):

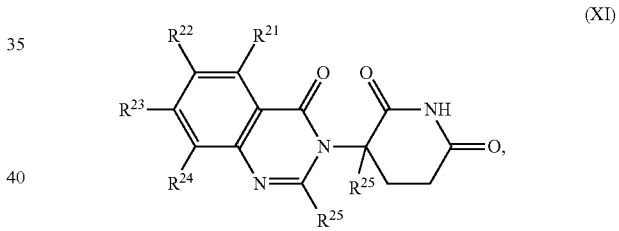

and pharmaceutically acceptable salts, solvates, and stereoisomers thereof, wherein:

$R^{21}$ is hydrogen;

$R^{22}$, $R^{23}$, and $R^{24}$ are each independently: halo; —$(CH_2)_n$OH; $(C_1-C_6)$alkyl, optionally substituted with one or more halo; $(C_1-C_6)$alkoxy, optionally substituted with one or more halo; or two of $R^{21}$-$R^{24}$ together form a 5 to 6 membered ring, optionally substituted with one or more of: halo; $(C_1-C_6)$alkyl, optionally substituted with one or more halo; and $(C_1-C_6)$alkoxy, optionally substituted with one or more halo;

$R^{25}$ is: hydrogen; —$(CH_2)_n$OH; phenyl; —O—$(C_1-C_6)$alkyl; or $(C_1-C_6)$alkyl, optionally substituted with one or more halo;

$R^{26}$ is: hydrogen; or $(C_1-C_6)$alkyl, optionally substituted with one or more halo; and n is 0, 1, or 2.

In one embodiment, two of $R^{22}$-$R^{24}$ are halo. In another embodiment, two of $R^{22}$-$R^{24}$ are $(C_1-C_6)$alkyl, optionally substituted with one or more halo. In another embodiment, two of $R^{22}$-$R^{24}$ are $(C_1-C_6)$alkoxy, optionally substituted with one or more halo.

In another embodiment, one of $R^{22}$-$R^{24}$ are is halo, and another one of $R^{22}$-$R^{24}$ is $(C_1-C_6)$alkyl, optionally substituted with one or more halo. In another embodiment, one of $R^{22}$-$R^{24}$ is halo, and another one of $R^{22}$-$R^{24}$ is $(C_1$-$C_6)$ alkoxy, optionally substituted with one or more halo. In another embodiment, one of $R^{22}$-$R^{24}$ is $(C_1$-$C_6)$alkoxy, optionally substituted with one or more halo, and another one of $R^{22}$-$R^{24}$ is $(C_1$-$C_6)$alkyl, optionally substituted with one or more halo.

In another embodiment, two of $R^{22}$-$R^{24}$ together form a 5 to 6 membered ring. In one specific embodiment, $R^{22}$ and $R^{23}$ together form a 5 to 6 membered ring. In one specific embodiment, $R^{22}$ and $R^{23}$ together form phenyl ring. In another embodiment, the ring formed by $R^{22}$ and $R^{23}$ is optionally substituted with one or more of: halo; $(C_1$-$C_6)$ alkyl, optionally substituted with one or more halo; and $(C_1$-$C_6)$alkoxy, optionally substituted with one or more halo.

In one embodiment, $R^{25}$ is hydrogen. In another embodiment, $R^{25}$ is —$(CH_2)_n$OH or hydroxyl. In another embodiment, $R^{25}$ is phenyl. In another embodiment, $R^{25}$ is —O—$(C_1$-$C_6)$alkyl, optionally substituted with one or more halo. In another embodiment, $R^{25}$ is $(C_1$-$C_6)$alkyl, optionally substituted with one or more halo.

In one embodiment, $R^{26}$ is hydrogen. In another embodiment, $R^{26}$ is $(C_1$-$C_6)$alkyl, optionally substituted with one or more halo.

In one embodiment, n is 0. In another embodiment, n is 1. In another embodiment, n is 2.

5-Substituted Quinazolinone Compounds provided herein encompass any of the combinations of $R^{21}$, $R^{22}$, $R^{23}$, $R^{24}$, $R^{25}$, $R^{26}$, and n described above.

Specific 5-Substituted Quinazolinone Compounds include, but are not limited to:

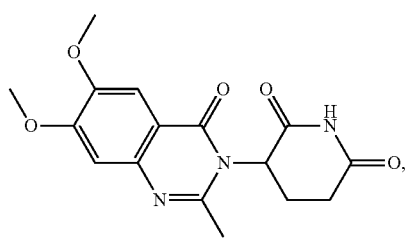

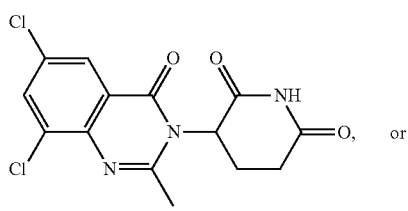

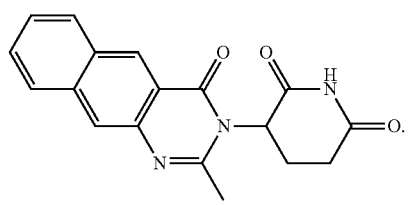

In one embodiment, the 5-Substituted Quinazolinone Compound is:

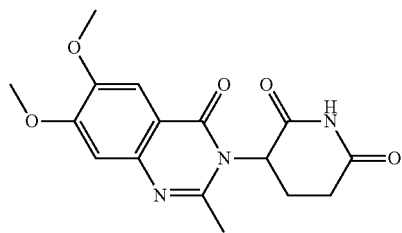 [SMILES: COc1cc2nc(C)n(C3CCC(=O)NC3=O)c(=O)c2cc1OC]

or a pharmaceutically acceptable salt, solvate, prodrug, or stereoisomer thereof.

All of the 5-Substituted Quinazolinone Compounds described can either be commercially purchased or prepared according to the methods described in the patents or patent publications disclosed herein. Further, optically pure 5-Substituted Quinazolinone Compounds can be asymmetrically synthesized or resolved using known resolving agents or chiral columns as well as other standard synthetic organic chemistry techniques.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Still other specific immunomodulatory drugs provided herein belong to a class of 5-substituted isoindole compounds disclosed in U.S. Patent Application Publication No. US 2009/0142297, the entirety of which is incorporated herein by reference. Representative compounds are of formula XI:

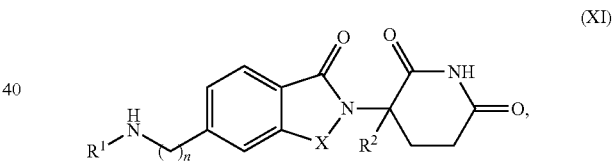

(XI)

and pharmaceutically acceptable salts, solvates, stereoisomers, and prodrugs thereof,
wherein:
n is 0 or 1;
X is $CH_2$, C=O, or C=S;
$R^1$ is:
 a) —$(CH_2)_mR^3$ or —$CO(CH_2)_mR^3$, wherein
  m is 0, 1, 2, or 3; and
  $R^3$ is 5-10 membered aryl or heteroaryl, optionally substituted with one or more halogen;
 b) —C=Y$R^4$, wherein
  Y is O or S; and
  $R^4$ is: $(C_1$-$C_{10})$alkyl; $(C_1$-$C_{10})$alkoxy; $(C_0$-$C_{10})$alkyl-(5 to 10 membered heteroaryl or heterocycle), said heteroaryl or heterocycle optionally substituted with one or more of $(C_1$-$C_6)$alkyl, halogen, oxo, $(C_1$-$C_6)$alkoxy, or —Z—$(C_1$-$C_6)$alkyl, wherein Z is S or $SO_2$, and wherein said $(C_1$-$C_6)$ alkyl may be optionally substituted with one or more halogen; $(C_0$-$C_{10})$alkyl-(5 to 10 membered aryl), said aryl optionally substituted with one or more of: halogen; $(C_1$-$C_6)$alkoxy, itself optionally substituted with one or more halogen; $(C_1$-$C_6)$alkyl, itself optionally substituted with one or more halogen; or —Z—$(C_1$-$C_6)$alkyl, wherein Z is S or $SO_2$, and wherein said $(C_1-C_6)$alkyl may be optionally substituted with one or more halogen; or $(C_1-C_6)$alkyl-CO—O—$R^{12}$, wherein $R^{12}$ is H or $(C_1-C_6)$alkyl; or c) —C=ZNHR$^6$, wherein Z is O or S; and $R^6$ is: $(C_1-C_{10})$alkyl; $(C_1-C_{10})$alkoxy; 5 to 10 membered aryl or heteroaryl, optionally substituted with one or more of: halogen; cyano; $(C_1-C_6)$alkylenedioxy; $(C_1-C_6)$alkoxy, itself optionally substituted with one or more halogen; $(C_1-C_6)$alkyl, itself optionally substituted with one or more halogen; or $(C_1-C_6)$alkylthio, itself optionally substituted with one or more halogen; and $R^2$ is H or $(C_1-C_6)$alkyl.

Representative compounds are of formula:

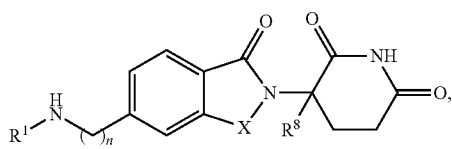

and pharmaceutically acceptable salts, solvates, stereoisomers, and prodrugs thereof, wherein:

n is 0 or 1;

X is $CH_2$ or C=O;

$R^7$ is —$(CH_2)_m R^9$, wherein m is 0, 1, 2, or 3, and $R^9$ is 5-10 membered aryl or heteroaryl, optionally substituted with one or more halogen; and $R^8$ is H or $(C_1-C_6)$alkyl.

In one embodiment, X is C=O. In another embodiment, X is $CH_2$.

In one embodiment, n is 0. In another embodiment, n is 1.

In one embodiment, m is 0. In another embodiment, m is 1. In another embodiment, m is 2. In another embodiment, m is 3.

In one embodiment, $R^9$ is 5-10 membered aryl. In certain specific embodiments, $R^9$ is phenyl, optionally substituted with one or more halogen.

In one embodiment, $R^9$ is 5-10 membered heteroaryl. In certain specific embodiments, $R^9$ is furyl or benzofuryl.

In one embodiment, $R^8$ is H. In another embodiment, $R^8$ is $(C_1-C_6)$alkyl. In certain specific embodiments, $R^8$ is methyl.

All of the combinations of the above embodiments are encompassed by this invention.

Examples include, but are not limited to, those listed below, or a pharmaceutically acceptable salt, solvate (e.g., hydrate), prodrug or stereoisomer thereof:

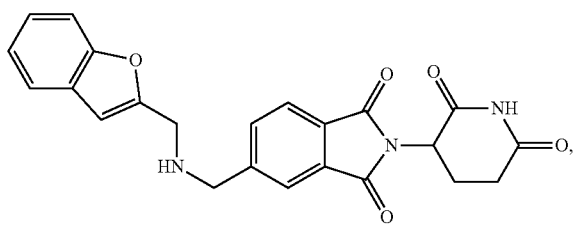

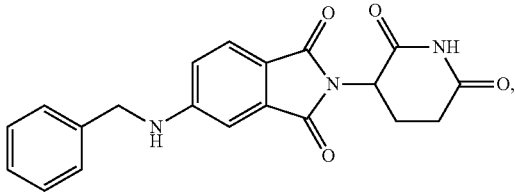

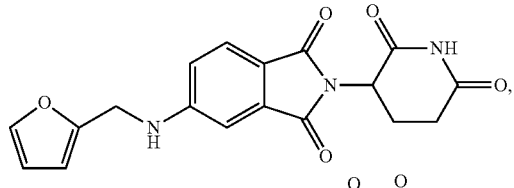

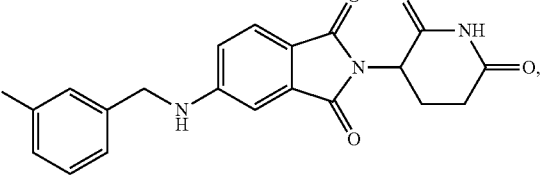

or

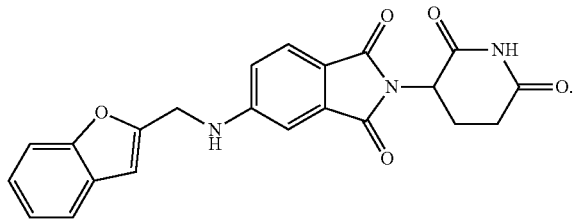

Other representative compounds are of formula:

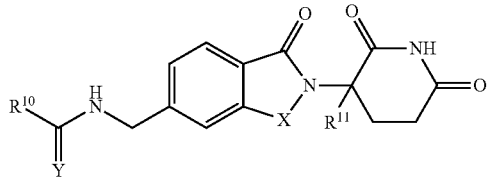

and pharmaceutically acceptable salts, solvates, stereoisomers, and prodrugs thereof, wherein:

X is $CH_2$ or C=O;

Y is O or S;

$R^{10}$ is: $(C_1-C_{10})$alkyl; $(C_1-C_{10})$alkoxy; $(C_0-C_{10})$alkyl-(5 to 10 membered heteroaryl or heterocycle), said heteroaryl or heterocycle optionally substituted with one or more of: $(C_1-C_6)$alkyl, itself substituted with one or more halogen; halogen; oxo; $(C_1-C_6)$alkoxy, itself substituted with one or more halogen; or —Z—$(C_1-C_6)$alkyl, wherein Z is S or $SO_2$, and wherein said $(C_1-C_6)$alkyl may be optionally substituted with one or more halogen; $(C_0-C_{10})$alkyl-(5 to 10 membered aryl), said aryl optionally substituted with one or more of: halogen; $(C_1-C_6)$alkoxy, itself optionally substituted with one or more halogen; $(C_1-C_6)$alkyl, itself optionally substituted with one or more halogen; or —Z—$(C_1-C_6)$alkyl, wherein Z is S or $SO_2$, and wherein said $(C_1-C_6)$alkyl may be optionally substituted with one or more halogen; or $(C_1-C_6)$alkyl-CO—O—$R^{12}$, wherein $R^{12}$ is H or $(C_1-C_6)$alkyl; and $R^{11}$ is H or $(C_1-C_6)$alkyl.

In one embodiment, X is $CH_2$. In another embodiment, X is C=O.

In one embodiment, Y is O. In another embodiment, Y is S.

In one embodiment, $R^{10}$ is $(C_1-C_{10})$alkyl. In certain specific embodiments, $R^{10}$ is $(C_5-C_{10})$alkyl. In certain specific embodiments, $R^{10}$ is pentyl or hexyl.

In one embodiment, $R^{10}$ is $(C_1-C_{10})$alkoxy. In certain specific embodiments, $R^{10}$ is $(C_5-C_{10})$alkoxy. In certain specific embodiments, $R^{10}$ is pentyloxy or hexyloxy.

In one embodiment, $R^{10}$ is 5 to 10 membered heteroaryl. In certain specific embodiments, $R^{10}$ is thiopheneyl or furyl.

In one embodiment, $R^{10}$ is 5 to 10 membered aryl, optionally substituted with one or more halogen. In certain specific embodiments, $R^{10}$ is phenyl, optionally substituted with one or more halogen.

In one embodiment, $R^{10}$ is 5 to 10 membered aryl or heteroaryl, optionally substituted with $(C_1-C_6)$alkyl or $(C_1-C_6)$alkoxy, themselves optionally substituted with one or more halogen. In certain specific embodiments, $R^{10}$ is phenyl substituted with $(C_1-C_3)$alkyl or $(C_1-C_3)$alkoxy, substituted with one or more halogen. In certain specific embodiments, $R^{10}$ is phenyl substituted with methyl or methoxy, substituted with 1, 2, or 3 halogens.

In one embodiment, $R^{10}$ is aryl or heteroaryl substituted with —S—$(C_1-C_6)$alkyl, wherein said alkyl itself optionally substituted with one or more halogen. In another embodiment, $R^{10}$ is aryl or heteroaryl substituted with —SO$_2$—$(C_1-C_6)$alkyl, wherein said alkyl itself optionally substituted with one or more halogen.

In one embodiment, $R^{10}$ is $(C_1-C_6)$alkyl-CO—O—$R^{12}$, and $R^{12}$ is $(C_1-C_6)$alkyl. In one specific embodiment, $R^{10}$ is butyl-CO—O-tBu.

In one embodiment, $R^{10}$ is $(C_1-C_6)$alkyl-CO—O—$R^{12}$, and $R^{12}$ is H. In one specific embodiment, $R^{10}$ is butyl-COOH.

In one embodiment, $R^{11}$ is H. In another embodiment, $R^{11}$ is $(C_1-C_6)$alkyl. In certain specific embodiments, $R^{11}$ is methyl.

All of the combinations of the above embodiments are encompassed by this invention.

Examples include, but are not limited to, those listed in Table J, below, or a pharmaceutically acceptable salt, solvate (e.g., hydrate), or stereoisomer thereof:

TABLE J

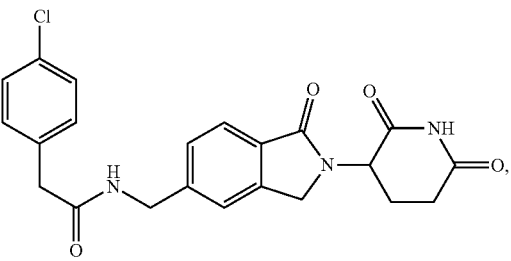 [SMILES: O=C(Cc1ccc(Cl)cc1)NCc1ccc2c(c1)CN(C1CCC(=O)NC1=O)C2=O]

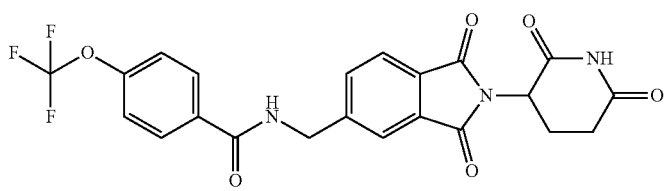 [SMILES: O=C1CCC(N2C(=O)c3ccc(CNC(=O)c4ccc(OC(F)(F)F)cc4)cc3C2=O)C(=O)N1]

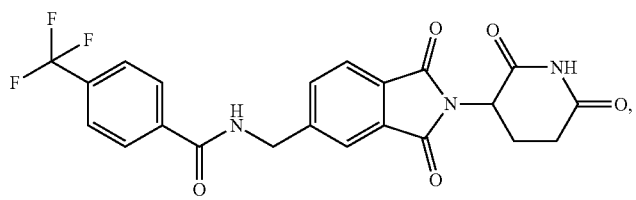 [SMILES: O=C1CCC(N2C(=O)c3ccc(CNC(=O)c4ccc(C(F)(F)F)cc4)cc3C2=O)C(=O)N1]

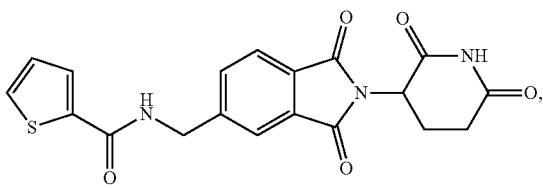 [SMILES: O=C1CCC(N2C(=O)c3ccc(CNC(=O)c4cccs4)cc3C2=O)C(=O)N1]

TABLE J-continued
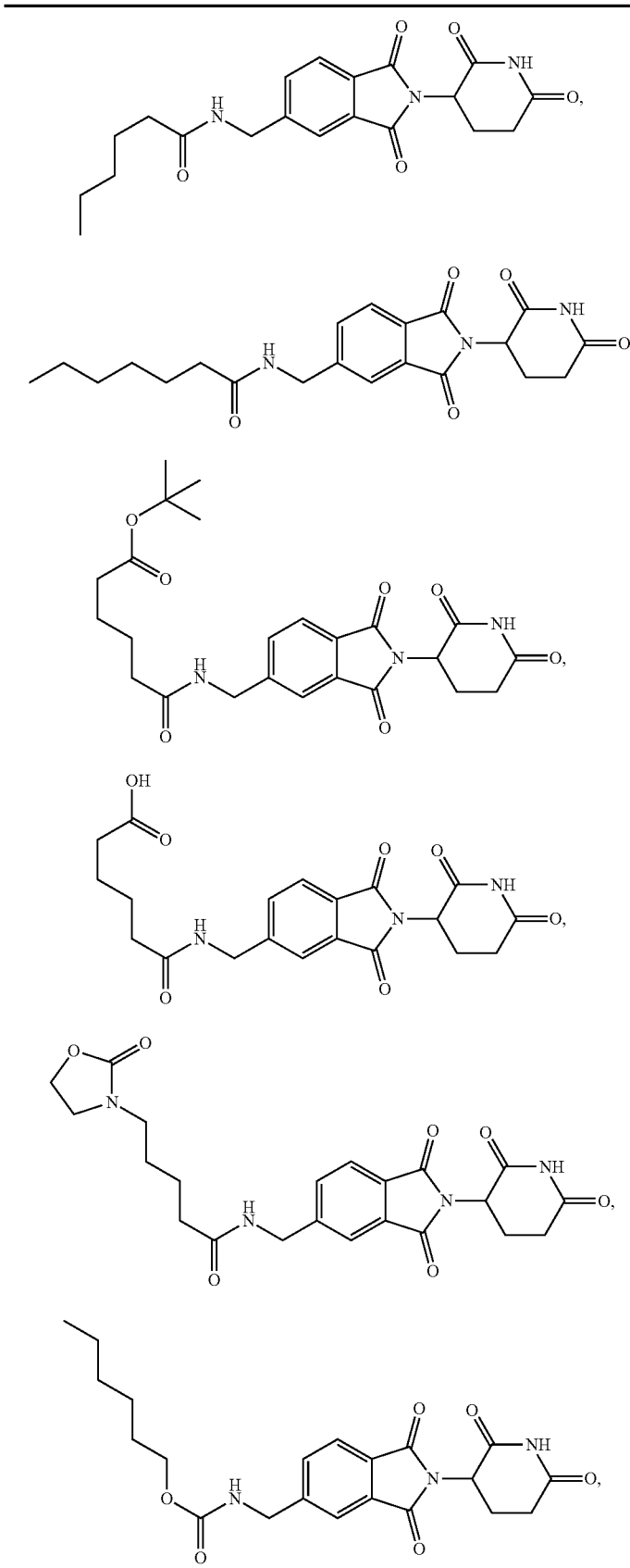

TABLE J-continued
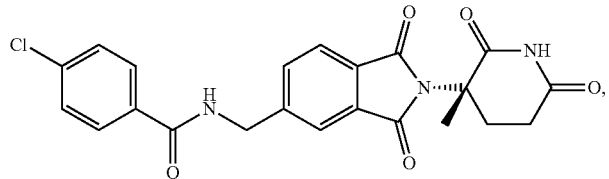
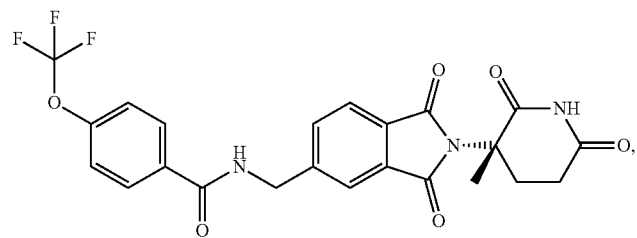
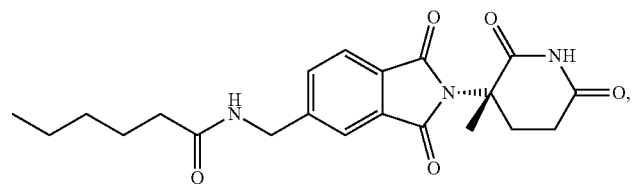
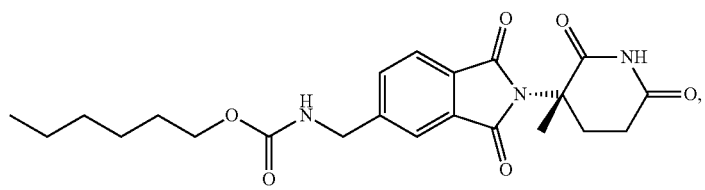
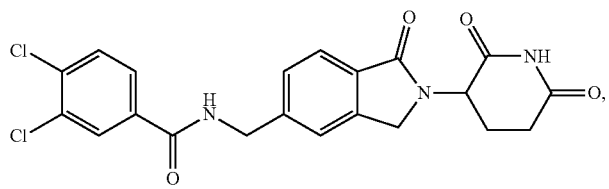 [SMILES: O=C1CCC(N2Cc3cc(CNC(=O)c4ccc(Cl)c(Cl)c4)ccc3C2=O)C(=O)N1]
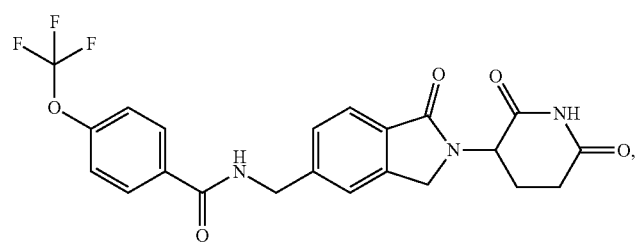 [SMILES: O=C1CCC(N2Cc3cc(CNC(=O)c4ccc(OC(F)(F)F)cc4)ccc3C2=O)C(=O)N1]
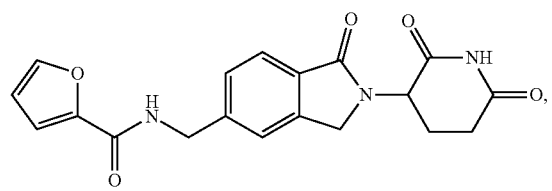 [SMILES: O=C1CCC(N2Cc3cc(CNC(=O)c4ccco4)ccc3C2=O)C(=O)N1]

TABLE J-continued
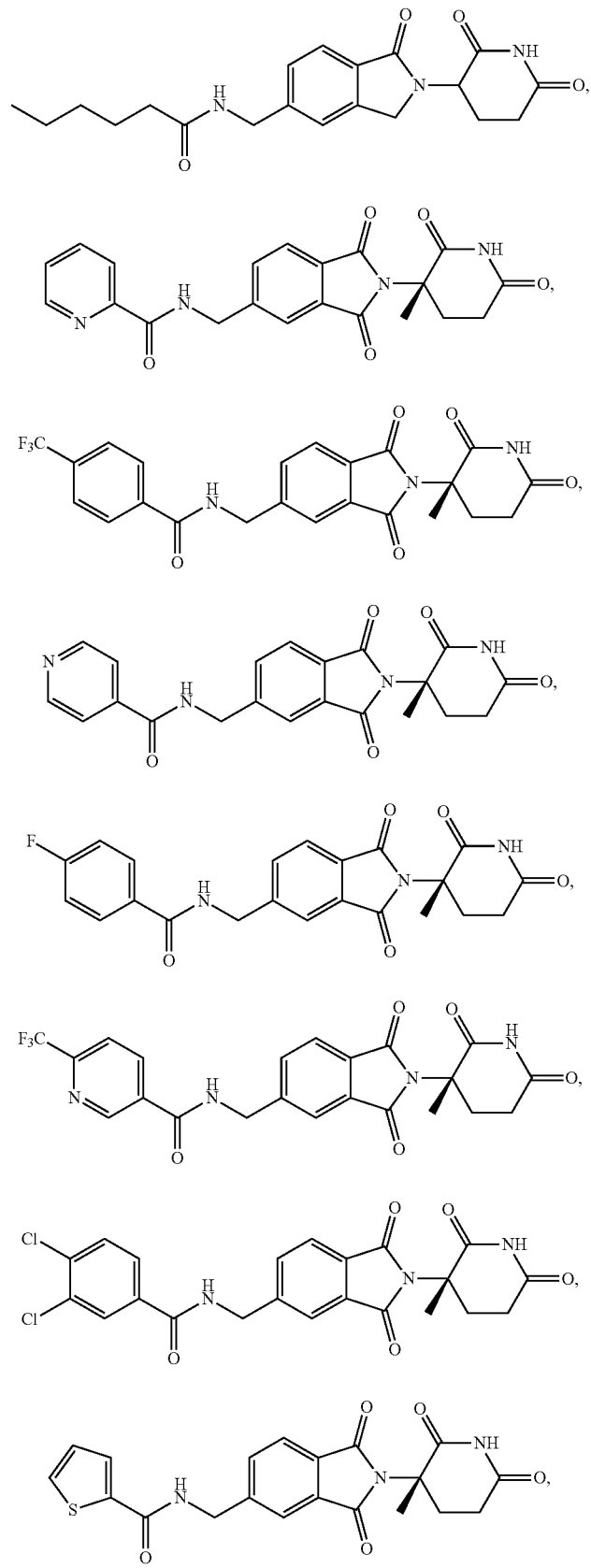

TABLE J-continued
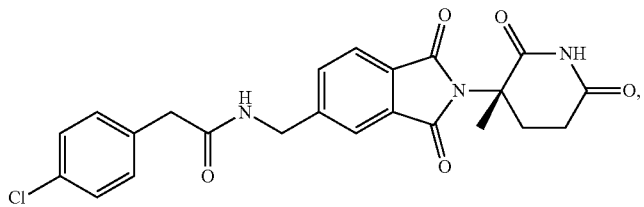 [SMILES: C[C@]1(N2C(=O)c3ccc(CNC(=O)Cc4ccc(Cl)cc4)cc3C2=O)CCC(=O)NC1=O]
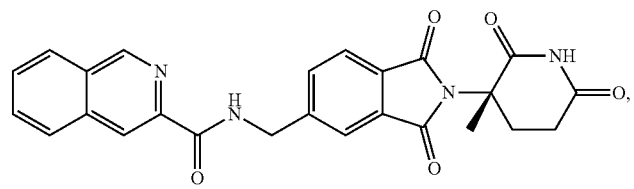 [SMILES: C[C@]1(N2C(=O)c3ccc(CNC(=O)c4cc5ccccc5cn4)cc3C2=O)CCC(=O)NC1=O]
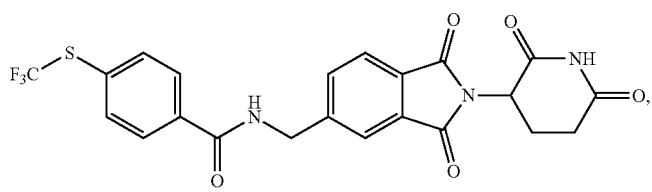 [SMILES: O=C1CCC(N2C(=O)c3ccc(CNC(=O)c4ccc(SC(F)(F)F)cc4)cc3C2=O)C(=O)N1]
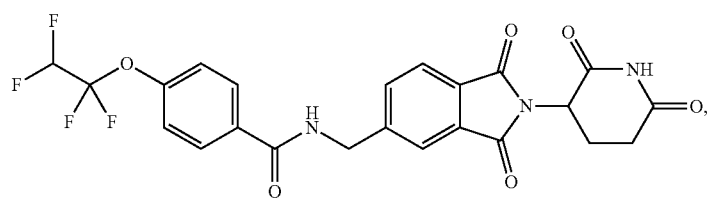 [SMILES: O=C1CCC(N2C(=O)c3ccc(CNC(=O)c4ccc(OC(F)(F)C(F)F)cc4)cc3C2=O)C(=O)N1]
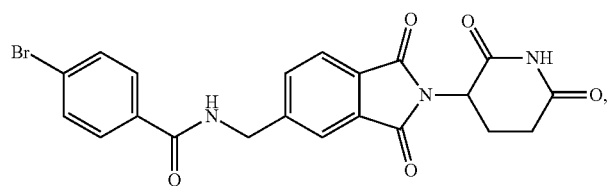 [SMILES: O=C1CCC(N2C(=O)c3ccc(CNC(=O)c4ccc(Br)cc4)cc3C2=O)C(=O)N1]
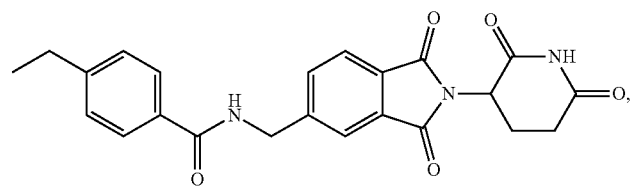 [SMILES: CCc1ccc(C(=O)NCc2ccc3c(c2)C(=O)N(C2CCC(=O)NC2=O)C3=O)cc1]
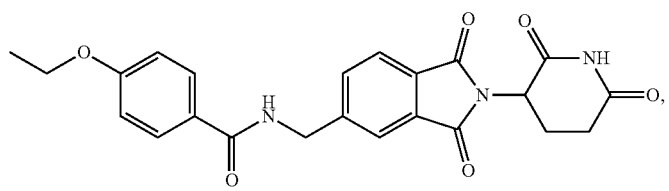 [SMILES: CCOc1ccc(C(=O)NCc2ccc3c(c2)C(=O)N(C2CCC(=O)NC2=O)C3=O)cc1]
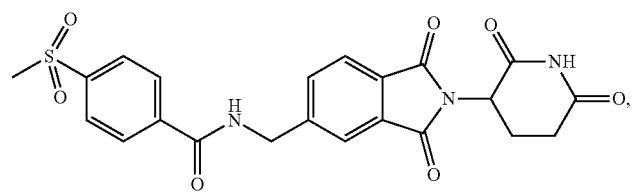 [SMILES: CS(=O)(=O)c1ccc(C(=O)NCc2ccc3c(c2)C(=O)N(C2CCC(=O)NC2=O)C3=O)cc1]

TABLE J-continued
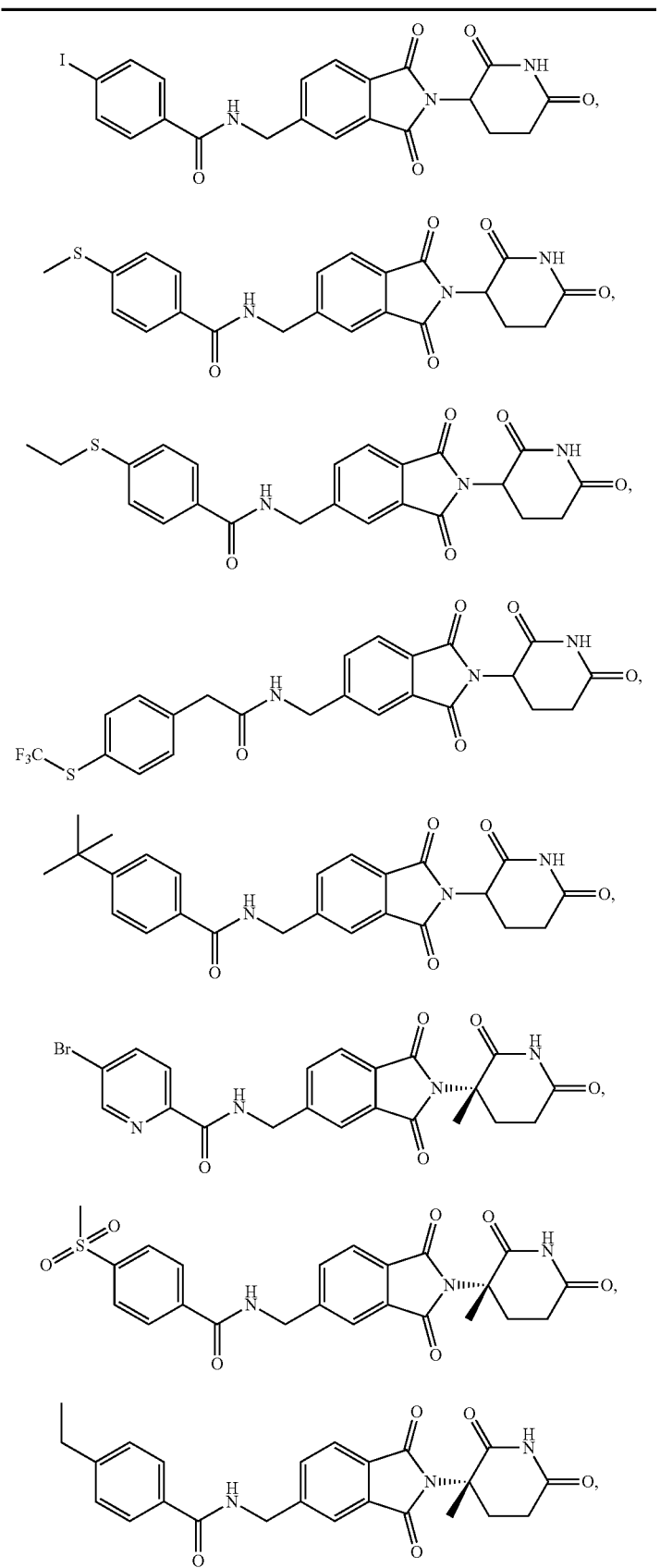

TABLE J-continued
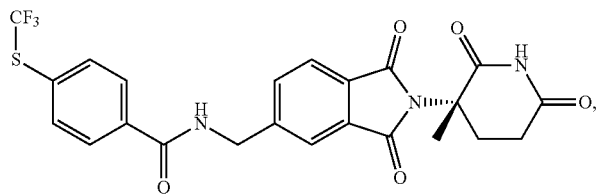 [SMILES: C[C@]1(N2C(=O)c3ccc(CNC(=O)c4ccc(SC(F)(F)F)cc4)cc3C2=O)CCC(=O)NC1=O]
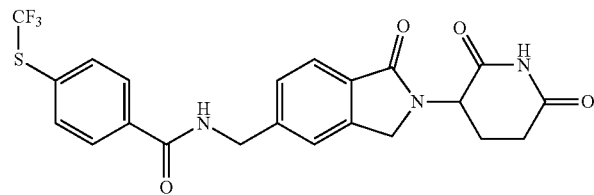 [SMILES: O=C1CCC(N2Cc3cc(CNC(=O)c4ccc(SC(F)(F)F)cc4)ccc3C2=O)C(=O)N1]
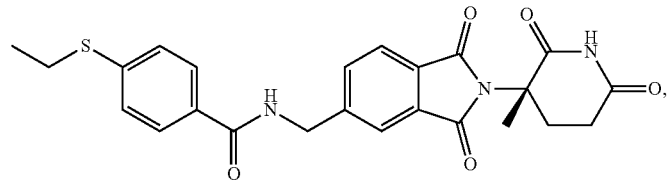 [SMILES: CCSc1ccc(C(=O)NCc2ccc3c(c2)C(=O)N([C@@]2(C)CCC(=O)NC2=O)C3=O)cc1]
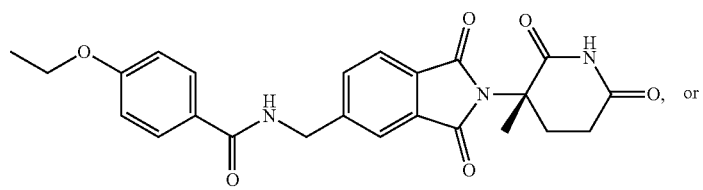 [SMILES: CCOc1ccc(C(=O)NCc2ccc3c(c2)C(=O)N([C@@]2(C)CCC(=O)NC2=O)C3=O)cc1 ; "or"]
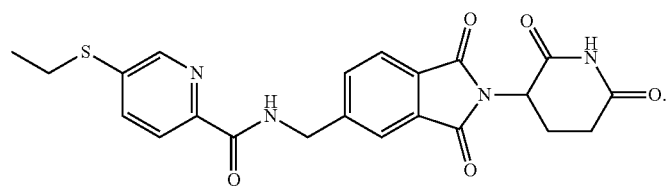 [SMILES: CCSc1ccc(C(=O)NCc2ccc3c(c2)C(=O)N(C2CCC(=O)NC2=O)C3=O)nc1]
Other examples include, but are not limited to, those listed in Table K, below, or a pharmaceutically acceptable salt, solvate (e.g., hydrate), or stereoisomer thereof:
TABLE K
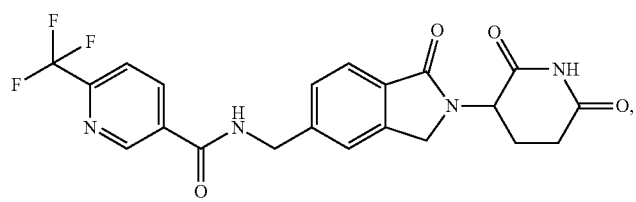 [SMILES: O=C1CCC(N2Cc3cc(CNC(=O)c4ccc(C(F)(F)F)nc4)ccc3C2=O)C(=O)N1]
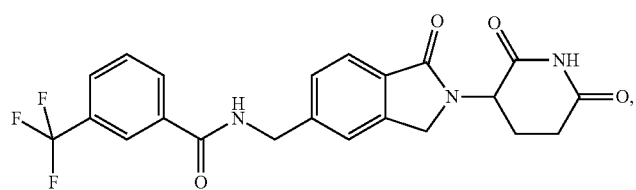 [SMILES: O=C1CCC(N2Cc3cc(CNC(=O)c4cccc(C(F)(F)F)c4)ccc3C2=O)C(=O)N1]

TABLE K-continued
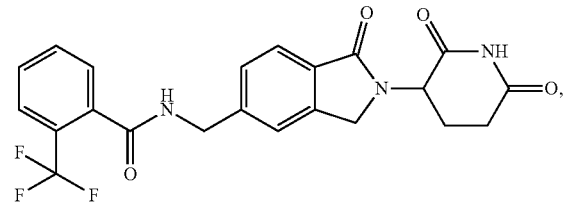 [SMILES: O=C1CCC(N2Cc3cc(CNC(=O)c4ccccc4C(F)(F)F)ccc3C2=O)C(=O)N1]
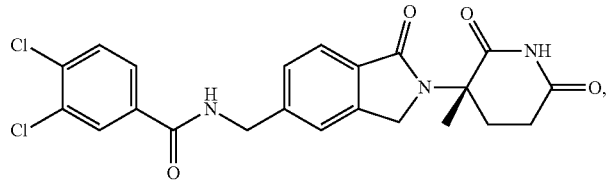 [SMILES: C[C@]1(N2Cc3cc(CNC(=O)c4ccc(Cl)c(Cl)c4)ccc3C2=O)CCC(=O)NC1=O]
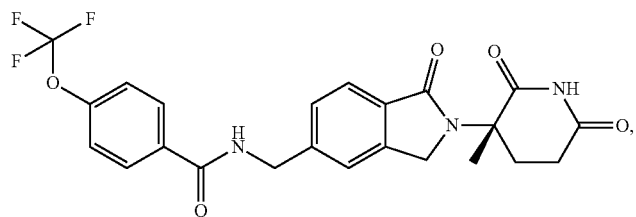 [SMILES: C[C@]1(N2Cc3cc(CNC(=O)c4ccc(OC(F)(F)F)cc4)ccc3C2=O)CCC(=O)NC1=O]
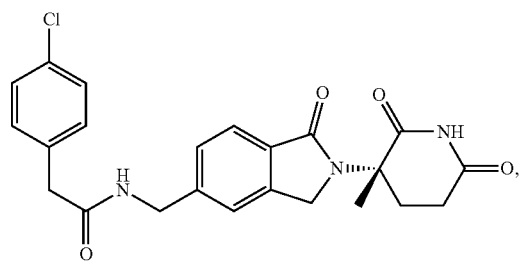 [SMILES: C[C@]1(N2Cc3cc(CNC(=O)Cc4ccc(Cl)cc4)ccc3C2=O)CCC(=O)NC1=O]
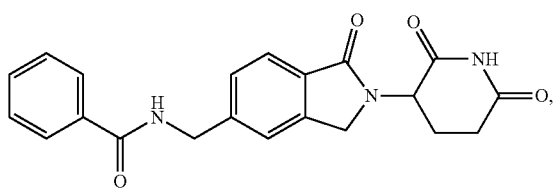 [SMILES: O=C1CCC(N2Cc3cc(CNC(=O)c4ccccc4)ccc3C2=O)C(=O)N1]
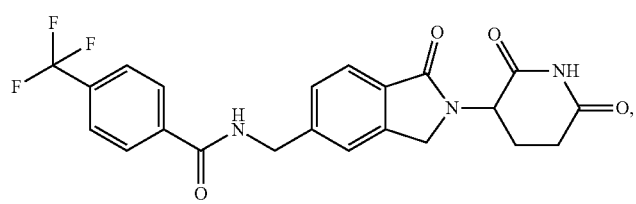 [SMILES: O=C1CCC(N2Cc3cc(CNC(=O)c4ccc(C(F)(F)F)cc4)ccc3C2=O)C(=O)N1]
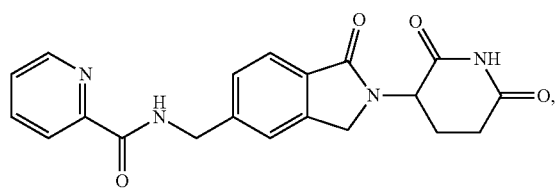 [SMILES: O=C1CCC(N2Cc3cc(CNC(=O)c4ccccn4)ccc3C2=O)C(=O)N1]

TABLE K-continued
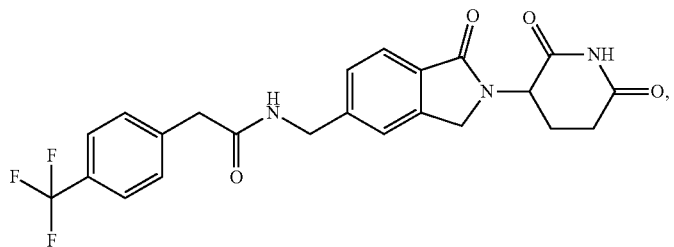 [SMILES: O=C(Cc1ccc(C(F)(F)F)cc1)NCc1ccc2c(c1)CN(C1CCC(=O)NC1=O)C2=O]
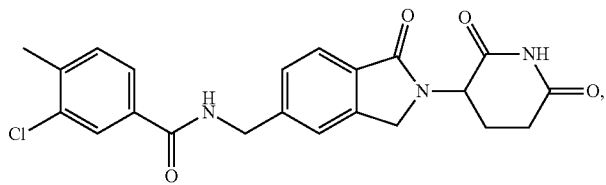 [SMILES: Cc1ccc(C(=O)NCc2ccc3c(c2)CN(C2CCC(=O)NC2=O)C3=O)cc1Cl]
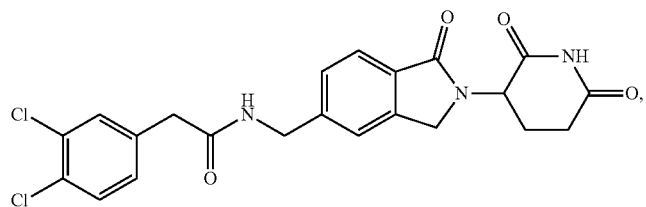 [SMILES: O=C(Cc1ccc(Cl)c(Cl)c1)NCc1ccc2c(c1)CN(C1CCC(=O)NC1=O)C2=O]
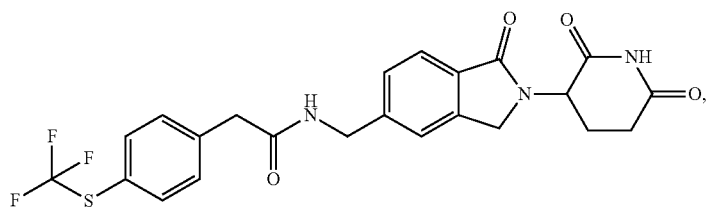 [SMILES: O=C(Cc1ccc(SC(F)(F)F)cc1)NCc1ccc2c(c1)CN(C1CCC(=O)NC1=O)C2=O]
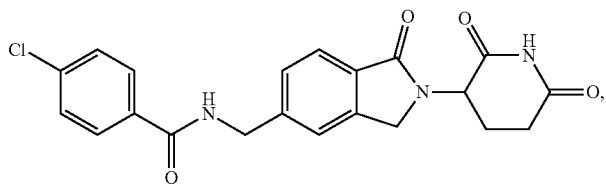 [SMILES: O=C1CCC(N2Cc3cc(CNC(=O)c4ccc(Cl)cc4)ccc3C2=O)C(=O)N1]
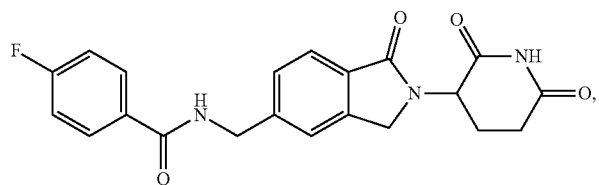 [SMILES: O=C1CCC(N2Cc3cc(CNC(=O)c4ccc(F)cc4)ccc3C2=O)C(=O)N1]
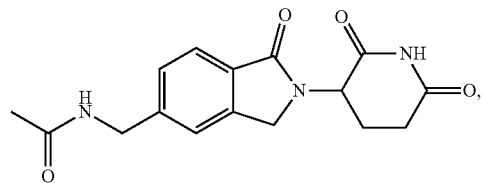 [SMILES: CC(=O)NCc1ccc2c(c1)CN(C1CCC(=O)NC1=O)C2=O]
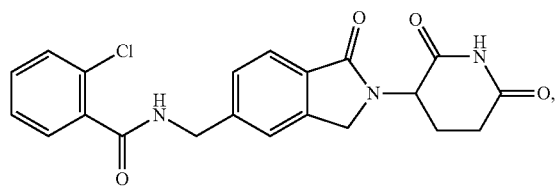 [SMILES: O=C1CCC(N2Cc3cc(CNC(=O)c4ccccc4Cl)ccc3C2=O)C(=O)N1]

TABLE K-continued
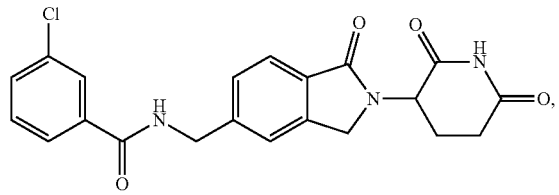 [SMILES: O=C1CCC(N2Cc3cc(CNC(=O)c4cccc(Cl)c4)ccc3C2=O)C(=O)N1]
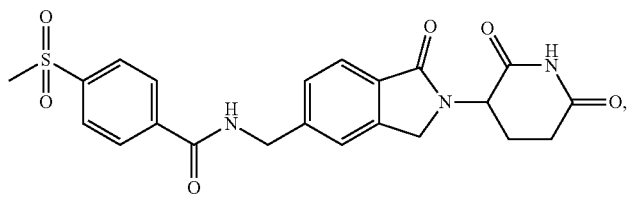 [SMILES: CS(=O)(=O)c1ccc(C(=O)NCc2ccc3c(c2)CN(C2CCC(=O)NC2=O)C3=O)cc1]
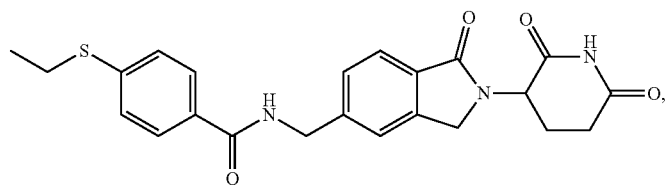 [SMILES: CCSc1ccc(C(=O)NCc2ccc3c(c2)CN(C2CCC(=O)NC2=O)C3=O)cc1]
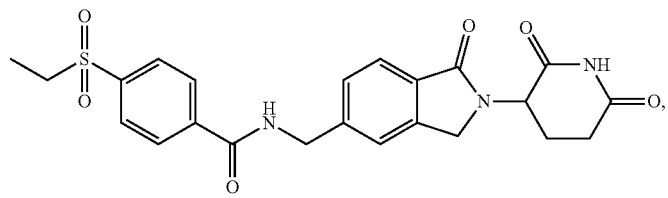 [SMILES: CCS(=O)(=O)c1ccc(C(=O)NCc2ccc3c(c2)CN(C2CCC(=O)NC2=O)C3=O)cc1]
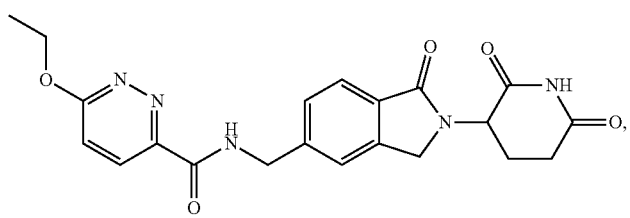 [SMILES: CCOc1ccc(C(=O)NCc2ccc3c(c2)CN(C2CCC(=O)NC2=O)C3=O)cn1]
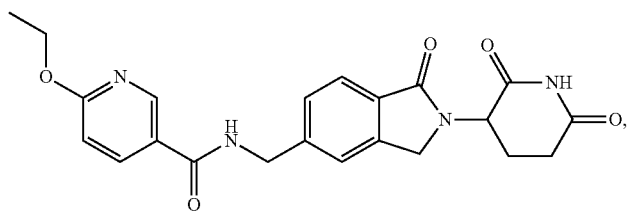
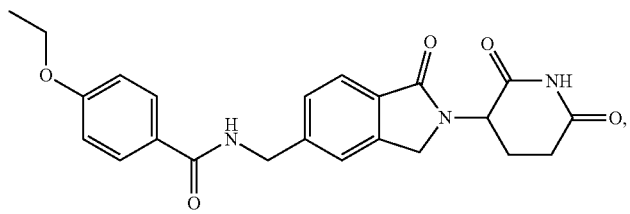 [SMILES: CCOc1ccc(C(=O)NCc2ccc3c(c2)CN(C2CCC(=O)NC2=O)C3=O)cc1]

TABLE K-continued
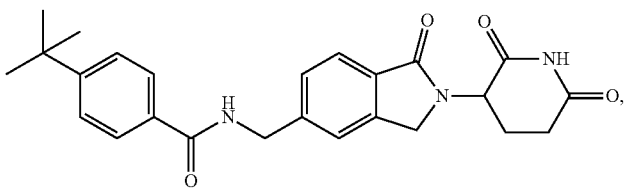 [SMILES: CC(C)(C)c1ccc(C(=O)NCc2ccc3c(c2)CN(C2CCC(=O)NC2=O)C3=O)cc1]
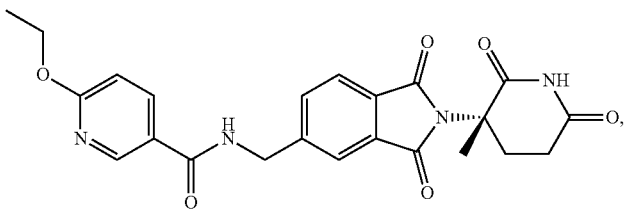 [SMILES: CCOc1ccc(C(=O)NCc2ccc3c(c2)C(=O)N([C@@]2(C)CCC(=O)NC2=O)C3=O)cn1]
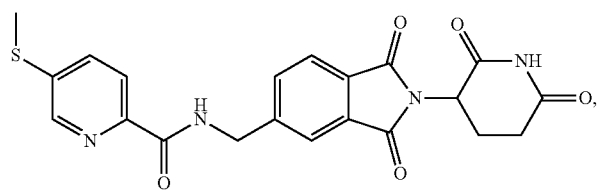 [SMILES: CSc1ccc(C(=O)NCc2ccc3c(c2)C(=O)N(C2CCC(=O)NC2=O)C3=O)nc1]
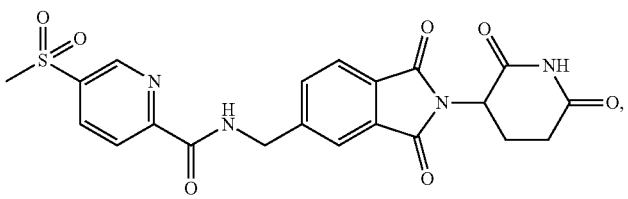 [SMILES: CS(=O)(=O)c1ccc(C(=O)NCc2ccc3c(c2)C(=O)N(C2CCC(=O)NC2=O)C3=O)nc1]
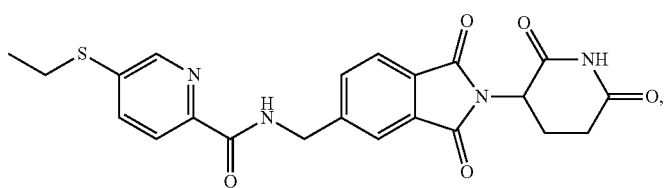 [SMILES: CCSc1ccc(C(=O)NCc2ccc3c(c2)C(=O)N(C2CCC(=O)NC2=O)C3=O)nc1]
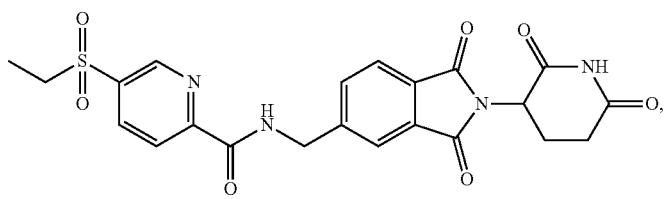 [SMILES: CCS(=O)(=O)c1ccc(C(=O)NCc2ccc3c(c2)C(=O)N(C2CCC(=O)NC2=O)C3=O)nc1]
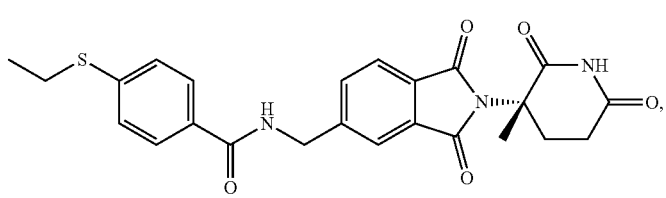 [SMILES: CCSc1ccc(C(=O)NCc2ccc3c(c2)C(=O)N([C@@]2(C)CCC(=O)NC2=O)C3=O)cc1]
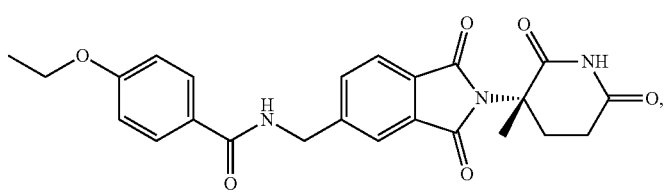

TABLE K-continued
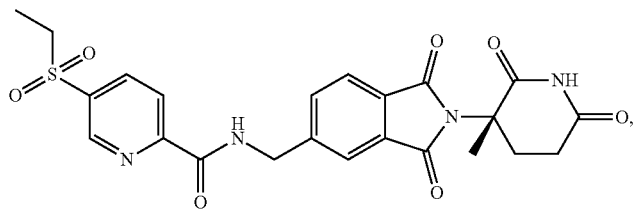 [SMILES: CCS(=O)(=O)c1ccc(C(=O)NCc2ccc3c(c2)C(=O)N([C@@]2(C)CCC(=O)NC2=O)C3=O)nc1]
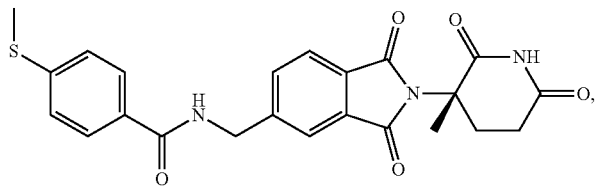 [SMILES: CSc1ccc(C(=O)NCc2ccc3c(c2)C(=O)N([C@@]2(C)CCC(=O)NC2=O)C3=O)cc1]
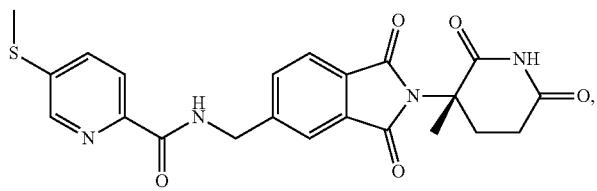 [SMILES: CSc1ccc(C(=O)NCc2ccc3c(c2)C(=O)N([C@@]2(C)CCC(=O)NC2=O)C3=O)nc1]
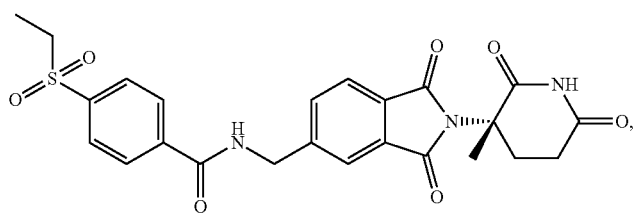 [SMILES: CCS(=O)(=O)c1ccc(C(=O)NCc2ccc3c(c2)C(=O)N([C@@]2(C)CCC(=O)NC2=O)C3=O)cc1]
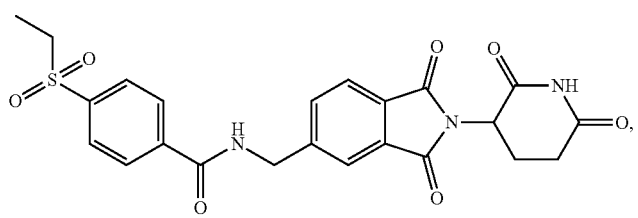 [SMILES: CCS(=O)(=O)c1ccc(C(=O)NCc2ccc3c(c2)C(=O)N(C2CCC(=O)NC2=O)C3=O)cc1]
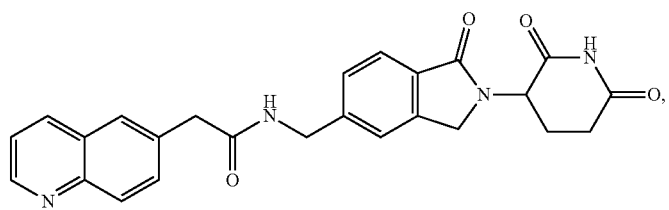 [SMILES: O=C(Cc1ccc2ncccc2c1)NCc1ccc2c(c1)CN(C1CCC(=O)NC1=O)C2=O]
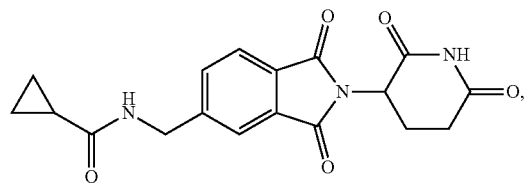 [SMILES: O=C1CCC(N2C(=O)c3ccc(CNC(=O)C4CC4)cc3C2=O)C(=O)N1]

TABLE K-continued
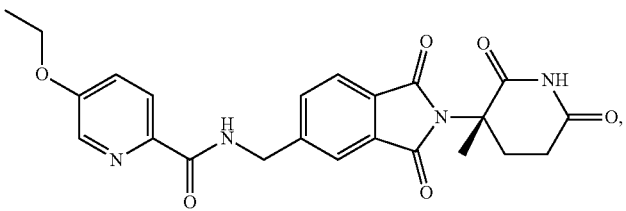
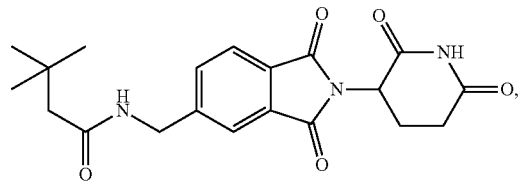 [SMILES: CC(C)(C)CC(=O)NCc1ccc2c(c1)C(=O)N(C1CCC(=O)NC1=O)C2=O]
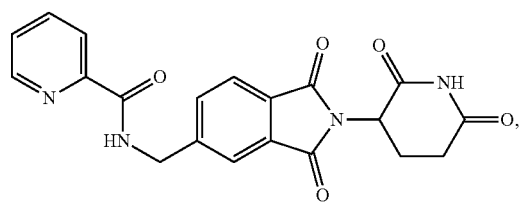 [SMILES: O=C1CCC(N2C(=O)c3ccc(CNC(=O)c4ccccn4)cc3C2=O)C(=O)N1]
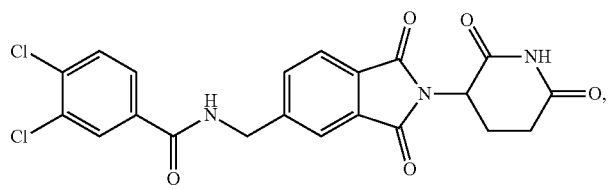 [SMILES: O=C1CCC(N2C(=O)c3ccc(CNC(=O)c4ccc(Cl)c(Cl)c4)cc3C2=O)C(=O)N1]
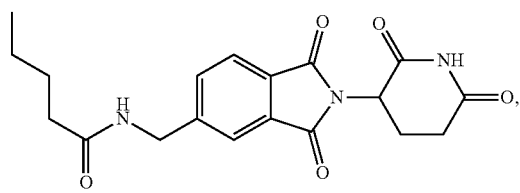 [SMILES: CCCCC(=O)NCc1ccc2c(c1)C(=O)N(C1CCC(=O)NC1=O)C2=O]
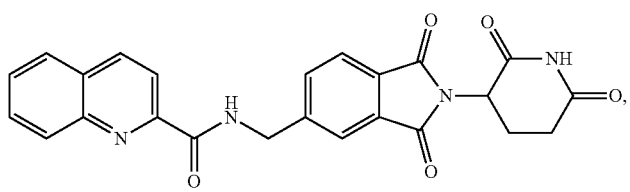 [SMILES: O=C1CCC(N2C(=O)c3ccc(CNC(=O)c4ccc5ccccc5n4)cc3C2=O)C(=O)N1]
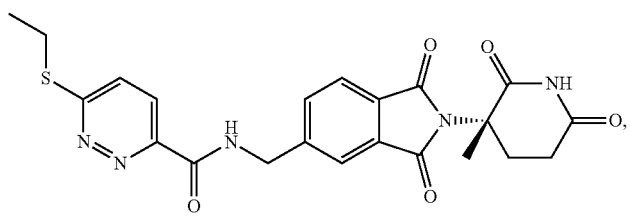
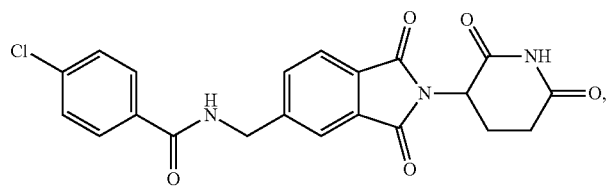 [SMILES: O=C1CCC(N2C(=O)c3ccc(CNC(=O)c4ccc(Cl)cc4)cc3C2=O)C(=O)N1]

TABLE K-continued
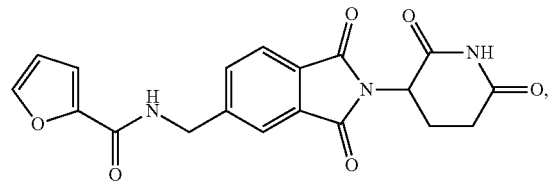
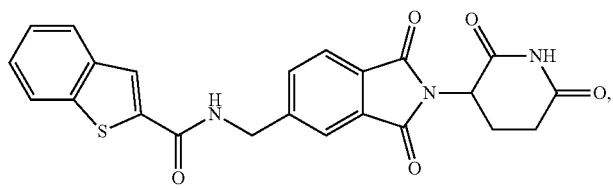 [SMILES: O=C1CCC(N2C(=O)c3ccc(CNC(=O)c4cc5ccccc5s4)cc3C2=O)C(=O)N1]
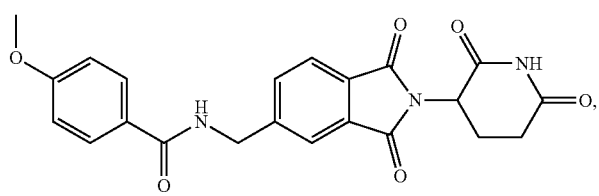 [SMILES: COc1ccc(C(=O)NCc2ccc3c(c2)C(=O)N(C2CCC(=O)NC2=O)C3=O)cc1]
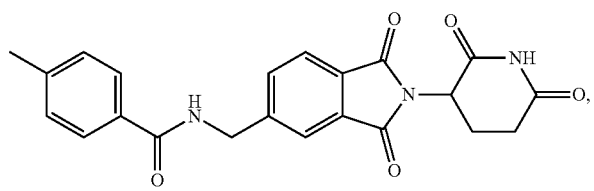 [SMILES: Cc1ccc(C(=O)NCc2ccc3c(c2)C(=O)N(C2CCC(=O)NC2=O)C3=O)cc1]
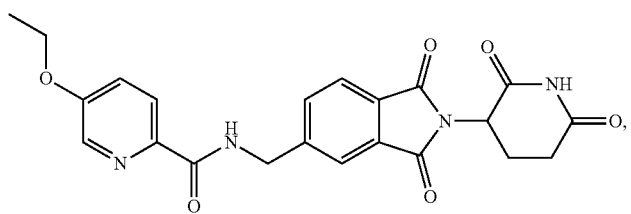 [SMILES: CCOc1ccc(C(=O)NCc2ccc3c(c2)C(=O)N(C2CCC(=O)NC2=O)C3=O)nc1]
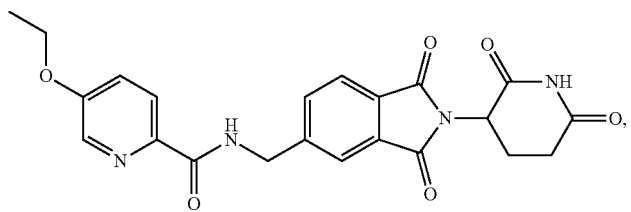
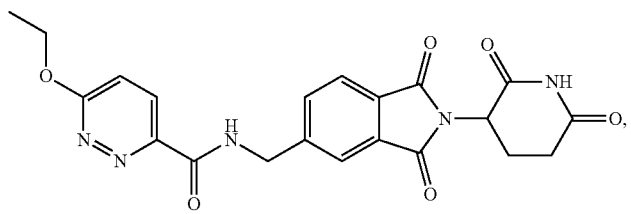 [SMILES: CCOc1ccc(C(=O)NCc2ccc3c(c2)C(=O)N(C2CCC(=O)NC2=O)C3=O)nc1]

TABLE K-continued
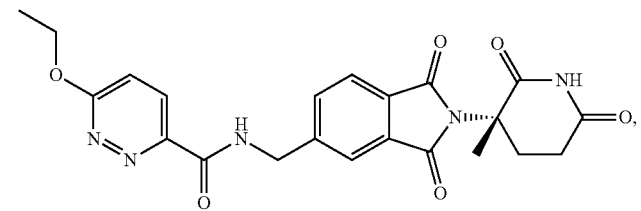 [SMILES: CCOc1ccc(C(=O)NCc2ccc3c(c2)C(=O)N([C@@]2(C)CCC(=O)NC2=O)C3=O)nn1]
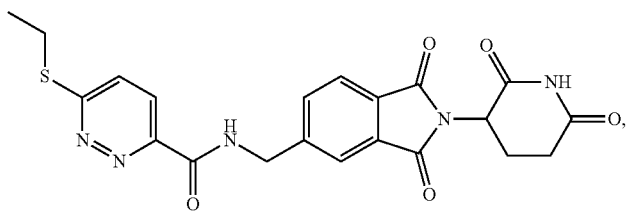
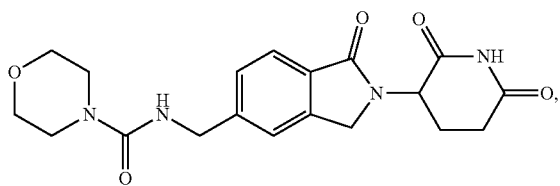 [SMILES: O=C1CCC(N2Cc3cc(CNC(=O)N4CCOCC4)ccc3C2=O)C(=O)N1]
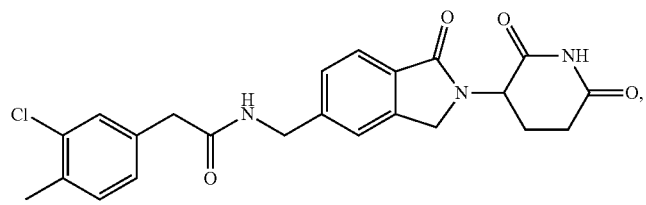 [SMILES: Cc1ccc(CC(=O)NCc2ccc3c(c2)CN(C2CCC(=O)NC2=O)C3=O)cc1Cl]
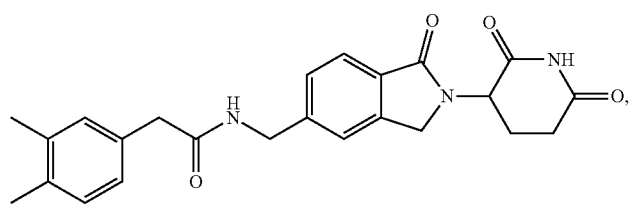 [SMILES: Cc1ccc(CC(=O)NCc2ccc3c(c2)CN(C2CCC(=O)NC2=O)C3=O)cc1C]
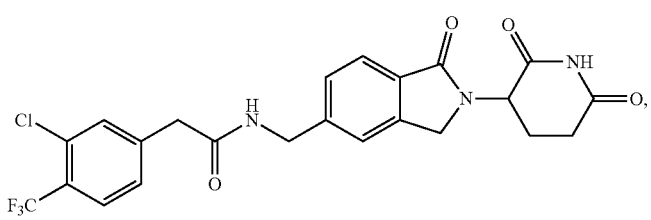 [SMILES: O=C(Cc1ccc(C(F)(F)F)c(Cl)c1)NCc1ccc2c(c1)CN(C1CCC(=O)NC1=O)C2=O]
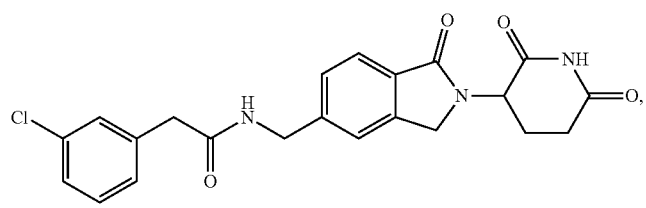 [SMILES: O=C(Cc1cccc(Cl)c1)NCc1ccc2c(c1)CN(C1CCC(=O)NC1=O)C2=O]

TABLE K-continued
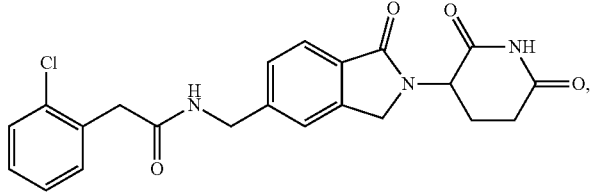
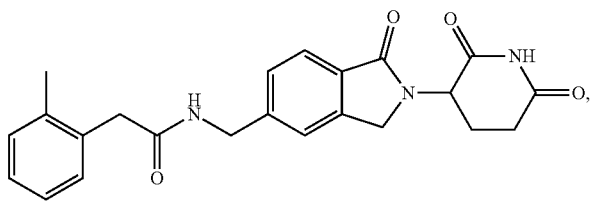 [SMILES: Cc1ccccc1CC(=O)NCc1ccc2c(c1)CN(C1CCC(=O)NC1=O)C2=O]
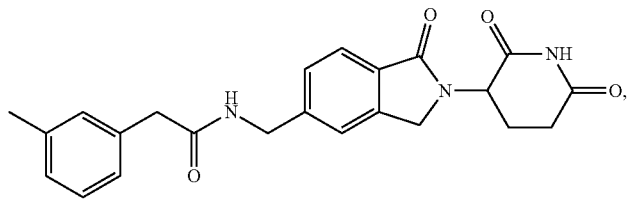 [SMILES: Cc1cccc(CC(=O)NCc2ccc3c(c2)CN(C2CCC(=O)NC2=O)C3=O)c1]
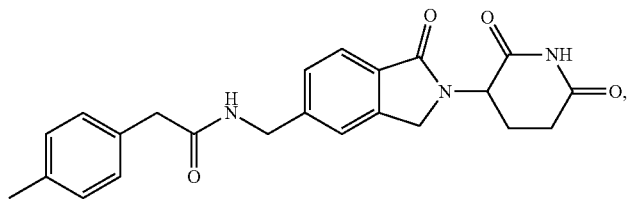 [SMILES: Cc1ccc(CC(=O)NCc2ccc3c(c2)CN(C2CCC(=O)NC2=O)C3=O)cc1]
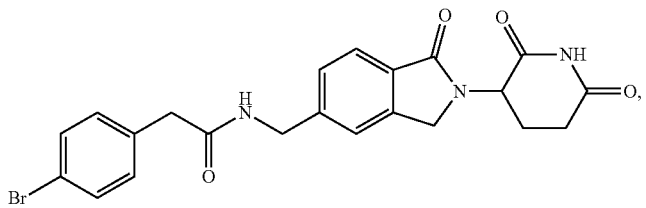
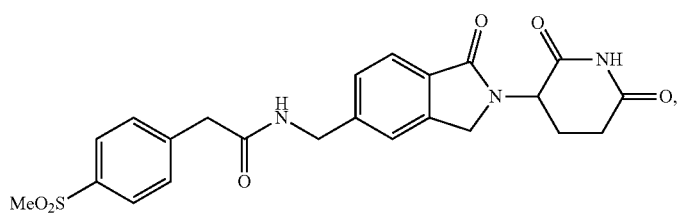 [SMILES: CS(=O)(=O)c1ccc(CC(=O)NCc2ccc3c(c2)CN(C2CCC(=O)NC2=O)C3=O)cc1]
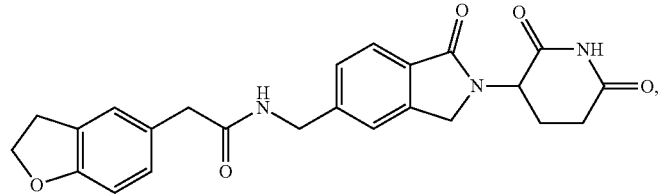 [SMILES: O=C(Cc1ccc2c(c1)CCO2)NCc1ccc2c(c1)CN(C1CCC(=O)NC1=O)C2=O]

TABLE K-continued
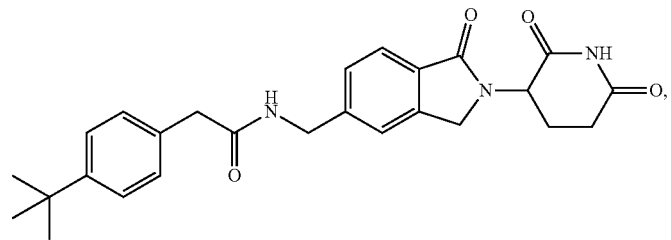 [SMILES: CC(C)(C)c1ccc(CC(=O)NCc2ccc3c(c2)CN(C2CCC(=O)NC2=O)C3=O)cc1]
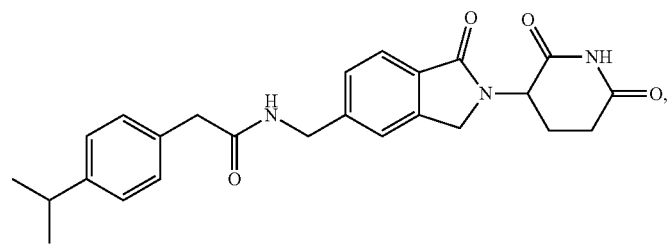 [SMILES: CC(C)c1ccc(CC(=O)NCc2ccc3c(c2)CN(C2CCC(=O)NC2=O)C3=O)cc1]
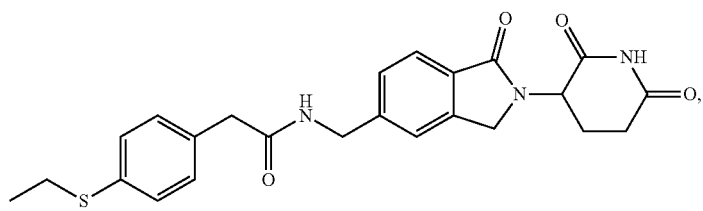 [SMILES: CCSc1ccc(CC(=O)NCc2ccc3c(c2)CN(C2CCC(=O)NC2=O)C3=O)cc1]
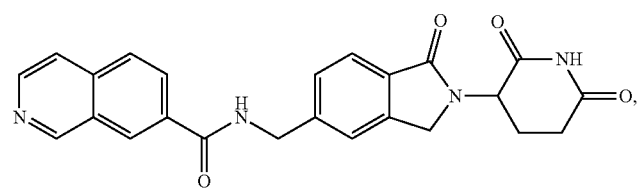 [SMILES: O=C1CCC(N2Cc3cc(CNC(=O)c4ccc5ccncc5c4)ccc3C2=O)C(=O)N1]
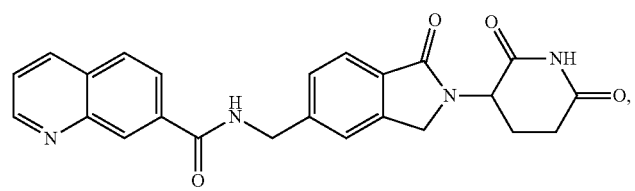 [SMILES: O=C1CCC(N2Cc3cc(CNC(=O)c4ccc5cccnc5c4)ccc3C2=O)C(=O)N1]
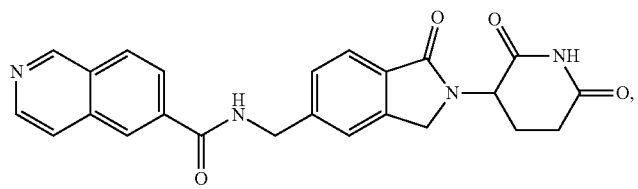 [SMILES: O=C1CCC(N2Cc3cc(CNC(=O)c4ccc5cnccc5c4)ccc3C2=O)C(=O)N1]
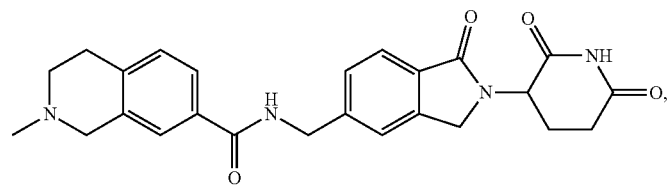 [SMILES: CN1CCc2ccc(C(=O)NCc3ccc4c(c3)CN(C3CCC(=O)NC3=O)C4=O)cc2C1]

TABLE K-continued
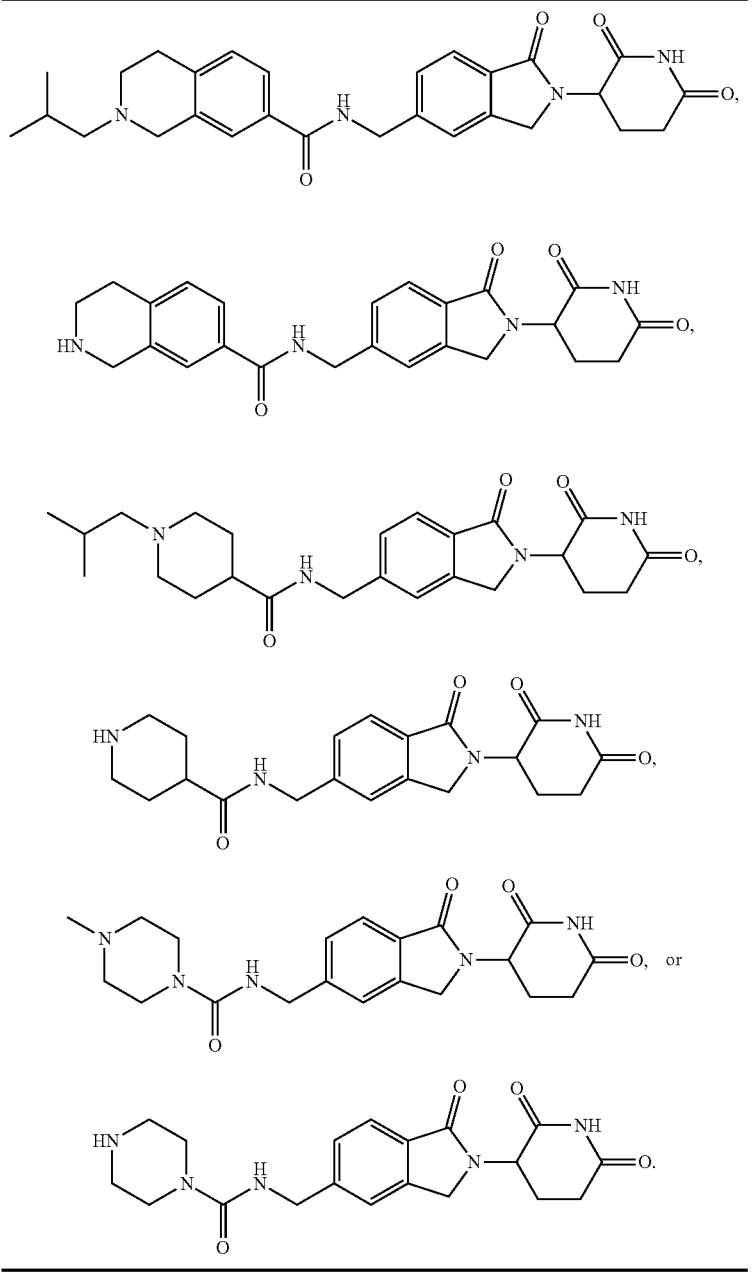
In one embodiment, the immunomodulatory compound is:
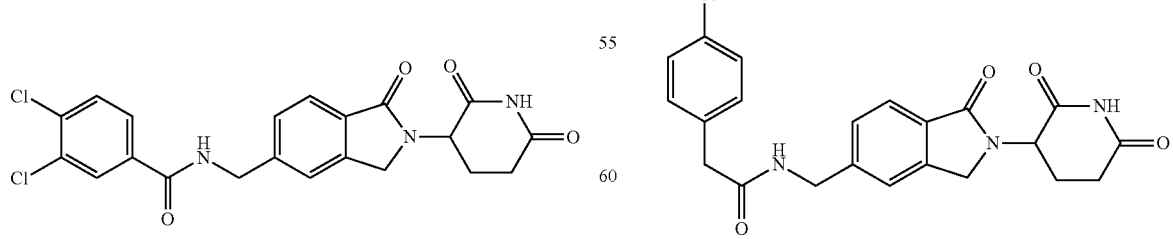
or a pharmaceutically acceptable salt, solvate, prodrug, or stereoisomer thereof.
In one embodiment, the immunomodulatory compound is:
or a pharmaceutically acceptable salt, solvate, prodrug, or stereoisomer thereof.

Still other representative compounds of formula:

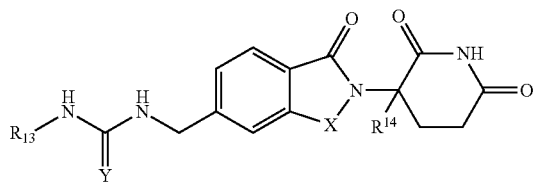

and pharmaceutically acceptable salts, solvates, stereoisomers, and prodrugs thereof,
wherein:
X is $CH_2$ or C=O;
Y is O or S;
$R^{13}$ is: $(C_1-C_{10})$alkyl; $(C_1-C_{10})$alkoxy; 5 to 10 membered aryl or heteroaryl, optionally substituted with one or more of: halogen; cyano; $(C_1-C_6)$alkylenedioxy; $(C_1-C_6)$alkoxy, itself optionally substituted with one or more halogen; $(C_1-C_6)$alkyl, itself optionally substituted with one or more halogen; or $(C_1-C_6)$alkylthio, itself optionally substituted with one or more halogen; and
$R^{14}$ is H or $(C_1-C_6)$alkyl.

In one embodiment, X is $CH_2$. In another embodiment, X is C=O.

In one embodiment, Y is O. In another embodiment, Y is S.

In one embodiment, $R^{13}$ is $(C_1-C_{10})$alkyl. In certain specific embodiments, $R^{13}$ is $(C_1-C_6)$alkyl. In certain specific embodiments, $R^{13}$ is propyl, butyl, pentyl, or hexyl.

In one embodiment, $R^{13}$ is $(C_1-C_{10})$alkoxy.

In one embodiment, $R^{13}$ is 5 to 10 membered aryl or heteroaryl, optionally substituted with cyano. In certain specific embodiments, $R^{13}$ is phenyl, optionally substituted with cyano.

In one embodiment, $R^{13}$ is 5 to 10 membered aryl or heteroaryl, optionally substituted with $(C_1-C_6)$alkylenedioxy. In certain specific embodiments, $R^{13}$ is phenyl, optionally substituted with methylenedioxy.

In one embodiment, $R^{13}$ is 5 to 10 membered aryl or heteroaryl, optionally substituted with one or more halogen. In certain specific embodiments, $R^{13}$ is phenyl, optionally substituted with one or more halogen.

In another embodiment, $R^{13}$ is 5 to 10 membered aryl or heteroaryl, optionally substituted with $(C_1-C_6)$alkyl or $(C_1-C_6)$alkoxy, themselves optionally substituted with one or more halogens. In certain specific embodiments, $R^{13}$ is phenyl, optionally substituted with methyl or methoxy, themselves optionally substituted with 1, 2, or 3 halogens.

In another embodiment, $R^{13}$ is 5 to 10 membered aryl or heteroaryl, optionally substituted with $(C_1-C_6)$alkylthio, itself optionally substituted with one or more halogens.

In another embodiment, $R^{14}$ is H. In another embodiment, $R^{14}$ is $(C_1-C_6)$alkyl. In certain specific embodiments, $R^{14}$ is methyl.

All of the combinations of the above embodiments are encompassed by this invention.

Examples include, but are not limited to, those listed in Table L, below, or a pharmaceutically acceptable salt, solvate (e.g., hydrate), prodrug or stereoisomer thereof:

TABLE L

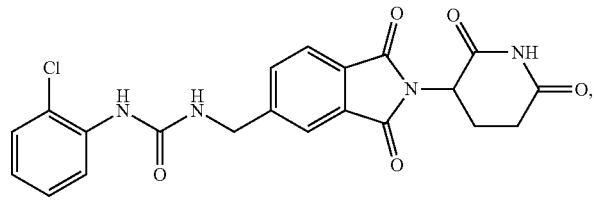 [SMILES: O=C1CCC(N2C(=O)c3ccc(CNC(=O)Nc4ccccc4Cl)cc3C2=O)C(=O)N1]

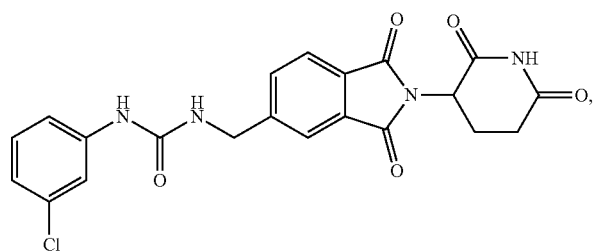 [SMILES: O=C1CCC(N2C(=O)c3ccc(CNC(=O)Nc4cccc(Cl)c4)cc3C2=O)C(=O)N1]

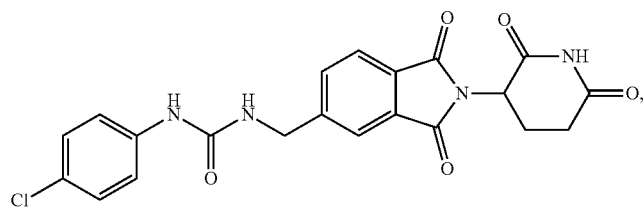

TABLE L-continued
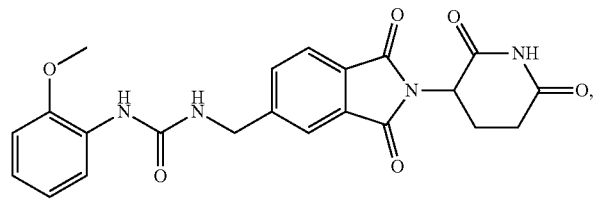 [SMILES: COc1ccccc1NC(=O)NCc1ccc2c(c1)C(=O)N(C1CCC(=O)NC1=O)C2=O]
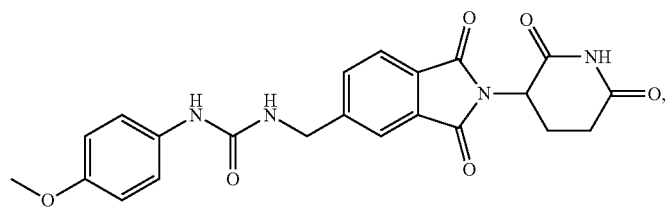 [SMILES: COc1ccc(NC(=O)NCc2ccc3c(c2)C(=O)N(C2CCC(=O)NC2=O)C3=O)cc1]
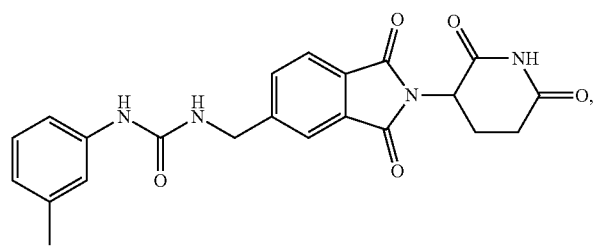 [SMILES: Cc1cccc(NC(=O)NCc2ccc3c(c2)C(=O)N(C2CCC(=O)NC2=O)C3=O)c1]
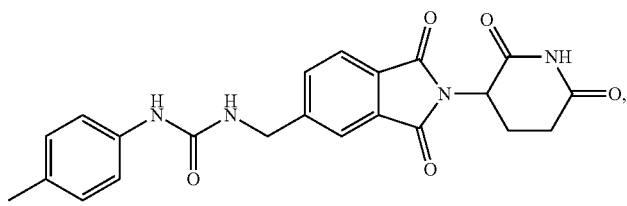 [SMILES: Cc1ccc(NC(=O)NCc2ccc3c(c2)C(=O)N(C2CCC(=O)NC2=O)C3=O)cc1]
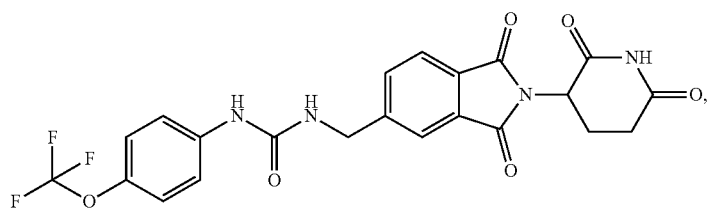 [SMILES: O=C1CCC(N2C(=O)c3ccc(CNC(=O)Nc4ccc(OC(F)(F)F)cc4)cc3C2=O)C(=O)N1]
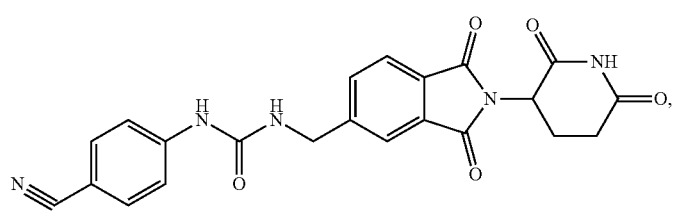 [SMILES: N#Cc1ccc(NC(=O)NCc2ccc3c(c2)C(=O)N(C2CCC(=O)NC2=O)C3=O)cc1]
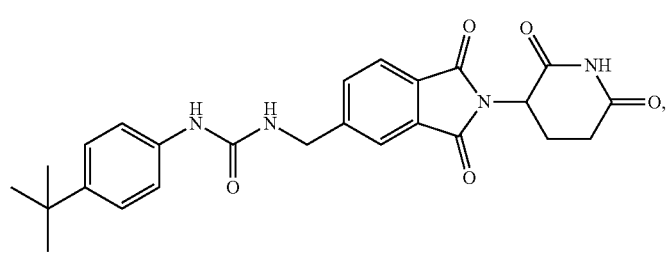 [SMILES: CC(C)(C)c1ccc(NC(=O)NCc2ccc3c(c2)C(=O)N(C2CCC(=O)NC2=O)C3=O)cc1]

TABLE L-continued
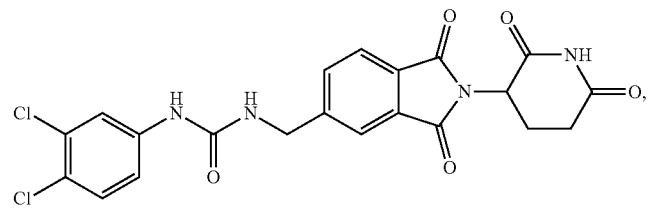 [SMILES: O=C1CCC(N2C(=O)c3ccc(CNC(=O)Nc4ccc(Cl)c(Cl)c4)cc3C2=O)C(=O)N1]
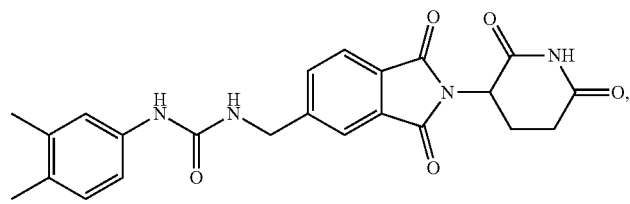 [SMILES: Cc1ccc(NC(=O)NCc2ccc3c(c2)C(=O)N(C2CCC(=O)NC2=O)C3=O)cc1C]
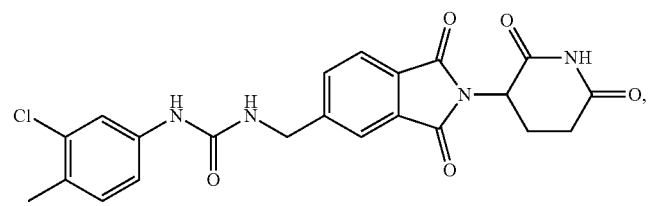 [SMILES: Cc1ccc(NC(=O)NCc2ccc3c(c2)C(=O)N(C2CCC(=O)NC2=O)C3=O)cc1Cl]
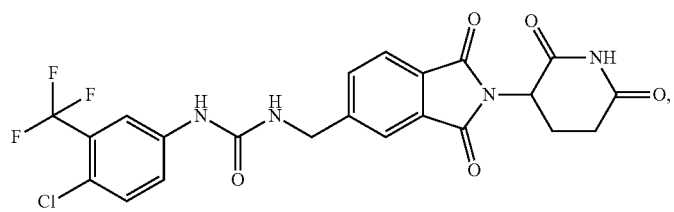 [SMILES: O=C1CCC(N2C(=O)c3ccc(CNC(=O)Nc4ccc(Cl)c(C(F)(F)F)c4)cc3C2=O)C(=O)N1]
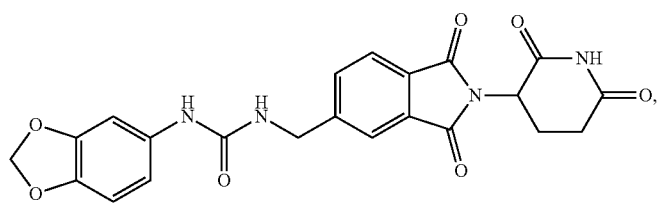 [SMILES: O=C1CCC(N2C(=O)c3ccc(CNC(=O)Nc4ccc5c(c4)OCO5)cc3C2=O)C(=O)N1]
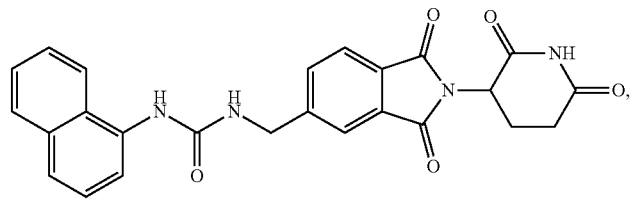 [SMILES: O=C1CCC(N2C(=O)c3ccc(CNC(=O)Nc4cccc5ccccc45)cc3C2=O)C(=O)N1]
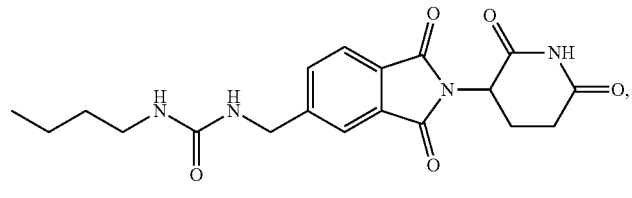 [SMILES: CCCCNC(=O)NCc1ccc2c(c1)C(=O)N(C1CCC(=O)NC1=O)C2=O]
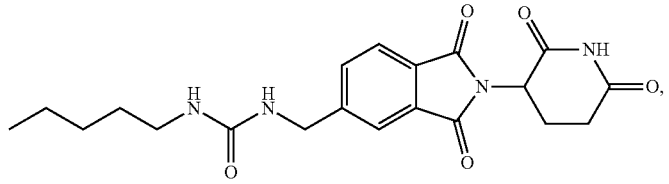 [SMILES: CCCCCNC(=O)NCc1ccc2c(c1)C(=O)N(C1CCC(=O)NC1=O)C2=O]

TABLE L-continued
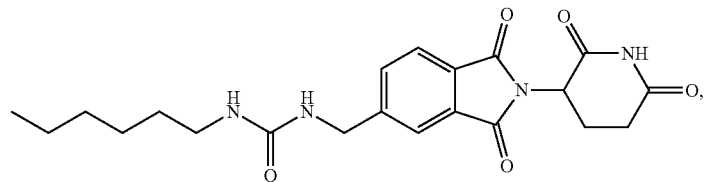 [SMILES: CCCCCCNC(=O)NCc1ccc2c(c1)C(=O)N(C1CCC(=O)NC1=O)C2=O]
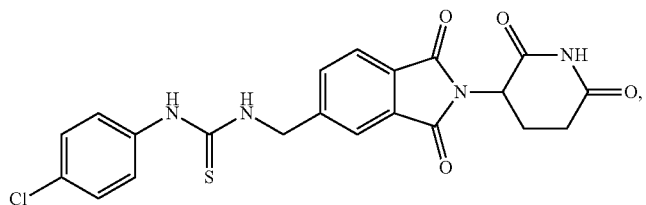 [SMILES: O=C1CCC(N2C(=O)c3ccc(CNC(=S)Nc4ccc(Cl)cc4)cc3C2=O)C(=O)N1]
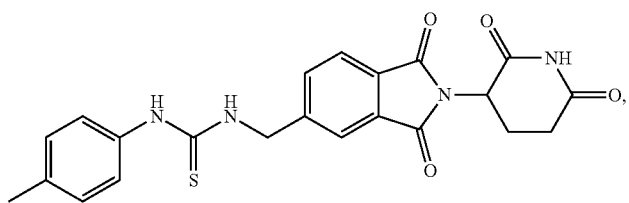
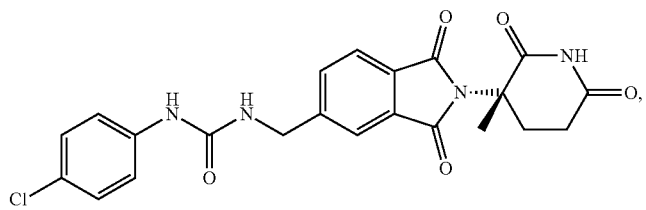
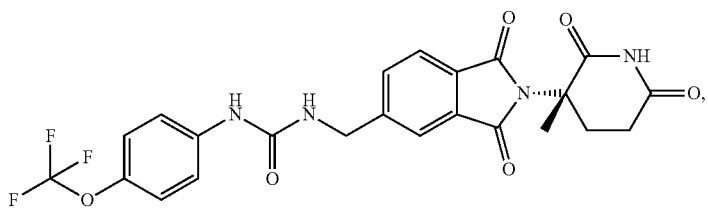
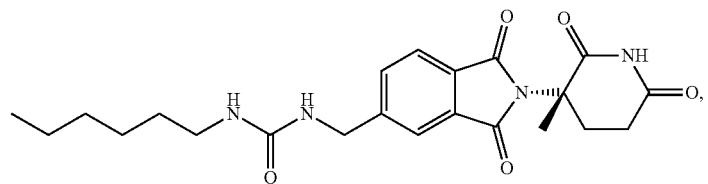
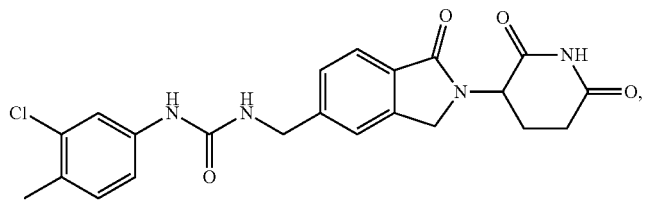

TABLE L-continued
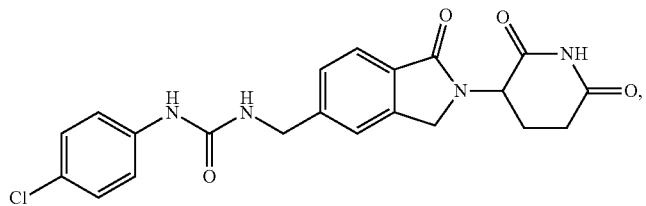 [SMILES: O=C1CCC(N2Cc3cc(CNC(=O)Nc4ccc(Cl)cc4)ccc3C2=O)C(=O)N1]
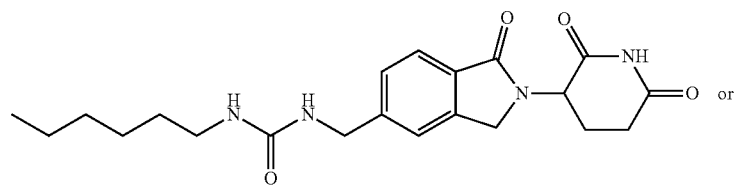 [SMILES: CCCCCCNC(=O)NCc1ccc2c(c1)CN(C1CCC(=O)NC1=O)C2=O]
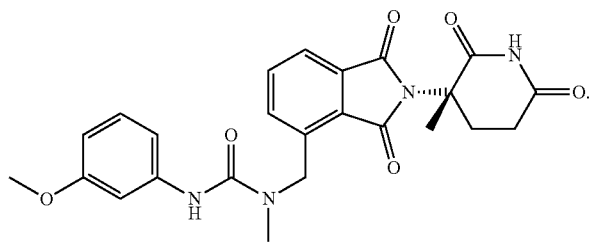
Other examples include, but are not limited to, those listed in Table M, below, or a pharmaceutically acceptable salt, solvate (e.g., hydrate), prodrug or stereoisomer thereof:
TABLE M
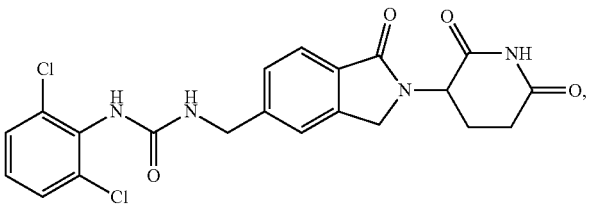 [SMILES: O=C1CCC(N2Cc3cc(CNC(=O)Nc4c(Cl)cccc4Cl)ccc3C2=O)C(=O)N1]
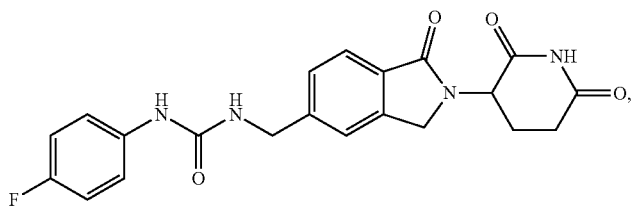 [SMILES: O=C1CCC(N2Cc3cc(CNC(=O)Nc4ccc(F)cc4)ccc3C2=O)C(=O)N1]
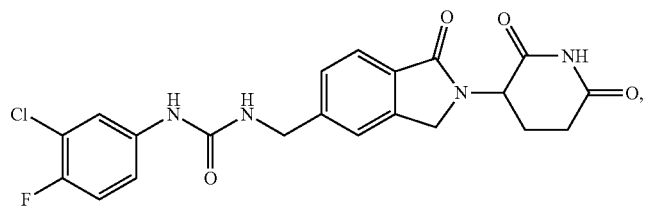 [SMILES: O=C1CCC(N2Cc3cc(CNC(=O)Nc4ccc(F)c(Cl)c4)ccc3C2=O)C(=O)N1]

TABLE M-continued
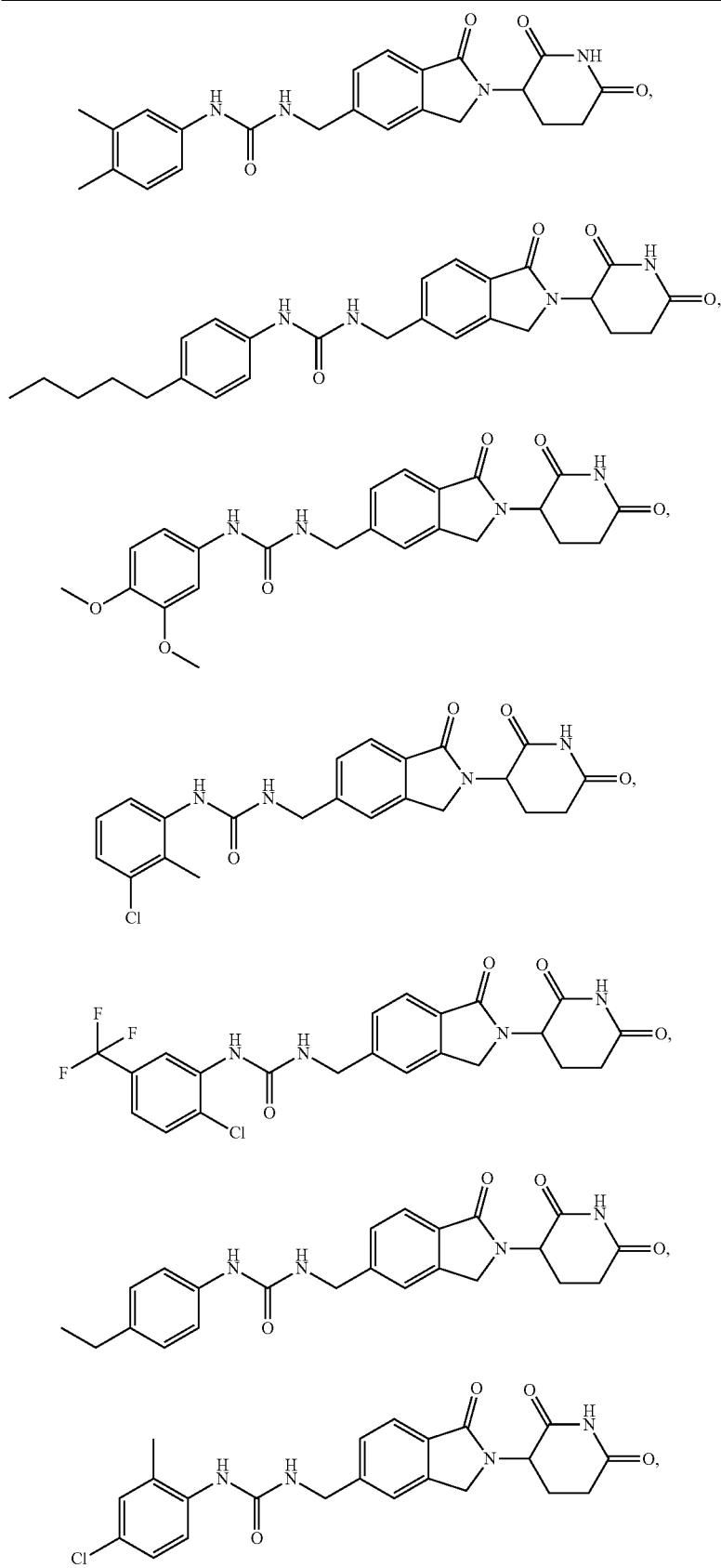

TABLE M-continued
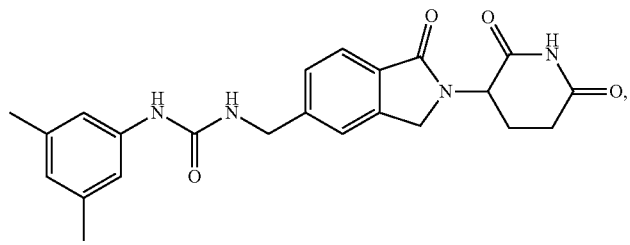 [SMILES: Cc1cc(C)cc(NC(=O)NCc2ccc3c(c2)CN(C2CCC(=O)NC2=O)C3=O)c1]
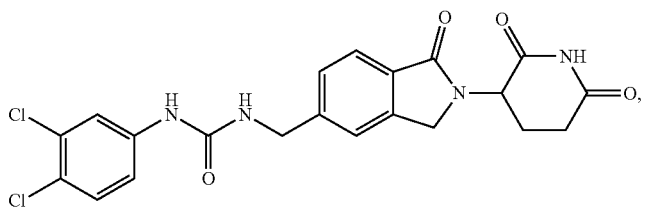 [SMILES: O=C1CCC(N2Cc3cc(CNC(=O)Nc4ccc(Cl)c(Cl)c4)ccc3C2=O)C(=O)N1]
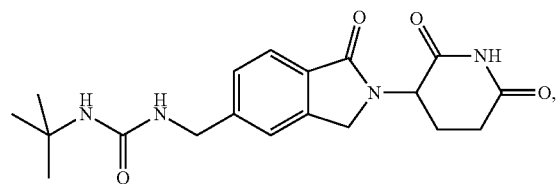 [SMILES: CC(C)(C)NC(=O)NCc1ccc2c(c1)CN(C1CCC(=O)NC1=O)C2=O]
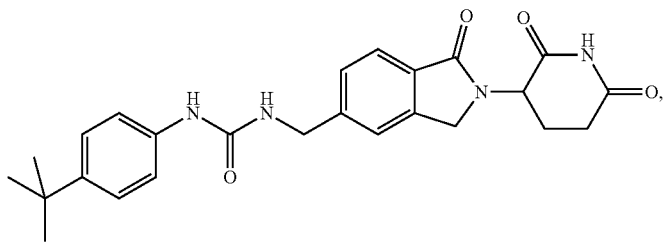 [SMILES: CC(C)(C)c1ccc(NC(=O)NCc2ccc3c(c2)CN(C2CCC(=O)NC2=O)C3=O)cc1]
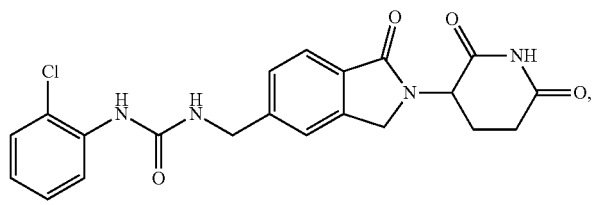 [SMILES: O=C1CCC(N2Cc3cc(CNC(=O)Nc4ccccc4Cl)ccc3C2=O)C(=O)N1]
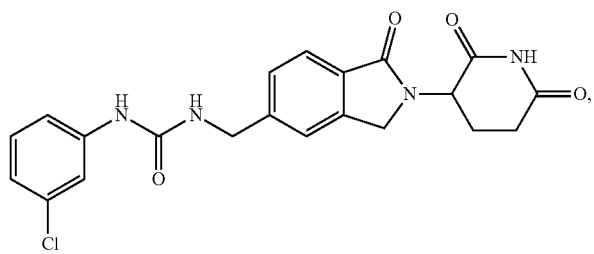 [SMILES: O=C1CCC(N2Cc3cc(CNC(=O)Nc4cccc(Cl)c4)ccc3C2=O)C(=O)N1]
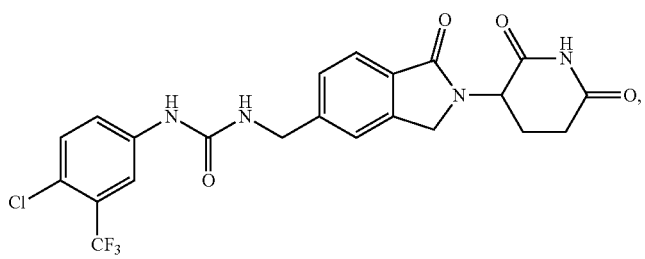 [SMILES: O=C1CCC(N2Cc3cc(CNC(=O)Nc4ccc(Cl)c(C(F)(F)F)c4)ccc3C2=O)C(=O)N1]

TABLE M-continued
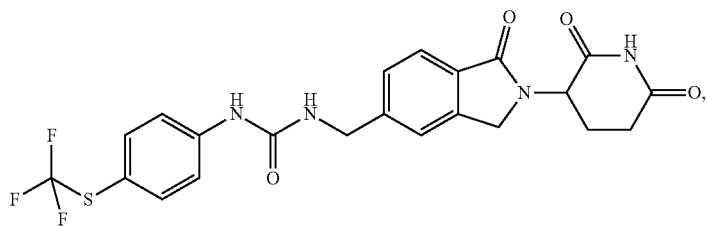 [SMILES: O=C1CCC(N2Cc3cc(CNC(=O)Nc4ccc(SC(F)(F)F)cc4)ccc3C2=O)C(=O)N1]
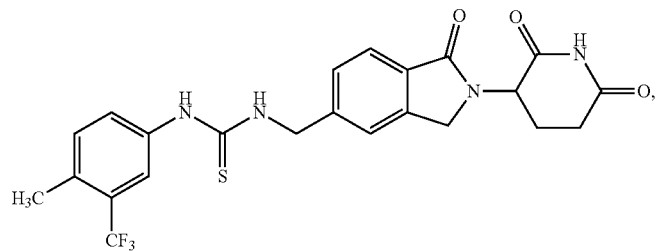 [SMILES: Cc1ccc(NC(=S)NCc2ccc3c(c2)CN(C2CCC(=O)NC2=O)C3=O)cc1C(F)(F)F]
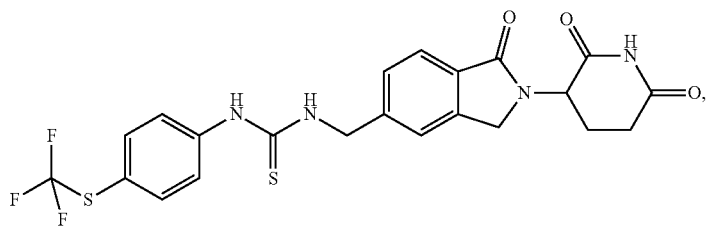 [SMILES: O=C1CCC(N2Cc3cc(CNC(=S)Nc4ccc(SC(F)(F)F)cc4)ccc3C2=O)C(=O)N1]
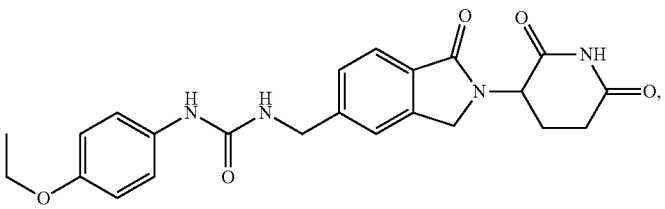 [SMILES: CCOc1ccc(NC(=O)NCc2ccc3c(c2)CN(C2CCC(=O)NC2=O)C3=O)cc1]
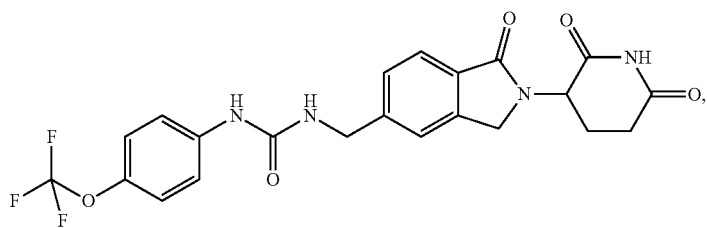 [SMILES: O=C1CCC(N2Cc3cc(CNC(=O)Nc4ccc(OC(F)(F)F)cc4)ccc3C2=O)C(=O)N1]
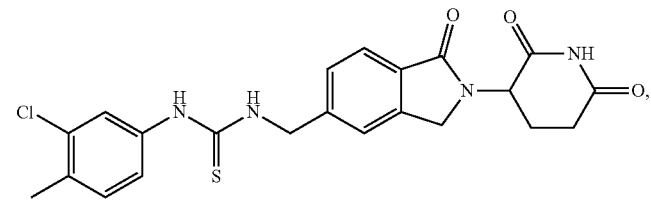 [SMILES: Cc1ccc(NC(=S)NCc2ccc3c(c2)CN(C2CCC(=O)NC2=O)C3=O)cc1Cl]
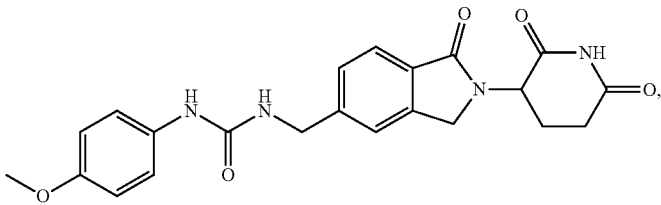 [SMILES: COc1ccc(NC(=O)NCc2ccc3c(c2)CN(C2CCC(=O)NC2=O)C3=O)cc1]

TABLE M-continued
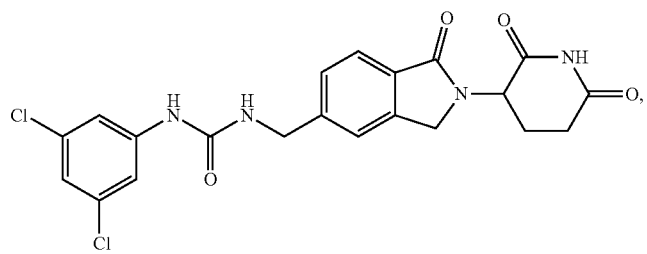 [SMILES: O=C1CCC(N2Cc3cc(CNC(=O)Nc4cc(Cl)cc(Cl)c4)ccc3C2=O)C(=O)N1]
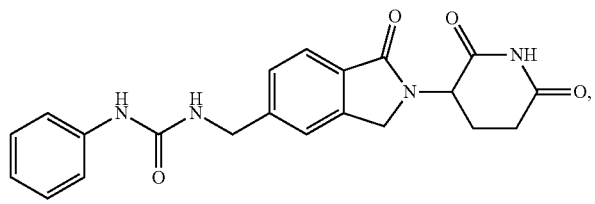 [SMILES: O=C1CCC(N2Cc3cc(CNC(=O)Nc4ccccc4)ccc3C2=O)C(=O)N1]
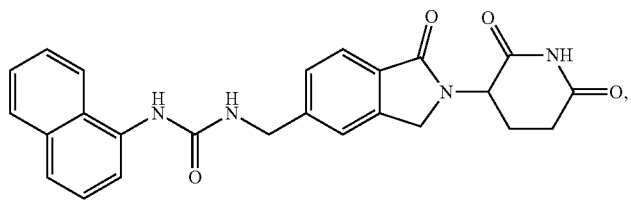 [SMILES: O=C1CCC(N2Cc3cc(CNC(=O)Nc4cccc5ccccc45)ccc3C2=O)C(=O)N1]
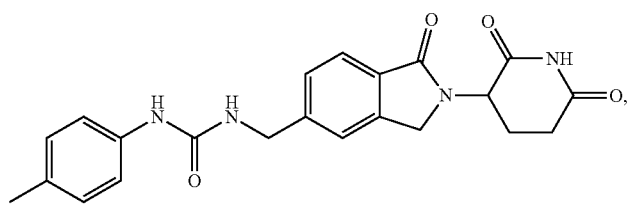 [SMILES: Cc1ccc(NC(=O)NCc2ccc3c(c2)CN(C2CCC(=O)NC2=O)C3=O)cc1]
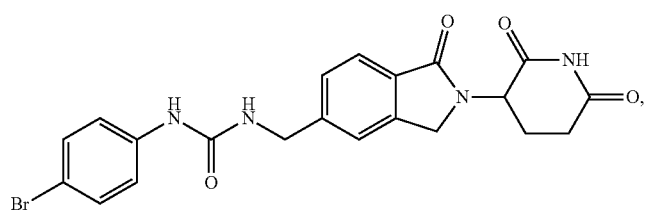
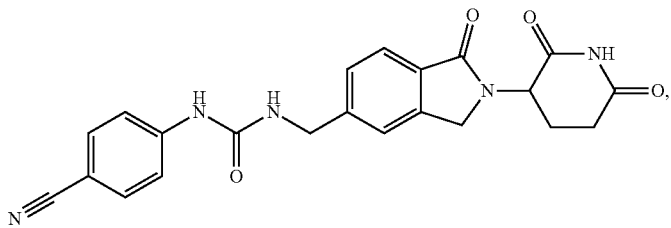 [SMILES: N#Cc1ccc(NC(=O)NCc2ccc3c(c2)CN(C2CCC(=O)NC2=O)C3=O)cc1]
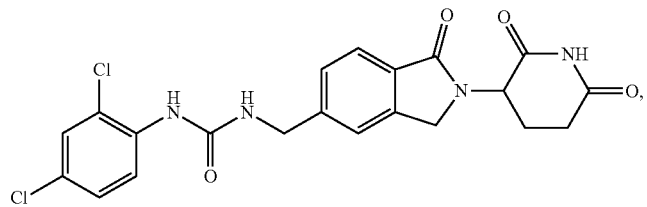 [SMILES: O=C1CCC(N2Cc3cc(CNC(=O)Nc4ccc(Cl)cc4Cl)ccc3C2=O)C(=O)N1]

TABLE M-continued
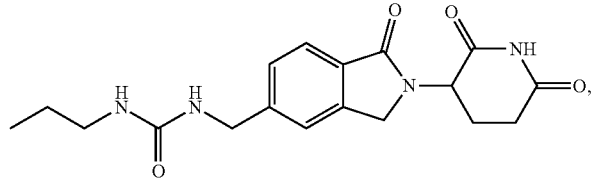 [SMILES: CCCNC(=O)NCc1ccc2c(c1)CN(C1CCC(=O)NC1=O)C2=O]
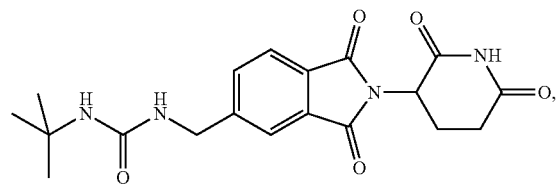 [SMILES: CC(C)(C)NC(=O)NCc1ccc2c(c1)C(=O)N(C1CCC(=O)NC1=O)C2=O]
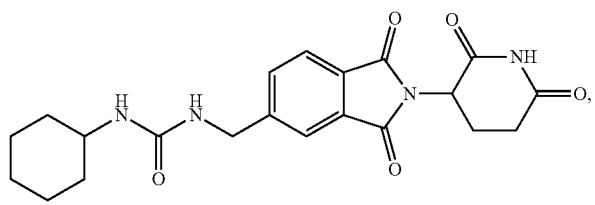 [SMILES: O=C1CCC(N2C(=O)c3ccc(CNC(=O)NC4CCCCC4)cc3C2=O)C(=O)N1]
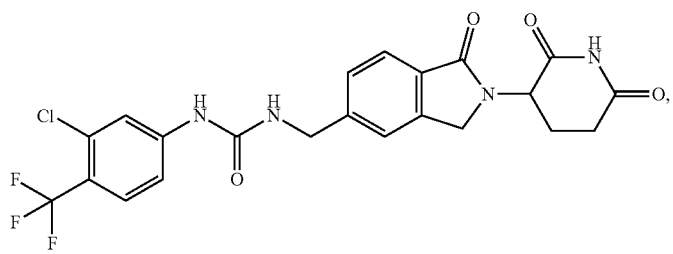 [SMILES: O=C1CCC(N2Cc3cc(CNC(=O)Nc4ccc(C(F)(F)F)c(Cl)c4)ccc3C2=O)C(=O)N1]
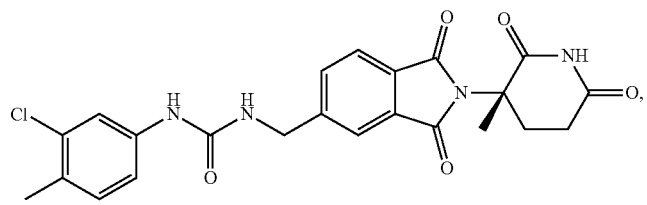 [SMILES: Cc1ccc(NC(=O)NCc2ccc3c(c2)C(=O)N([C@@]2(C)CCC(=O)NC2=O)C3=O)cc1Cl]
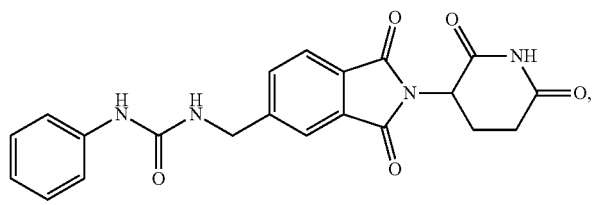 [SMILES: O=C1CCC(N2C(=O)c3ccc(CNC(=O)Nc4ccccc4)cc3C2=O)C(=O)N1]
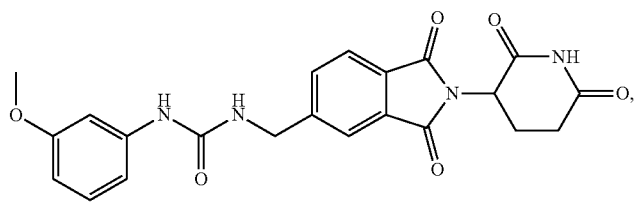 [SMILES: COc1cccc(NC(=O)NCc2ccc3c(c2)C(=O)N(C2CCC(=O)NC2=O)C3=O)c1]

TABLE M-continued
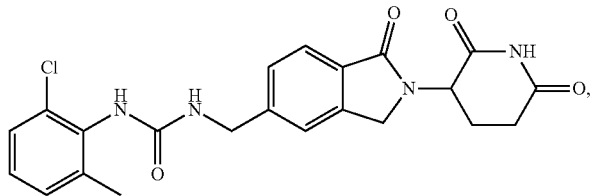 [SMILES: Cc1cccc(Cl)c1NC(=O)NCc1ccc2c(c1)CN(C1CCC(=O)NC1=O)C2=O]
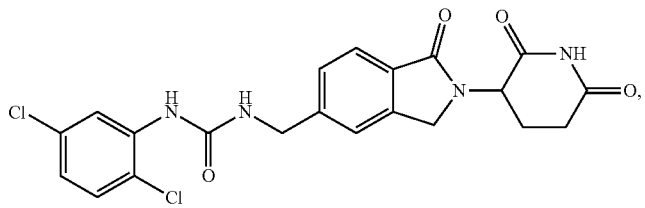 [SMILES: O=C1CCC(N2Cc3cc(CNC(=O)Nc4cc(Cl)ccc4Cl)ccc3C2=O)C(=O)N1]
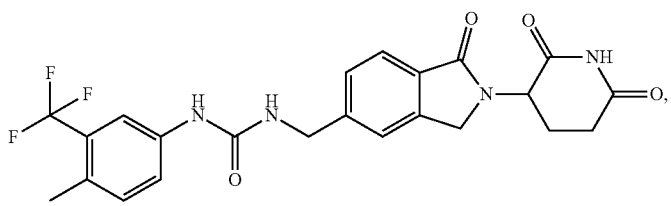 [SMILES: Cc1ccc(NC(=O)NCc2ccc3c(c2)CN(C2CCC(=O)NC2=O)C3=O)cc1C(F)(F)F]
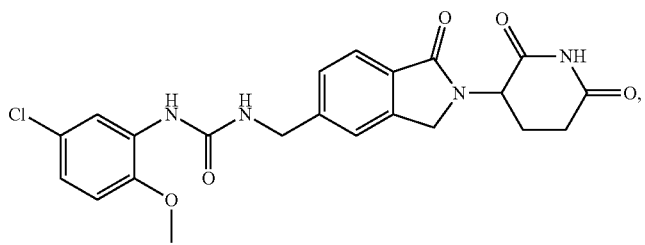 [SMILES: COc1ccc(Cl)cc1NC(=O)NCc1ccc2c(c1)CN(C1CCC(=O)NC1=O)C2=O]
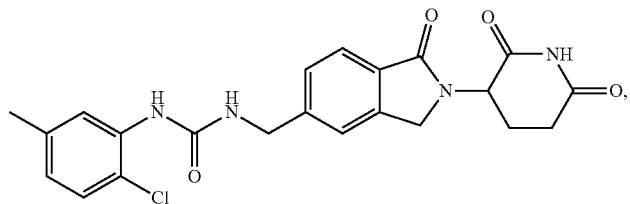 [SMILES: Cc1ccc(Cl)c(NC(=O)NCc2ccc3c(c2)CN(C2CCC(=O)NC2=O)C3=O)c1]
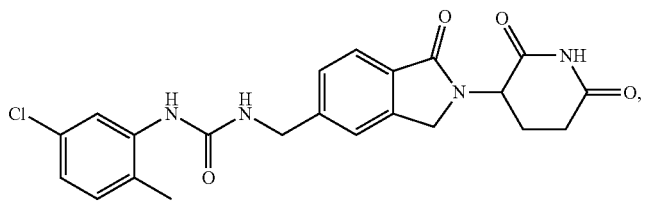 [SMILES: Cc1ccc(Cl)cc1NC(=O)NCc1ccc2c(c1)CN(C1CCC(=O)NC1=O)C2=O]
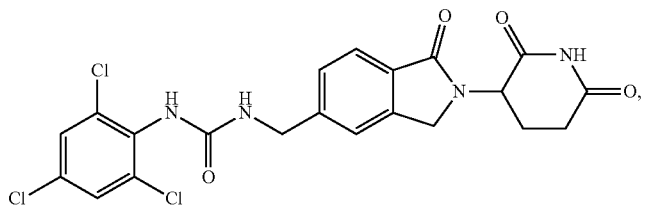 [SMILES: O=C1CCC(N2Cc3cc(CNC(=O)Nc4c(Cl)cc(Cl)cc4Cl)ccc3C2=O)C(=O)N1]

TABLE M-continued
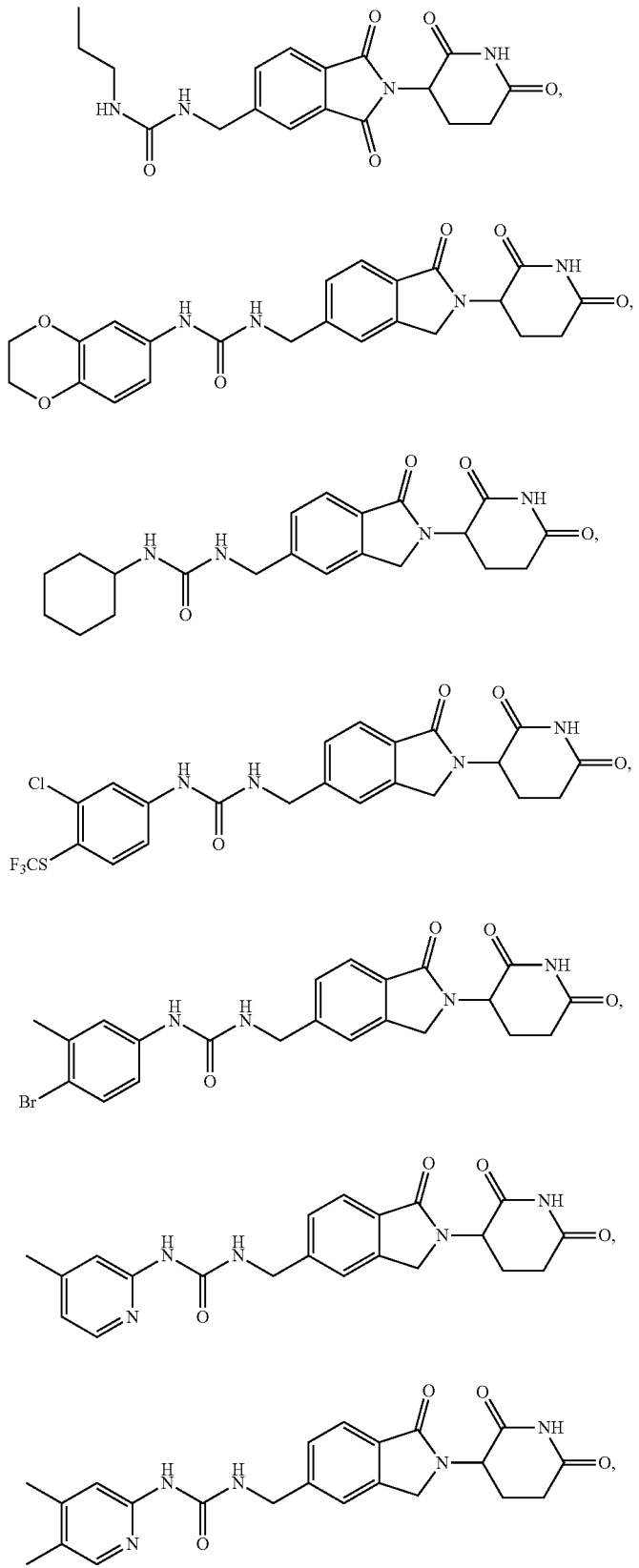

TABLE M-continued
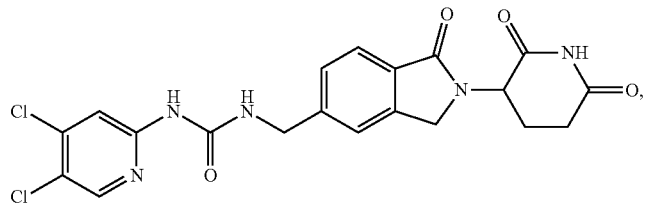
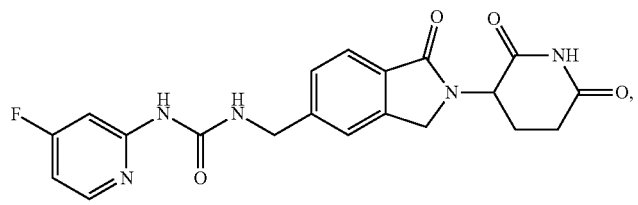 [SMILES: O=C1CCC(N2Cc3cc(CNC(=O)Nc4cc(F)ccn4)ccc3C2=O)C(=O)N1]
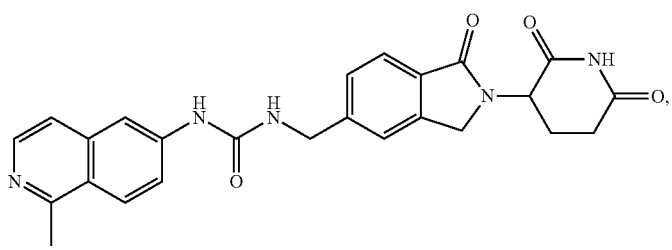 [SMILES: Cc1nccc2cc(NC(=O)NCc3ccc4c(c3)CN(C3CCC(=O)NC3=O)C4=O)ccc12]
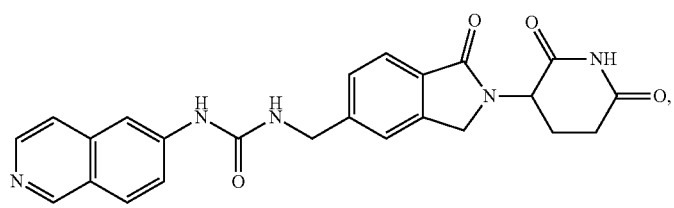 [SMILES: O=C1CCC(N2Cc3cc(CNC(=O)Nc4ccc5cnccc5c4)ccc3C2=O)C(=O)N1]
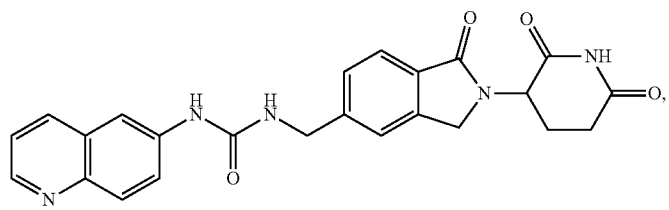 [SMILES: O=C1CCC(N2Cc3cc(CNC(=O)Nc4ccc5ncccc5c4)ccc3C2=O)C(=O)N1]
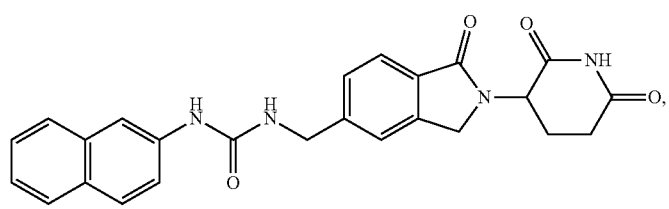 [SMILES: O=C1CCC(N2Cc3cc(CNC(=O)Nc4ccc5ccccc5c4)ccc3C2=O)C(=O)N1]
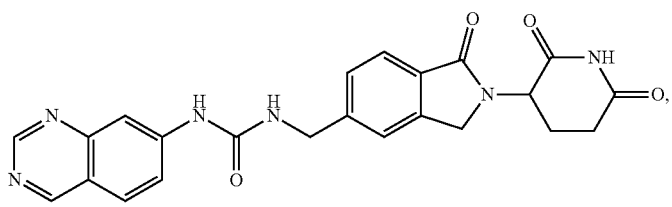 [SMILES: O=C1CCC(N2Cc3cc(CNC(=O)Nc4ccc5cncnc5c4)ccc3C2=O)C(=O)N1]

TABLE M-continued

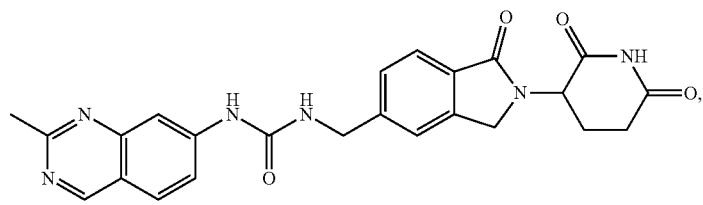 [SMILES: Cc1ncc2ccc(NC(=O)NCc3ccc4c(c3)CN(C3CCC(=O)NC3=O)C4=O)cc2n1]

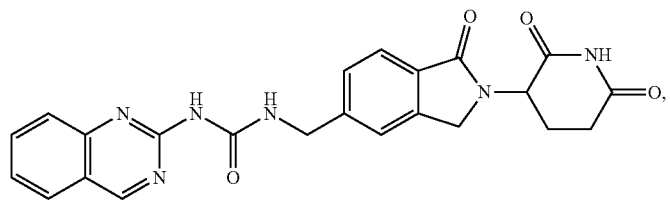 [SMILES: O=C1CCC(N2Cc3cc(CNC(=O)Nc4ncc5ccccc5n4)ccc3C2=O)C(=O)N1]

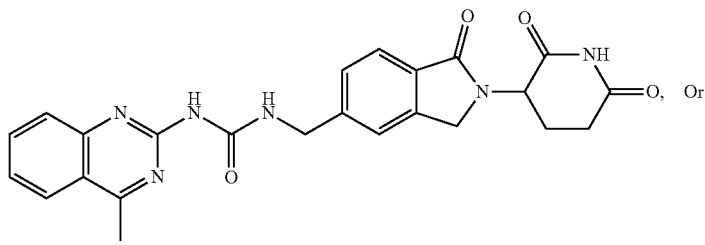 [SMILES: Cc1nc(NC(=O)NCc2ccc3c(c2)CN(C2CCC(=O)NC2=O)C3=O)nc2ccccc12]

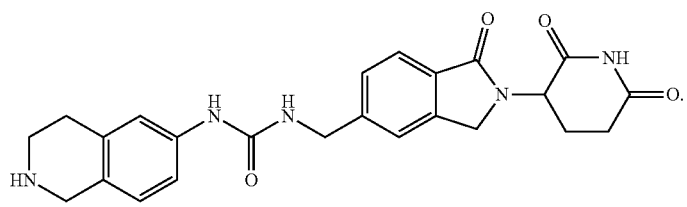 [SMILES: O=C1CCC(N2Cc3cc(CNC(=O)Nc4ccc5c(c4)CCNC5)ccc3C2=O)C(=O)N1]

In one embodiment, the immunomodulatory compound is:

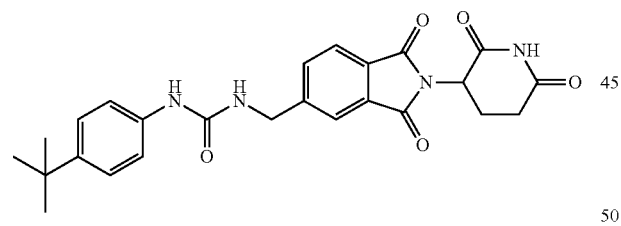

or a pharmaceutically acceptable salt, solvate, prodrug, or stereoisomer thereof.

In one embodiment, the immunomodulatory compound is:

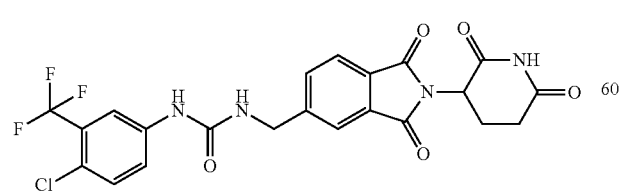

or a pharmaceutically acceptable salt, solvate, prodrug, or stereoisomer thereof.

In one embodiment, the immunomodulatory compound is:

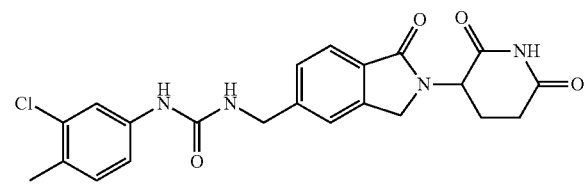 [SMILES: Cc1ccc(NC(=O)NCc2ccc3c(c2)CN(C2CCC(=O)NC2=O)C3=O)cc1Cl]

or a pharmaceutically acceptable salt, solvate, prodrug, or stereoisomer thereof.

In one embodiment, the immunomodulatory compound is:

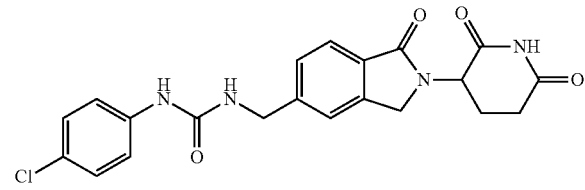 [SMILES: O=C1CCC(N2Cc3cc(CNC(=O)Nc4ccc(Cl)cc4)ccc3C2=O)C(=O)N1]

or a pharmaceutically acceptable salt, solvate, prodrug, or stereoisomer thereof.

In one embodiment, the immunomodulatory compound is:

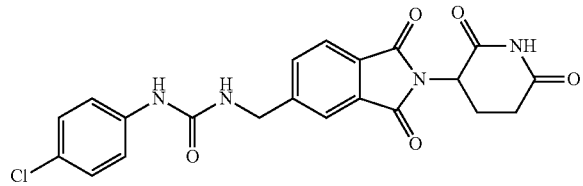 [SMILES: O=C1CCC(N2C(=O)c3ccc(CNC(=O)Nc4ccc(Cl)cc4)cc3C2=O)C(=O)N1]

or a pharmaceutically acceptable salt, solvate, prodrug, or stereoisomer thereof.

Still other specific immunomodulatory drugs provided herein belong to a class of isoindoline compounds disclosed in U.S. Pat. No. 8,129,375, the entirety of which is incorporated herein by reference. Representative compounds are of formula XIII:

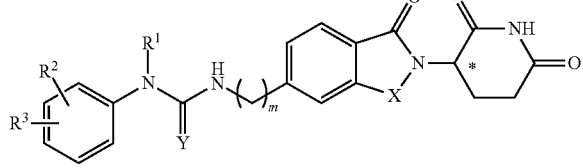

or a pharmaceutically acceptable salt, solvate, prodrug, or stereoisomer thereof, wherein:

X is C(=O) or $CH_2$;
Y is O, cyanamido (N=N), or amido (NH);
m is an integer of 0, 1, 2, or 3;
$R^1$ is hydrogen or $C_{1-6}$ alkyl;
$R^2$ is hydrogen, $-NO_2$, $C_{1-10}$ alkyl, $C_{0-6}$ alkyl-(5 to 10 membered heteroaryl), $C_{0-6}$alkyl-(5 to 6 membered heterocyclyl), $C_{0-6}$alkyl-OH, $C_{0-4}$ alkyl-$NH_2$, $-NHCO-C_{1-6}$ alkyl, $-OR^{21}$, or $-(CH_2-Z)_{0-2}$-(5 to 10 membered heteroaryl), where each heteroaryl and heterocyclyl is optionally substituted with one or more $C_{1-6}$ alkyl;
$R^3$ is hydrogen, halogen, $-NO_2$, $C_{0-6}$ alkyl-(5 to 10 membered heteroaryl), $C_{0-6}$ alkyl-(5 to 6 membered heterocyclyl), $C_{0-6}$alkyl-OH, $C_{0-4}$ alkyl-$NH_2$, $-NHCO-C_{1-6}$ alkyl, $-OR^{21}$, or $-(CH_2-Z)_{0-2}$-(5 to 10 membered heteroaryl), where each heteroaryl and heterocyclyl is optionally substituted with one or more $C_{1-6}$ alkyl;
$R^{21}$ is $C_{6-10}$ aryl, 5 to 10 membered heteroaryl, 5 to 6 membered heterocyclyl, or $-CO(CH_2)_{0-2}R^{22}$, wherein the aryl, heteroaryl, and heterocyclyl are each optionally substituted with one or more $C_{1-6}$ alkyl;
$R^{22}$ is $-NH_2$ or 5 to 6 membered heterocyclyl; and
Z is $CH_2$, NH, or O;
with the proviso that when $R^1$ is hydrogen, then $R^2$ is not hydrogen or $C_{1-10}$ alkyl;
with the proviso that when Y is O, then $R^3$ is not halogen; and
with the proviso that when Y is O and $R^3$ is halogen, then $R^2$ is $C_{0-6}$alkyl-(5-6 membered heterocyclyl).

In certain embodiments, X is $CH_2$. In certain embodiments, X is C(=O).

In certain embodiments, Y is O. In certain embodiments, Y is cyanamido. In certain embodiments, Y is amido.

In certain embodiments, Z is $CH_2$. In certain embodiments, Z is NH. In certain embodiments, Z is O.

In certain embodiments, m is 0. In certain embodiments, m is 1. In certain embodiments, m is 2. In certain embodiments, m is 3.

In certain embodiments, $R^1$ is hydrogen. In certain embodiments, $R^1$ is $C_{1-6}$ alkyl, optionally substituted with one, two, or three substituents Q as described herein. In certain embodiments, $R^1$ is methyl.

In certain embodiments, $R^2$ is hydrogen. In certain embodiments, $R^2$ is halogen. In certain embodiments, $R^2$ is nitro. In certain embodiments, $R^2$ is $C_{1-10}$ alkyl. In certain embodiments, $R^2$ is $C_{0-6}$alkyl-(5 to 10 membered heteroaryl), where the heteroaryl is optionally substituted with one or more $C_{1-6}$ alkyl. In certain embodiments, $R^2$ is $C_{0-6}$alkyl-(5 to 6 membered heterocyclyl), where the heterocyclyl is optionally substituted with one or more $C_{1-6}$ alkyl. In certain embodiments, $R^2$ is $C_{0-6}$alkyl-OH. In certain embodiments, $R^2$ is $C_{0-4}$ alkyl-$NH_2$. In certain embodiments, $R^2$ is $-NHCO-C_{1-6}$ alkyl. In certain embodiments, $R^2$ is $-OR^{21}$, wherein $R^{21}$ is as described herein. In certain embodiments, $R^2$ is or $-(CH_2-Y)_{0-2}$-(5 to 10 membered heteroaryl), where the heteroaryl is optionally substituted with one or more $C_{1-6}$ alkyl. In certain embodiments, $R^2$ is hydrogen, amino, acetamido, hydroxy, nitro, aminomethyl, hydroxymethyl, 2-methyl-1H-imidazol-1-yl, 3-methyl-1,2,4-oxadiazol-5-yl, 4-methylpiperazin-1-yl)methyl, 2-methyl-2H-pyrazol-3-yl, 1-methyl-1H-pyrazol-3-yl, 2-methylthiazol-4-yl, 4-methyl-4H-1,2,4-triazol-3-yl, morpholinomethyl, (pyridin-4-yl)methyl, (pyridin-4-yloxy)methyl, pheoxy, pyridin-2-yloxy, piperidin-4-yloxy, 2-aminoacetoxy, or 2-piperazin-1-ylacetoxy.

In certain embodiments, $R^3$ is hydrogen. In certain embodiments, $R^3$ is nitro. In certain embodiments, $R^3$ is $C_{0-6}$ alkyl-(5 to 10 membered heteroaryl), where the heteroaryl is optionally substituted with one or more $C_{1-6}$ alkyl. In certain embodiments, $R^3$ is $C_{0-6}$ alkyl-(5 to 6 membered heterocyclyl), where the heterocyclyl is optionally substituted with one or more $C_{1-6}$ alkyl. In certain embodiments, $R^3$ is $C_{0-6}$alkyl-OH. In certain embodiments, $R^3$ is $C_{0-4}$ alkyl-$NH_2$. In certain embodiments, $R^3$ is $-NHCO-C_{1-6}$ alkyl. In certain embodiments, $R^3$ is $-OR^{21}$, wherein $R^{21}$ is as described herein. In certain embodiments, $R^3$ is or $-(CH_2-Y)_{0-2}$-(5 to 10 membered heteroaryl), where the heteroaryl is optionally substituted with one or more $C_{1-6}$ alkyl. In certain embodiments, $R^3$ is hydrogen, amino, acetamido, hydroxy, nitro, methyl, aminomethyl, hydroxymethyl, 2-methyl-1H-imidazol-1-yl, 3-methyl-1,2,4-oxadiazol-5-yl, 4-methylpiperazin-1-yl)methyl, 2-methyl-2H-pyrazol-3-yl, 1-methyl-1H-pyrazol-3-yl, 2-methylthiazol-4-yl, 4-methyl-4H-1,2,4-triazol-3-yl, morpholinomethyl, (pyridin-4-yl)methyl, (pyridin-4-yloxy)methyl, pheoxy, pyridin-2-yloxy, piperidin-4-yloxy, 2-aminoacetoxy, or 2-piperazin-1-ylacetoxy.

In one embodiment, the compound is selected from those listed in Table Q, below:

TABLE Q
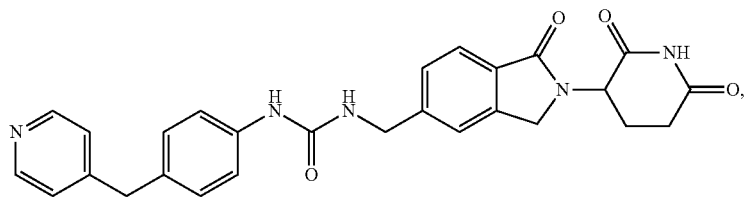 [SMILES: O=C1CCC(N2Cc3cc(CNC(=O)Nc4ccc(Cc5ccncc5)cc4)ccc3C2=O)C(=O)N1]
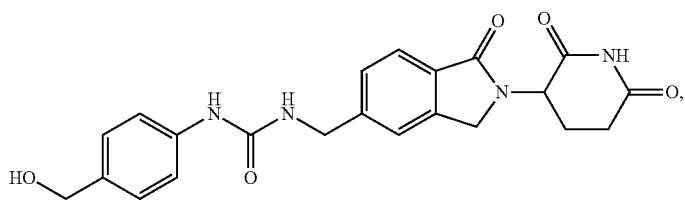 [SMILES: O=C1CCC(N2Cc3cc(CNC(=O)Nc4ccc(CO)cc4)ccc3C2=O)C(=O)N1]
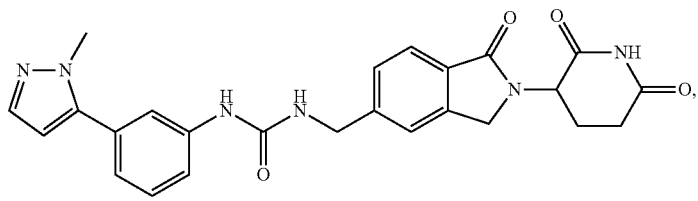 [SMILES: Cn1nccc1-c1cccc(NC(=O)NCc2ccc3c(c2)CN(C2CCC(=O)NC2=O)C3=O)c1]
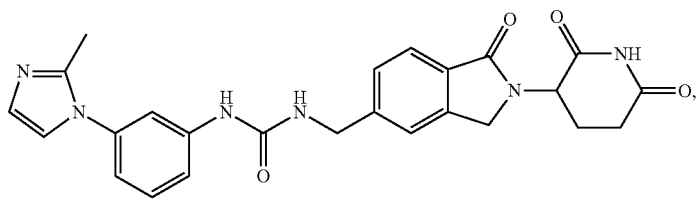 [SMILES: Cc1nccn1-c1cccc(NC(=O)NCc2ccc3c(c2)CN(C2CCC(=O)NC2=O)C3=O)c1]
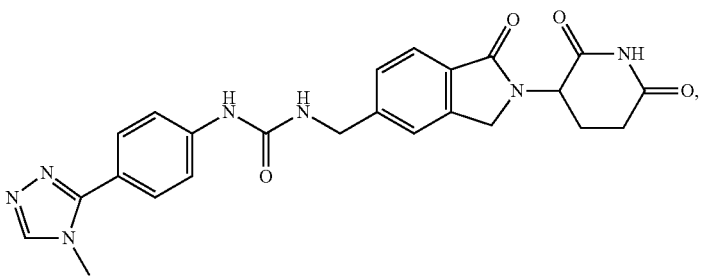 [SMILES: Cn1cnnc1-c1ccc(NC(=O)NCc2ccc3c(c2)CN(C2CCC(=O)NC2=O)C3=O)cc1]
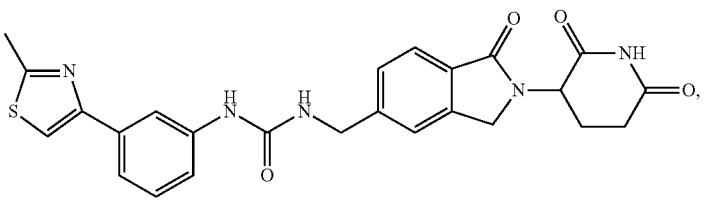 [SMILES: Cc1nc(-c2cccc(NC(=O)NCc3ccc4c(c3)CN(C3CCC(=O)NC3=O)C4=O)c2)cs1]
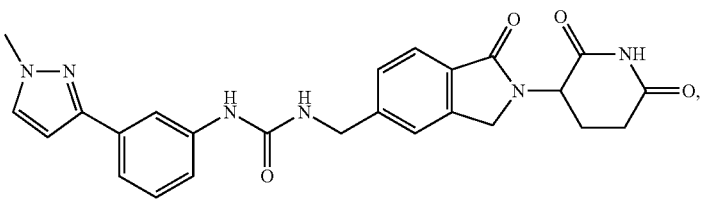 [SMILES: Cn1ccc(-c2cccc(NC(=O)NCc3ccc4c(c3)CN(C3CCC(=O)NC3=O)C4=O)c2)n1]

TABLE Q-continued
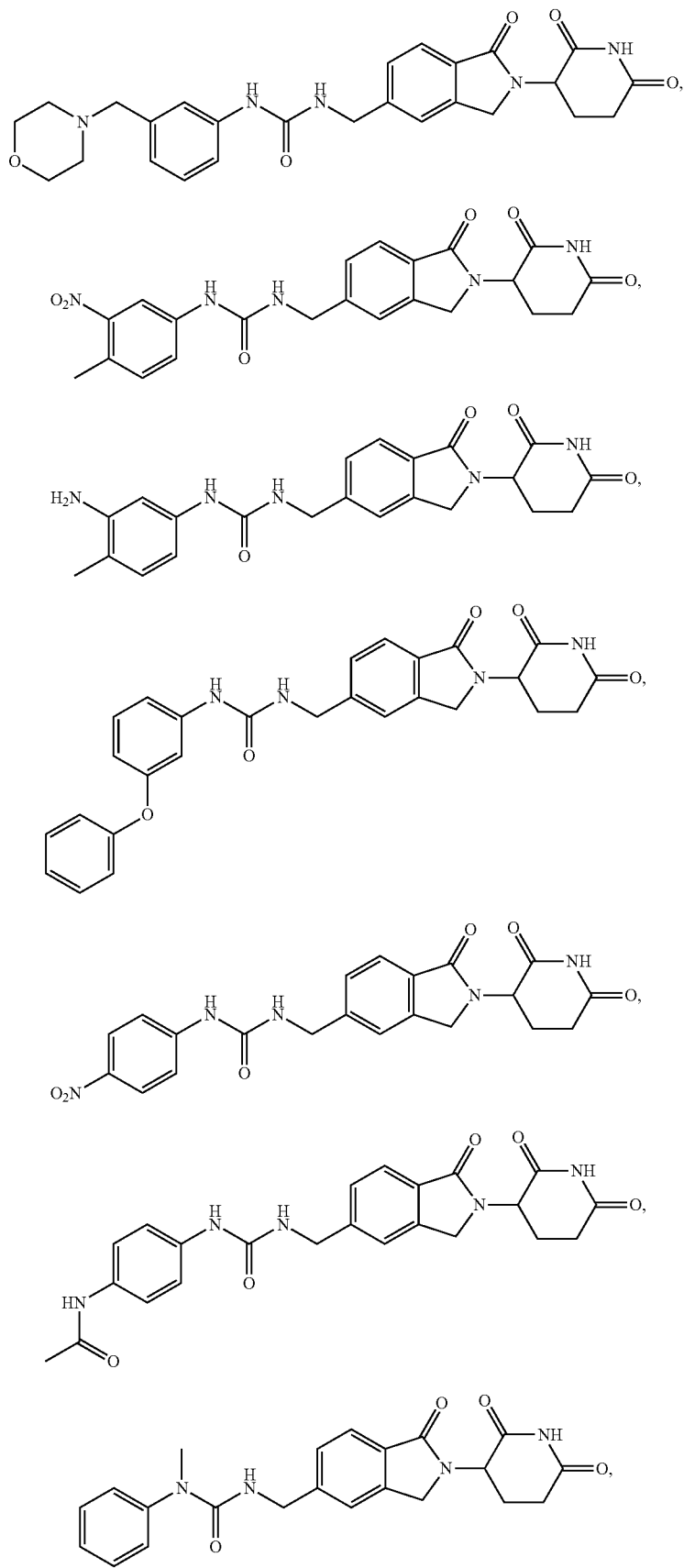

TABLE Q-continued
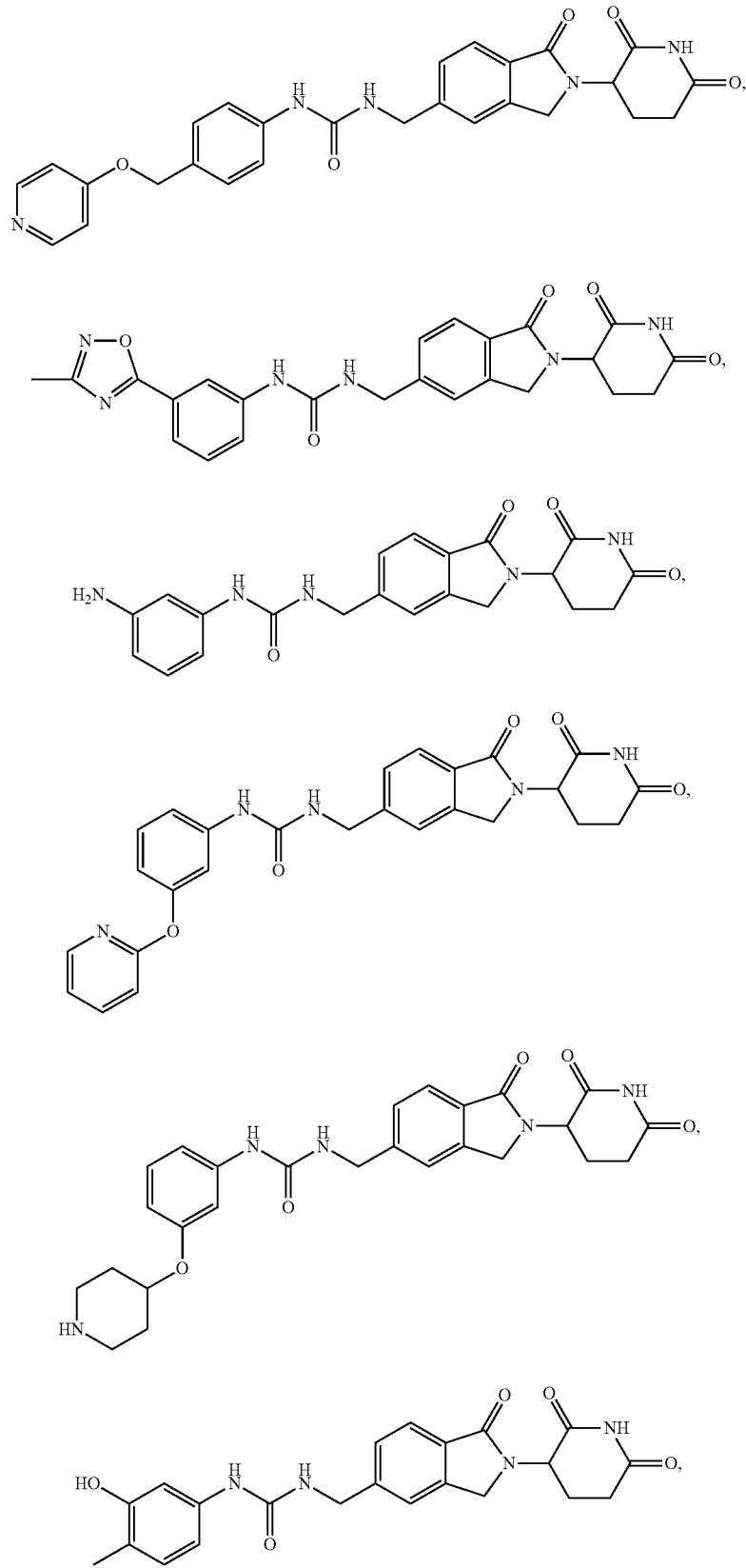

TABLE Q-continued
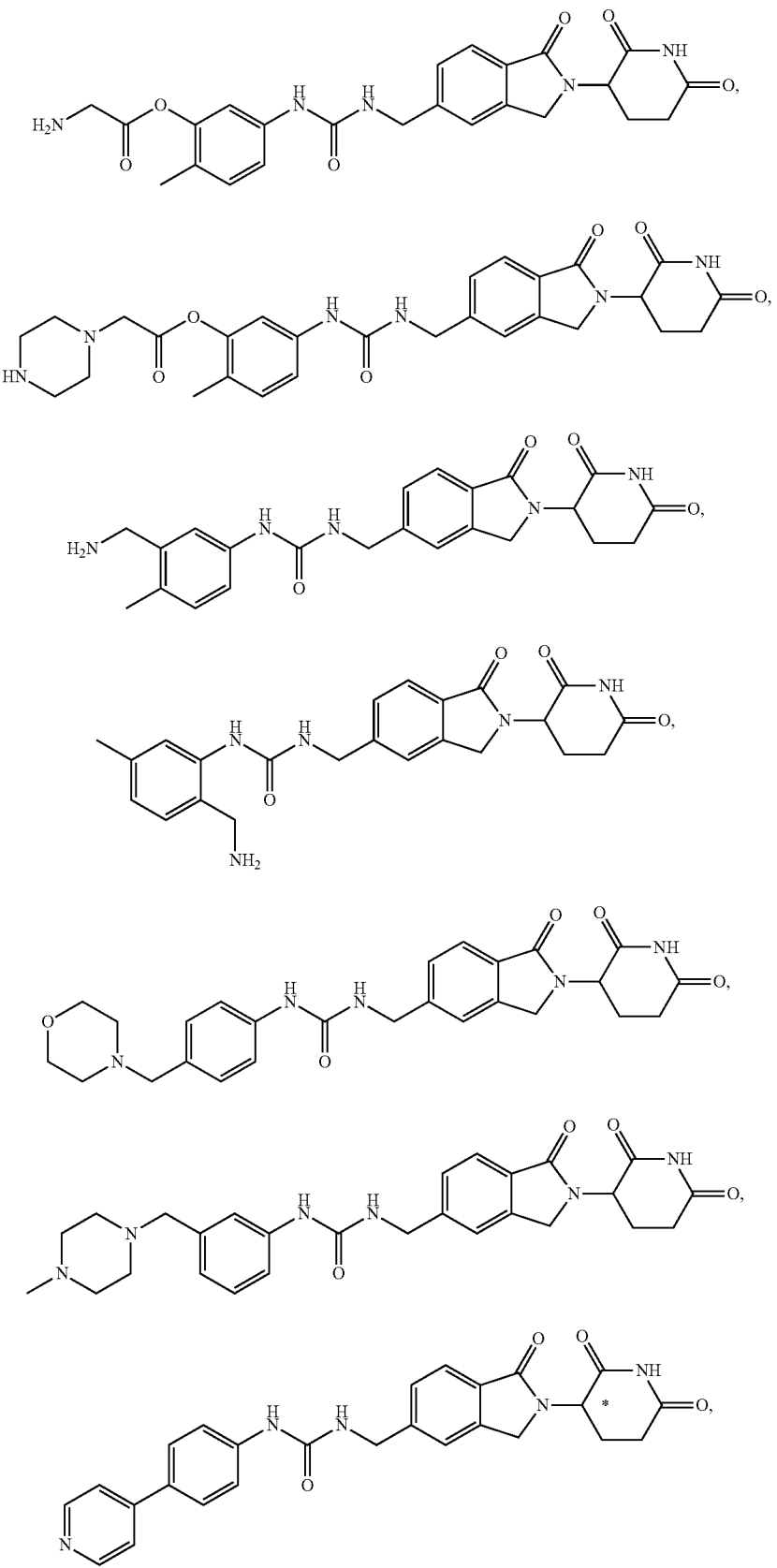

TABLE Q-continued
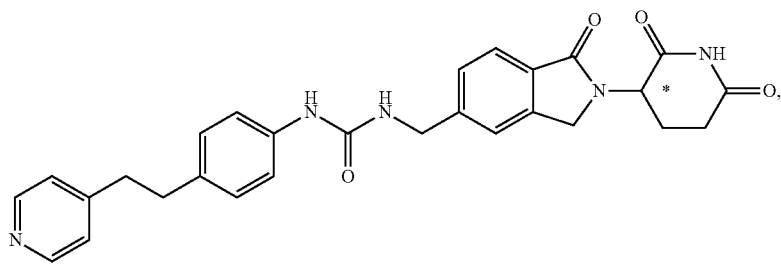 [SMILES: O=C1CCC(N2Cc3cc(CNC(=O)Nc4ccc(CCc5ccncc5)cc4)ccc3C2=O)C(=O)N1]
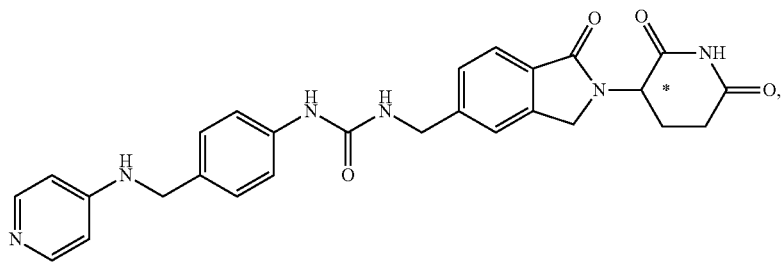 [SMILES: O=C1CCC(N2Cc3cc(CNC(=O)Nc4ccc(CNc5ccncc5)cc4)ccc3C2=O)C(=O)N1]
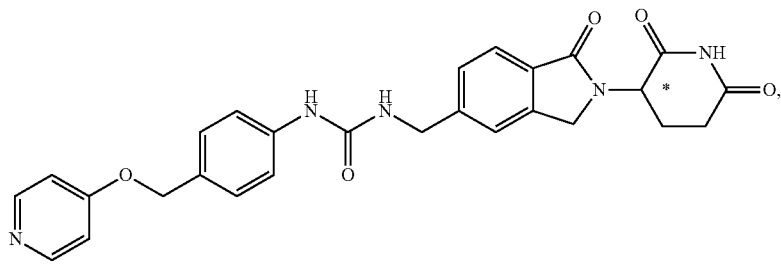 [SMILES: O=C1CCC(N2Cc3cc(CNC(=O)Nc4ccc(COc5ccncc5)cc4)ccc3C2=O)C(=O)N1]
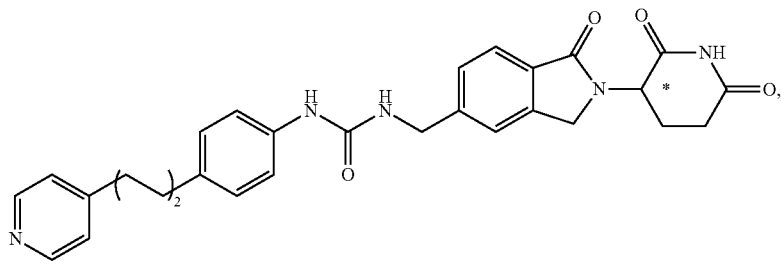
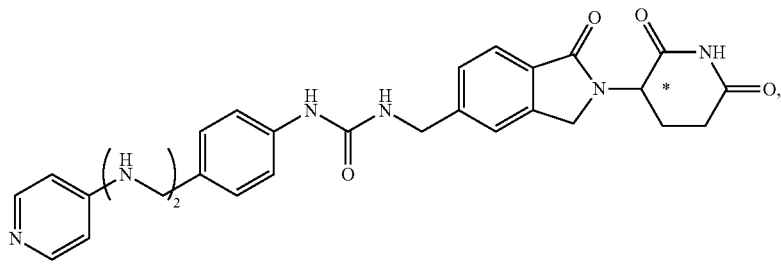
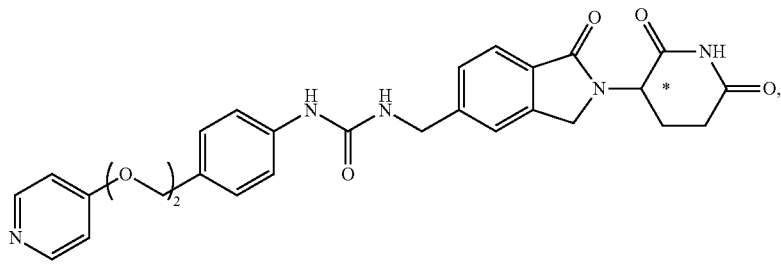

TABLE Q-continued
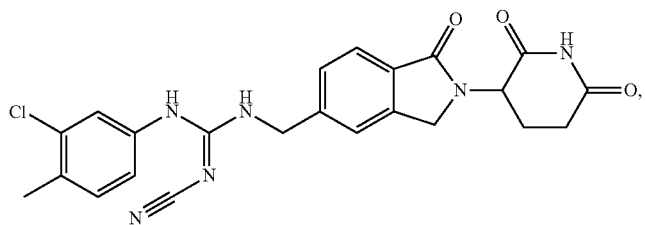 [SMILES: Cc1ccc(N/C(=N\C#N)NCc2ccc3c(c2)CN(C2CCC(=O)NC2=O)C3=O)cc1Cl]
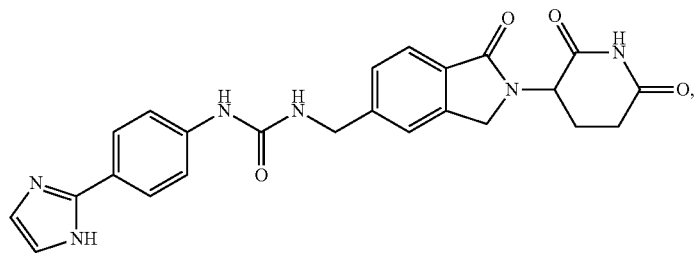 [SMILES: O=C1CCC(N2Cc3cc(CNC(=O)Nc4ccc(-c5ncc[nH]5)cc4)ccc3C2=O)C(=O)N1]
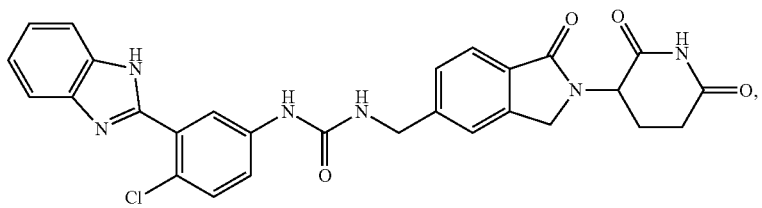 [SMILES: O=C1CCC(N2Cc3cc(CNC(=O)Nc4ccc(Cl)c(-c5nc6ccccc6[nH]5)c4)ccc3C2=O)C(=O)N1]
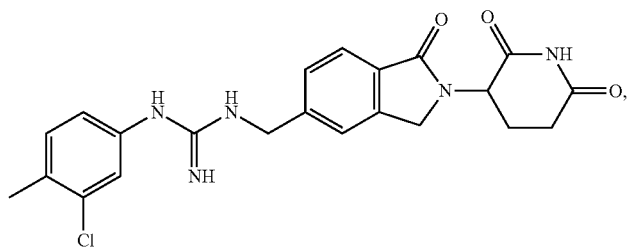 [SMILES: Cc1ccc(NC(=N)NCc2ccc3c(c2)CN(C2CCC(=O)NC2=O)C3=O)cc1Cl]
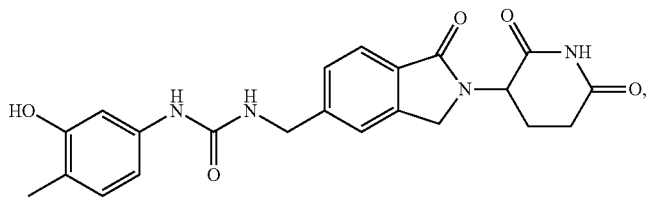 [SMILES: Cc1ccc(NC(=O)NCc2ccc3c(c2)CN(C2CCC(=O)NC2=O)C3=O)cc1O]
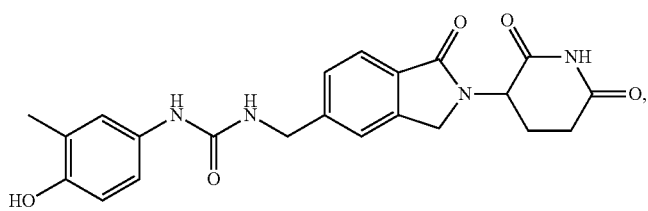 [SMILES: Cc1cc(NC(=O)NCc2ccc3c(c2)CN(C2CCC(=O)NC2=O)C3=O)ccc1O]
or a pharmaceutically acceptable salt, solvate, prodrug, and stereoisomer thereof.
In another embodiment, representative compounds are of Formula XIV:

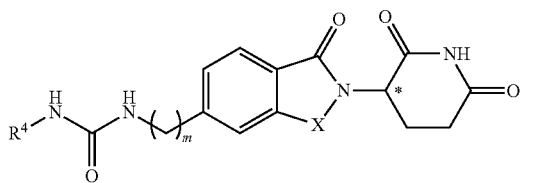

or a pharmaceutically acceptable salt, solvate, prodrug, or stereoisomer thereof, wherein:

X is C(=O) or $CH_2$;

m is an integer of 0, 1, 2, or 3;

$R^4$ is $C_{3-10}$ cycloalkyl, 5 to 10 membered heterocyclyl, 5 to 10 membered heteroaryl, or $C_{0-4}$ alkyl-$NR^{41}R^{42}$; wherein the cycloalkyl, heterocyclyl, and heteroaryl are each optionally substituted with one or more halogen, $C_{1-6}$ alkyl, —CO—$NR^{43}R^{44}$, —$COOR^{45}$, or $C_{0-4}$ alkyl-$C_{6-10}$ aryl, wherein the aryl itself may be optionally substituted with one or more halogen; and $R^{41}$, $R^{42}$, $R^{43}$, $R^{44}$, and $R^{45}$ are each independently hydrogen or $C_{1-6}$ alkyl.

In certain embodiments, X is $CH_2$. In certain embodiments, X is C(=O).

In certain embodiments, m is 0. In certain embodiments, m is 1. In certain embodiments, m is 2. In certain embodiments, m is 3.

In certain embodiments, $R^4$ is $C_{3-10}$ cycloalkyl, optionally substituted with one or more ($C_{1-6}$) alkyl or $C_{0-4}$ alkyl-$C_6$10 aryl. In certain embodiments, $R^4$ is 5 to 6 membered heterocyclyl, optionally substituted with one or more ($C_{1-6}$) alkyl or $C_{0-4}$ alkyl-$C_{6-10}$ aryl. In certain embodiments, $R^4$ is $C_{0-4}$alkyl-$NR^{41}R^{42}$, wherein $R^{41}$ and $R^{42}$ are each described herein.

In certain embodiments, $R^4$ is 3-(N,N-diethylamino)propyl, 4-acetamidophenyl, 3-(2-aminoacetoxy)-4-methylphenyl, 3-aminomethyl-4-methylphenyl, 2-aminomethyl-5-methylphenyl, 3-aminophenyl, 3-amino-4-methylphenyl, 3-chloro-4-methylphenyl, 4-hydroxymethylphenyl, 3-hydroxy-4-methylphenyl, 3-(2-methyl-1H-imidazol-1-yl)phenyl, 4-methyl-3-nitrophenyl, 3-(3-methyl-1,2,4-oxadiazol-5-yl)phenyl, 4-methyl-3-(2-piperazin-1-ylacetoxy)-phenyl, 3-((4-methylpiperazin-1-yl)methyl)phenyl, 3-(1-methyl-1H-pyrazol-3-yl)phenyl, 3-(2-methyl-2H-pyrazol-3-yl)phenyl, 3-(2-methylthiazol-4-yl)phenyl, 4-(4-methyl-4H-1,2,4-triazol-3-yl)phenyl, 3-(morpholinomethyl)phenyl, 4-(morpholinomethyl)phenyl, 4-nitrophenyl, phenyl, 3-(piperidin-4-yloxy)phenyl, 4-(pyridin-4-yl)methylphenyl, 4-((pyridin-4-yloxy)methyl)phenyl, 3-(pyridin-2-yloxy)phenyl, 3-phenoxyphenyl, 4-tert-butylcyclohexyl, cis-4-tert-butylcyclohexyl, trans-4-tert-butylcyclohexyl, 4-methylcyclohexyl, cis-4-methylcyclohexyl, trans-4-methylcyclohexyl, 1-benzylpiperidin-4-yl, 4-methyltetrahydro-2H-pyran-4-yl, piperidin-4-yl, 4-phenylcyclohexyl, cis-4-phenylcyclohexyl, or trans-4-phenylcyclohexyl.

In one embodiment, the compound is selected from those listed in Table R, below:

TABLE R

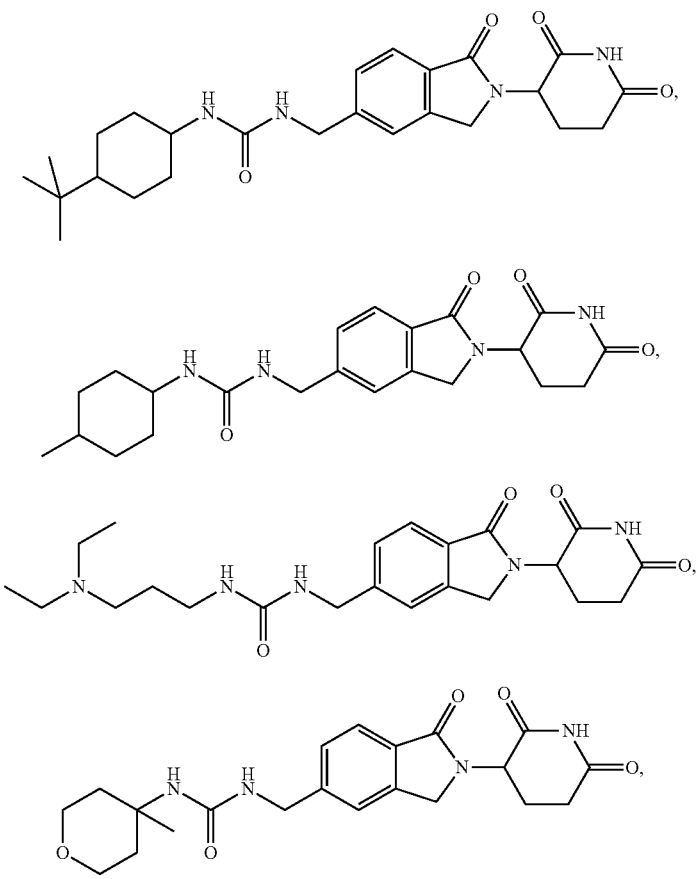

TABLE R-continued
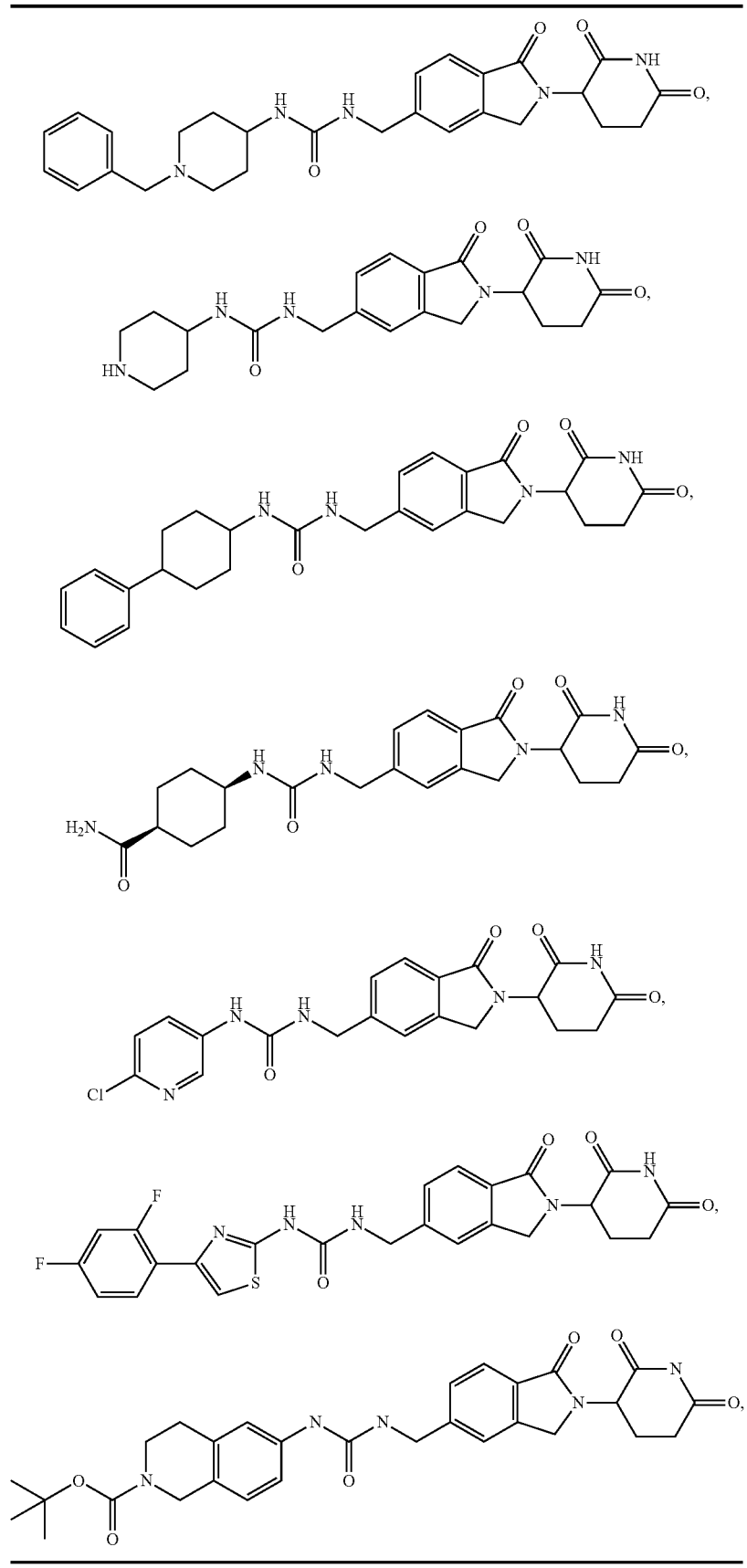

or a pharmaceutically acceptable salt, solvate, prodrug, or stereoisomer thereof.

In yet another embodiment, representative compounds are of Formula XV:

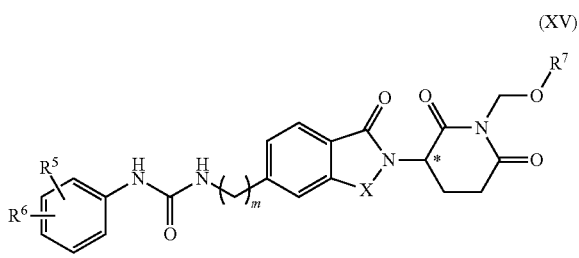

(XV)

or a pharmaceutically acceptable salt, solvate, prodrug, or stereoisomer thereof, wherein:
X is C(=O) or CH$_2$;
m is an integer of 0, 1, 2, or 3;
R$^5$ and R$^6$ are each independently: hydrogen, halo, C$_{1-6}$ alkyl, oxo, —NO$_2$, C$_{1-6}$ alkoxy, —Z—C$_{1-6}$alkyl, C$_{0-6}$alkyl-(5 to 10 membered heteroaryl), C$_{0-6}$alkyl-(5 to 6 membered heterocyclyl), C$_{0-6}$ alkyl-OH, C$_{0-4}$ alkyl-NH$_2$, —NHCO—C$_{1-6}$alkyl, —OR$^{21}$, or —(CH$_2$—Y)$_{0-2}$-(5 to 10 membered heteroaryl),
wherein Z is S or SO$_2$;
wherein R$^{21}$ is as defined above;
wherein each heteroaryl and heterocyclyl above is optionally substituted with one or more C$_{1-6}$ alkyl; and
wherein the alkyl or alkoxy above may be optionally substituted with one or more: halogen; cyano; nitro; amino; C$_{1-6}$ alkylidenedioxy; C$_{1-6}$ alkoxy, itself optionally substituted with one or more halogens; or C$_{1-6}$ alkylthio, itself optionally substituted with one or more halogens;
R$^7$ is —COR$^{71}$ or —PO(OR$^{72}$)(OR$^{73}$);
R$^{71}$ is C$_{1-10}$ alkyl, C$_{6-10}$ aryl, or 5 to 6 membered heterocyclyl; wherein the alkyl, aryl, heterocyclyl may be optionally substituted with one or more amino, C$_{1-6}$ alkylamino, di(C$_{1-6}$ alkyl)amino, or —COOR$^{74}$; and
R$^{72}$, R$^{73}$, and R$^{74}$ are each independently hydrogen or C$_{1-10}$ alkyl.

In certain embodiments, X is CH2. In certain embodiments, X is C(=O).

In certain embodiments, m is 0. In certain embodiments, m is 1. In certain embodiments, m is 2. In certain embodiments, m is 3.

In certain embodiments, R5 is hydrogen. In certain embodiments, R5 is halo.

In certain embodiments, R5 is fluoro or chloro.

In certain embodiments, R6 is hydrogen. In certain embodiments, R6 is halo.

In certain embodiments, R6 is fluoro or chloro.

In certain embodiments, R7 is —COR41, wherein R41 is as described herein.

In certain embodiments, R7 is —PO(OR42))(OR43), wherein R42 and R43 are each as described herein.

In one embodiment, the compound is selected from those listed in Table S, below:

TABLE S

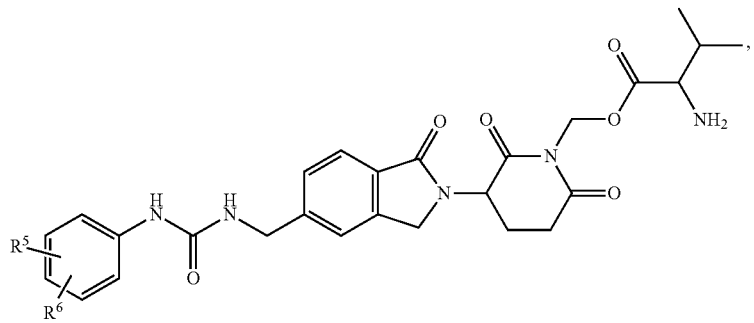

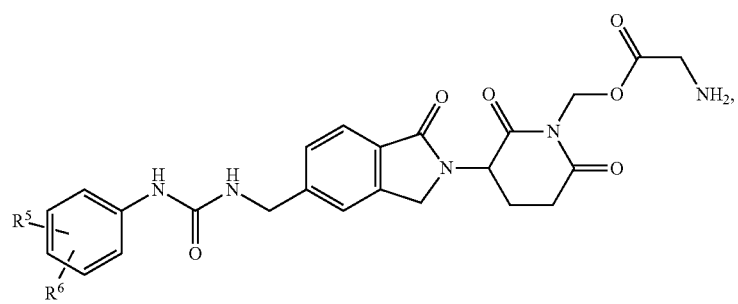

TABLE S-continued
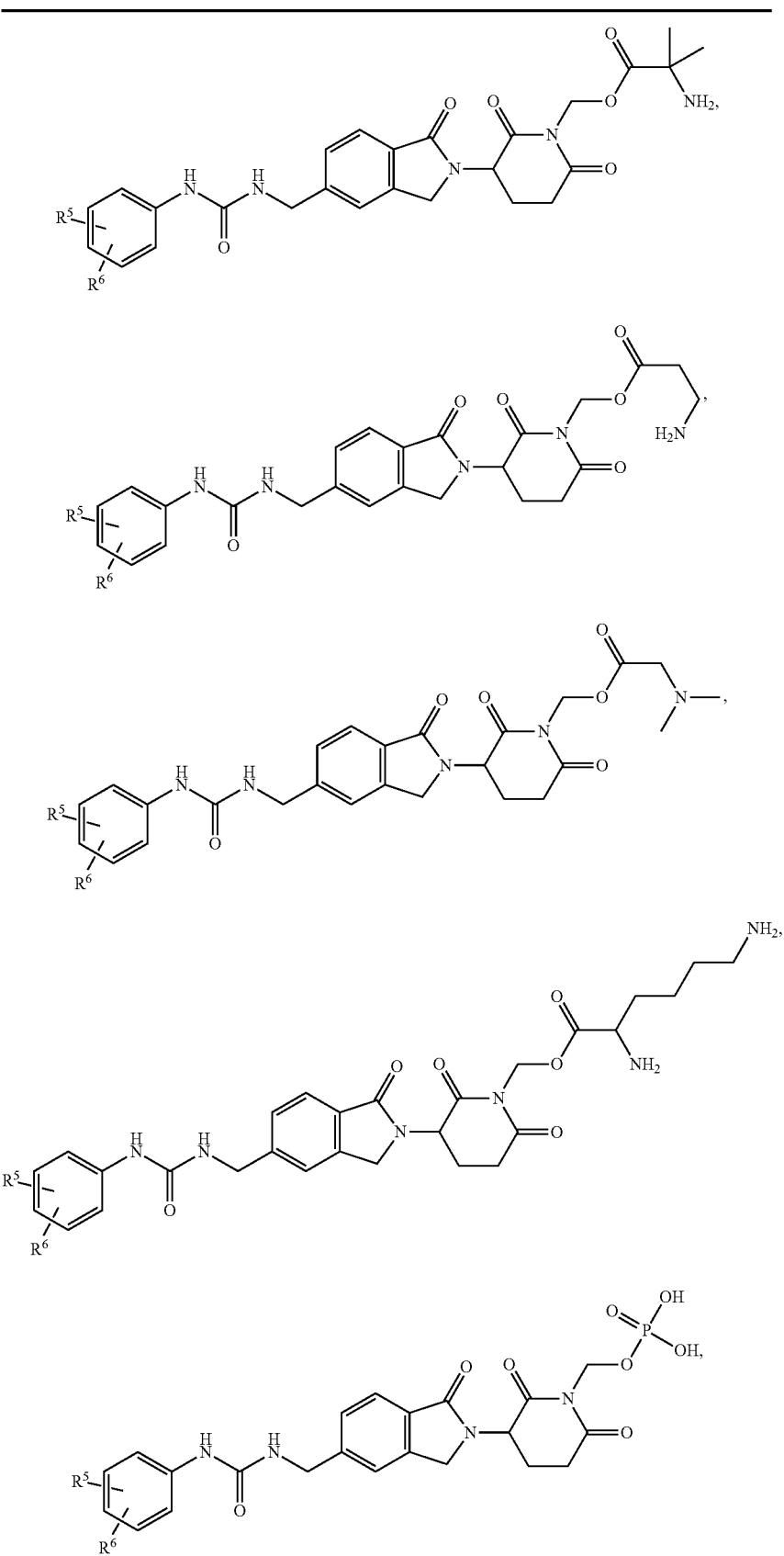

TABLE S-continued
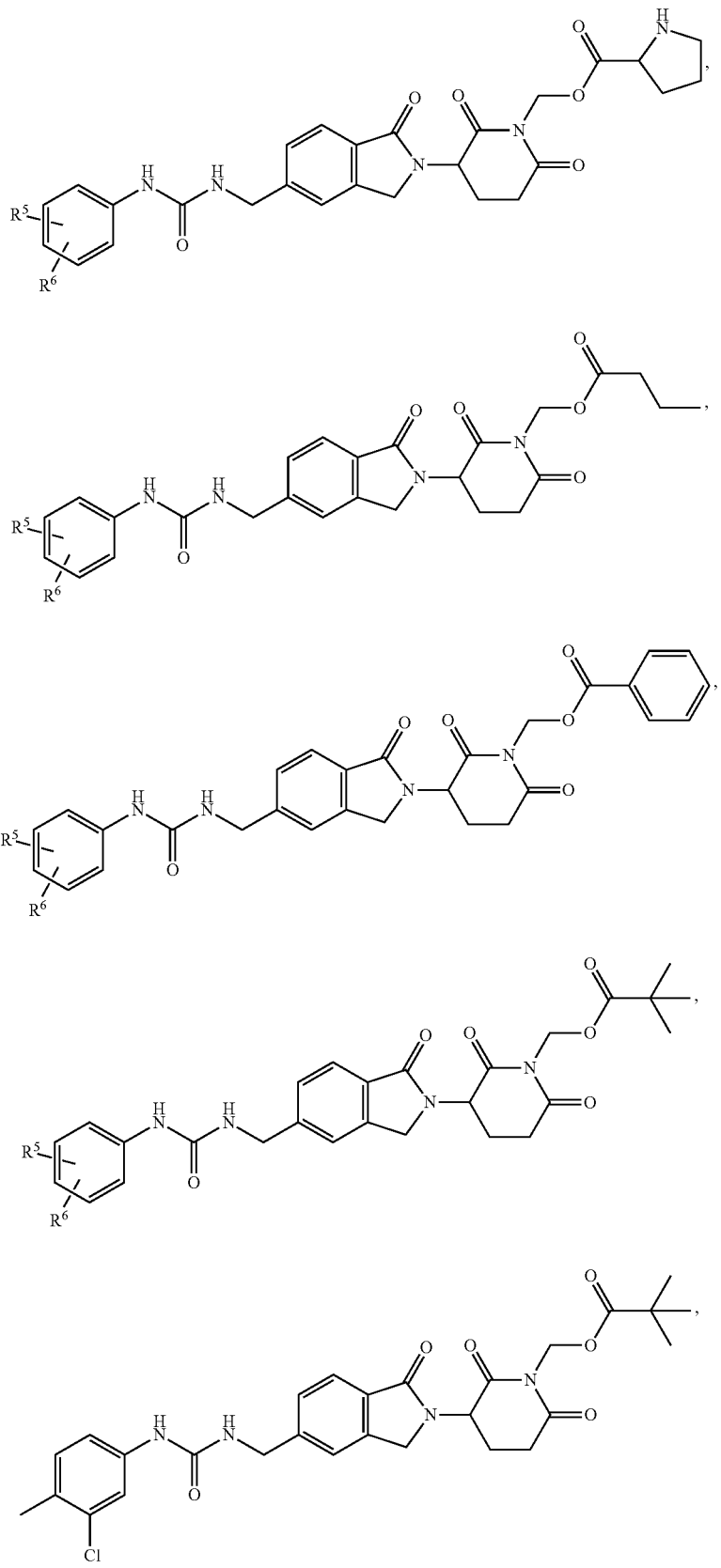

TABLE S-continued

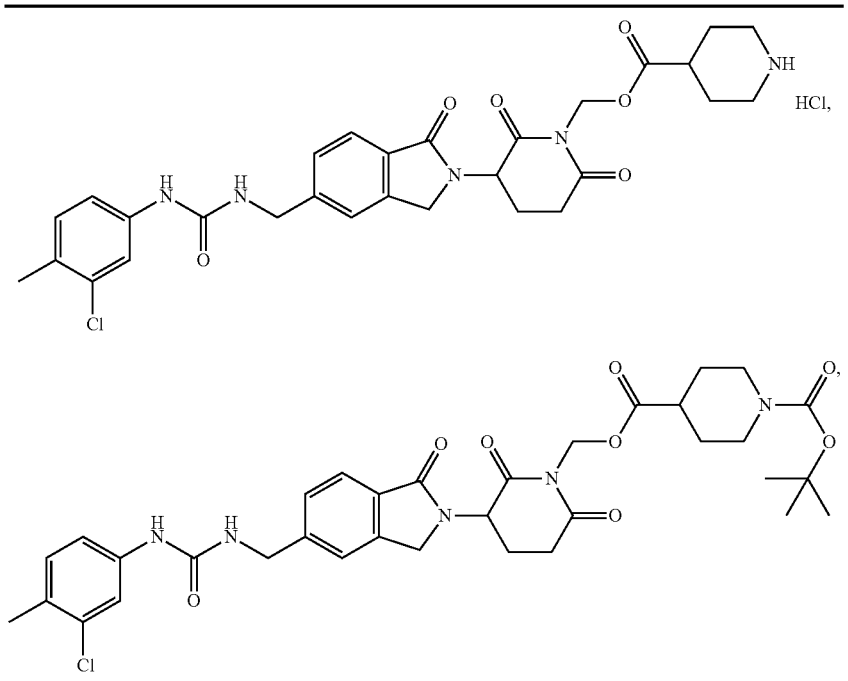

or a pharmaceutically acceptable salt, solvate, prodrug, or stereoisomer thereof, wherein $R^5$ and $R^6$ are as defined above.

In yet another embodiment, representative compounds are of Formula XVI:

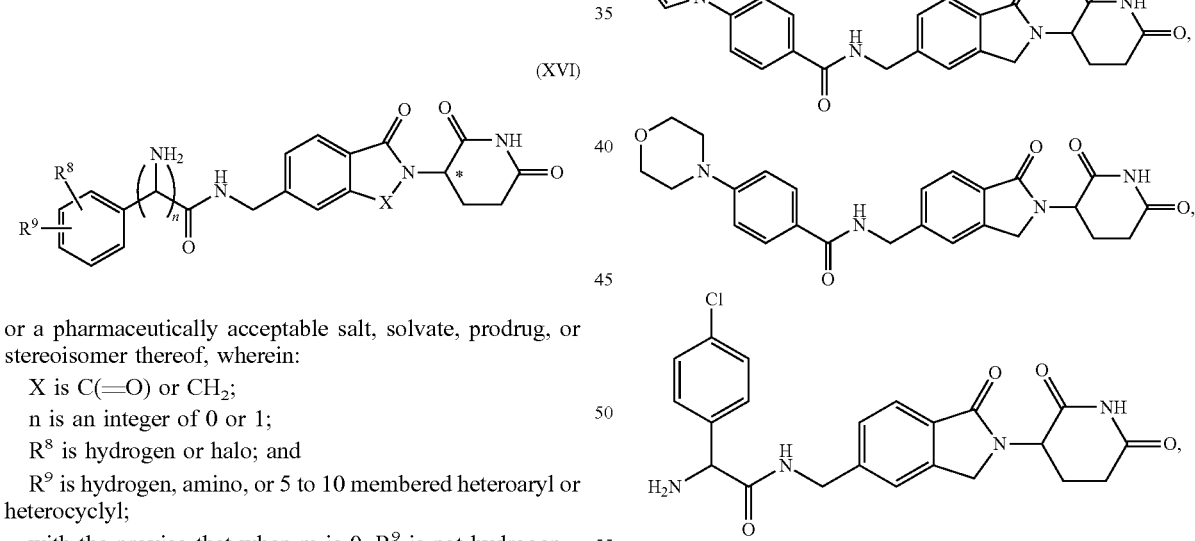

(XVI)

or a pharmaceutically acceptable salt, solvate, prodrug, or stereoisomer thereof, wherein:

X is C(=O) or $CH_2$;

n is an integer of 0 or 1;

$R^8$ is hydrogen or halo; and $R^9$ is hydrogen, amino, or 5 to 10 membered heteroaryl or heterocyclyl;

with the proviso that when m is 0, $R^9$ is not hydrogen.

In certain embodiments, X is $CH_2$. In certain embodiments, X is C(=O).

In certain embodiments, n is 0. In certain embodiments, n is 1.

In certain embodiments, $R^8$ is hydrogen. In certain embodiments, $R^8$ is halo. In certain embodiments, $R^8$ is fluoro or chloro.

In certain embodiments, $R^9$ is hydrogen. In certain embodiments, $R^9$ is amino. In certain embodiments, $R^9$ is 5 to 10 membered heteroaryl. In certain embodiments, $R^9$ is 5 to 10 membered heterocyclyl.

In one embodiment, the compound is:

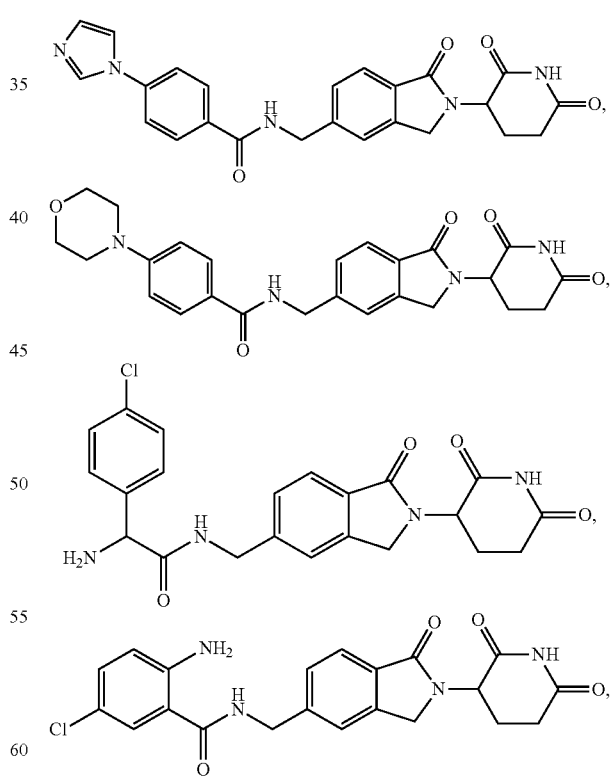

or a pharmaceutically acceptable salt, solvate, prodrug, or stereoisomer thereof.

In yet another embodiment, representative compounds are of Formula XVII:

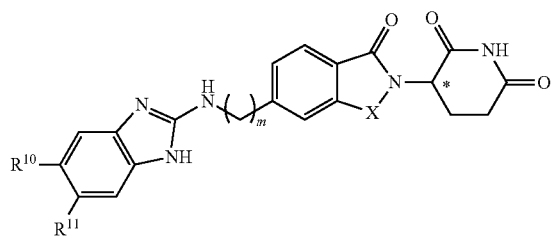

(XVII)

or a pharmaceutically acceptable salt, solvate, prodrug, or stereoisomer thereof, wherein:

X is C(=O) or CH$_2$;

m is an integer of 0, 1, 2, or 3;

R$^{10}$ and R$^{11}$ are each independently hydrogen, halo, C$_{1-6}$ alkyl, or C$_{6-10}$ aryloxy, wherein the alkyl and aryl are each optionally substituted with one or more halo.

In certain embodiments, X is CH$_2$. In certain embodiments, X is C(=O).

In certain embodiments, m is 0. In certain embodiments, m is 1. In certain embodiments, m is 2. In certain embodiments, m is 3.

In certain embodiments, R$^{10}$ is hydrogen. In certain embodiments, R$^{10}$ is halo. In certain embodiments, R$^{10}$ is fluoro or chloro. In certain embodiments, R$^{10}$ is C$_{1-6}$ alkyl, optionally substituted with one or more halo. In certain embodiments, R$^{10}$ is C$_{6-10}$ aryloxy, optionally substituted with one or more halo.

In certain embodiments, R$^{11}$ is hydrogen. In certain embodiments, R$^{11}$ is halo. In certain embodiments, R$^{11}$ is fluoro or chloro. In certain embodiments, R$^{11}$ is C$_{1-6}$ alkyl, optionally substituted with one or more halo. In certain embodiments, R$^{1}$ is C$_{6-10}$ aryloxy, optionally substituted with one or more halo.

In one embodiment, the compound is selected from those listed in Table T, below:

TABLE T

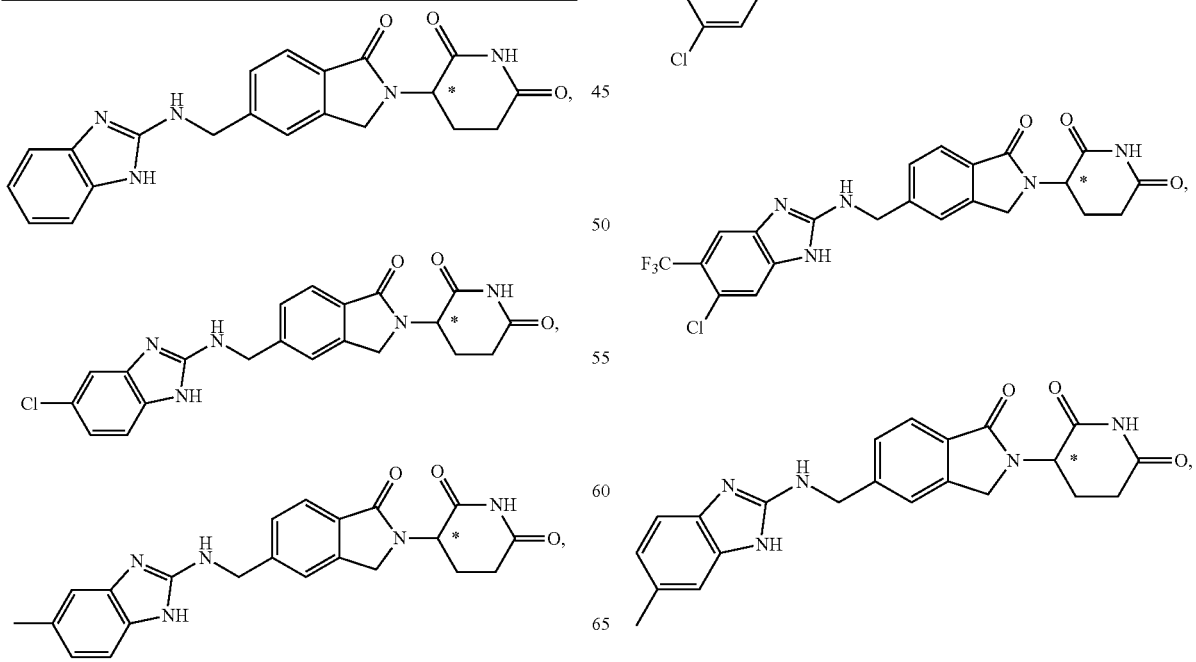

TABLE T-continued

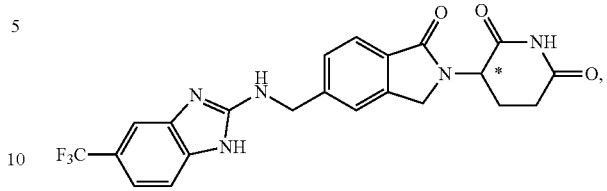

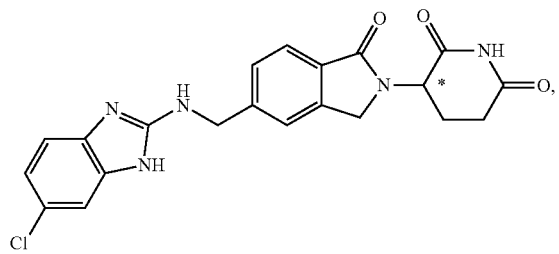 [SMILES: O=C1CCC(N2Cc3cc(CNc4nc5ccc(Cl)cc5[nH]4)ccc3C2=O)C(=O)N1]

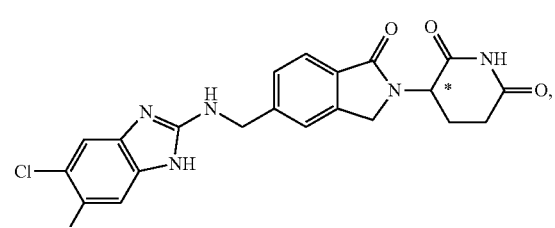

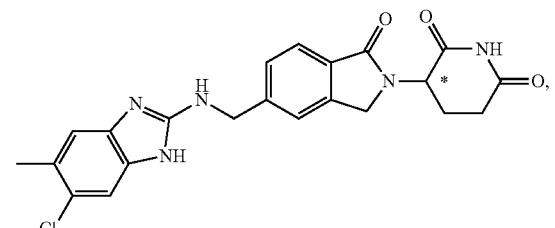

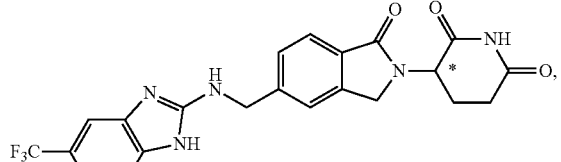

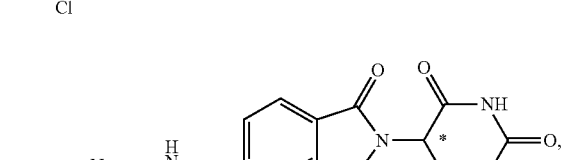

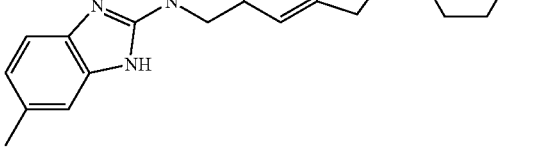

TABLE T-continued
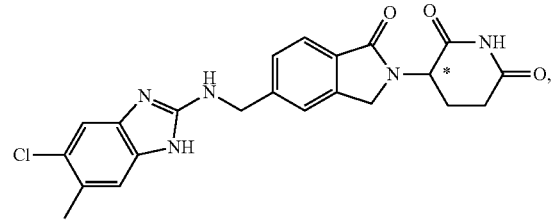 [SMILES: Cc1cc2[nH]c(NCc3ccc4c(c3)CN(C3CCC(=O)NC3=O)C4=O)nc2cc1Cl]
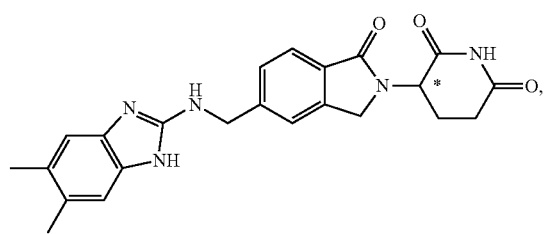 [SMILES: Cc1cc2nc(NCc3ccc4c(c3)CN(C3CCC(=O)NC3=O)C4=O)[nH]c2cc1C]
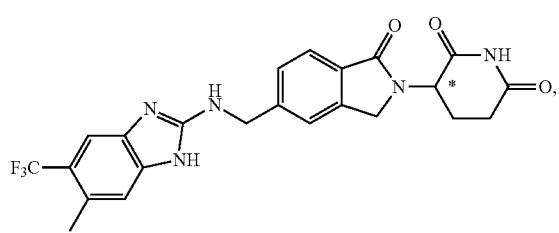 [SMILES: Cc1cc2[nH]c(NCc3ccc4c(c3)CN(C3CCC(=O)NC3=O)C4=O)nc2cc1C(F)(F)F]
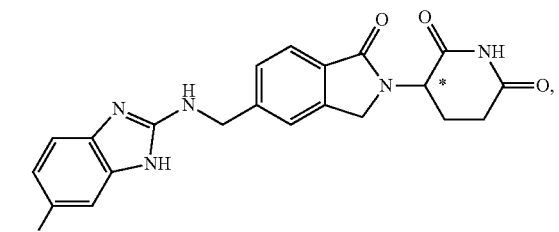
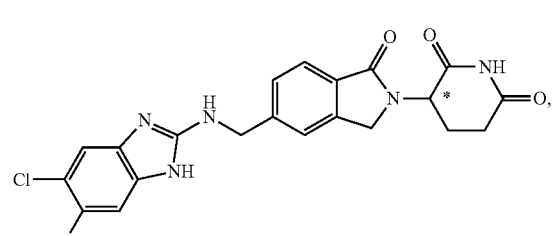
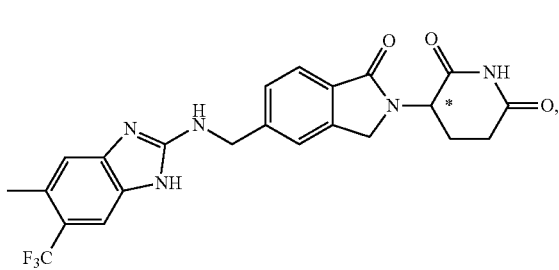 [SMILES: Cc1cc2nc(NCc3ccc4c(c3)CN(C3CCC(=O)NC3=O)C4=O)[nH]c2cc1C(F)(F)F]
TABLE T-continued
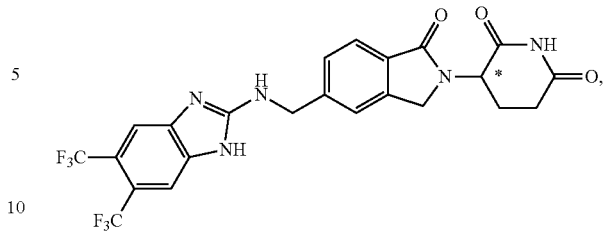
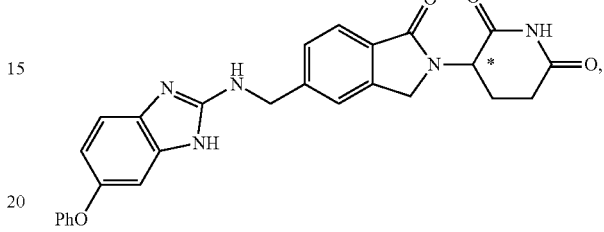
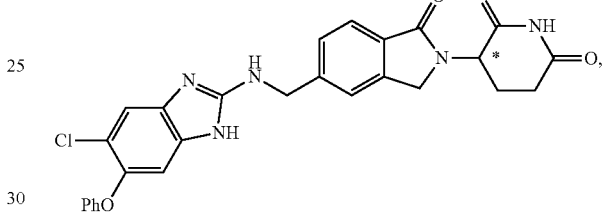
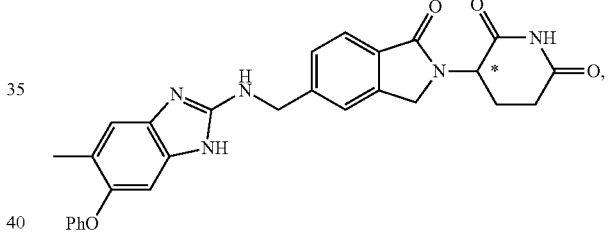
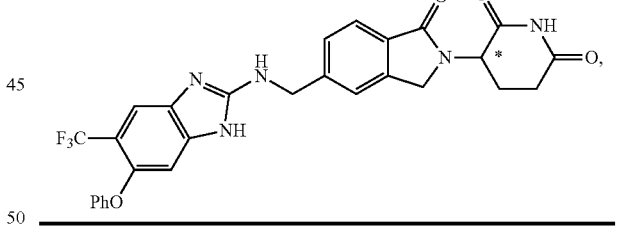
or a pharmaceutically acceptable salt, solvate, prodrug, or stereoisomer thereof.
In yet another embodiment, representative compounds are of Formula XVIII:
(XVIII)
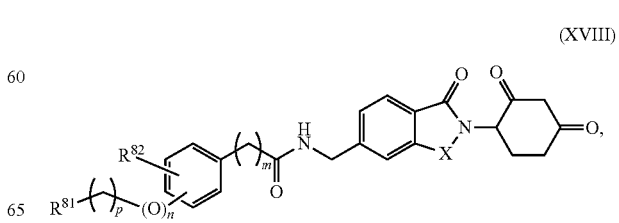

or a pharmaceutically acceptable salt, solvate, prodrug, or stereoisomer thereof, wherein:

X is $CH_2$ or C=O m and n are each independently 0 or 1;

p is 0, 1, 2, or 3;

$R^{81}$ is 5 to 6 membered heterocyclyl, optionally substituted with $C_{1-6}$ alkyl; and $R^{82}$ is hydrogen or halogen.

In one embodiment, X is $CH_2$. In another embodiment, X is C=O.

In one embodiment, m is 0. In another embodiment, m is 1. In another embodiment, n is 0. In another embodiment, n is 1.

In one embodiment, p is 0. In another embodiment, p is 1. In another embodiment, p is 2. In another embodiment, p is 3.

In one embodiment, $R^{81}$ is 5 membered heterocycle. In another embodiment, the 5 membered heterocycle is substituted with $C_{1-6}$ alkyl. In another embodiment, $R^{81}$ is 6 membered heterocycle. In another embodiment, the 6 membered heterocycle is substituted with $C_{1-6}$ alkyl.

In one embodiment, $R^{82}$ is hydrogen. In another embodiment, $R^{82}$ is halogen.

In one embodiment, the compound is selected from those listed in Table U, below:

TABLE U

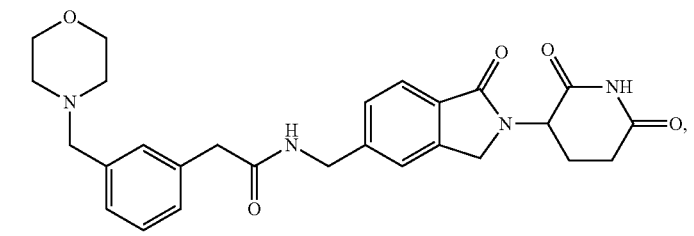 [SMILES: O=C(Cc1cccc(CN2CCOCC2)c1)NCc1ccc2c(c1)CN(C1CCC(=O)NC1=O)C2=O]

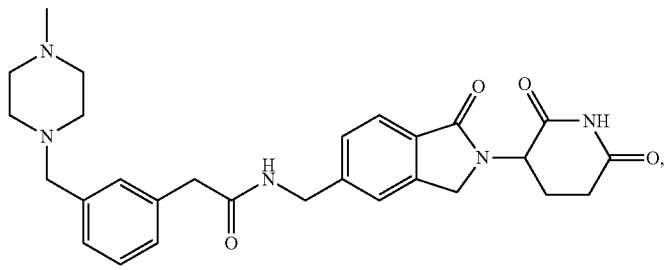 [SMILES: CN1CCN(Cc2cccc(CC(=O)NCc3ccc4c(c3)CN(C3CCC(=O)NC3=O)C4=O)c2)CC1]

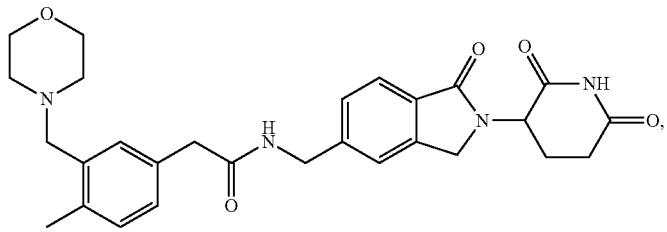 [SMILES: Cc1ccc(CC(=O)NCc2ccc3c(c2)CN(C2CCC(=O)NC2=O)C3=O)cc1CN1CCOCC1]

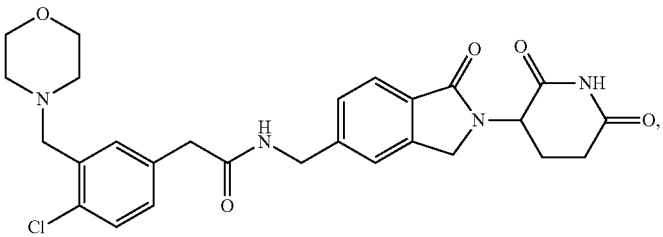 [SMILES: O=C(Cc1ccc(Cl)c(CN2CCOCC2)c1)NCc1ccc2c(c1)CN(C1CCC(=O)NC1=O)C2=O]

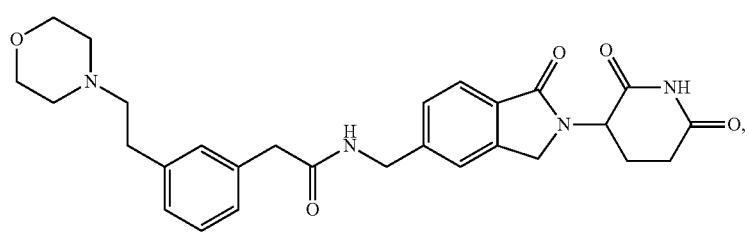 [SMILES: O=C(Cc1cccc(CCN2CCOCC2)c1)NCc1ccc2c(c1)CN(C1CCC(=O)NC1=O)C2=O]

TABLE U-continued
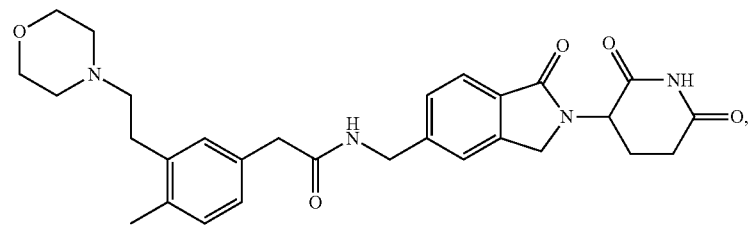 [SMILES: Cc1ccc(CC(=O)NCc2ccc3c(c2)CN(C2CCC(=O)NC2=O)C3=O)cc1CCN1CCOCC1]
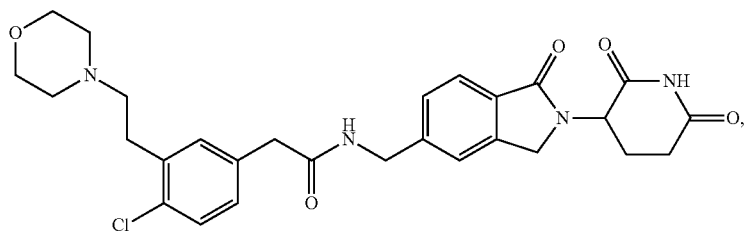 [SMILES: O=C(Cc1ccc(Cl)c(CCN2CCOCC2)c1)NCc1ccc2c(c1)CN(C1CCC(=O)NC1=O)C2=O]
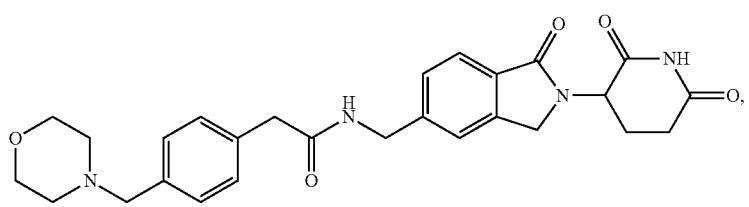 [SMILES: O=C(Cc1ccc(CN2CCOCC2)cc1)NCc1ccc2c(c1)CN(C1CCC(=O)NC1=O)C2=O]
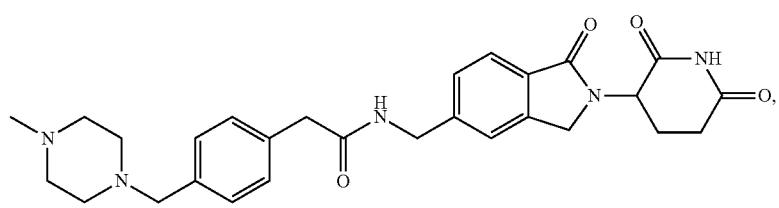 [SMILES: CN1CCN(Cc2ccc(CC(=O)NCc3ccc4c(c3)CN(C3CCC(=O)NC3=O)C4=O)cc2)CC1]
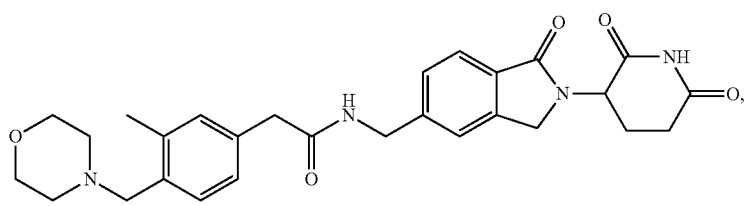 [SMILES: Cc1cc(CC(=O)NCc2ccc3c(c2)CN(C2CCC(=O)NC2=O)C3=O)ccc1CN1CCOCC1]
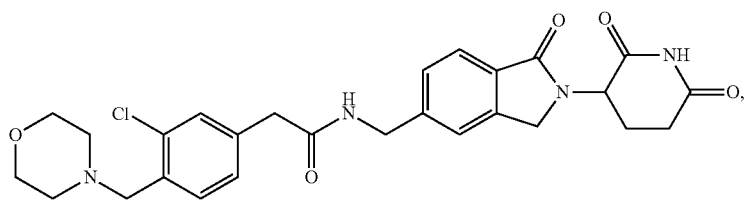 [SMILES: O=C(Cc1ccc(CN2CCOCC2)c(Cl)c1)NCc1ccc2c(c1)CN(C1CCC(=O)NC1=O)C2=O]
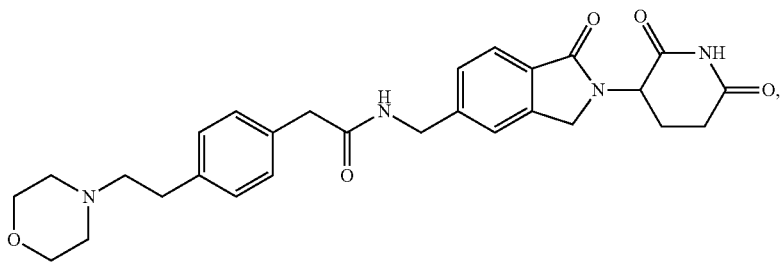 [SMILES: O=C(Cc1ccc(CCN2CCOCC2)cc1)NCc1ccc2c(c1)CN(C1CCC(=O)NC1=O)C2=O]

TABLE U-continued
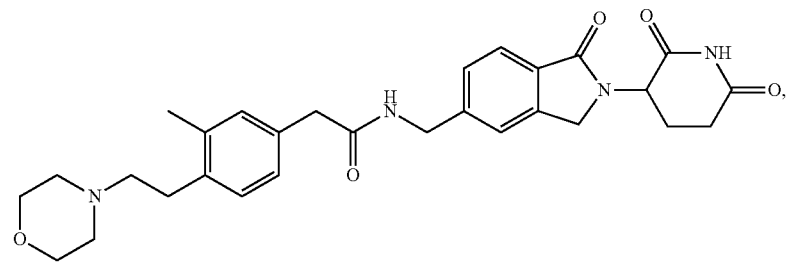
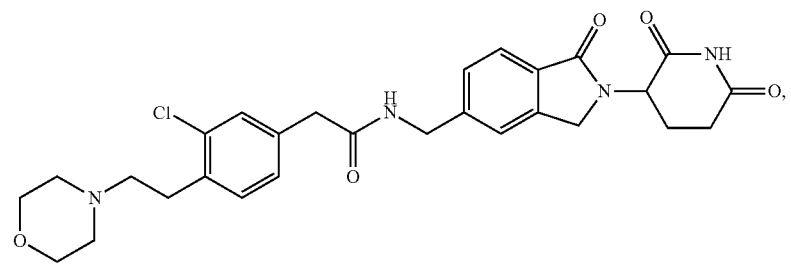 [SMILES: Cc1cc(CC(=O)NCc2ccc3c(c2)CN(C2CCC(=O)NC2=O)C3=O)ccc1CCN1CCOCC1]
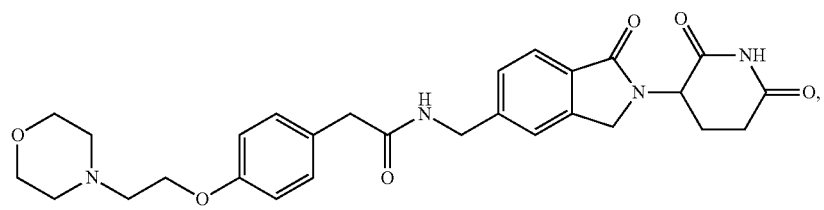 [SMILES: O=C(Cc1ccc(OCCN2CCOCC2)cc1)NCc1ccc2c(c1)CN(C1CCC(=O)NC1=O)C2=O]
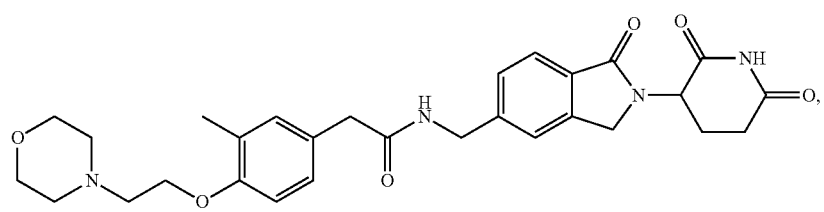 [SMILES: Cc1cc(CC(=O)NCc2ccc3c(c2)CN(C2CCC(=O)NC2=O)C3=O)ccc1OCCN1CCOCC1]
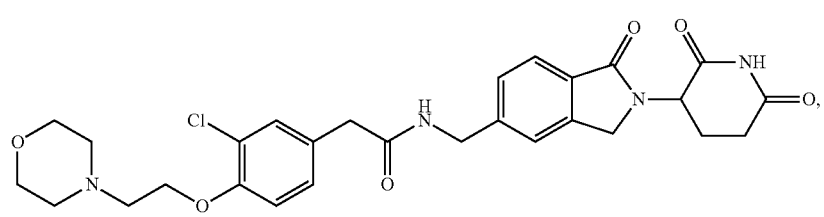 [SMILES: O=C(Cc1ccc(OCCN2CCOCC2)c(Cl)c1)NCc1ccc2c(c1)CN(C1CCC(=O)NC1=O)C2=O]
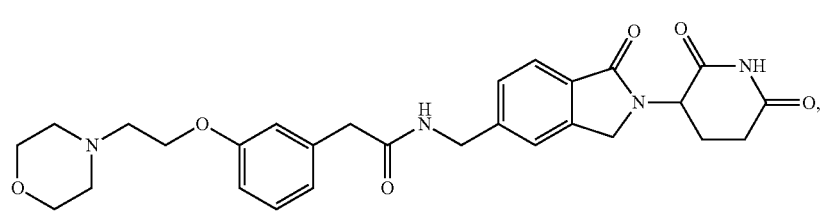 [SMILES: O=C(Cc1cccc(OCCN2CCOCC2)c1)NCc1ccc2c(c1)CN(C1CCC(=O)NC1=O)C2=O]
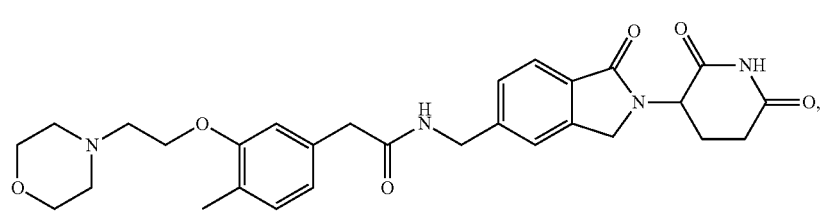 [SMILES: Cc1ccc(CC(=O)NCc2ccc3c(c2)CN(C2CCC(=O)NC2=O)C3=O)cc1OCCN1CCOCC1]

TABLE U-continued
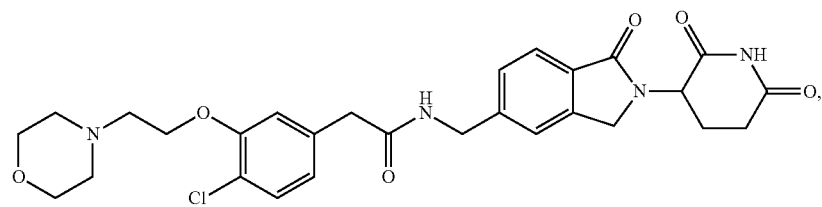 [SMILES: O=C(Cc1ccc(Cl)c(OCCN2CCOCC2)c1)NCc1ccc2c(c1)CN(C1CCC(=O)NC1=O)C2=O]
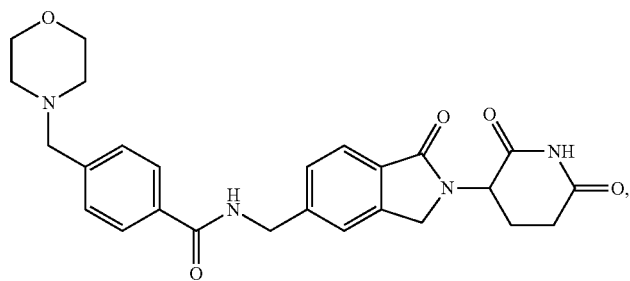 [SMILES: O=C1CCC(N2Cc3cc(CNC(=O)c4ccc(CN5CCOCC5)cc4)ccc3C2=O)C(=O)N1]
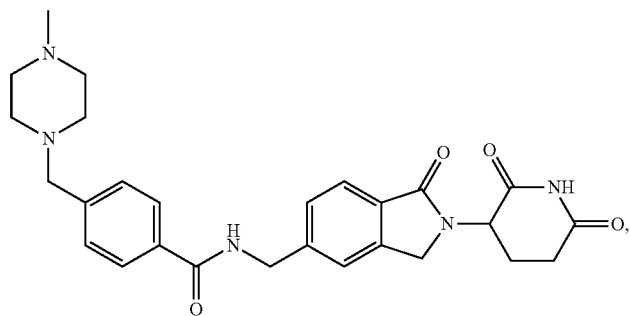 [SMILES: CN1CCN(Cc2ccc(C(=O)NCc3ccc4c(c3)CN(C3CCC(=O)NC3=O)C4=O)cc2)CC1]
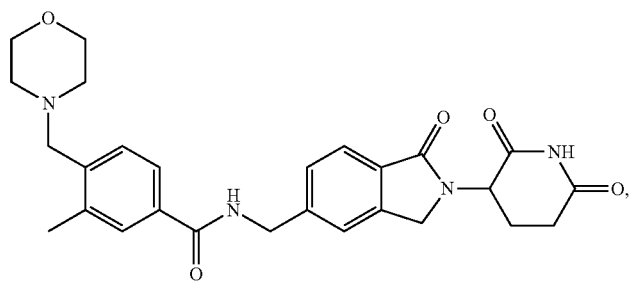 [SMILES: Cc1cc(C(=O)NCc2ccc3c(c2)CN(C2CCC(=O)NC2=O)C3=O)ccc1CN1CCOCC1]
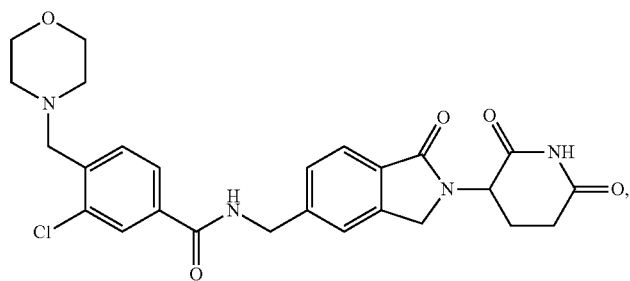

TABLE U-continued
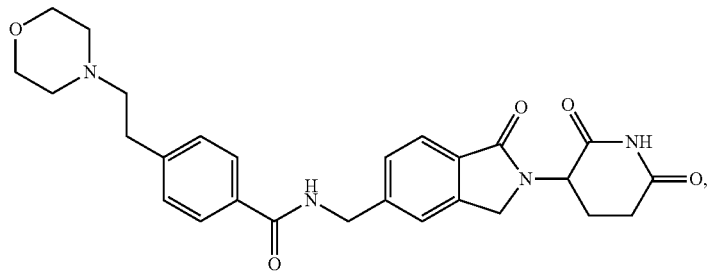 [SMILES: O=C1CCC(N2Cc3cc(CNC(=O)c4ccc(CCN5CCOCC5)cc4)ccc3C2=O)C(=O)N1]
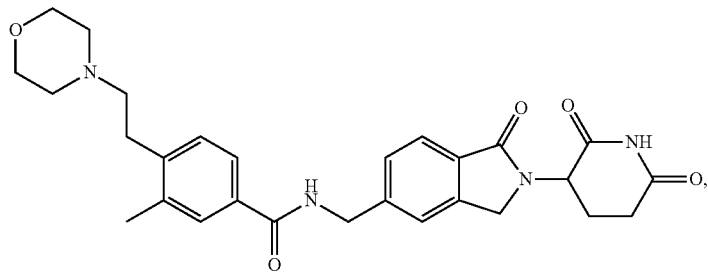 [SMILES: Cc1cc(C(=O)NCc2ccc3c(c2)CN(C2CCC(=O)NC2=O)C3=O)ccc1CCN1CCOCC1]
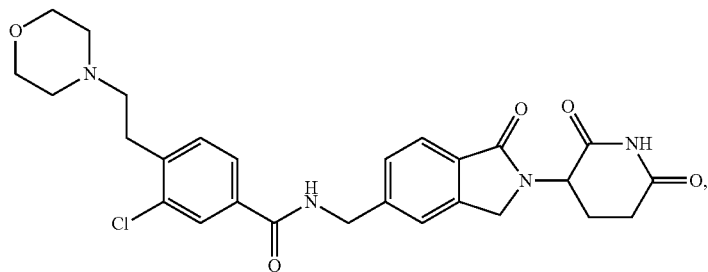 [SMILES: O=C1CCC(N2Cc3cc(CNC(=O)c4ccc(CCN5CCOCC5)c(Cl)c4)ccc3C2=O)C(=O)N1]
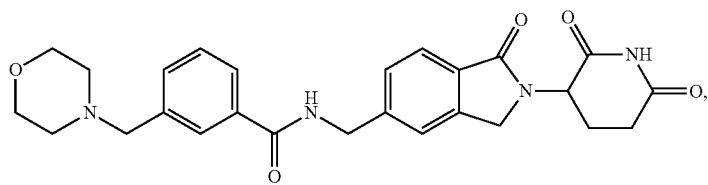 [SMILES: O=C1CCC(N2Cc3cc(CNC(=O)c4cccc(CN5CCOCC5)c4)ccc3C2=O)C(=O)N1]
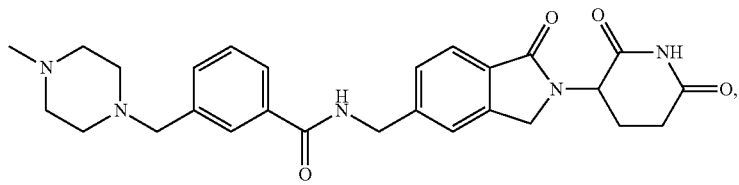 [SMILES: CN1CCN(Cc2cccc(C(=O)NCc3ccc4c(c3)CN(C3CCC(=O)NC3=O)C4=O)c2)CC1]
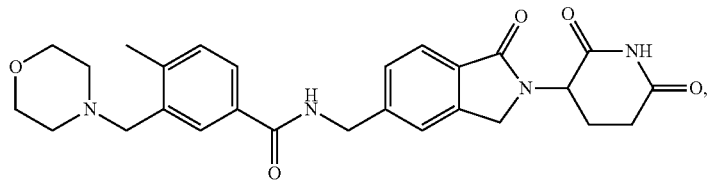 [SMILES: Cc1ccc(C(=O)NCc2ccc3c(c2)CN(C2CCC(=O)NC2=O)C3=O)cc1CN1CCOCC1]
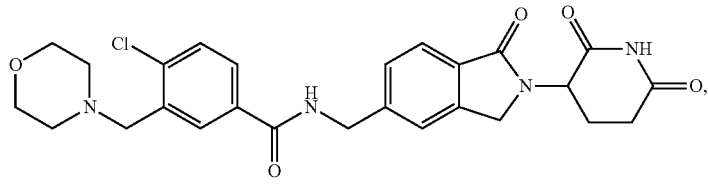 [SMILES: O=C1CCC(N2Cc3cc(CNC(=O)c4ccc(Cl)c(CN5CCOCC5)c4)ccc3C2=O)C(=O)N1]

TABLE U-continued
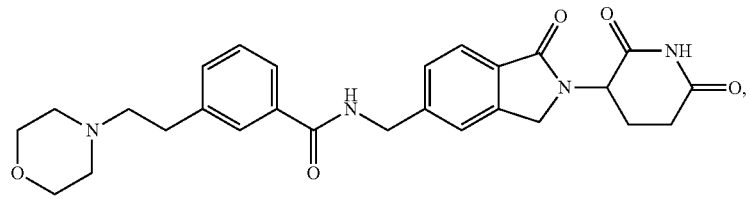 [SMILES: O=C1CCC(N2Cc3cc(CNC(=O)c4cccc(CCN5CCOCC5)c4)ccc3C2=O)C(=O)N1]
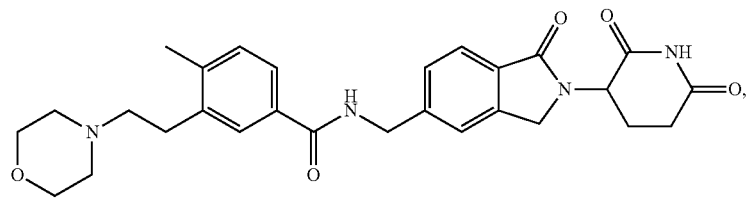 [SMILES: Cc1ccc(C(=O)NCc2ccc3c(c2)CN(C2CCC(=O)NC2=O)C3=O)cc1CCN1CCOCC1]
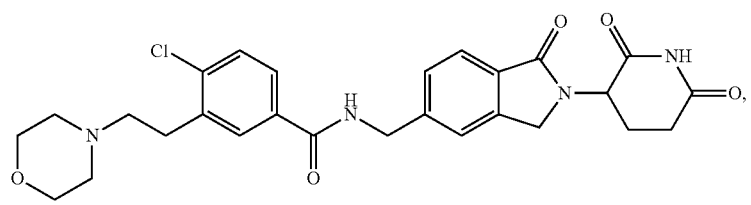 [SMILES: O=C1CCC(N2Cc3cc(CNC(=O)c4ccc(Cl)c(CCN5CCOCC5)c4)ccc3C2=O)C(=O)N1]
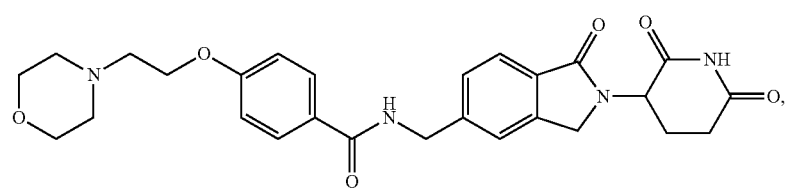 [SMILES: O=C1CCC(N2Cc3cc(CNC(=O)c4ccc(OCCN5CCOCC5)cc4)ccc3C2=O)C(=O)N1]
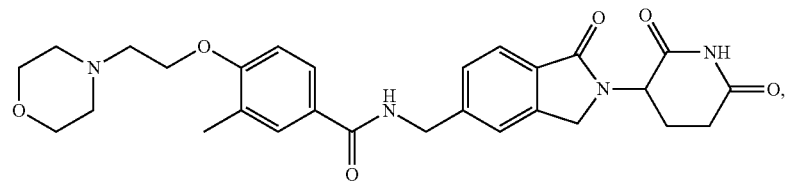 [SMILES: Cc1cc(C(=O)NCc2ccc3c(c2)CN(C2CCC(=O)NC2=O)C3=O)ccc1OCCN1CCOCC1]
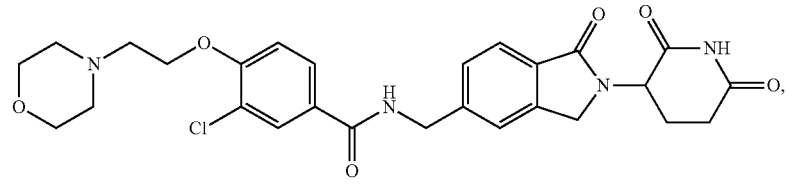 [SMILES: O=C1CCC(N2Cc3cc(CNC(=O)c4ccc(OCCN5CCOCC5)c(Cl)c4)ccc3C2=O)C(=O)N1]
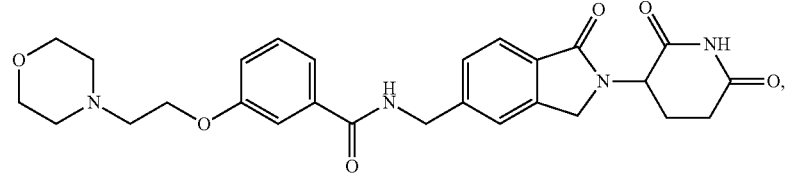 [SMILES: O=C1CCC(N2Cc3cc(CNC(=O)c4cccc(OCCN5CCOCC5)c4)ccc3C2=O)C(=O)N1]
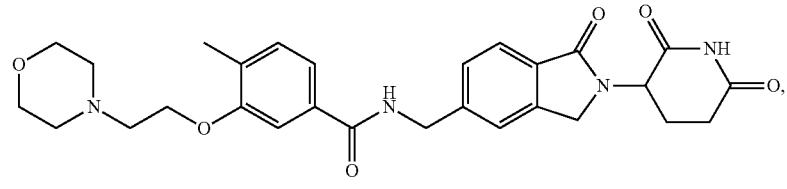 [SMILES: Cc1ccc(C(=O)NCc2ccc3c(c2)CN(C2CCC(=O)NC2=O)C3=O)cc1OCCN1CCOCC1]

TABLE U-continued
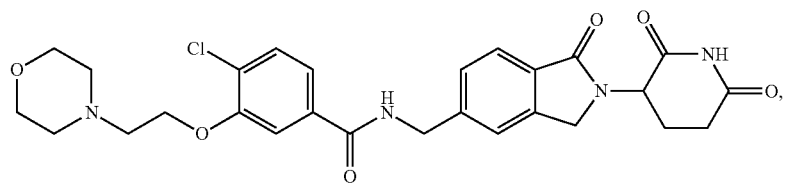 [SMILES: O=C1CCC(N2Cc3cc(CNC(=O)c4ccc(Cl)c(OCCN5CCOCC5)c4)ccc3C2=O)C(=O)N1]
or a pharmaceutically acceptable salt, solvate, prodrug, or stereoisomer thereof.
In yet another embodiment, representative compounds are of the following formula in Table V, below:
TABLE V
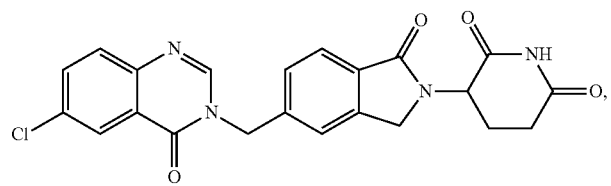 [SMILES: O=C1CCC(N2Cc3cc(Cn4cnc5ccc(Cl)cc5c4=O)ccc3C2=O)C(=O)N1]
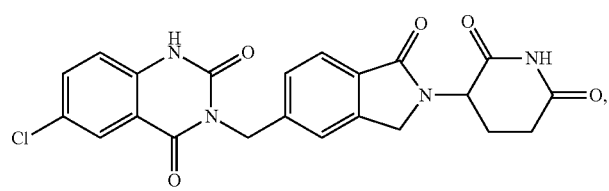 [SMILES: O=C1CCC(N2Cc3cc(Cn4c(=O)[nH]c5ccc(Cl)cc5c4=O)ccc3C2=O)C(=O)N1]
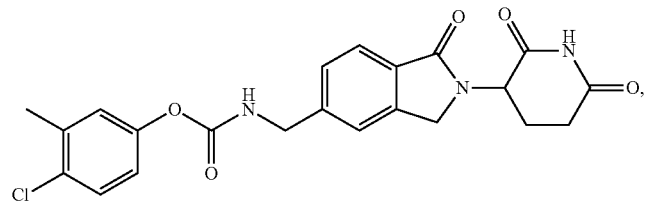 [SMILES: Cc1cc(OC(=O)NCc2ccc3c(c2)CN(C2CCC(=O)NC2=O)C3=O)ccc1Cl]
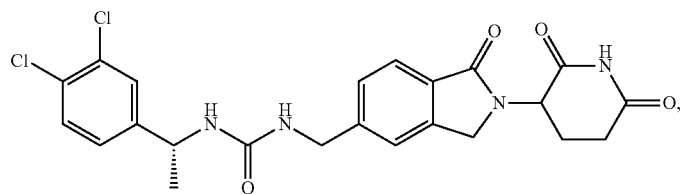 [SMILES: C[C@@H](NC(=O)NCc1ccc2c(c1)CN(C1CCC(=O)NC1=O)C2=O)c1ccc(Cl)c(Cl)c1]
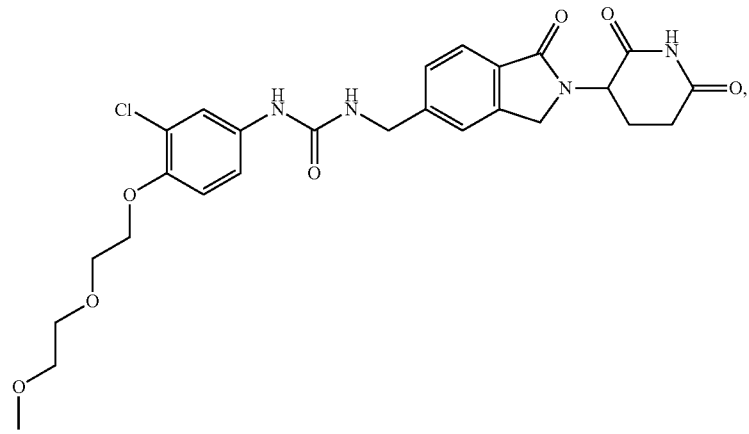 [SMILES: COCCOCCOc1ccc(NC(=O)NCc2ccc3c(c2)CN(C2CCC(=O)NC2=O)C3=O)cc1Cl]

TABLE V-continued

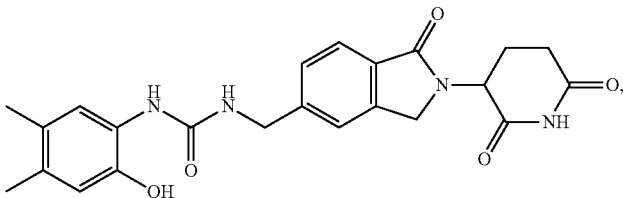 [SMILES: Cc1cc(O)c(NC(=O)NCc2ccc3c(c2)CN(C2CCC(=O)NC2=O)C3=O)cc1C]

or a pharmaceutically acceptable salt, solvate, prodrug, or stereoisomer thereof.

Still other specific immunomodulatory drugs provided herein belong to a class of 4'-arylmethoxy isoindoline compounds disclosed in U.S. Patent Application Publication No. US 2011/0196150, the entirety of which is incorporated herein by reference. Representative compounds are of formula XIX:

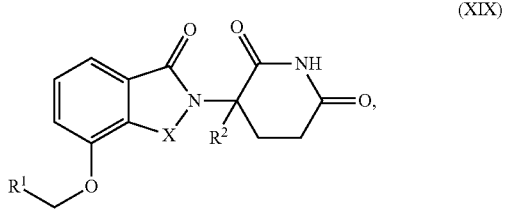

or a pharmaceutically acceptable salt, solvate or stereoisomer thereof, wherein:

X is C=O or $CH_2$;
$R^1$ is —Y—$R^3$;
$R^2$ is H or ($C_1$-$C_6$)alkyl;
Y is: 6 to 10 membered aryl, heteroaryl or heterocycle, each of which may be optionally substituted with one or more halogen; or a bond;
$R^3$ is: —$(CH_2)_n$-aryl, —O—$(CH_2)_n$-aryl or —$(CH_2)_n$—O-aryl, wherein the aryl is optionally substituted with one or more: ($C_1$-$C_6$)alkyl, itself optionally substituted with one or more halogen; ($C_1$-$C_6$)alkoxy, itself substituted with one or more halogen; oxo; amino; carboxyl; cyano; hydroxyl; halogen; deuterium; 6 to 10 membered aryl or heteroaryl, optionally substituted with one or more ($C_1$-$C_6$)alkyl, ($C_1$-$C_6$)alkoxy or halogen; —$CONH_2$; or —COO—($C_1$-$C_6$)alkyl, wherein the alkyl may be optionally substituted with one or more halogen; —$(CH_2)_n$-heterocycle, —O—$(CH_2)_n$-heterocycle or —$(CH_2)_n$—O-heterocycle, wherein the heterocycle is optionally substituted with one or more: ($C_1$-$C_6$)alkyl, itself optionally substituted with one or more halogen; ($C_1$-$C_6$)alkoxy, itself substituted with one or more halogen; oxo; amino; carboxyl; cyano; hydroxyl; halogen; deuterium; 6 to 10 membered aryl or heteroaryl, optionally substituted with one or more ($C_1$-$C_6$)alkyl, ($C_1$-$C_6$)alkoxy or halogen; —$CONH_2$; or —COO—($C_1$-$C_6$)alkyl, wherein the alkyl may be optionally substituted with one or more halogen; or —$(CH_2)_n$-heteroaryl, —O—$(CH_2)_n$-heteroaryl or —$(CH_2)_n$—O-heteroaryl, wherein the heteroaryl is optionally substituted with one or more: ($C_1$-$C_6$)alkyl, itself optionally substituted with one or more halogen; ($C_1$-$C_6$)alkoxy, itself substituted with one or more halogen; oxo; amino; carboxyl; cyano; hydroxyl; halogen; deuterium; 6 to 10 membered aryl or heteroaryl, optionally substituted with one or more ($C_1$-$C_6$)alkyl, ($C_1$-$C_6$)alkoxy or halogen; —$CONH_2$; or —COO—($C_1$-$C_6$)alkyl, wherein the alkyl may be optionally substituted with one or more halogen; and n is 0, 1, 2 or 3.

In one embodiment, X is C=O. In another embodiment, C is $CH_2$.

In one embodiment, $R^2$ is H. In another embodiment, $R^2$ is ($C_1$-$C_6$)alkyl.

In one embodiment, Y is aryl. In another embodiment, Y is heteroaryl. In another embodiment, Y is heterocycle. In another embodiment, Y is a bond.

In one embodiment, $R^3$ is unsubstituted —$(CH_2)_n$-aryl. In another embodiment, $R^3$ is —$(CH_2)_n$-aryl substituted with one or more ($C_1$-$C_6$)alkyl, itself optionally substituted with one or more halogen. In another embodiment, $R^3$ is —$(CH_2)_n$-aryl substituted with one or more ($C_1$-$C_6$)alkoxy, itself substituted with one or more halogen. In another embodiment, $R^3$ is —$(CH_2)_n$-aryl substituted with one or more oxo. In another embodiment, $R^3$ is —$(CH_2)_n$-aryl substituted with one or more amino. In another embodiment, $R^3$ is —$(CH_2)_n$-aryl substituted with one or more carboxyl. In another embodiment, $R^3$ is —$(CH_2)_n$-aryl substituted with one or more cyano. In another embodiment, $R^3$ is —$(CH_2)_n$-aryl substituted with one or more hydroxyl. In another embodiment, $R^3$ is —$(CH_2)_n$-aryl substituted with one or more halogen. In another embodiment, $R^3$ is —$(CH_2)_n$-aryl substituted with one or more deuterium. In another embodiment, $R^3$ is —$(CH_2)_n$-aryl substituted with one or more 6 to 10 membered aryl, optionally substituted with one or more ($C_1$-$C_6$)alkyl. In another embodiment, $R^3$ is —$(CH_2)_n$-aryl substituted with one or more 6 to 10 membered heteroaryl, optionally substituted with one or more ($C_1$-$C_6$)alkyl, ($C_1$-$C_6$)alkoxy or halogen. In another embodiment, $R^3$ is —$(CH_2)_n$-aryl substituted with one or more —$CONH_2$. In another embodiment, $R^3$ is —$(CH_2)_n$-aryl substituted with one or more —COO—($C_1$-$C_6$)alkyl, wherein the alkyl may be optionally substituted with one or more halogen.

In one embodiment, $R^3$ is unsubstituted —O—$(CH_2)_n$-aryl. In another embodiment, $R^3$ is —O—$(CH_2)_n$-aryl substituted with one or more ($C_1$-$C_6$)alkyl, itself optionally substituted with one or more halogen. In another embodiment, $R^3$ is —O—$(CH_2)_n$-aryl substituted with one or more ($C_1$-$C_6$)alkoxy, itself substituted with one or more halogen. In another embodiment, $R^3$ is —O—$(CH_2)_n$-aryl substituted with one or more oxo. In another embodiment, $R^3$ is —O—$(CH_2)_n$-aryl substituted with one or more amino. In another embodiment, $R^3$ is —O—$(CH_2)_n$-aryl substituted with one or more carboxyl. In another embodiment, $R^3$ is —O—$(CH_2)_n$-aryl substituted with one or more cyano. In another embodiment, $R^3$ is —O—$(CH_2)_n$-aryl substituted with one or more hydroxyl. In another embodiment, $R^3$ is —O—$(CH_2)_n$-aryl substituted with one or more halogen. In another embodiment, $R^3$ is —O—$(CH_2)_n$-aryl substituted with one or more deuterium. In another embodiment, $R^3$ is —O—$(CH_2)_n$-aryl substituted with one or more 6 to 10 membered aryl, optionally substituted with one or more ($C_1$-$C_6$)alkyl. In another embodiment, $R^3$ is —O—($CH_2$)$_n$-aryl substituted with one or more 6 to 10 membered heteroaryl, optionally substituted with one or more ($C_1$-$C_6$)alkyl, ($C_1$-$C_6$)alkoxy or halogen. In another embodiment, $R^3$ is —O—($CH_2$)-aryl substituted with one or more —CONH$_2$. In another embodiment, $R^3$ is —O—($CH_2$)$_n$-aryl substituted with one or more —COO—($C_1$-$C_6$)alkyl, wherein the alkyl may be optionally substituted with one or more halogen.

In one embodiment, $R^3$ is unsubstituted —($CH_2$)$_n$—O-aryl. In another embodiment, $R^3$ is —($CH_2$)$_n$—O-aryl substituted with one or more ($C_1$-$C_6$)alkyl, itself optionally substituted with one or more halogen. In another embodiment, $R^3$ is —($CH_2$)$_n$—O-aryl substituted with one or more ($C_1$-$C_6$)alkoxy, itself substituted with one or more halogen. In another embodiment, $R^3$ is —($CH_2$)$_n$—O-aryl substituted with one or more oxo. In another embodiment, $R^3$ is —($CH_2$)$_n$—O-aryl substituted with one or more amino. In another embodiment, $R^3$ is —($CH_2$)$_n$—O-aryl substituted with one or more carboxyl. In another embodiment, $R^3$ is —($CH_2$)$_n$—O-aryl substituted with one or more cyano. In another embodiment, $R^3$ is —($CH_2$)$_n$—O-aryl substituted with one or more hydroxyl. In another embodiment, $R^3$ is —($CH_2$)$_n$—O-aryl substituted with one or more halogen. In another embodiment, $R^3$ is —($CH_2$)$_n$—O-aryl substituted with one or more deuterium. In another embodiment, $R^3$ is —($CH_2$)$_n$—O-aryl substituted with one or more 6 to 10 membered aryl, optionally substituted with one or more ($C_1$-$C_6$)alkyl. In another embodiment, $R^3$ is —($CH_2$)$_n$—O-aryl substituted with one or more 6 to 10 membered heteroaryl, optionally substituted with one or more ($C_1$-$C_6$)alkyl, ($C_1$-$C_6$)alkoxy or halogen. In another embodiment, $R^3$ is —($CH_2$)$_n$—O-aryl substituted with one or more —CONH$_2$. In another embodiment, $R^3$ is —($CH_2$)$_n$—O-aryl substituted with one or more —COO—($C_1$-$C_6$)alkyl, wherein the alkyl may be optionally substituted with one or more halogen.

In one embodiment, $R^3$ is unsubstituted —($CH_2$)$_n$-heterocycle. In another embodiment, $R^3$ is —($CH_2$)$_n$-heterocycle substituted with one or more ($C_1$-$C_6$)alkyl, itself optionally substituted with one or more halogen. In another embodiment, $R^3$ is —($CH_2$)$_n$-heterocycle substituted with one or more ($C_1$-$C_6$)alkoxy, itself substituted with one or more halogen. In another embodiment, $R^3$ is —($CH_2$)$_n$-heterocycle substituted with one or more oxo. In another embodiment, $R^3$ is —($CH_2$)$_n$-heterocycle substituted with one or more amino. In another embodiment, $R^3$ is —($CH_2$)$_n$-heterocycle substituted with one or more carboxyl. In another embodiment, $R^3$ is —($CH_2$)$_n$-heterocycle substituted with one or more cyano. In another embodiment, $R^3$ is —($CH_2$)$_n$-heterocycle substituted with one or more hydroxyl. In another embodiment, $R^3$ is —($CH_2$)$_n$-heterocycle substituted with one or more halogen. In another embodiment, $R^3$ is —($CH_2$)$_n$-heterocycle substituted with one or more deuterium. In another embodiment, $R^3$ is —($CH_2$)$_n$-heterocycle substituted with one or more 6 to 10 membered aryl, optionally substituted with one or more ($C_1$-$C_6$)alkyl. In another embodiment, $R^3$ is —($CH_2$)$_n$-heterocycle substituted with one or more 6 to 10 membered heteroaryl, optionally substituted with one or more ($C_1$-$C_6$)alkyl, ($C_1$-$C_6$)alkoxy or halogen. In another embodiment, $R^3$ is —($CH_2$)$_n$-heterocycle substituted with one or more —CONH$_2$. In another embodiment, $R^3$ is —($CH_2$)$_n$-heterocycle substituted with one or more —COO—($C_1$-$C_6$)alkyl, wherein the alkyl may be optionally substituted with one or more halogen.

In one embodiment, $R^3$ is unsubstituted —O—($CH_2$)$_n$-heterocycle. In another embodiment, $R^3$ is —O—($CH_2$)$_n$-heterocycle substituted with one or more ($C_1$-$C_6$)alkyl, itself optionally substituted with one or more halogen. In another embodiment, $R^3$ is —O—($CH_2$)-heterocycle substituted with one or more ($C_1$-$C_6$)alkoxy, itself substituted with one or more halogen. In another embodiment, $R^3$ is —O—($CH_2$)$_n$-heterocycle substituted with one or more oxo. In another embodiment, $R^3$ is —O—($CH_2$)$_n$-heterocycle substituted with one or more amino. In another embodiment, $R^3$ is —O—($CH_2$)$_n$-heterocycle substituted with one or more carboxyl. In another embodiment, $R^3$ is —O—($CH_2$)$_n$-heterocycle substituted with one or more cyano. In another embodiment, $R^3$ is —O—($CH_2$)$_n$-heterocycle substituted with one or more hydroxyl. In another embodiment, $R^3$ is —O—($CH_2$)$_n$-heterocycle substituted with one or more halogen. In another embodiment, $R^3$ is —O—($CH_2$)$_n$-heterocycle substituted with one or more deuterium. In another embodiment, $R^3$ is —O—($CH_2$)$_n$-heterocycle substituted with one or more 6 to 10 membered aryl, optionally substituted with one or more ($C_1$-$C_6$)alkyl. In another embodiment, $R^3$ is —O—($CH_2$)$_n$-heterocycle substituted with one or more 6 to 10 membered heteroaryl, optionally substituted with one or more ($C_1$-$C_6$)alkyl, ($C_1$-$C_6$)alkoxy or halogen. In another embodiment, $R^3$ is —O—($CH_2$)$_n$-heterocycle substituted with one or more —CONH$_2$. In another embodiment, $R^3$ is —O—($CH_2$)$_n$-heterocycle substituted with one or more —COO—($C_1$-$C_6$)alkyl, wherein the alkyl may be optionally substituted with one or more halogen.

In one embodiment, $R^3$ is unsubstituted —($CH_2$)$_n$—O-heterocycle. In another embodiment, $R^3$ is —($CH_2$)$_n$—O-heterocycle substituted with one or more ($C_1$-$C_6$)alkyl, itself optionally substituted with one or more halogen. In another embodiment, $R^3$ is —($CH_2$)$_n$—O-heterocycle substituted with one or more ($C_1$-$C_6$)alkoxy, itself substituted with one or more halogen. In another embodiment, $R^3$ is —($CH_2$)$_n$—O-heterocycle substituted with one or more oxo. In another embodiment, $R^3$ is —($CH_2$)$_n$—O-heterocycle substituted with one or more amino. In another embodiment, $R^3$ is —($CH_2$)$_n$—O-heterocycle substituted with one or more carboxyl. In another embodiment, $R^3$ is —($CH_2$)$_n$—O-heterocycle substituted with one or more cyano. In another embodiment, $R^3$ is —($CH_2$)$_n$—O-heterocycle substituted with one or more hydroxyl. In another embodiment, $R^3$ is —($CH_2$)$_n$—O-heterocycle substituted with one or more halogen. In another embodiment, $R^3$ is —($CH_2$)$_n$—O-heterocycle substituted with one or more deuterium. In another embodiment, $R^3$ is —($CH_2$)$_n$—O-heterocycle substituted with one or more 6 to 10 membered aryl, optionally substituted with one or more ($C_1$-$C_6$)alkyl. In another embodiment, $R^3$ is —($CH_2$)$_n$—O-heterocycle substituted with one or more 6 to 10 membered heteroaryl, optionally substituted with one or more ($C_1$-$C_6$)alkyl, ($C_1$-$C_6$)alkoxy or halogen. In another embodiment, $R^3$ is —($CH_2$)$_n$—O-heterocycle substituted with one or more —CONH$_2$. In another embodiment, $R^3$ is —($CH_2$)$_n$—O-heterocycle substituted with one or more —COO—($C_1$-$C_6$)alkyl, wherein the alkyl may be optionally substituted with one or more halogen.

In one embodiment, $R^3$ is unsubstituted —($CH_2$)$_n$-heteroaryl. In another embodiment, $R^3$ is —($CH_2$)$_n$-heteroaryl substituted with one or more ($C_1$-$C_6$)alkyl, itself optionally substituted with one or more halogen. In another embodiment, $R^3$ is —($CH_2$)$_n$-heteroaryl substituted with one or more ($C_1$-$C_6$)alkoxy, itself substituted with one or more halogen. In another embodiment, $R^3$ is —($CH_2$)$_n$-heteroaryl substituted with one or more oxo. In another embodiment, $R^3$ is —($CH_2$)$_n$-heteroaryl substituted with one or more amino. In another embodiment, $R^3$ is —$(CH_2)_n$-heteroaryl substituted with one or more carboxyl. In another embodiment, $R^3$ is —$(CH_2)_n$-heteroaryl substituted with one or more cyano. In another embodiment, $R^3$ is —$(CH_2)_n$-heteroaryl substituted with one or more hydroxyl. In another embodiment, $R^3$ is —$(CH_2)_n$-heteroaryl substituted with one or more halogen. In another embodiment, $R^3$ is —$(CH_2)_n$-heteroaryl substituted with one or more deuterium. In another embodiment, $R^3$ is —$(CH_2)_n$-heteroaryl substituted with one or more 6 to 10 membered aryl, optionally substituted with one or more ($C_1$-$C_6$)alkyl. In another embodiment, $R^3$ is —$(CH_2)_n$-heteroaryl substituted with one or more 6 to 10 membered heteroaryl, optionally substituted with one or more ($C_1$-$C_6$)alkyl, ($C_1$-$C_6$)alkoxy or halogen. In another embodiment, $R^3$ is —$(CH_2)_n$-heteroaryl substituted with one or more —$CONH_2$. In another embodiment, $R^3$ is —$(CH_2)_n$-heteroaryl substituted with one or more —COO—($C_1$-$C_6$)alkyl, wherein the alkyl may be optionally substituted with one or more halogen.

In one embodiment, $R^3$ is unsubstituted —O—$(CH_2)_n$-heteroaryl. In another embodiment, $R^3$ is —O—$(CH_2)_n$-heteroaryl substituted with one or more ($C_1$-$C_6$)alkyl, itself optionally substituted with one or more halogen. In another embodiment, $R^3$ is —O—$(CH_2)_n$-heteroaryl substituted with one or more ($C_1$-$C_6$)alkoxy, itself substituted with one or more halogen. In another embodiment, $R^3$ is —O—$(CH_2)_n$-heteroaryl substituted with one or more oxo. In another embodiment, $R^3$ is —O—$(CH_2)_n$-heteroaryl substituted with one or more amino. In another embodiment, $R^3$ is —O—$(CH_2)_n$-heteroaryl substituted with one or more carboxyl. In another embodiment, $R^3$ is —O—$(CH_2)_n$-heteroaryl substituted with one or more cyano. In another embodiment, $R^3$ is —O—$(CH_2)_n$-heteroaryl substituted with one or more hydroxyl. In another embodiment, $R^3$ is —O—$(CH_2)_n$-heteroaryl substituted with one or more halogen. In another embodiment, $R^3$ is —O—$(CH_2)_n$-heteroaryl substituted with one or more deuterium. In another embodiment, $R^3$ is —O—$(CH_2)_n$-heteroaryl substituted with one or more 6 to 10 membered aryl, optionally substituted with one or more ($C_1$-$C_6$)alkyl. In another embodiment, $R^3$ is —O—$(CH_2)_n$-heteroaryl substituted with one or more 6 to 10 membered heteroaryl, optionally substituted with one or more ($C_1$-$C_6$)alkyl, ($C_1$-$C_6$)alkoxy or halogen. In another embodiment, $R^3$ is —O—$(CH_2)_n$-heteroaryl substituted with one or more —$CONH_2$. In another embodiment, $R^3$ is —O—$(CH_2)_n$-heteroaryl substituted with one or more —COO—($C_1$-$C_6$)alkyl, wherein the alkyl may be optionally substituted with one or more halogen.

In one embodiment, $R^3$ is unsubstituted —$(CH_2)_n$—O-heteroaryl. In another embodiment, $R^3$ is —$(CH_2)_n$—O-heteroaryl substituted with one or more ($C_1$-$C_6$)alkyl, itself optionally substituted with one or more halogen. In another embodiment, $R^3$ is —$(CH_2)_n$—O-heteroaryl substituted with one or more ($C_1$-$C_6$)alkoxy, itself substituted with one or more halogen. In another embodiment, $R^3$ is —$(CH_2)_n$—O-heteroaryl substituted with one or more oxo. In another embodiment, $R^3$ is —$(CH_2)_n$—O-heteroaryl substituted with one or more amino. In another embodiment, $R^3$ is —$(CH_2)_n$—O-heteroaryl substituted with one or more carboxyl. In another embodiment, $R^3$ is —$(CH_2)_n$—O-heteroaryl substituted with one or more cyano. In another embodiment, $R^3$ is —$(CH_2)_n$—O-heteroaryl substituted with one or more hydroxyl. In another embodiment, $R^3$ is —$(CH_2)_n$—O-heteroaryl substituted with one or more halogen. In another embodiment, $R^3$ is —$(CH_2)_n$—O-heteroaryl substituted with one or more deuterium. In another embodiment, $R^3$ is —$(CH_2)_n$—O-heteroaryl substituted with one or more 6 to 10 membered aryl, optionally substituted with one or more ($C_1$-$C_6$)alkyl. In another embodiment, $R^3$ is —$(CH_2)_n$—O-heteroaryl substituted with one or more 6 to 10 membered heteroaryl, optionally substituted with one or more ($C_1$-$C_6$)alkyl, ($C_1$-$C_6$)alkoxy or halogen. In another embodiment, $R^3$ is —$(CH_2)_n$—O-heteroaryl substituted with one or more —$CONH_2$. In another embodiment, $R^3$ is —$(CH_2)_n$—O-heteroaryl substituted with one or more —COO—($C_1$-$C_6$)alkyl, wherein the alkyl may be optionally substituted with one or more halogen.

In one embodiment, n is 0. In another embodiment, n is 1. In another embodiment, n is 2.

All of the specific combinations that can result from the definition provided herein for X, $R^1$, $R^2$, Y, $R^3$ and n are encompassed.

In one embodiment, X is $CH_2$.

In one embodiment, Y is aryl. In another embodiment, Y is phenyl.

In another embodiment wherein Y is phenyl, $R^3$ is —$(CH_2)_n$-heterocycle. In one embodiment, the heterocycle is morpholinyl, piperidinyl or pyrrolidinyl.

In one embodiment, Y is a heteroaryl. In another embodiment, Y is a 10 membered hetero aryl. In another embodiment, Y is benzo[d]thiazole. In another embodiment, Y is benzofuran. In another embodiment, Y is quinoline.

In another embodiment where Y is heteroaryl, $R^3$ is —$(CH_2)_n$-heterocycle. In one embodiment, the heterocycle is morpholinyl, piperidinyl or pyrrolidinyl.

In one embodiment, Y is a bond. In another embodiment where Y is a bond, $R^3$ is —$(CH_2)_n$-heterocycle or —$(CH_2)_n$-heteroaryl.

In one embodiment, examples include, but are not limited to those listed in Table W, below:

TABLE W

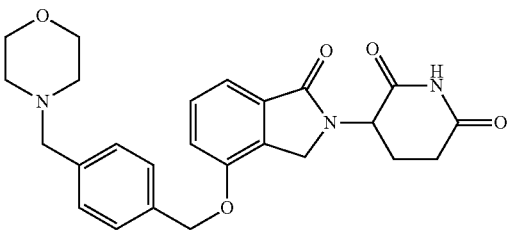

TABLE W-continued
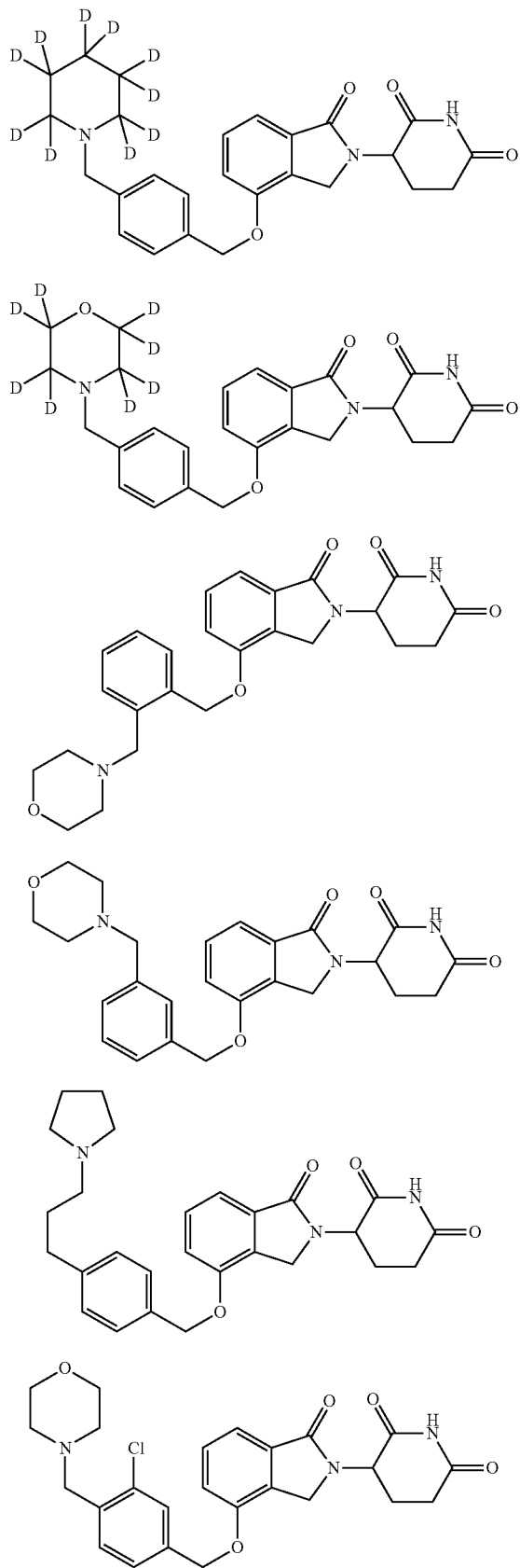

TABLE W-continued
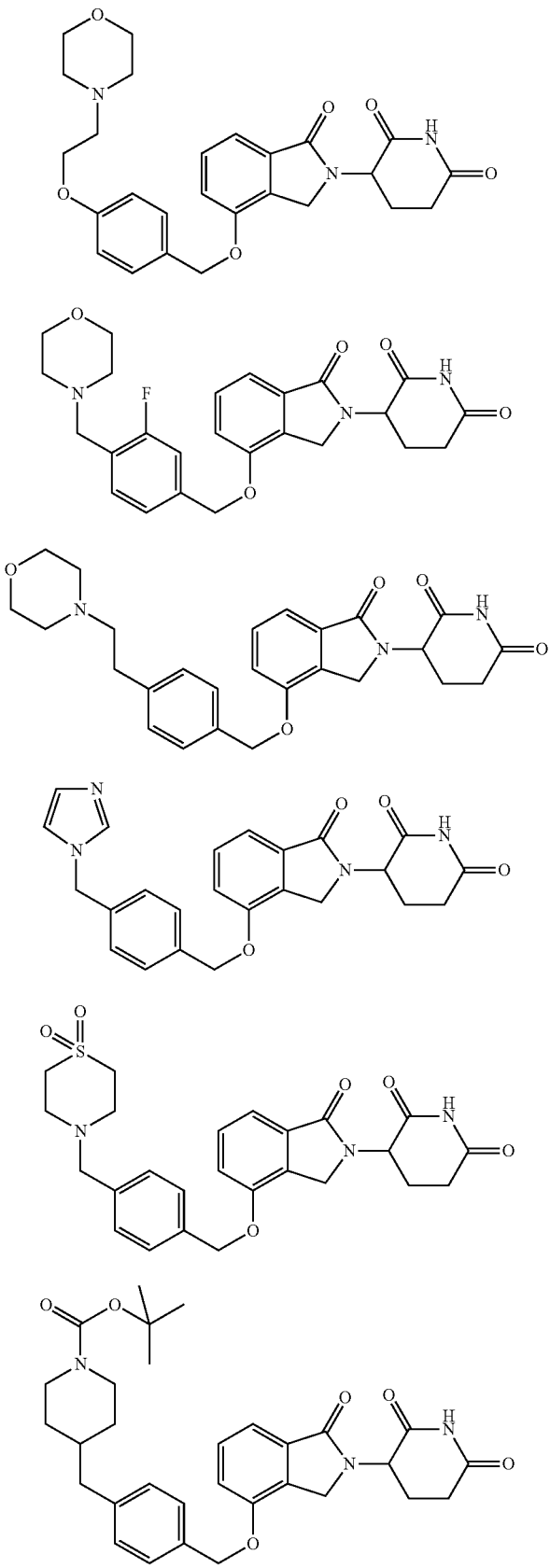

TABLE W-continued
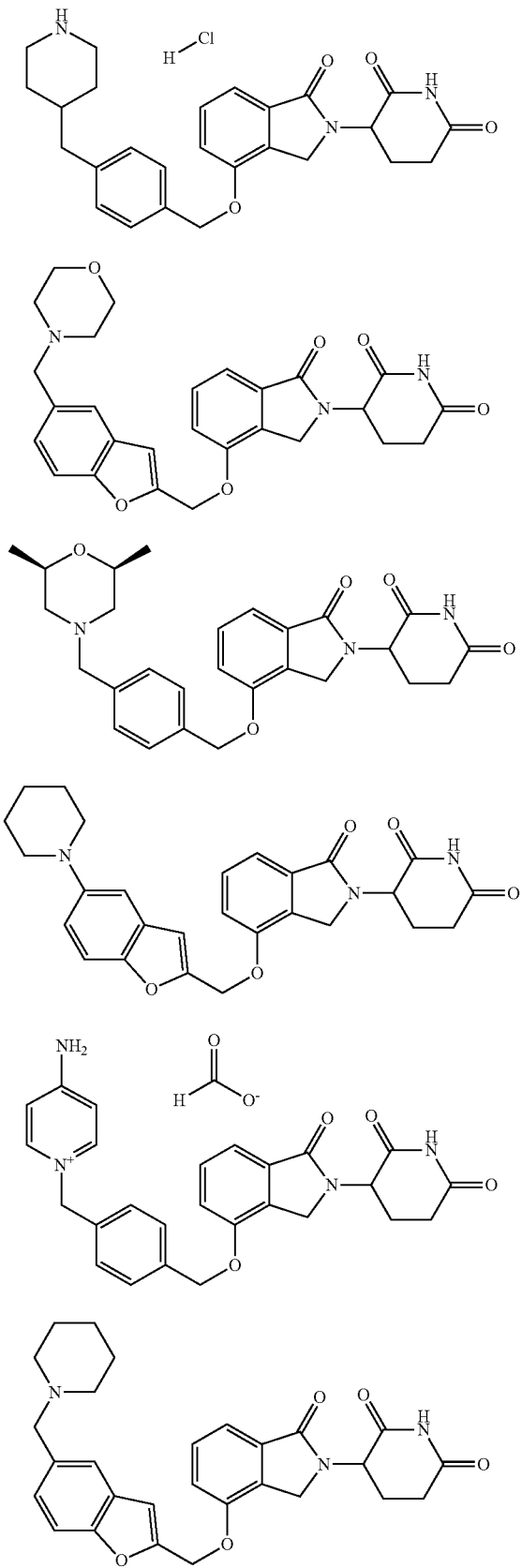

TABLE W-continued
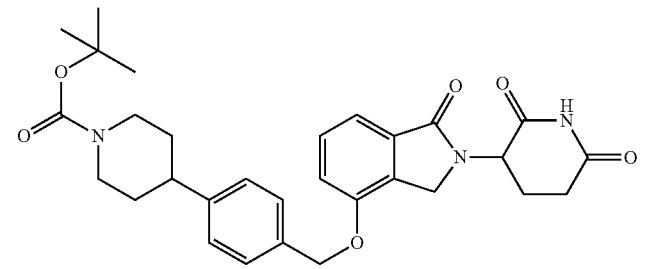 [SMILES: CC(C)(C)OC(=O)N1CCC(c2ccc(COc3cccc4c3CN(C3CCC(=O)NC3=O)C4=O)cc2)CC1]
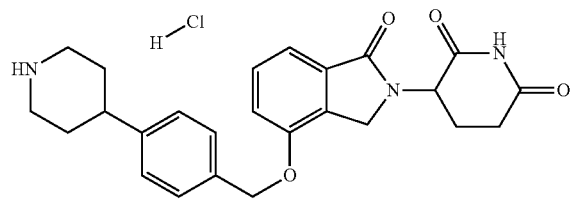
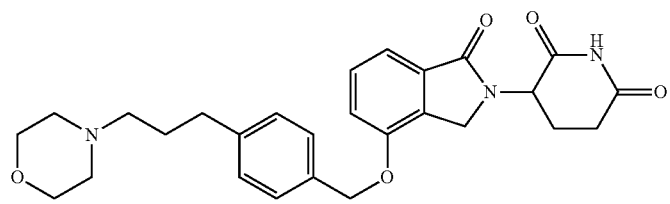 [SMILES: O=C1CCC(N2Cc3c(OCc4ccc(CCCN5CCOCC5)cc4)cccc3C2=O)C(=O)N1]
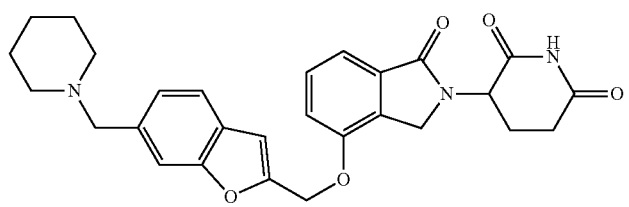 [SMILES: O=C1CCC(N2Cc3c(OCc4cc5ccc(CN6CCCCC6)cc5o4)cccc3C2=O)C(=O)N1]
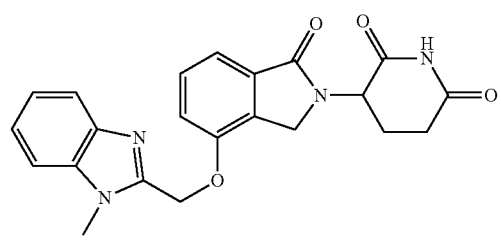 [SMILES: Cn1c(COc2cccc3c2CN(C2CCC(=O)NC2=O)C3=O)nc2ccccc21]
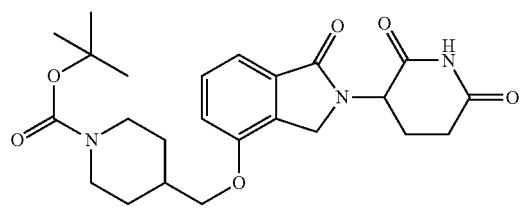 [SMILES: CC(C)(C)OC(=O)N1CCC(COc2cccc3c2CN(C2CCC(=O)NC2=O)C3=O)CC1]
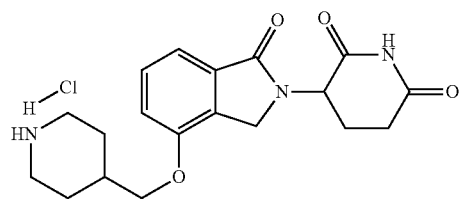

TABLE W-continued
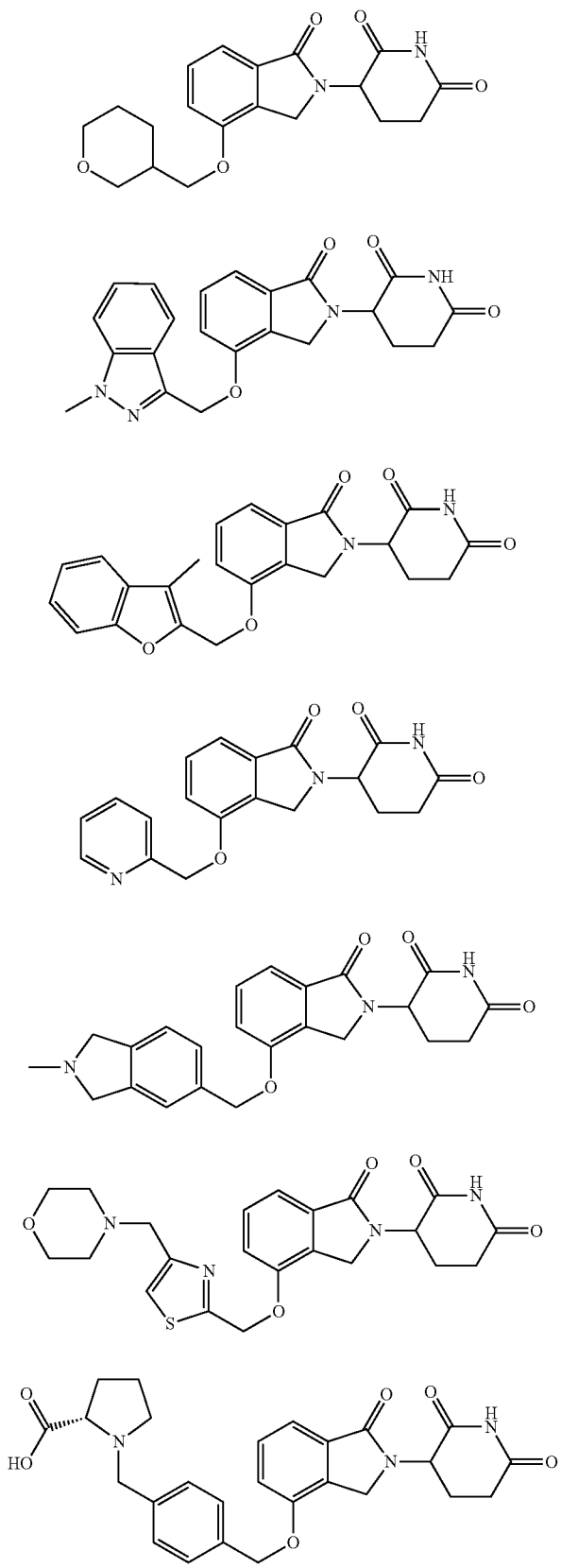

TABLE W-continued
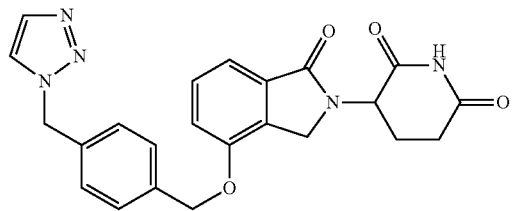
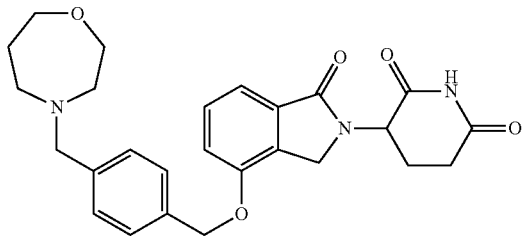 [SMILES: O=C1CCC(N2Cc3c(OCc4ccc(CN5CCCOCC5)cc4)cccc3C2=O)C(=O)N1]
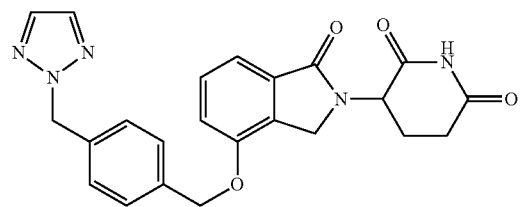 [SMILES: O=C1CCC(N2Cc3c(OCc4ccc(Cn5nccn5)cc4)cccc3C2=O)C(=O)N1]
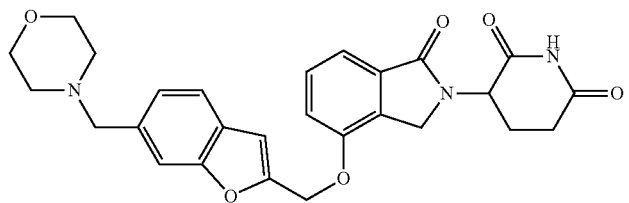 [SMILES: O=C1CCC(N2Cc3c(OCc4cc5ccc(CN6CCOCC6)cc5o4)cccc3C2=O)C(=O)N1]
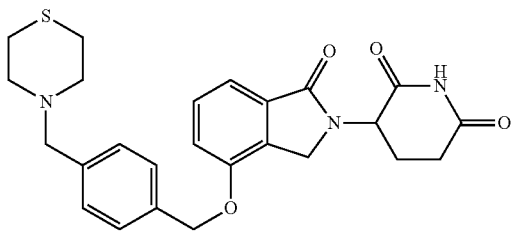 [SMILES: O=C1CCC(N2Cc3c(OCc4ccc(CN5CCSCC5)cc4)cccc3C2=O)C(=O)N1]
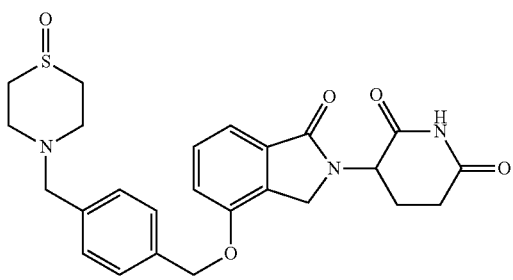 [SMILES: O=C1CCC(N2Cc3c(OCc4ccc(CN5CCS(=O)CC5)cc4)cccc3C2=O)C(=O)N1]
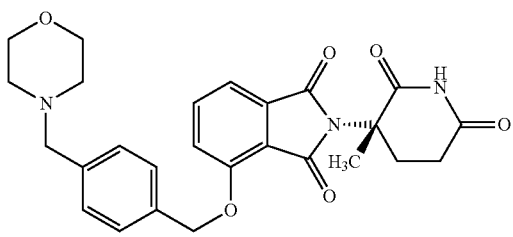

TABLE W-continued
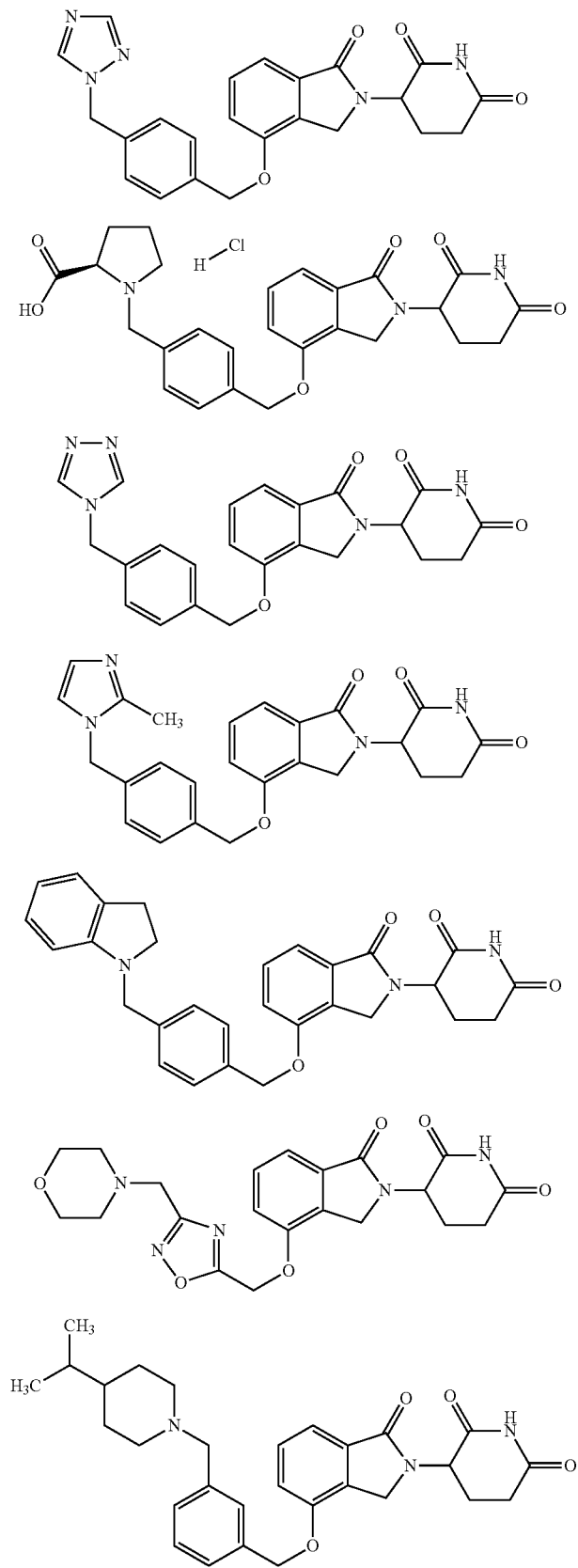

TABLE W-continued
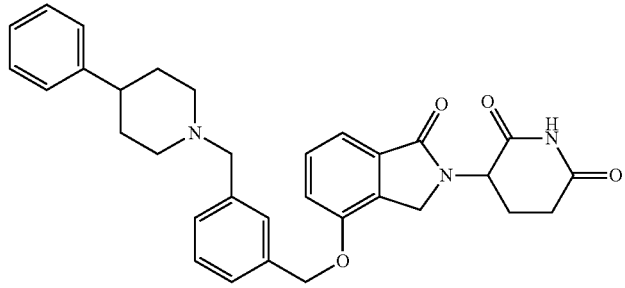 [SMILES: O=C1CCC(N2Cc3c(OCc4cccc(CN5CCC(c6ccccc6)CC5)c4)cccc3C2=O)C(=O)N1]
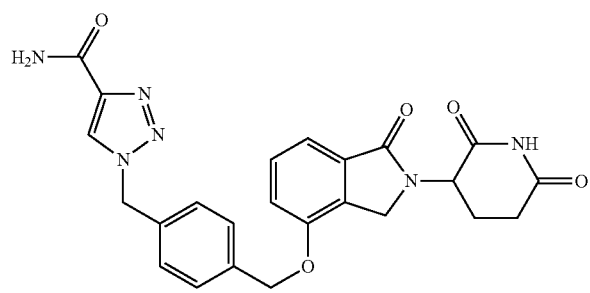 [SMILES: NC(=O)c1cn(Cc2ccc(COc3cccc4c3CN(C3CCC(=O)NC3=O)C4=O)cc2)nn1]
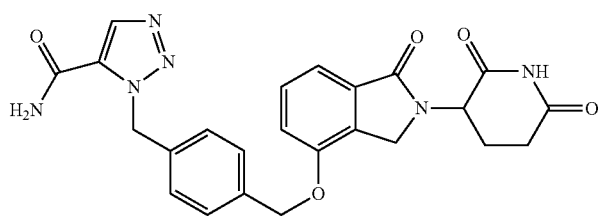 [SMILES: NC(=O)c1cnnn1Cc1ccc(COc2cccc3c2CN(C2CCC(=O)NC2=O)C3=O)cc1]
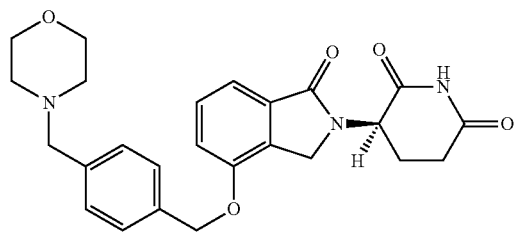 [SMILES: O=C1CC[C@@H](N2Cc3c(OCc4ccc(CN5CCOCC5)cc4)cccc3C2=O)C(=O)N1]
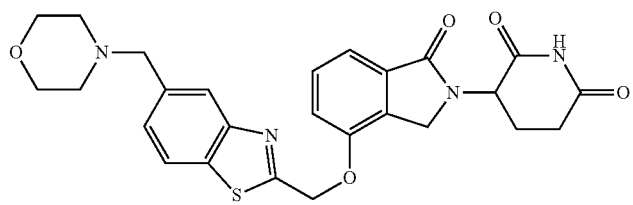 [SMILES: O=C1CCC(N2Cc3c(OCc4nc5cc(CN6CCOCC6)ccc5s4)cccc3C2=O)C(=O)N1]
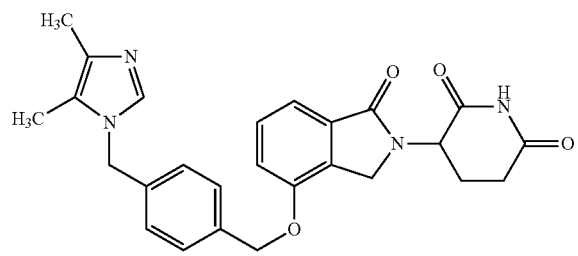 [SMILES: Cc1ncn(Cc2ccc(COc3cccc4c3CN(C3CCC(=O)NC3=O)C4=O)cc2)c1C]

TABLE W-continued
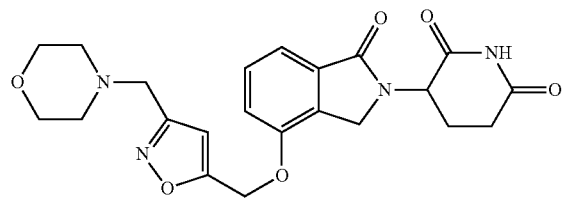 [SMILES: O=C1CCC(N2Cc3c(OCc4cc(CN5CCOCC5)no4)cccc3C2=O)C(=O)N1]
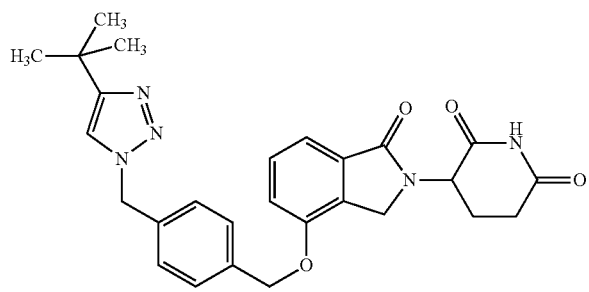 [SMILES: CC(C)(C)c1cn(Cc2ccc(COc3cccc4c3CN(C3CCC(=O)NC3=O)C4=O)cc2)nn1]
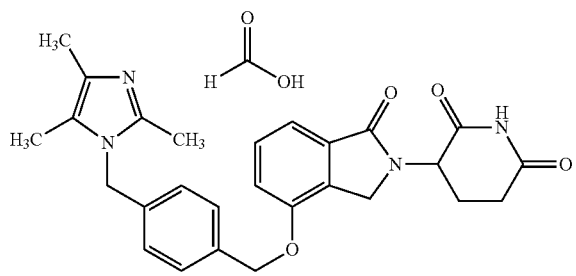
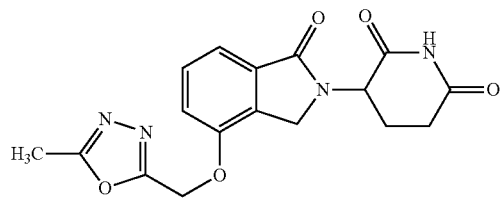 [SMILES: Cc1nnc(COc2cccc3c2CN(C2CCC(=O)NC2=O)C3=O)o1]
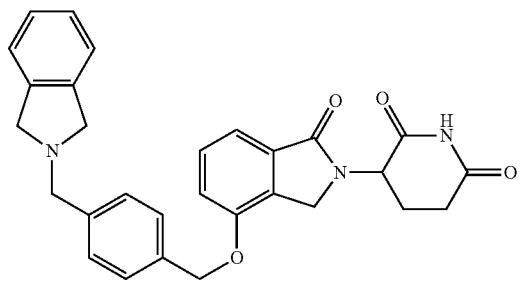 [SMILES: O=C1CCC(N2Cc3c(OCc4ccc(CN5Cc6ccccc6C5)cc4)cccc3C2=O)C(=O)N1]
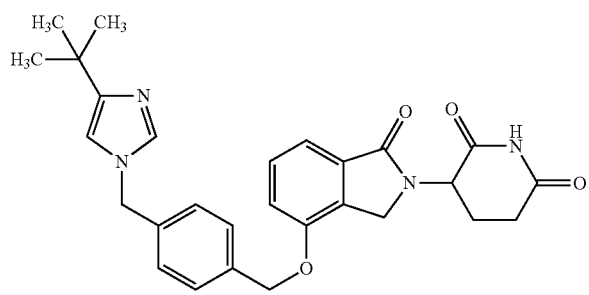 [SMILES: CC(C)(C)c1cn(Cc2ccc(COc3cccc4c3CN(C3CCC(=O)NC3=O)C4=O)cc2)cn1]

TABLE W-continued
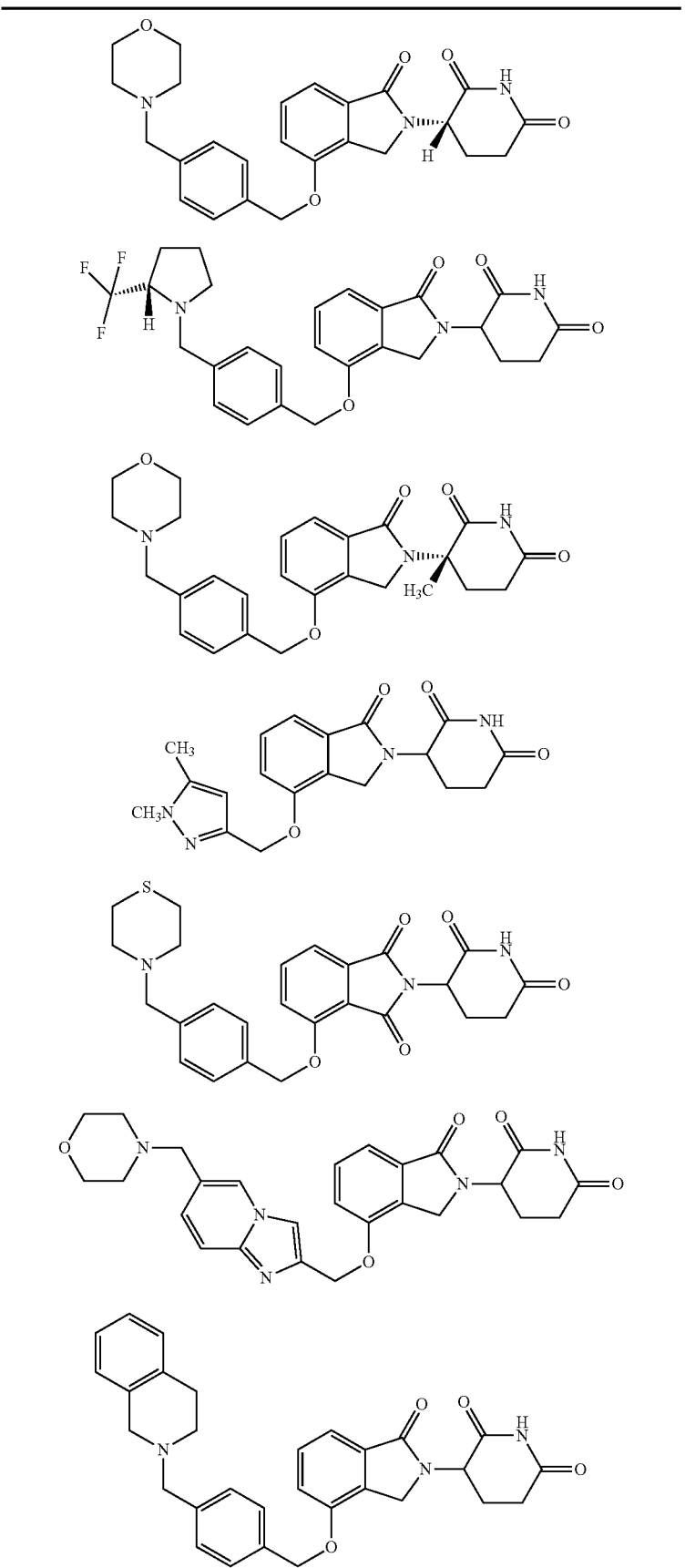

TABLE W-continued
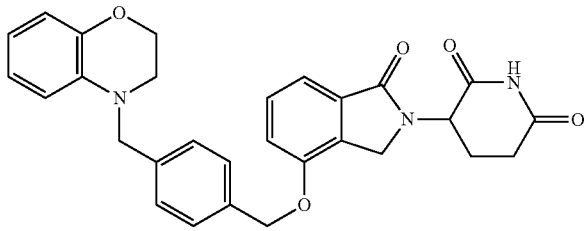 [SMILES: O=C1CCC(N2Cc3c(OCc4ccc(CN5CCOc6ccccc65)cc4)cccc3C2=O)C(=O)N1]
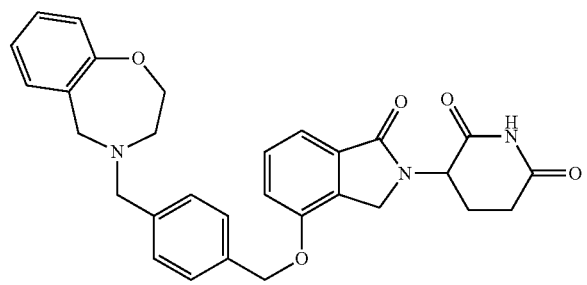 [SMILES: O=C1CCC(N2Cc3c(OCc4ccc(CN5CCOc6ccccc6C5)cc4)cccc3C2=O)C(=O)N1]
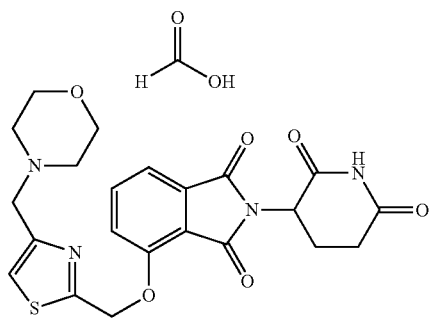 [SMILES: O=CO ; O=C1CCC(N2C(=O)c3cccc(OCc4nc(CN5CCOCC5)cs4)c3C2=O)C(=O)N1]
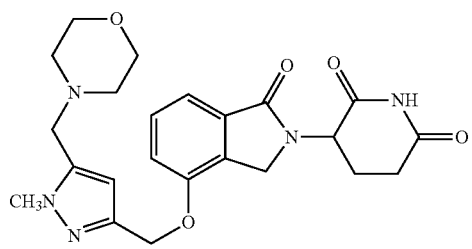
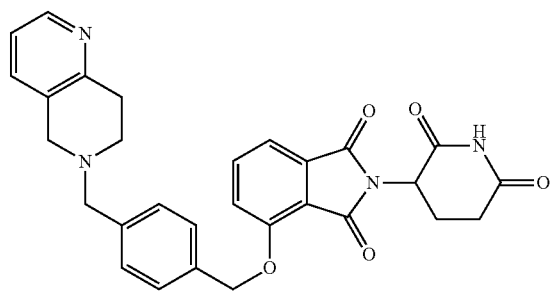 [SMILES: O=C1CCC(N2C(=O)c3cccc(OCc4ccc(CN5CCc6ncccc6C5)cc4)c3C2=O)C(=O)N1]

TABLE W-continued
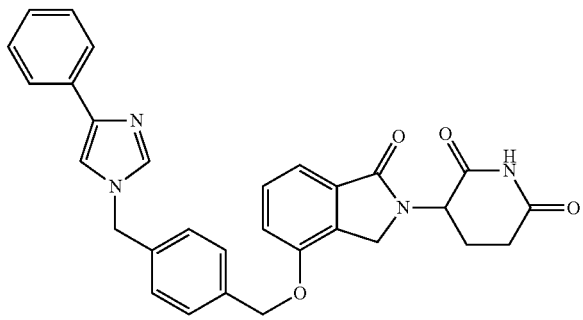 [SMILES: O=C1CCC(N2Cc3c(OCc4ccc(Cn5cnc(-c6ccccc6)c5)cc4)cccc3C2=O)C(=O)N1]
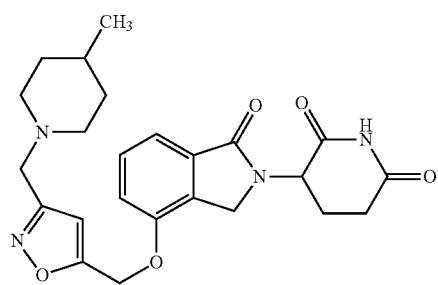 [SMILES: CC1CCN(Cc2cc(COc3cccc4c3CN(C3CCC(=O)NC3=O)C4=O)on2)CC1]
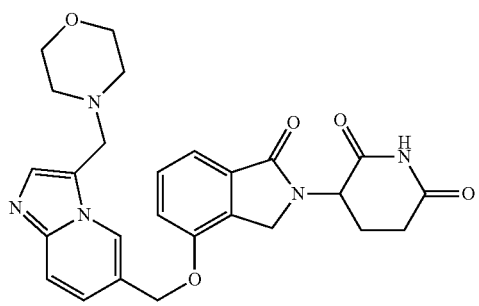 [SMILES: O=C1CCC(N2Cc3c(OCc4ccc5ncc(CN6CCOCC6)n5c4)cccc3C2=O)C(=O)N1]
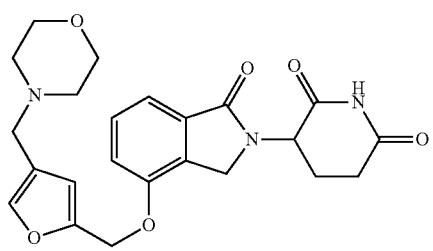 [SMILES: O=C1CCC(N2Cc3c(OCc4cc(CN5CCOCC5)co4)cccc3C2=O)C(=O)N1]
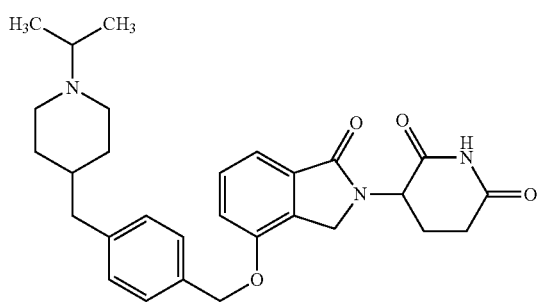 [SMILES: CC(C)N1CCC(Cc2ccc(COc3cccc4c3CN(C3CCC(=O)NC3=O)C4=O)cc2)CC1]

TABLE W-continued
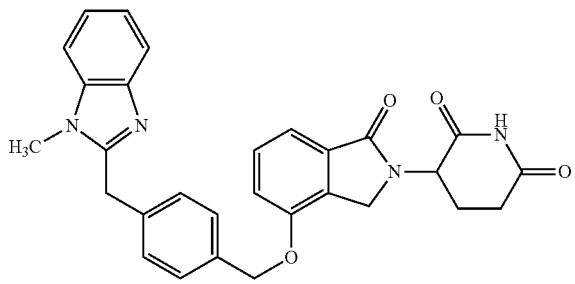 [SMILES: Cn1c(Cc2ccc(COc3cccc4c3CN(C3CCC(=O)NC3=O)C4=O)cc2)nc2ccccc21]
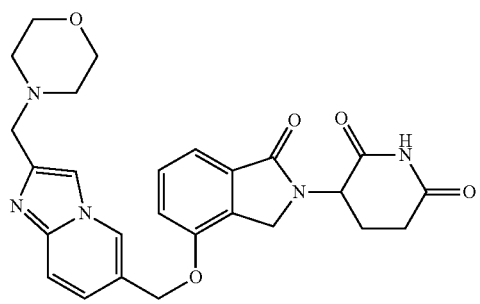 [SMILES: O=C1CCC(N2Cc3c(OCc4ccc5nc(CN6CCOCC6)cn5c4)cccc3C2=O)C(=O)N1]
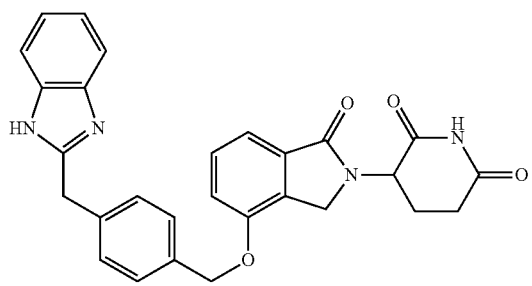 [SMILES: O=C1CCC(N2Cc3c(OCc4ccc(Cc5nc6ccccc6[nH]5)cc4)cccc3C2=O)C(=O)N1]
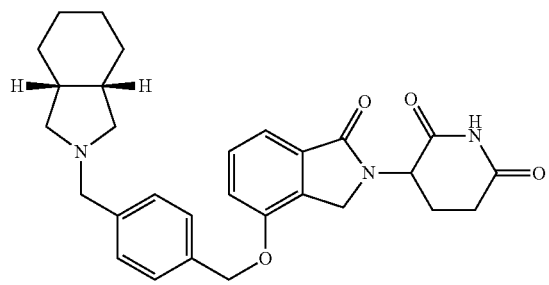 [SMILES: O=C1CCC(N2Cc3c(OCc4ccc(CN5C[C@H]6CCCC[C@H]6C5)cc4)cccc3C2=O)C(=O)N1]
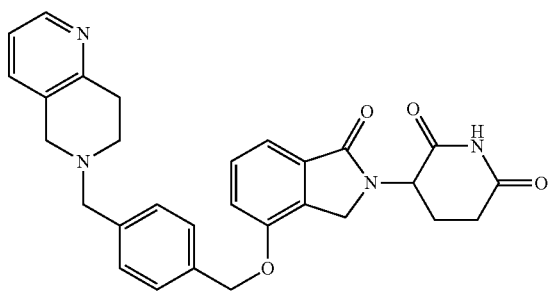 [SMILES: O=C1CCC(N2Cc3c(OCc4ccc(CN5CCc6ncccc6C5)cc4)cccc3C2=O)C(=O)N1]

TABLE W-continued
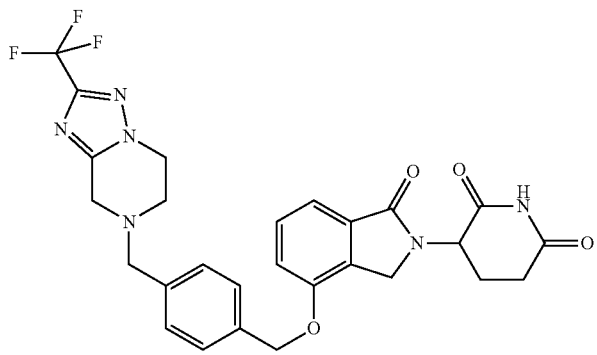
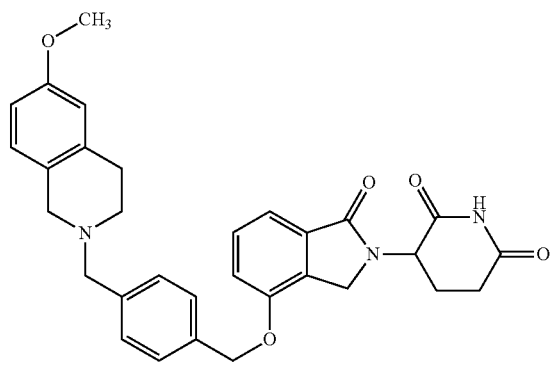 [SMILES: COc1ccc2c(c1)CCN(Cc1ccc(COc3cccc4c3CN(C3CCC(=O)NC3=O)C4=O)cc1)C2]
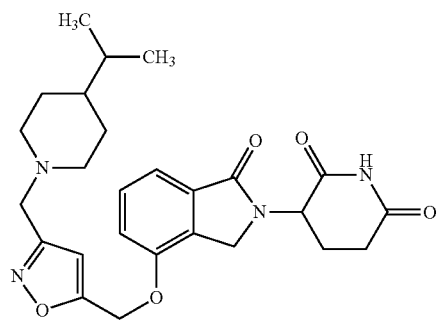 [SMILES: CC(C)C1CCN(Cc2cc(COc3cccc4c3CN(C3CCC(=O)NC3=O)C4=O)on2)CC1]
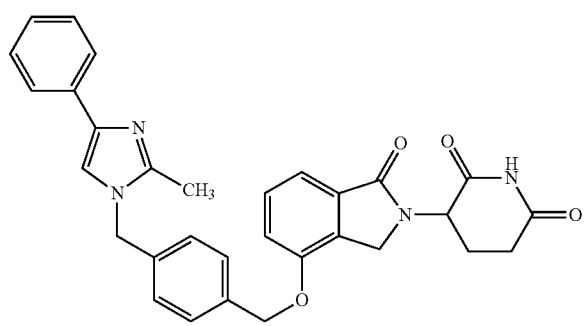 [SMILES: Cc1nc(-c2ccccc2)cn1Cc1ccc(COc2cccc3c2CN(C2CCC(=O)NC2=O)C3=O)cc1]

TABLE W-continued
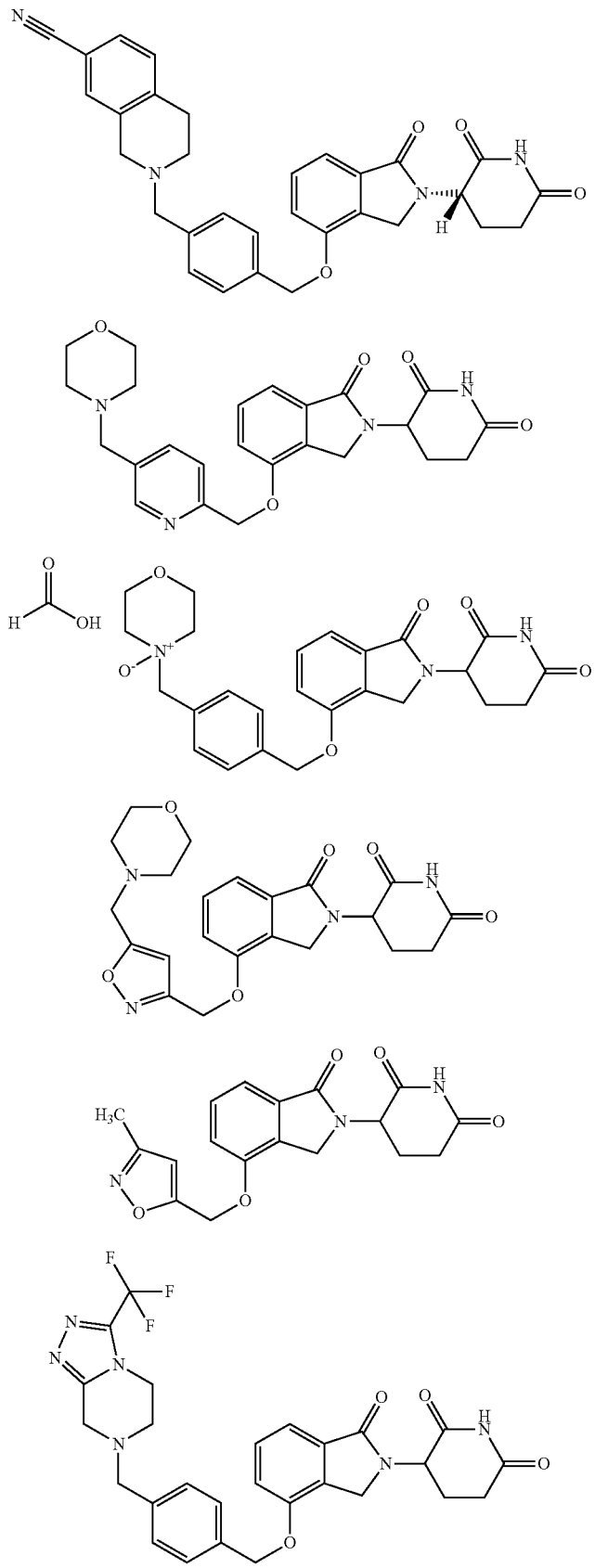

TABLE W-continued
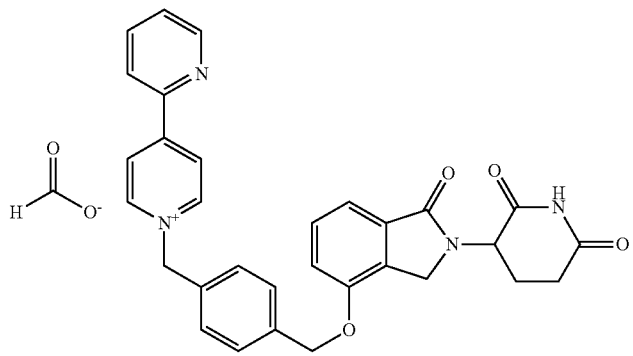
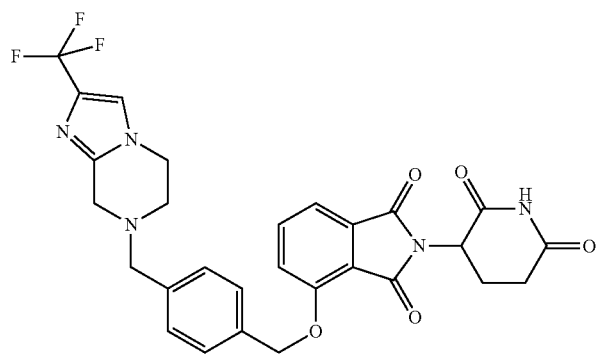 [SMILES: O=C1CCC(N2C(=O)c3cccc(OCc4ccc(CN5CCn6cc(C(F)(F)F)nc6C5)cc4)c3C2=O)C(=O)N1]
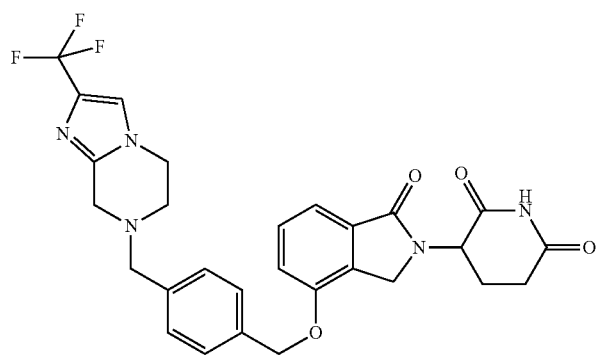 [SMILES: O=C1CCC(N2Cc3c(OCc4ccc(CN5CCn6cc(C(F)(F)F)nc6C5)cc4)cccc3C2=O)C(=O)N1]
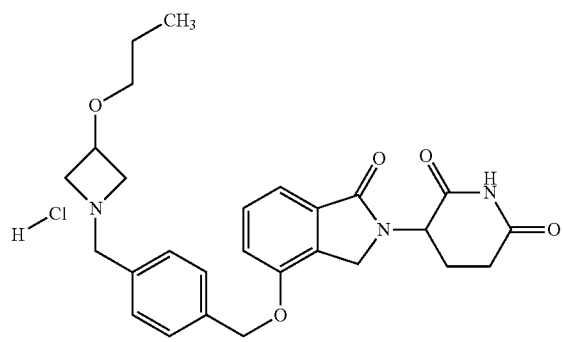
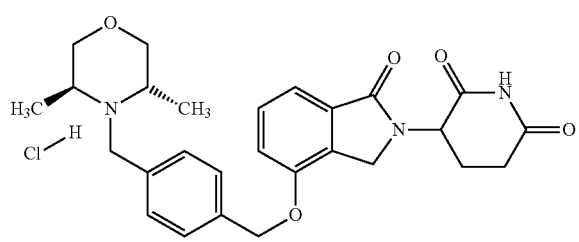

TABLE W-continued
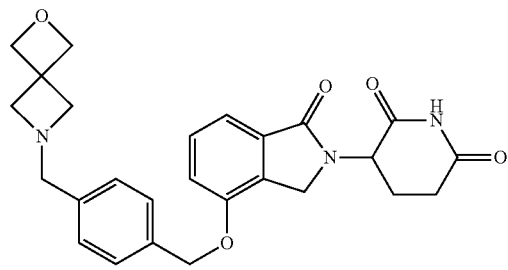 [SMILES: O=C1CCC(N2Cc3c(OCc4ccc(CN5CC6(COC6)C5)cc4)cccc3C2=O)C(=O)N1]
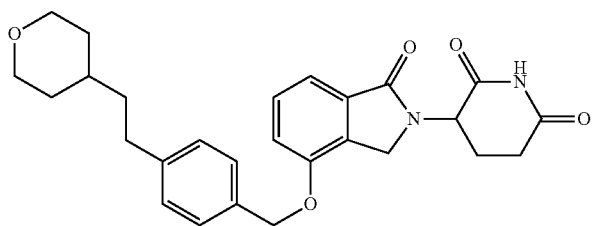 [SMILES: O=C1CCC(N2Cc3c(OCc4ccc(CCC5CCOCC5)cc4)cccc3C2=O)C(=O)N1]
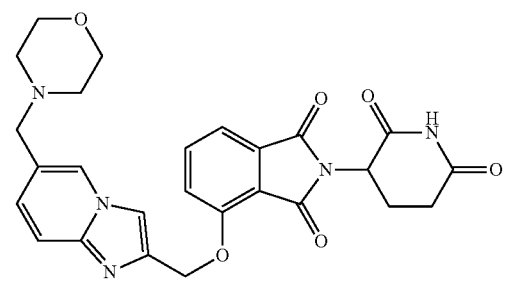 [SMILES: O=C1CCC(N2C(=O)c3cccc(OCc4cn5cc(CN6CCOCC6)ccc5n4)c3C2=O)C(=O)N1]
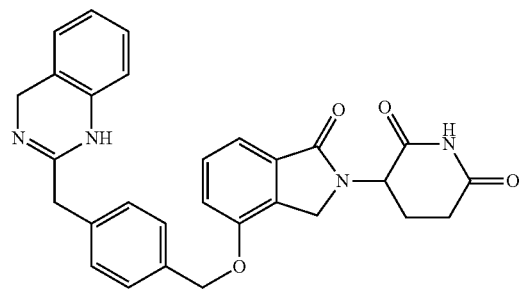 [SMILES: O=C1CCC(N2Cc3c(OCc4ccc(CC5=NCc6ccccc6N5)cc4)cccc3C2=O)C(=O)N1]
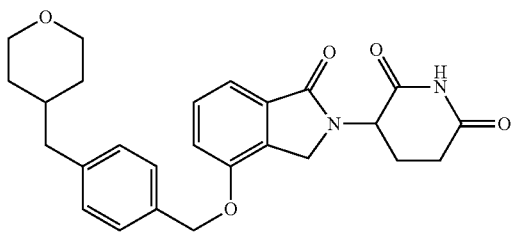 [SMILES: O=C1CCC(N2Cc3c(OCc4ccc(CC5CCOCC5)cc4)cccc3C2=O)C(=O)N1]

TABLE W-continued
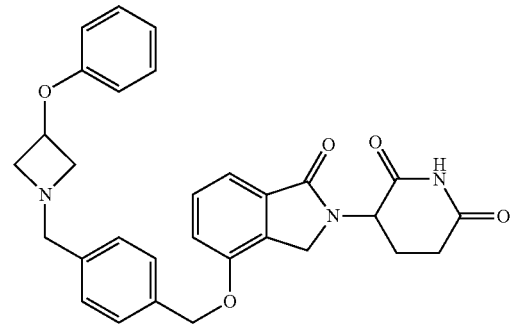 [SMILES: O=C1CCC(N2Cc3c(OCc4ccc(CN5CC(Oc6ccccc6)C5)cc4)cccc3C2=O)C(=O)N1]
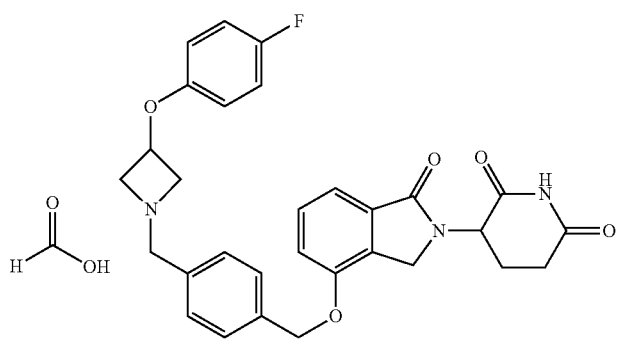 [SMILES: O=CO ; O=C1CCC(N2Cc3c(OCc4ccc(CN5CC(Oc6ccc(F)cc6)C5)cc4)cccc3C2=O)C(=O)N1]
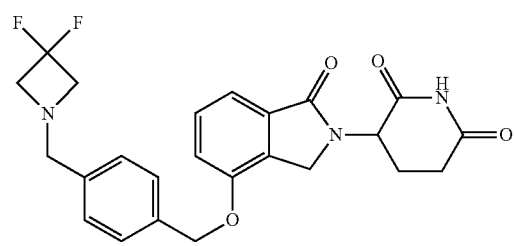 [SMILES: O=C1CCC(N2Cc3c(OCc4ccc(CN5CC(F)(F)C5)cc4)cccc3C2=O)C(=O)N1]
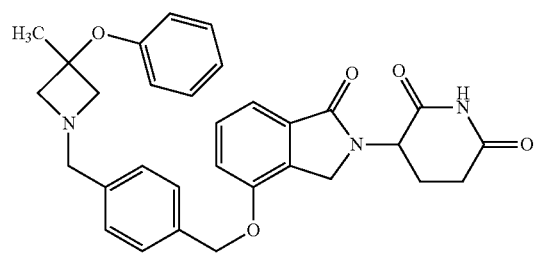 [SMILES: CC1(Oc2ccccc2)CN(Cc2ccc(COc3cccc4c3CN(C3CCC(=O)NC3=O)C4=O)cc2)C1]
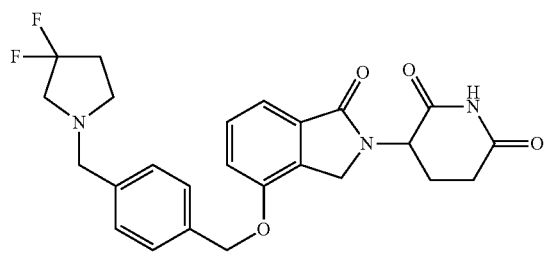 [SMILES: O=C1CCC(N2Cc3c(OCc4ccc(CN5CCC(F)(F)C5)cc4)cccc3C2=O)C(=O)N1]

TABLE W-continued
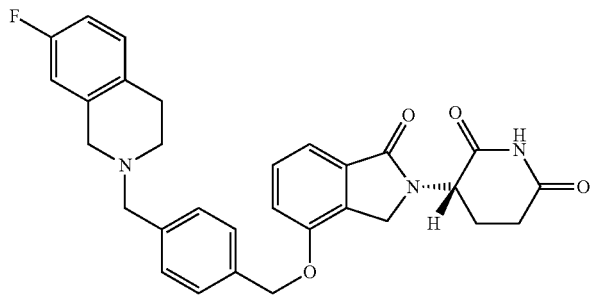
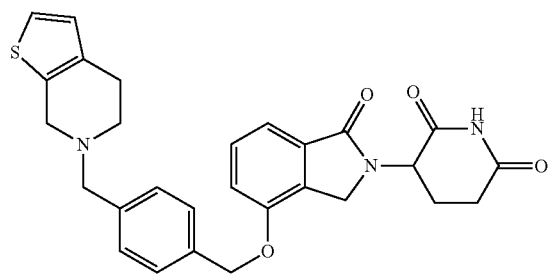 [SMILES: O=C1CCC(N2Cc3c(OCc4ccc(CN5CCc6ccsc6C5)cc4)cccc3C2=O)C(=O)N1]
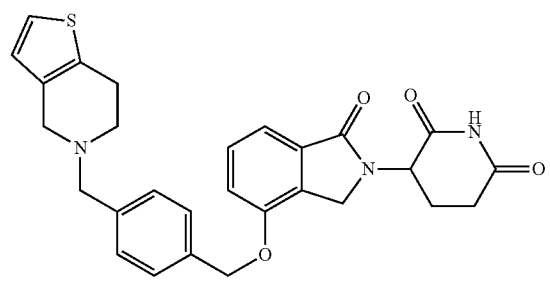 [SMILES: O=C1CCC(N2Cc3c(OCc4ccc(CN5CCc6sccc6C5)cc4)cccc3C2=O)C(=O)N1]
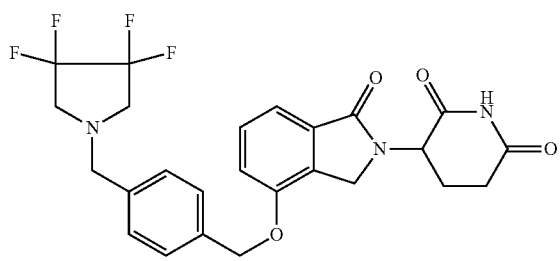 [SMILES: O=C1CCC(N2Cc3c(OCc4ccc(CN5CC(F)(F)C(F)(F)C5)cc4)cccc3C2=O)C(=O)N1]
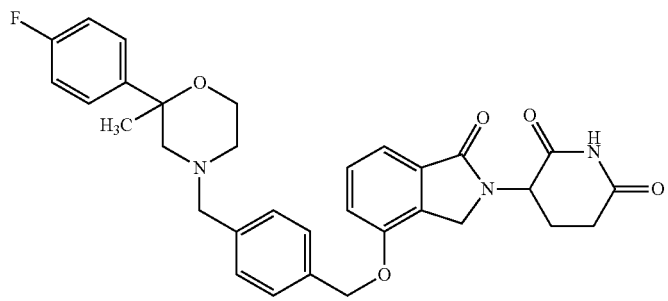 [SMILES: CC1(c2ccc(F)cc2)CN(Cc2ccc(COc3cccc4c3CN(C3CCC(=O)NC3=O)C4=O)cc2)CCO1]

TABLE W-continued
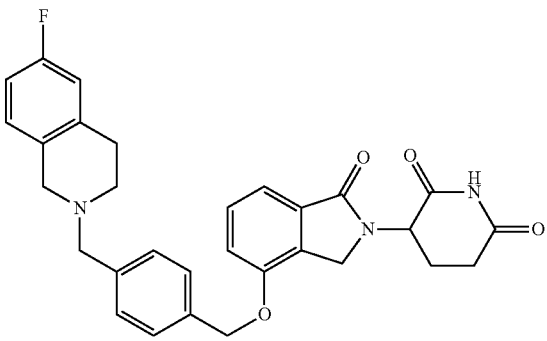 [SMILES: O=C1CCC(N2Cc3c(OCc4ccc(CN5CCc6cc(F)ccc6C5)cc4)cccc3C2=O)C(=O)N1]
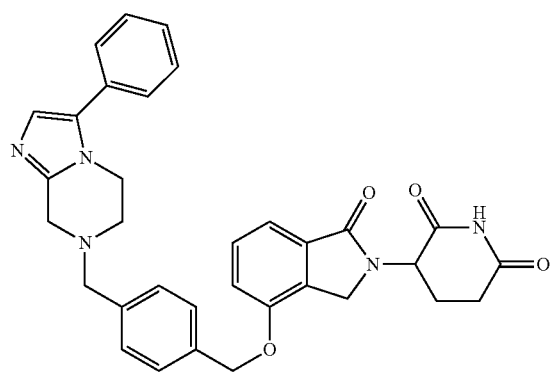 [SMILES: O=C1CCC(N2Cc3c(OCc4ccc(CN5CCn6c(-c7ccccc7)cnc6C5)cc4)cccc3C2=O)C(=O)N1]
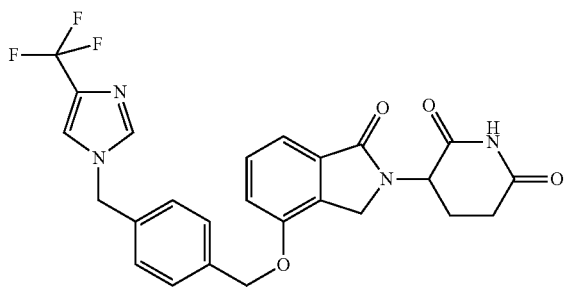 [SMILES: O=C1CCC(N2Cc3c(OCc4ccc(Cn5cnc(C(F)(F)F)c5)cc4)cccc3C2=O)C(=O)N1]
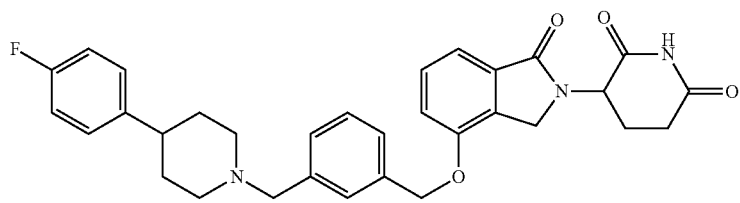 [SMILES: O=C1CCC(N2Cc3c(OCc4cccc(CN5CCC(c6ccc(F)cc6)CC5)c4)cccc3C2=O)C(=O)N1]
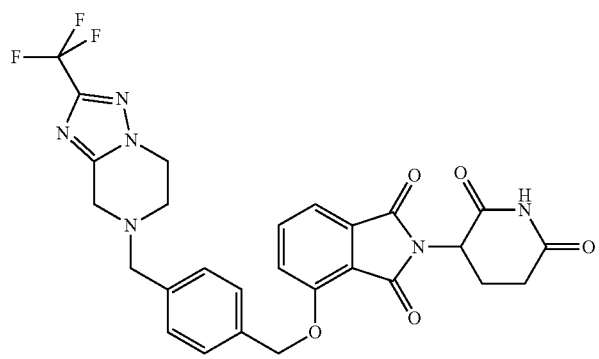 [SMILES: O=C1CCC(N2C(=O)c3cccc(OCc4ccc(CN5CCn6nc(C(F)(F)F)nc6C5)cc4)c3C2=O)C(=O)N1]

TABLE W-continued
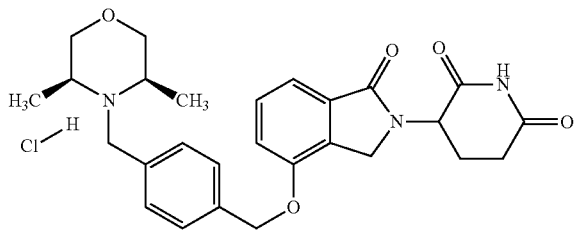
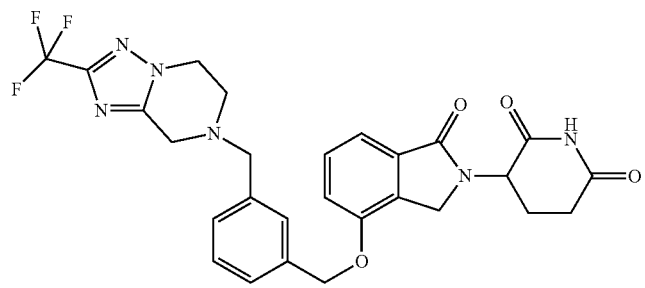 [SMILES: O=C1CCC(N2Cc3c(OCc4cccc(CN5CCn6nc(C(F)(F)F)nc6C5)c4)cccc3C2=O)C(=O)N1]
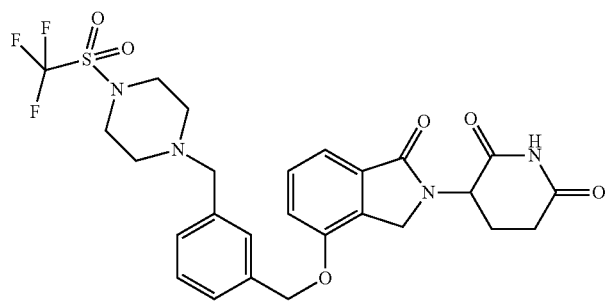 [SMILES: O=C1CCC(N2Cc3c(OCc4cccc(CN5CCN(S(=O)(=O)C(F)(F)F)CC5)c4)cccc3C2=O)C(=O)N1]
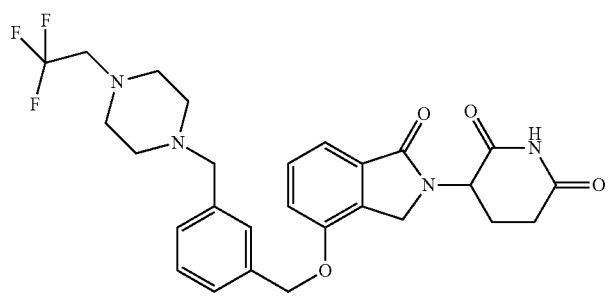 [SMILES: O=C1CCC(N2Cc3c(OCc4cccc(CN5CCN(CC(F)(F)F)CC5)c4)cccc3C2=O)C(=O)N1]
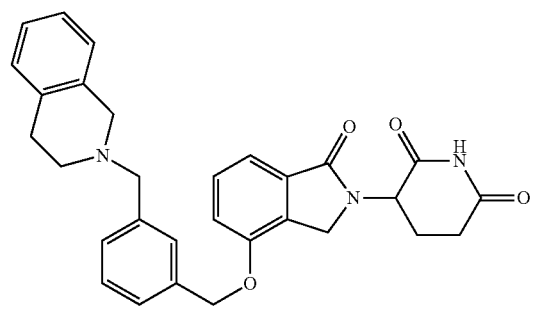 [SMILES: O=C1CCC(N2Cc3c(OCc4cccc(CN5CCc6ccccc6C5)c4)cccc3C2=O)C(=O)N1]

TABLE W-continued
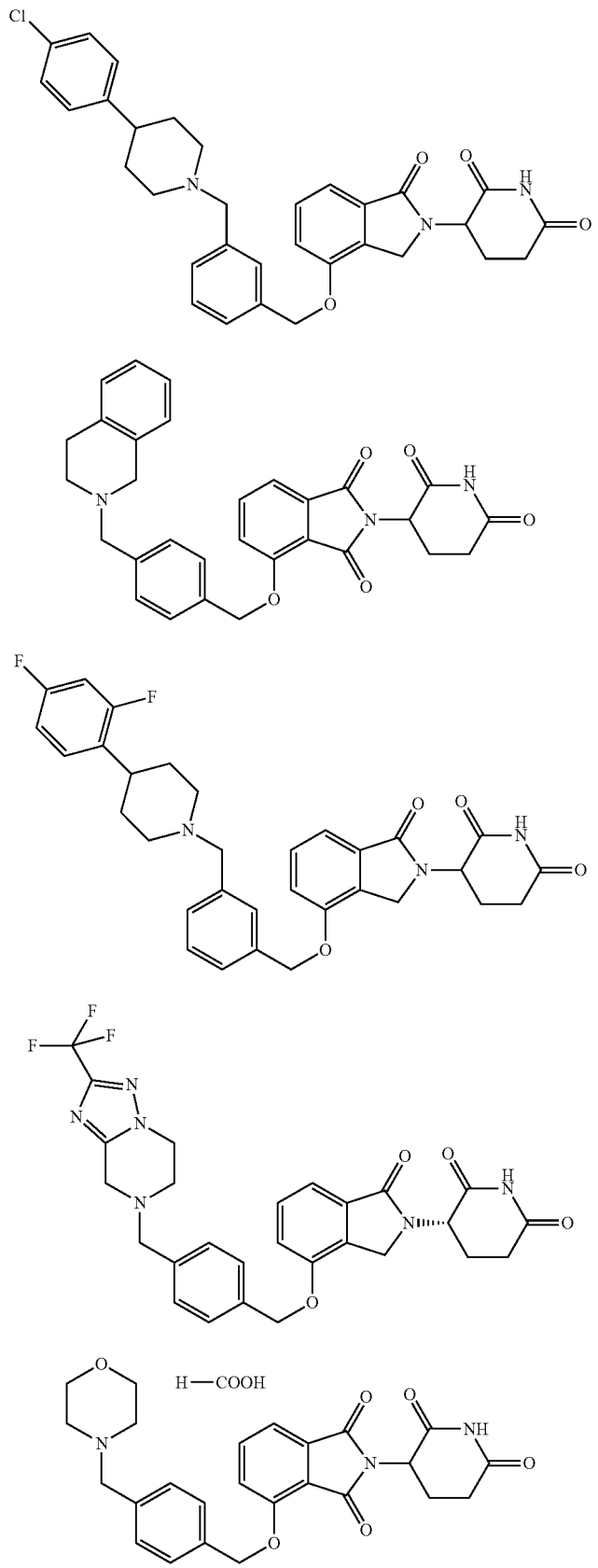

TABLE W-continued

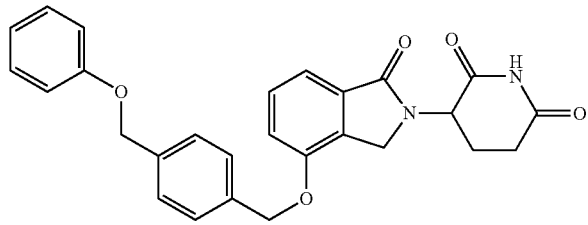 [SMILES: O=C1CCC(N2Cc3c(OCc4ccc(COc5ccccc5)cc4)cccc3C2=O)C(=O)N1]

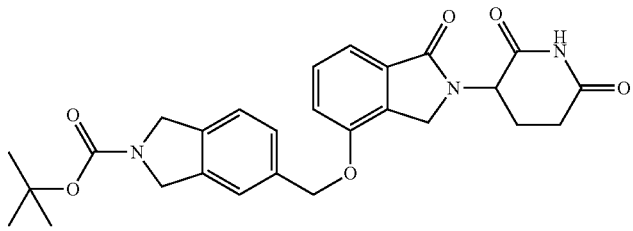 [SMILES: CC(C)(C)OC(=O)N1Cc2ccc(COc3cccc4c3CN(C3CCC(=O)NC3=O)C4=O)cc2C1]

or a pharmaceutically acceptable salt, solvate or stereoisomer thereof.

In another embodiment, representative compounds are of formula (XX):

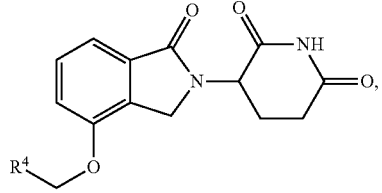

or a pharmaceutically acceptable salt, solvate or stereoisomer thereof, wherein: $R^4$ is unsubstituted 9 to 10 membered bicyclic ring is benzothiazole, quinoline, isoquinoline, naphthalene, 2,3-dihydro-1H-indene, benzo[d][1,2,3]triazole, imidazo[1,2-a]pyridine, benzofuran, 2,3-dihydrobenzofuran, benzothiophene, benzo[d]oxazole isoindoline or chroman; with the proviso that if the bicyclic ring is benzofuran or benzothiophene, then the ring is not connected to the isoindole ring through the 2-position.

In one embodiment, $R^4$ is benzothiazole. In another embodiment, $R^4$ is quinoline. In another embodiment, $R^4$ is isoquinoline. In another embodiment, $R^4$ is naphthalene. In another embodiment, $R^4$ is 2,3-dihydro-1H-indene. In another embodiment, $R^4$ is benzo[d][1,2,3]triazole. In another embodiment, $R^4$ is imidazo[1,2-a]pyridine. In another embodiment, $R^4$ is benzofuran. In another embodiment, $R^4$ is 2,3-dihydrobenzofuran. In another embodiment, $R^4$ is benzothiophene. In another embodiment, $R^4$ is benzo[d]oxazole isoindoline. In another embodiment, $R^4$ is chroman.

In one embodiment, specific examples include, but are not limited to those listed in Table X, below:

TABLE X

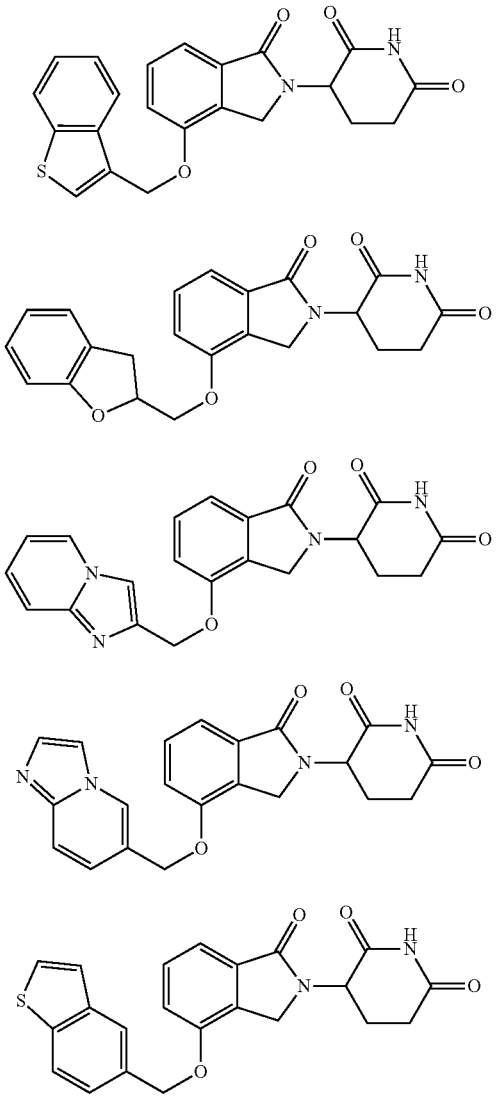

TABLE X-continued

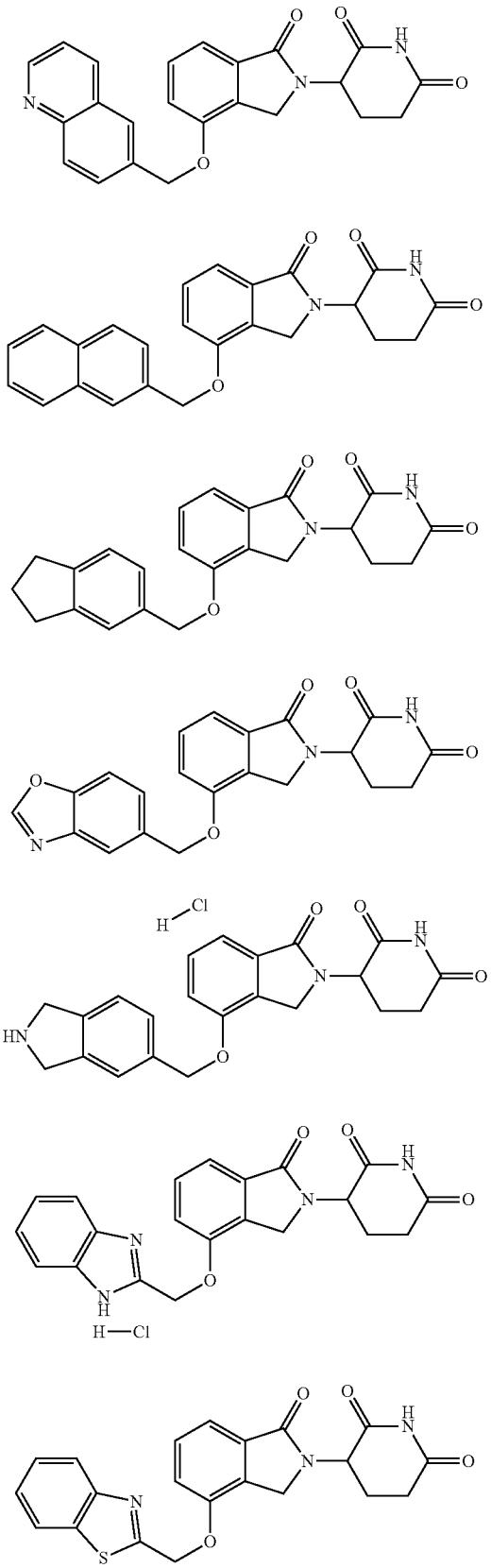

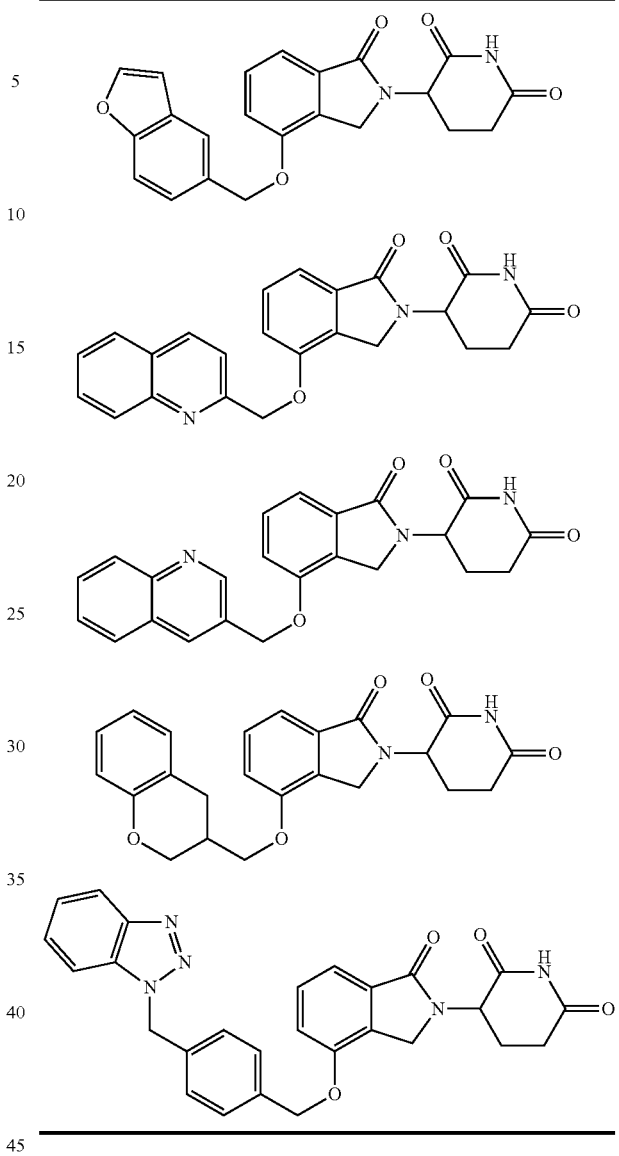

or a pharmaceutically acceptable salt, solvate or stereoisomer thereof.

In another embodiment, representative compounds are of formula (XXI):

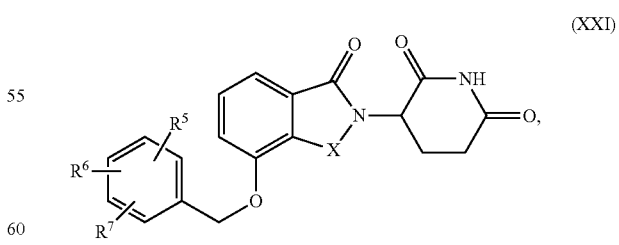

(XXI)

or a pharmaceutically acceptable salt, solvate or stereoisomer thereof, wherein:

X is $CH_2$ or C=O;

$R^5$, $R^6$ and $R^7$ are each independently hydrogen, halogen, nitro, carbamoyl, amino, —$SO_2R^8$, —$CONR^9R^{10}$, —($C_1$-

$C_6$)alkyl or —($C_1$-$C_6$)alkoxy, said alkyl or alkoxy may be optionally substituted with one or more halogen, amino, hydroxyl, or $NR^9R^{10}$;

$R^8$ is: ($C_1$-$C_6$)alkyl, optionally substituted with ($C_1$-$C_6$)alkyl or ($C_6$-$C_{10}$)aryl; amino, optionally substituted with ($C_1$-$C_6$) alkyl or ($C_6$-$C_{10}$)aryl; or 6 to 10 membered heterocycle, optionally substituted with ($C_1$-$C_6$)alkyl or ($C_6$-$C_{10}$)aryl;

$R^9$ and $R^{10}$ are each independently hydrogen, 6 to 10 membered aryl, —COO—($C_1$-$C_6$)alkyl, —($C_0$-$C_6$)alkyl-CHO, —($C_0$-$C_6$)alkyl-COOH, —($C_0$-$C_6$)alkyl-$NR^{9'}R^{10'}$, —($C_0$-$C_6$)alkyl-(5 to 10 membered heterocycle), —($C_1$-$C_6$) alkyl-OH, —($C_1$-$C_6$)alkyl-O—($C_1$-$C_6$)alkyl, ($C_1$-$C_6$)alkyl, or ($C_3$-$C_6$)cycloalkyl; or $R^9$ and $R^{10}$ together may form an optionally substituted 5 to 6 membered ring containing one or more heteroatoms; and $R^{9'}$ and $R^{10'}$ are each independently hydrogen or ($C_1$-$C_6$) alkyl;

with the proviso that all of $R^5$-$R^7$ cannot be hydrogen; and with the proviso that if one of $R^5$-$R^7$ is hydrogen and the remaining two of $R^5$-$R^7$ are both chloride, then the two chloride atoms cannot be on 3 and 4 position of the phenyl ring.

In one embodiment, $R^5$ is hydrogen. In another embodiment, $R^5$ is halogen. In another embodiment, $R^5$ is nitro. In another embodiment, $R^5$ is carbamoyl. In another embodiment, $R^5$ is amino. In another embodiment, $R^5$ is —$SO_2R^8$. In another embodiment, $R^5$ is —$CONR^9R^{10}$. In another embodiment, $R^5$ is —($C_1$-$C_6$)alkyl, optionally substituted with one or more halogen, amino, hydroxyl, or $NR^9R^{10}$. In another embodiment, $R^5$ is —($C_1$-$C_6$)alkoxy, optionally substituted with one or more halogen, amino, hydroxyl or $NR^9R^{10}$.

In one embodiment, $R^6$ is hydrogen. In another embodiment, $R^6$ is halogen. In another embodiment, $R^6$ is nitro. In another embodiment, $R^6$ is carbamoyl. In another embodiment, $R^6$ is amino. In another embodiment, $R^6$ is —$SO_2R^8$. In another embodiment, $R^6$ is —$CONR^9R^{10}$. In another embodiment, $R^6$ is —($C_1$-$C_6$)alkyl, optionally substituted with one or more halogen, amino, hydroxyl, or $NR^9R^{10}$. In another embodiment, $R^6$ is —($C_1$-$C_6$)alkoxy, optionally substituted with one or more halogen, amino, hydroxyl or $NR^9R^{10}$.

In one embodiment, $R^7$ is hydrogen. In another embodiment, $R^7$ is halogen. In another embodiment, $R^7$ is nitro. In another embodiment, $R^7$ is carbamoyl. In another embodiment, $R^7$ is amino. In another embodiment, $R^7$ is —$SO_2R^8$. In another embodiment, $R^7$ is —$CONR^9R^{10}$. In another embodiment, $R^7$ is —($C_1$-$C_6$)alkyl, optionally substituted with one or more halogen, amino, hydroxyl, or $NR^9R^{10}$. In another embodiment, $R^7$ is —($C_1$-$C_6$)alkoxy, optionally substituted with one or more halogen, amino, hydroxyl or $NR^9R^{10}$.

In one embodiment, $R^8$ is ($C_1$-$C_6$)alkyl, optionally substituted with ($C_1$-$C_6$)alkyl or ($C_6$-$C_{10}$)aryl. In another embodiment, $R^8$ is amino, optionally substituted with ($C_1$-$C_6$)alkyl or ($C_6$-$C_{10}$)aryl. In another embodiment, $R^8$ is 6 to 10 membered heterocycle, optionally substituted with ($C_1$-$C_6$)alkyl or ($C_6$-$C_{10}$)aryl.

In one embodiment, $R^9$ is hydrogen. In another embodiment, $R^9$ is 6 to 10 membered aryl. In another embodiment, $R^9$ is —COO—($C_1$-$C_6$)alkyl. In another embodiment, $R^9$ is —($C_0$-$C_6$)alkyl-CHO. In another embodiment, $R^9$ is —($C_0$-$C_6$)alkyl-COOH. In another embodiment, $R^9$ is —($C_0$-$C_6$)alkyl-$NR^{9'}R^{10'}$. In another embodiment, $R^9$ is —($C_0$-$C_6$)alkyl-(5 to 10 membered heterocycle). In another embodiment, $R^9$ is —($C_1$-$C_6$)alkyl-OH. In another embodiment, $R^9$ is —($C_1$-$C_6$)alkyl-O—($C_1$-$C_6$)alkyl. In another embodiment, $R^9$ is ($C_1$-$C_6$)alkyl. In another embodiment, $R^9$ is ($C_3$-$C_6$)cycloalkyl.

In one embodiment, $R^{10}$ is hydrogen. In another embodiment, $R^{10}$ is 6 to 10 membered aryl. In another embodiment, $R^{10}$ is —COO—($C_1$-$C_6$)alkyl. In another embodiment, $R^{10}$ is —($C_0$-$C_6$)alkyl-CHO. In another embodiment, $R^{10}$ is —($C_0$-$C_6$)alkyl-COOH. In another embodiment, $R^{10}$ is —($C_0$-$C_6$)alkyl-$NR^{9'}R^{10'}$. In another embodiment, $R^{10}$ is —($C_0$-$C_6$)alkyl-(5 to 10 membered heterocycle). In another embodiment, $R^{10}$ is —($C_1$-$C_6$)alkyl-OH. In another embodiment, $R^{10}$ is —($C_1$-$C_6$)alkyl-O—($C_1$-$C_6$)alkyl. In another embodiment, $R^{10}$ is ($C_1$-$C_6$)alkyl. In another embodiment, $R^{10}$ is ($C_3$-$C_6$)cycloalkyl.

In one embodiment, $R^9$ and $R^{10}$ together form a 5 to 6 membered ring. In one embodiment, the ring contains one or more heteroatoms. In one embodiment, the heteroatoms are selected from the group consisting of N, S and O.

In one embodiment, $R^{9'}$ is hydrogen. In another embodiment, $R^{9'}$ is ($C_1$-$C_6$)alkyl.

In one embodiment, $R^{10'}$ is hydrogen. In another embodiment, $R^{10'}$ is ($C_1$-$C_6$)alkyl.

In certain embodiments, provided herein are compounds that result from any combination of $R^5$-$R^{10}$ and $R^{9'}$-$R^{10'}$.

In one embodiment, one of $R^5$-$R^7$ is hydrogen and the remaining two of $R^5$-$R^7$ are halogen. In one embodiment, one of $R^5$-$R^7$ is hydrogen and the remaining two of $R^5$-$R^7$ are ($C_1$-$C_6$)alkoxy. In one embodiment, one of $R^5$-$R^7$ is hydrogen and the remaining two of $R^5$-$R^7$ are ($C_1$-$C_6$)alkyl. In one embodiment, $R^5$ is hydrogen, $R^6$ is halogen, and $R^7$ is ($C_1$-$C_6$)alkoxy.

In one embodiment, two of $R^5$-$R^7$ are hydrogen and the remaining one of $R^5$-$R^7$ is halogen. In one embodiment, two of $R^5$-$R^7$ are hydrogen and the remaining one of $R^5$-$R^7$ is ($C_1$-$C_6$)alkoxy. In one embodiment, two of $R^5$-$R^7$ are hydrogen and the remaining one of $R^5$-$R^7$ is ($C_1$-$C_6$)alkyl.

In one embodiment, specific examples include, but are not limited to those listed in Table Y, below:

TABLE Y

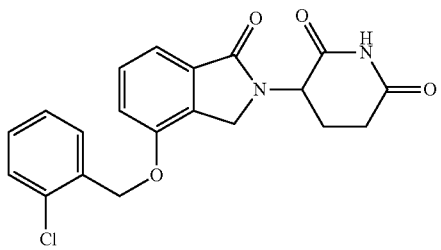 [SMILES: O=C1CCC(N2Cc3c(OCc4ccccc4Cl)cccc3C2=O)C(=O)N1]

TABLE Y-continued
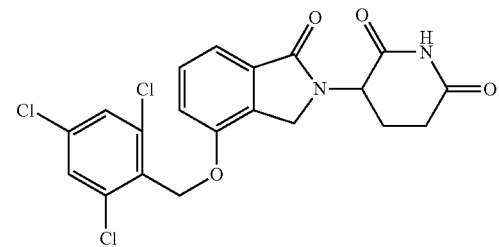 [SMILES: O=C1CCC(N2Cc3c(OCc4c(Cl)cc(Cl)cc4Cl)cccc3C2=O)C(=O)N1]
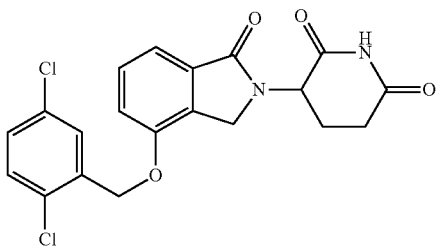 [SMILES: O=C1CCC(N2Cc3c(OCc4cc(Cl)ccc4Cl)cccc3C2=O)C(=O)N1]
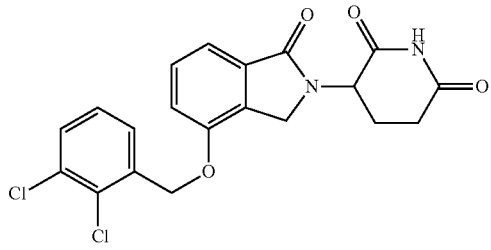 [SMILES: O=C1CCC(N2Cc3c(OCc4cccc(Cl)c4Cl)cccc3C2=O)C(=O)N1]
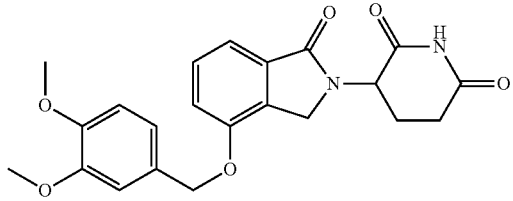 [SMILES: COc1ccc(COc2cccc3c2CN(C2CCC(=O)NC2=O)C3=O)cc1OC]
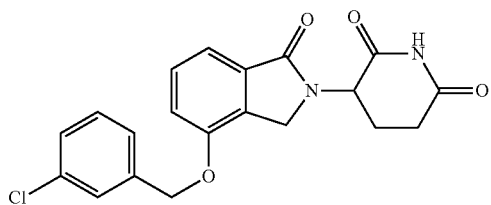 [SMILES: O=C1CCC(N2Cc3c(OCc4cccc(Cl)c4)cccc3C2=O)C(=O)N1]
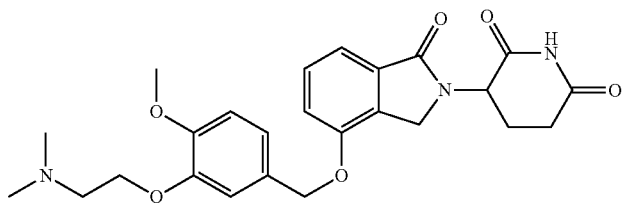 [SMILES: COc1ccc(COc2cccc3c2CN(C2CCC(=O)NC2=O)C3=O)cc1OCCN(C)C]
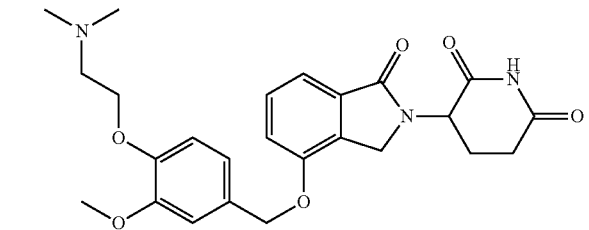 [SMILES: COc1cc(COc2cccc3c2CN(C2CCC(=O)NC2=O)C3=O)ccc1OCCN(C)C]

TABLE Y-continued
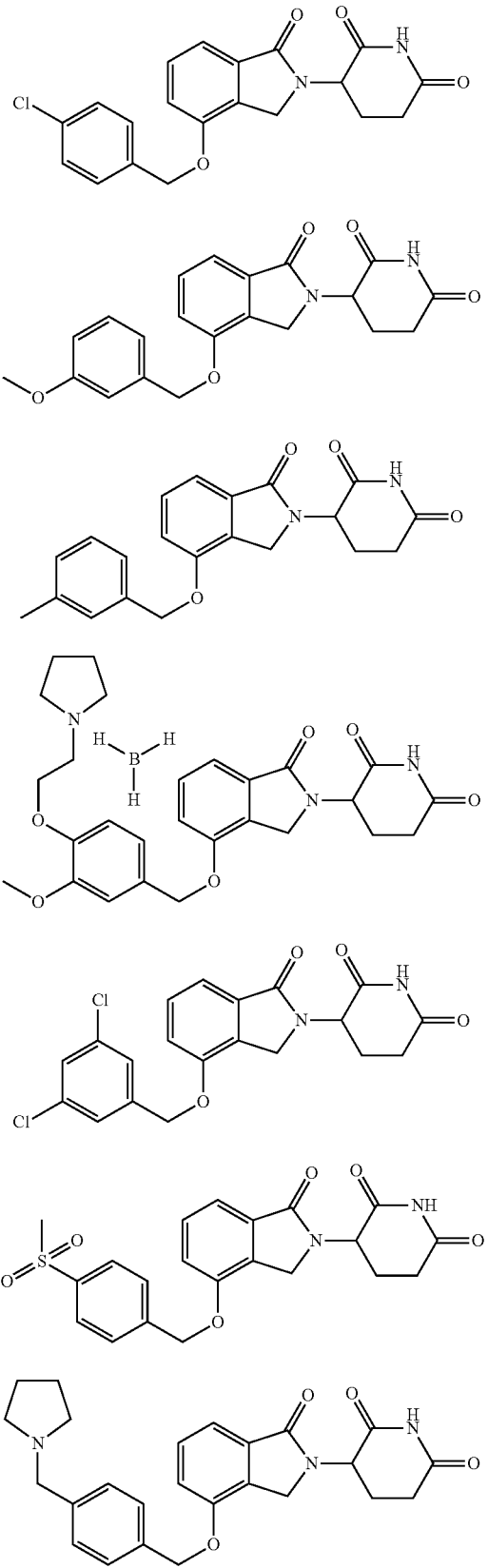

TABLE Y-continued
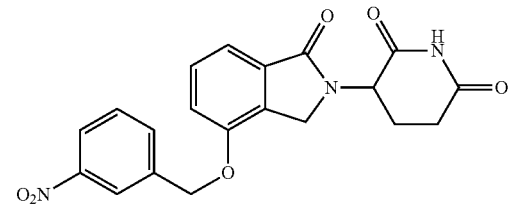 [SMILES: O=C1CCC(N2Cc3c(OCc4cccc([N+](=O)[O-])c4)cccc3C2=O)C(=O)N1]
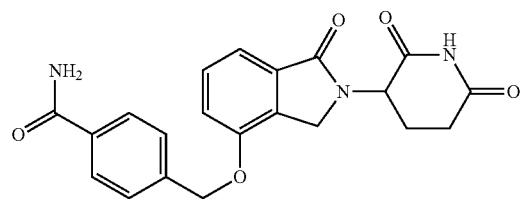 [SMILES: NC(=O)c1ccc(COc2cccc3c2CN(C2CCC(=O)NC2=O)C3=O)cc1]
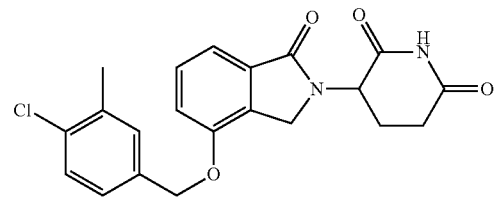 [SMILES: Cc1cc(COc2cccc3c2CN(C2CCC(=O)NC2=O)C3=O)ccc1Cl]
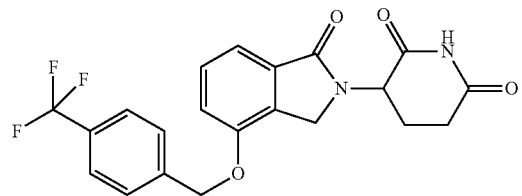
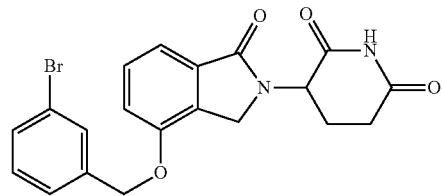 [SMILES: O=C1CCC(N2Cc3c(OCc4cccc(Br)c4)cccc3C2=O)C(=O)N1]
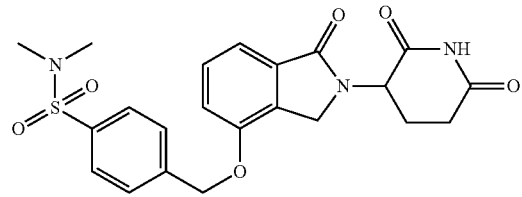 [SMILES: CN(C)S(=O)(=O)c1ccc(COc2cccc3c2CN(C2CCC(=O)NC2=O)C3=O)cc1]
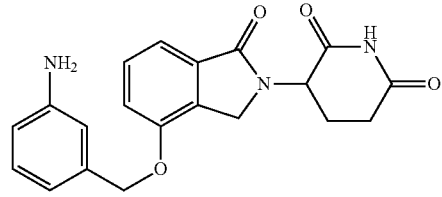 [SMILES: Nc1cccc(COc2cccc3c2CN(C2CCC(=O)NC2=O)C3=O)c1]

TABLE Y-continued
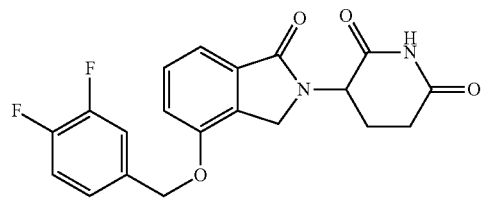 [SMILES: O=C1CCC(N2Cc3c(OCc4ccc(F)c(F)c4)cccc3C2=O)C(=O)N1]
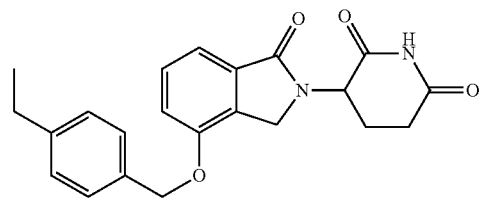 [SMILES: CCc1ccc(COc2cccc3c2CN(C2CCC(=O)NC2=O)C3=O)cc1]
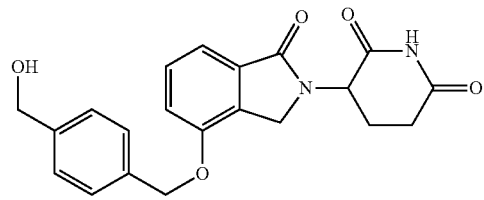 [SMILES: O=C1CCC(N2Cc3c(OCc4ccc(CO)cc4)cccc3C2=O)C(=O)N1]
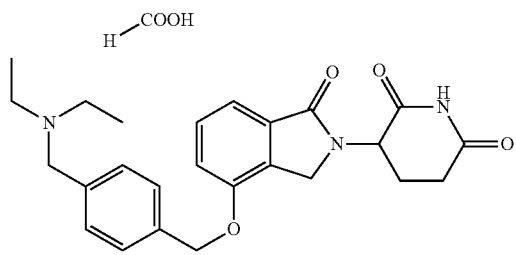 [SMILES: O=CO ; CCN(CC)Cc1ccc(COc2cccc3c2CN(C2CCC(=O)NC2=O)C3=O)cc1]
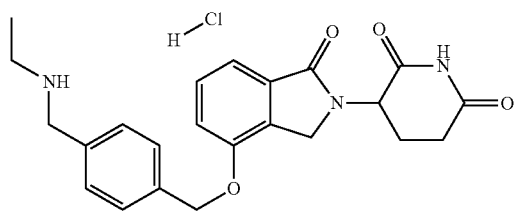
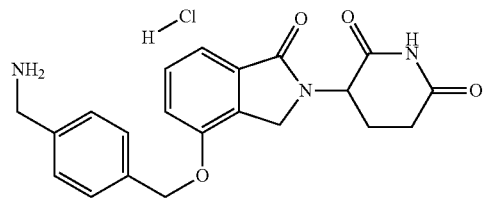
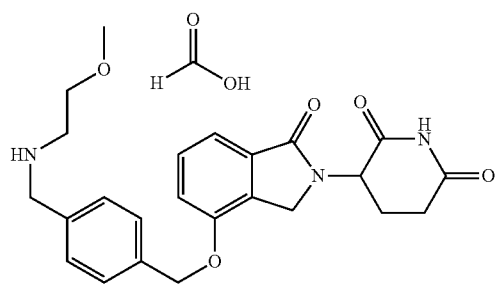

TABLE Y-continued
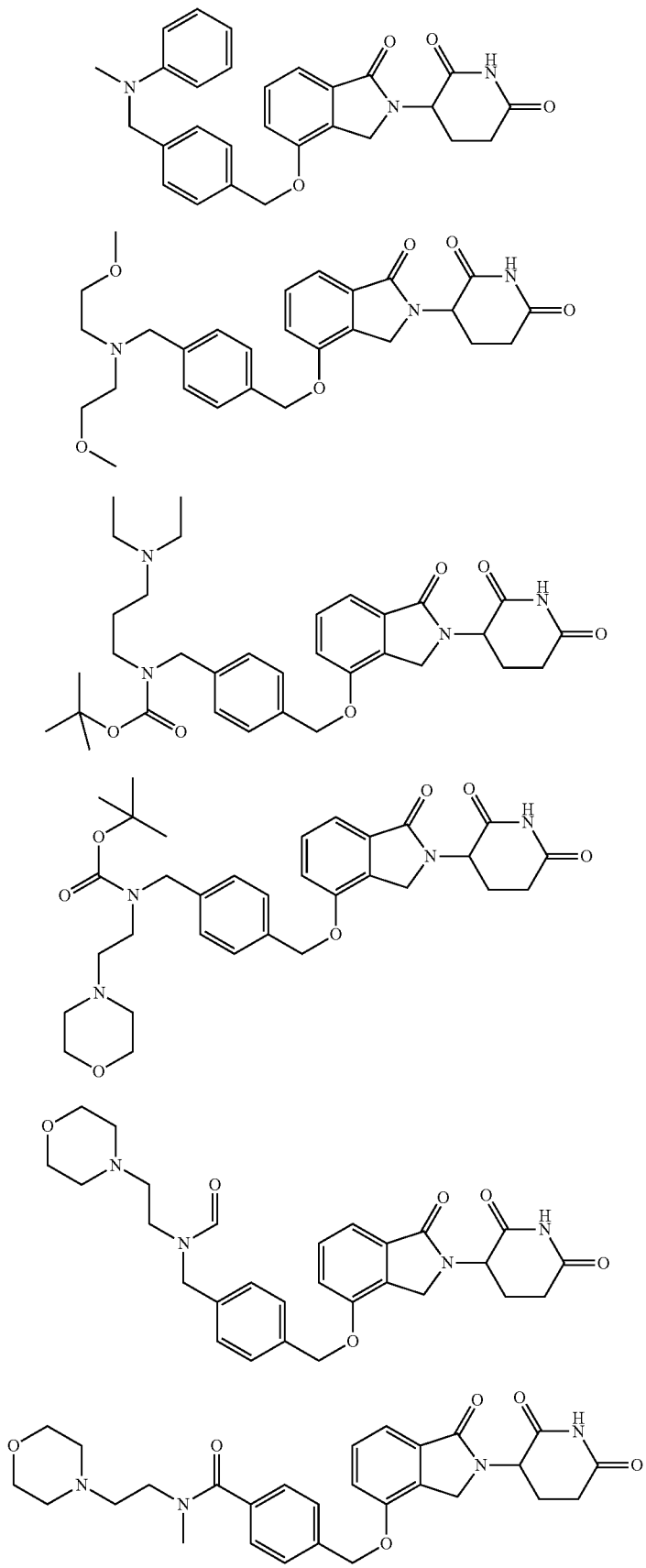

TABLE Y-continued
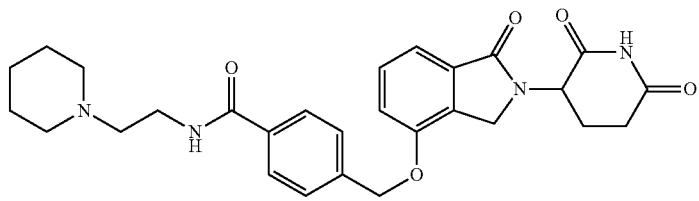 [SMILES: O=C1CCC(N2Cc3c(OCc4ccc(C(=O)NCCN5CCCCC5)cc4)cccc3C2=O)C(=O)N1]
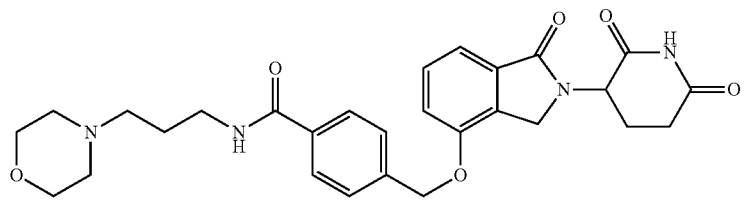 [SMILES: O=C1CCC(N2Cc3c(OCc4ccc(C(=O)NCCCN5CCOCC5)cc4)cccc3C2=O)C(=O)N1]
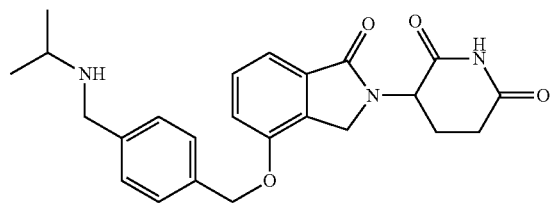 [SMILES: CC(C)NCc1ccc(COc2cccc3c2CN(C2CCC(=O)NC2=O)C3=O)cc1]
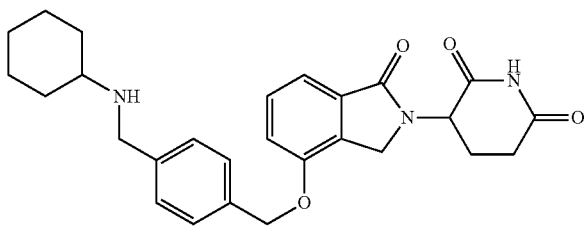 [SMILES: O=C1CCC(N2Cc3c(OCc4ccc(CNC5CCCCC5)cc4)cccc3C2=O)C(=O)N1]
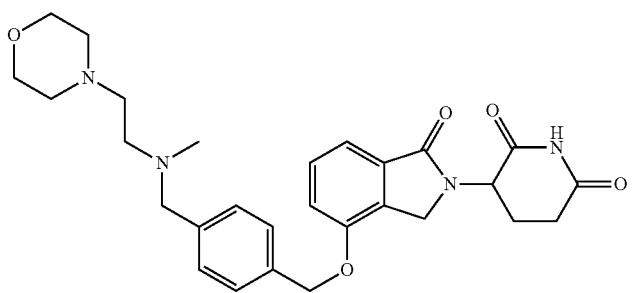 [SMILES: CN(CCN1CCOCC1)Cc1ccc(COc2cccc3c2CN(C2CCC(=O)NC2=O)C3=O)cc1]
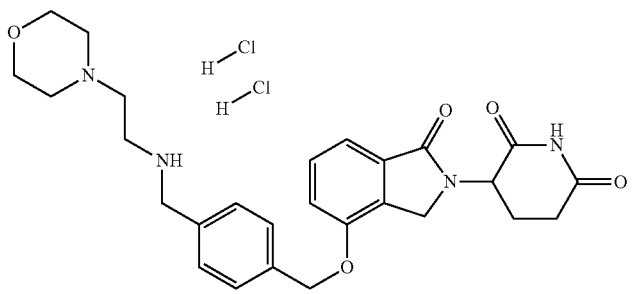

TABLE Y-continued
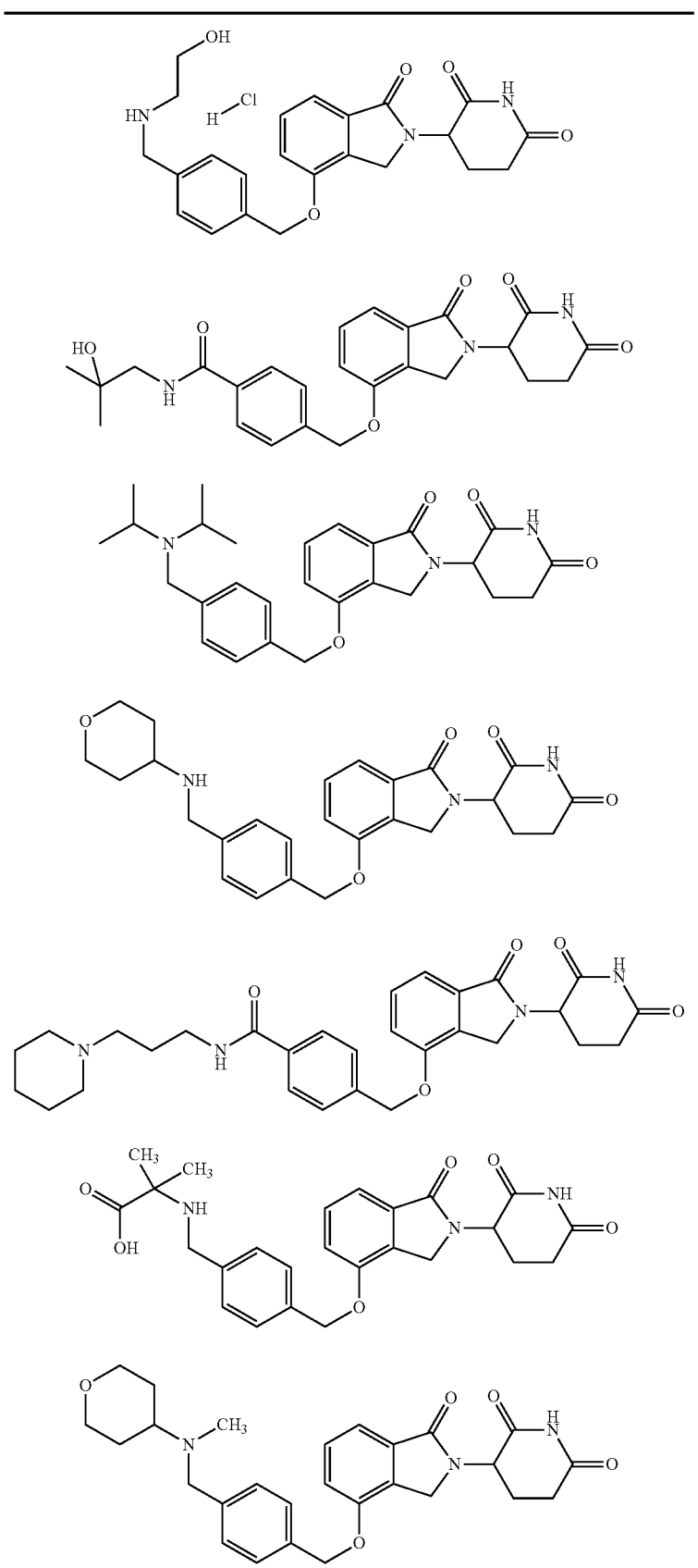

TABLE Y-continued
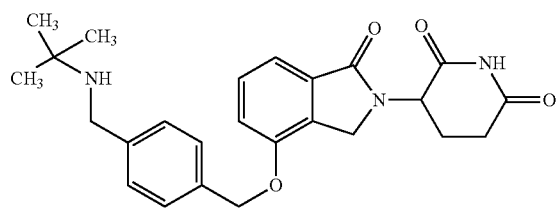 [SMILES: CC(C)(C)NCc1ccc(COc2cccc3c2CN(C2CCC(=O)NC2=O)C3=O)cc1]
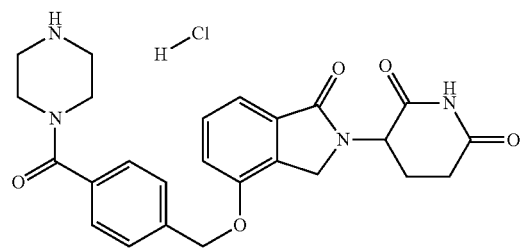 [SMILES: O=C1CCC(N2Cc3c(OCc4ccc(C(=O)N5CCNCC5)cc4)cccc3C2=O)C(=O)N1 ; Cl]
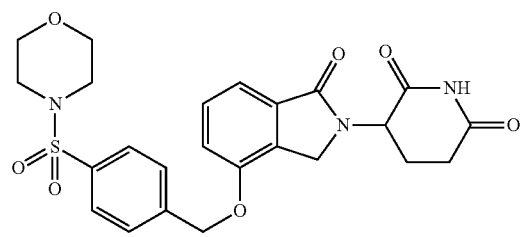 [SMILES: O=C1CCC(N2Cc3c(OCc4ccc(S(=O)(=O)N5CCOCC5)cc4)cccc3C2=O)C(=O)N1]
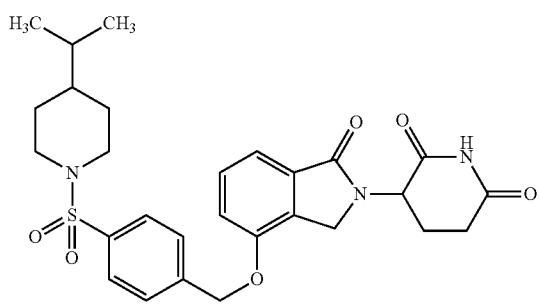 [SMILES: CC(C)C1CCN(S(=O)(=O)c2ccc(COc3cccc4c3CN(C3CCC(=O)NC3=O)C4=O)cc2)CC1]
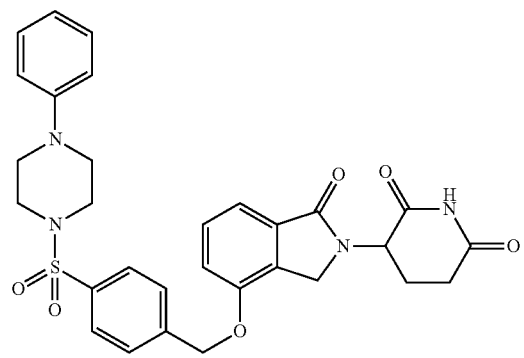 [SMILES: O=C1CCC(N2Cc3c(OCc4ccc(S(=O)(=O)N5CCN(c6ccccc6)CC5)cc4)cccc3C2=O)C(=O)N1]
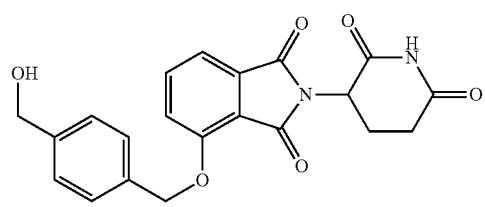 [SMILES: O=C1CCC(N2C(=O)c3cccc(OCc4ccc(CO)cc4)c3C2=O)C(=O)N1]

TABLE Y-continued

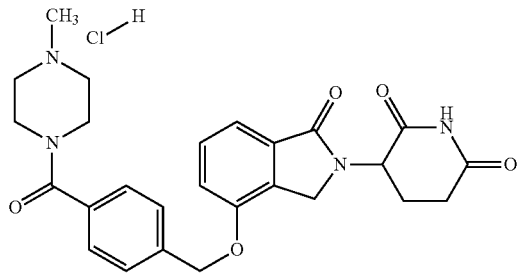

or a pharmaceutically acceptable salt, solvate or stereoisomer thereof.

In another embodiment, representative compounds are of formula (XXII):

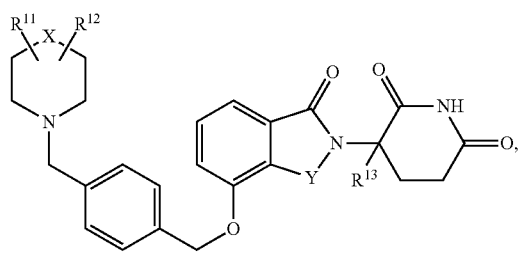

or a pharmaceutically acceptable salt, solvate or stereoisomer thereof, wherein:
X is N or C;
Y is $CH_2$ or C=O;
$R^{11}$ and $R^{12}$ are each independently hydrogen, —($C_1$-$C_6$) alkyl,
—($C_1$-$C_6$)alkyl-($C_3$-$C_6$)cycloalkyl, —($C_1$-$C_6$)alkoxy, —($C_6$-$C_{10}$)aryl, —CO($C_1$-$C_6$)alkyl, —CO($C_3$-$C_6$)cycloalkyl, —CO($C_6$-$C_{10}$)aryl, —COO($C_1$-$C_6$)alkyl, halogen, hydroxyl, oxo, 3 to 10 membered heterocycle, 6 to 10 membered heteroaryl, —NHCO($C_1$-$C_6$)alkyl, —($CH_2$)$_n$-phenyl, —$SO_2$($C_1$-$C_6$)alkyl, —$SO_2$($C_3$-$C_6$) cycloalkyl, —$SO_2$($C_6$-$C_1$)aryl or —$NR^{14}R^{15}$, wherein the alkyl, aryl or heteroaryl portion of each of the groups may be optionally substituted with one or more halogen, hydroxyl or —($C_1$-$C_6$)alkoxy;
$R^{13}$ is hydrogen or —($C_1$-$C_6$)alkyl;
$R^{14}$ and $R^{15}$ are each independently hydrogen or —($C_1$-$C_6$) alkyl; and
n is 0, 1, 2 or 3.

In one embodiment, X is N. In another embodiment, X is C.

In one embodiment, Y is $CH_2$. In another embodiment, Y is C=O.

In one embodiment, $R^{11}$ is hydrogen. In another embodiment, $R^{11}$ is —($C_1$-$C_6$)alkyl. In another embodiment, $R^{11}$ is —($C_1$-$C_6$)alkyl-($C_3$-$C_6$)cycloalkyl. In another embodiment, $R^{11}$ is —($C_1$-$C_6$)alkoxy. In another embodiment, $R^{11}$ is —(C6-C10)aryl. In another embodiment, $R^{11}$ is —CO($C_1$-$C_6$)alkyl. In another embodiment, $R^{11}$ is —CO($C_3$-$C_6$)cycloalkyl. In another embodiment, $R^{11}$ is —CO($C_6$-$C_{10}$)aryl. In another embodiment, $R^{11}$ is —COO($C_1$-$C_6$)alkyl. In another embodiment, $R^{11}$ is halogen. In another embodiment, $R^{11}$ is hydroxyl. In another embodiment, $R^{11}$ is oxo. In another embodiment, $R^{11}$ is 3 to 10 membered heterocycle. In another embodiment, $R^{11}$ is 6 to 10 membered heteroaryl. In another embodiment, $R^{11}$ is —NHCO($C_1$-$C_6$)alkyl. In another embodiment, $R^{11}$ is —($CH_2$)$_n$-phenyl. In another embodiment, $R^{11}$ is —$SO^2$($C_1$-$C_6$)alkyl. In another embodiment, $R^{11}$ is —$SO^2$($C_3$-$C_6$)cycloalkyl. In another embodiment, $R^{11}$ is —$SO_2$($C_6$-$C_{10}$)aryl. In another embodiment, $R^{11}$ is —$NR^{14}R^{15}$. In another embodiment, is the alkyl, aryl or heteroaryl portion of $R^{11}$ is substituted with one or more halogen, hydroxyl and/or —(C1-C6)alkoxy.

In one embodiment, $R^{12}$ is hydrogen. In another embodiment, $R^{12}$ is —($C_1$-$C_6$)alkyl. In another embodiment, $R^{12}$ is —($C_1$-$C_6$)alkyl-($C_3$-$C_6$)cycloalkyl. In another embodiment, $R^{12}$ is —($C_1$-$C_6$)alkoxy. In another embodiment, $R^{12}$ is —(C6-C10)aryl. In another embodiment, $R^{12}$ is —CO($C_1$-$C_6$)alkyl. In another embodiment, $R^{12}$ is —CO($C_3$-$C_6$)cycloalkyl. In another embodiment, $R^{12}$ is —CO($C_6$-$C_{10}$)aryl. In another embodiment, $R^{12}$ is —COO($C_1$-$C_6$)alkyl. In another embodiment, $R^{12}$ is halogen. In another embodiment, $R^{12}$ is hydroxyl. In another embodiment, $R^{12}$ is oxo. In another embodiment, $R^{12}$ is 3 to 10 membered heterocycle. In another embodiment, $R^{12}$ is 6 to 10 membered heteroaryl. In another embodiment, $R^{12}$ is —NHCO($C_1$-$C_6$) alkyl. In another embodiment, $R^{12}$ is —($CH_2$)$_n$-phenyl. In another embodiment, $R^{12}$ is —SO2($C_1$-$C_6$)alkyl. In another embodiment, $R^{12}$ is —$SO_2$($C_3$-$C_6$)cycloalkyl. In another embodiment, $R^{12}$ is —$SO_2$($C_6$-$C_{10}$)aryl. In another embodiment, $R^{12}$ is —NR14R15. In another embodiment, is the alkyl, aryl or heteroaryl portion of $R^{12}$ is substituted with one or more halogen, hydroxyl and/or —($C_1$-$C_6$)alkoxy.

In one embodiment, $R^{13}$ is hydrogen. In another embodiment, $R^{13}$ is —($C_1$-$C_6$)alkyl.

In one embodiment, $R^{14}$ is hydrogen. In another embodiment, $R^{14}$ is —($C_1$-$C_6$)alkyl.

In one embodiment, $R^5$ is hydrogen. In another embodiment, $R^5$ is —($C_1$-$C_6$)alkyl.

In one embodiment, n is 0. In another embodiment, n is 1. In another embodiment, n is 2. In another embodiment, n is 3.

In one embodiment, provided herein are compounds that result from any combination of X, Y, $R^{11}$-$R^{15}$ and n as defined above.

In one embodiment, specific examples include, but are not limited to those listed in Table Z, below:

TABLE Z
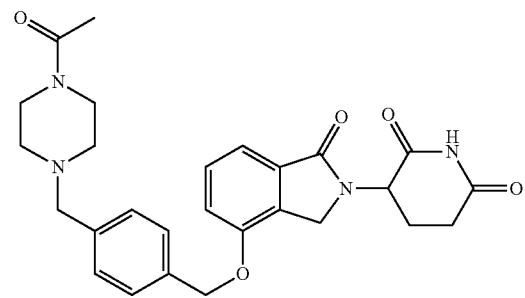 [SMILES: CC(=O)N1CCN(Cc2ccc(COc3cccc4c3CN(C3CCC(=O)NC3=O)C4=O)cc2)CC1]
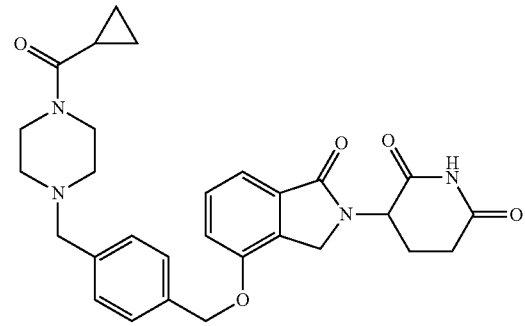 [SMILES: O=C1CCC(N2Cc3c(OCc4ccc(CN5CCN(C(=O)C6CC6)CC5)cc4)cccc3C2=O)C(=O)N1]
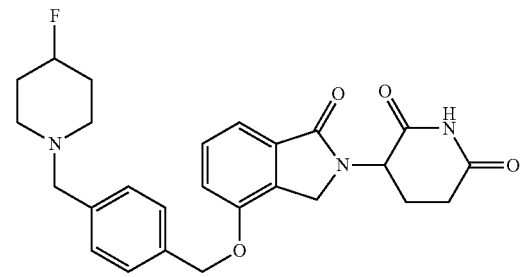
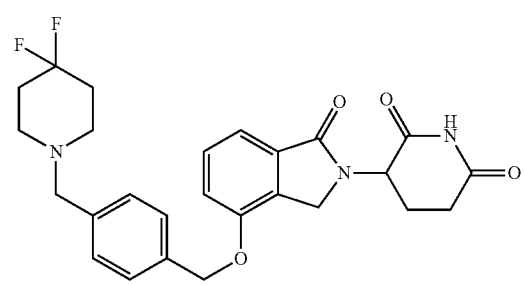
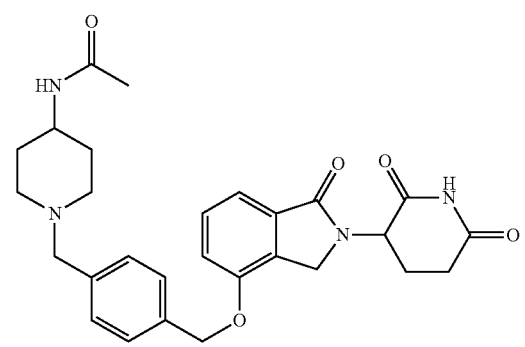 [SMILES: CC(=O)NC1CCN(Cc2ccc(COc3cccc4c3CN(C3CCC(=O)NC3=O)C4=O)cc2)CC1]
TABLE Z-continued
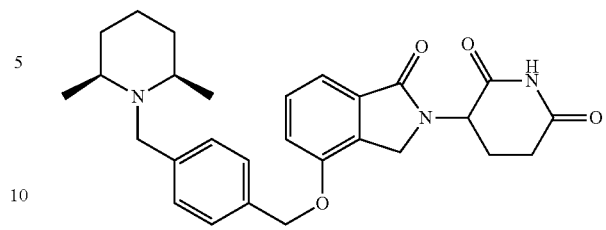
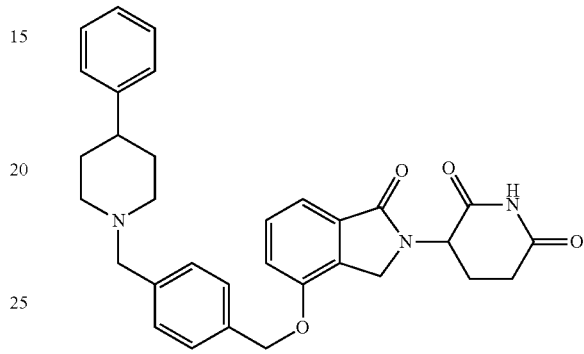
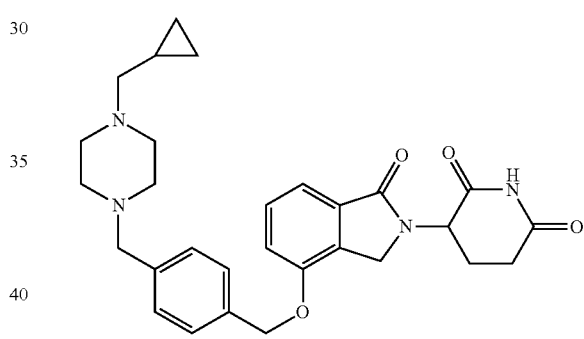
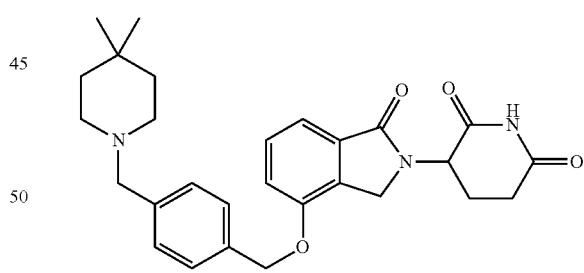
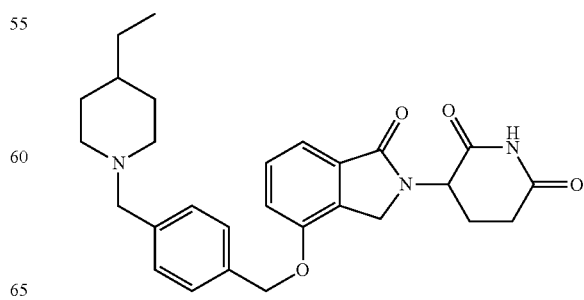

TABLE Z-continued
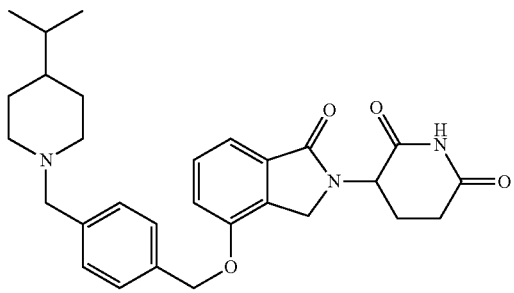 [SMILES: CC(C)C1CCN(Cc2ccc(COc3cccc4c3CN(C3CCC(=O)NC3=O)C4=O)cc2)CC1]
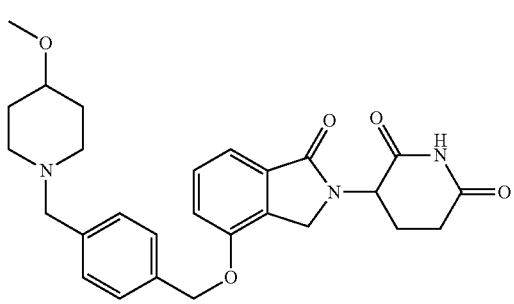 [SMILES: COC1CCN(Cc2ccc(COc3cccc4c3CN(C3CCC(=O)NC3=O)C4=O)cc2)CC1]
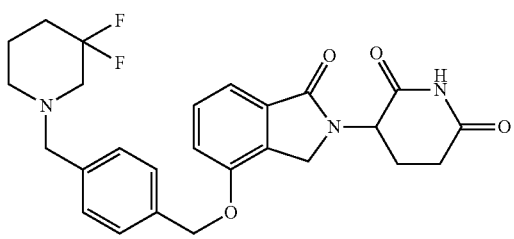 [SMILES: O=C1CCC(N2Cc3c(OCc4ccc(CN5CCCC(F)(F)C5)cc4)cccc3C2=O)C(=O)N1]
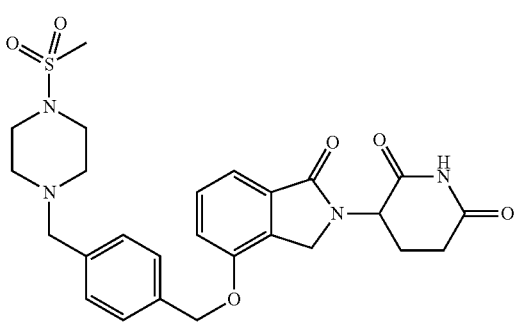 [SMILES: CS(=O)(=O)N1CCN(Cc2ccc(COc3cccc4c3CN(C3CCC(=O)NC3=O)C4=O)cc2)CC1]
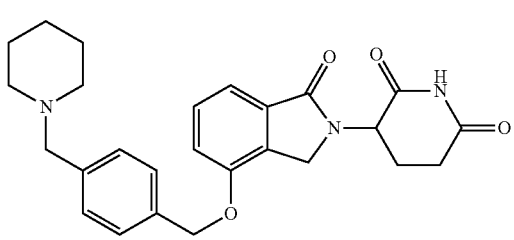 [SMILES: O=C1CCC(N2Cc3c(OCc4ccc(CN5CCCCC5)cc4)cccc3C2=O)C(=O)N1]
TABLE Z-continued
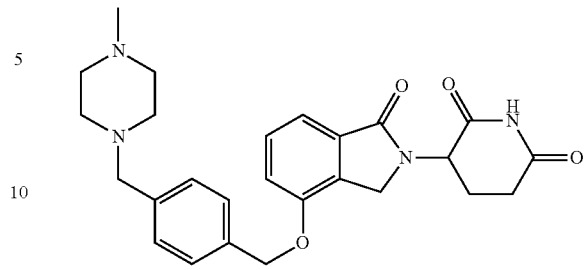
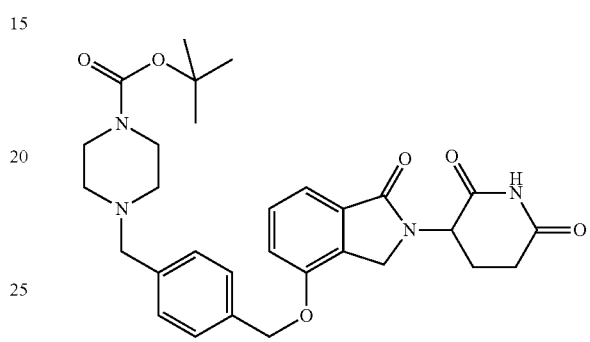
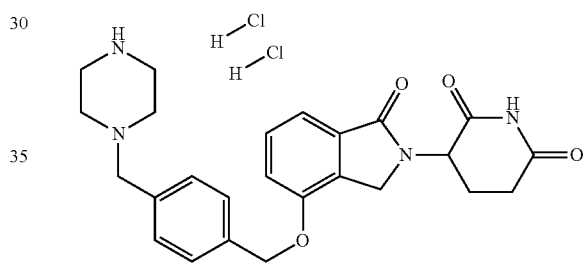
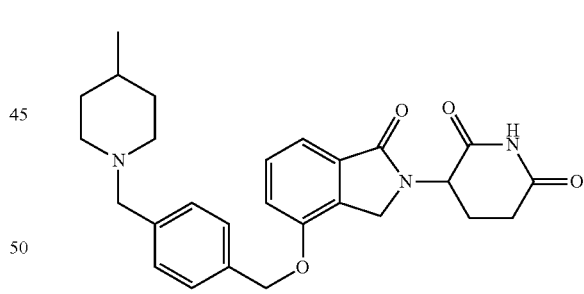
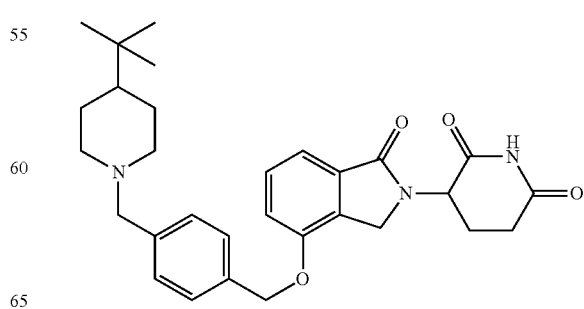

TABLE Z-continued
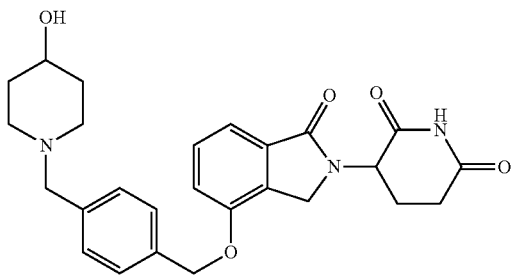
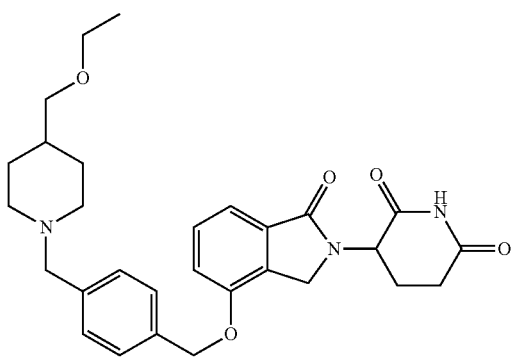 [SMILES: CCOCC1CCN(Cc2ccc(COc3cccc4c3CN(C3CCC(=O)NC3=O)C4=O)cc2)CC1]
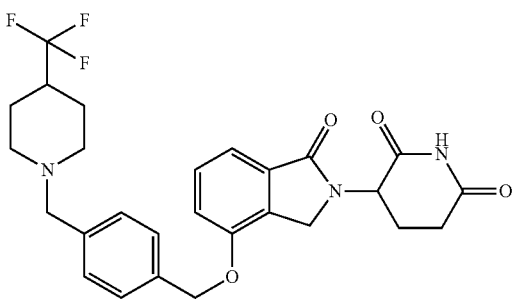 [SMILES: O=C1CCC(N2Cc3c(OCc4ccc(CN5CCC(C(F)(F)F)CC5)cc4)cccc3C2=O)C(=O)N1]
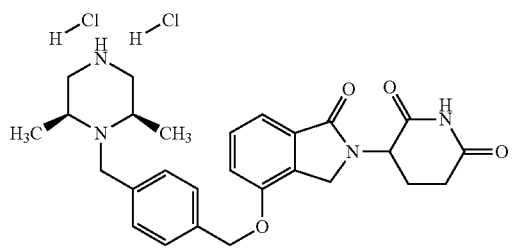
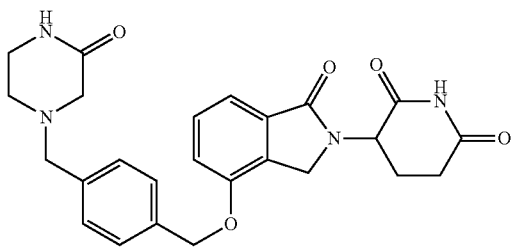 [SMILES: O=C1CN(Cc2ccc(COc3cccc4c3CN(C3CCC(=O)NC3=O)C4=O)cc2)CCN1]
TABLE Z-continued
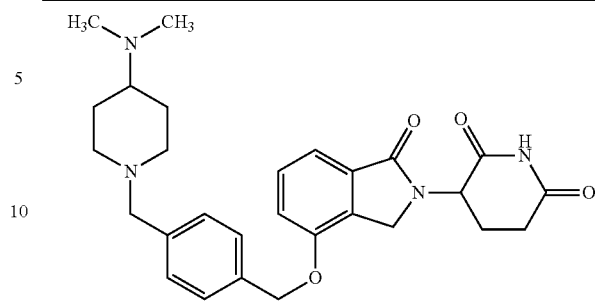
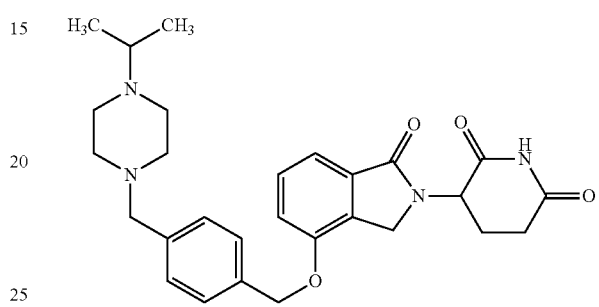
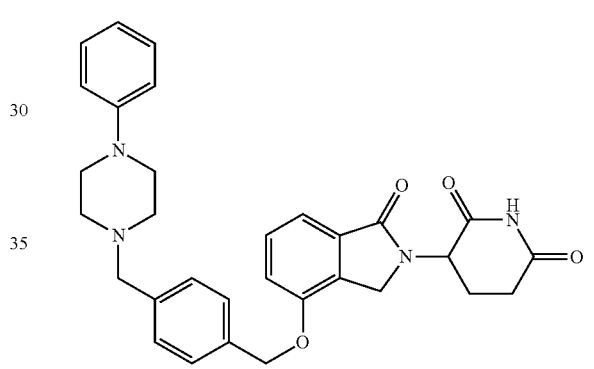
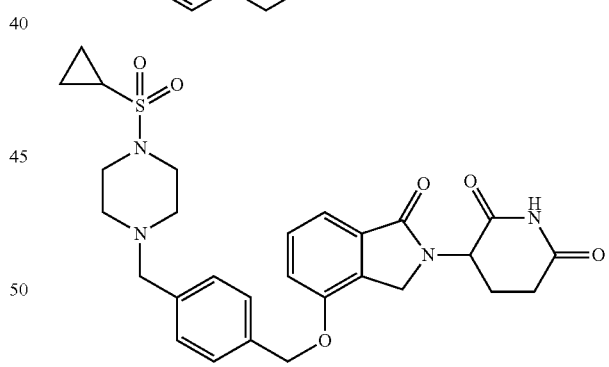
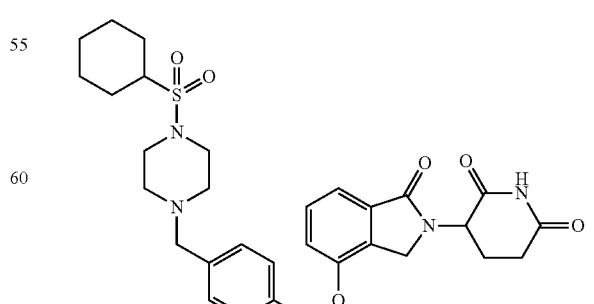

237
TABLE Z-continued
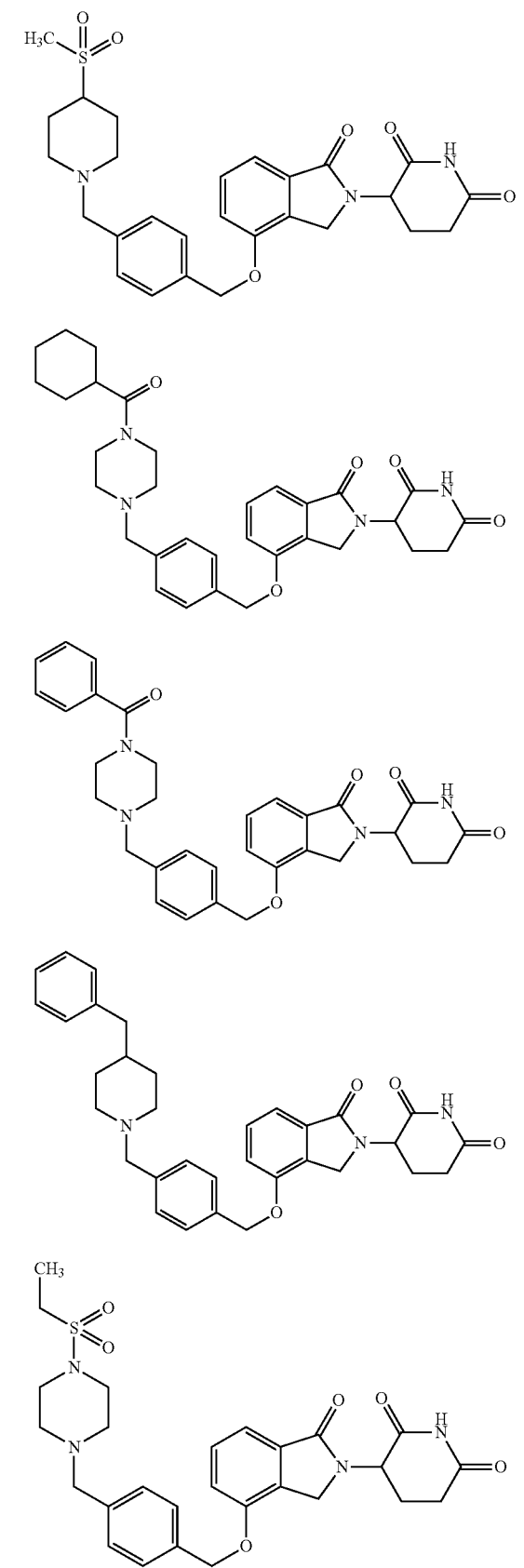
238
TABLE Z-continued
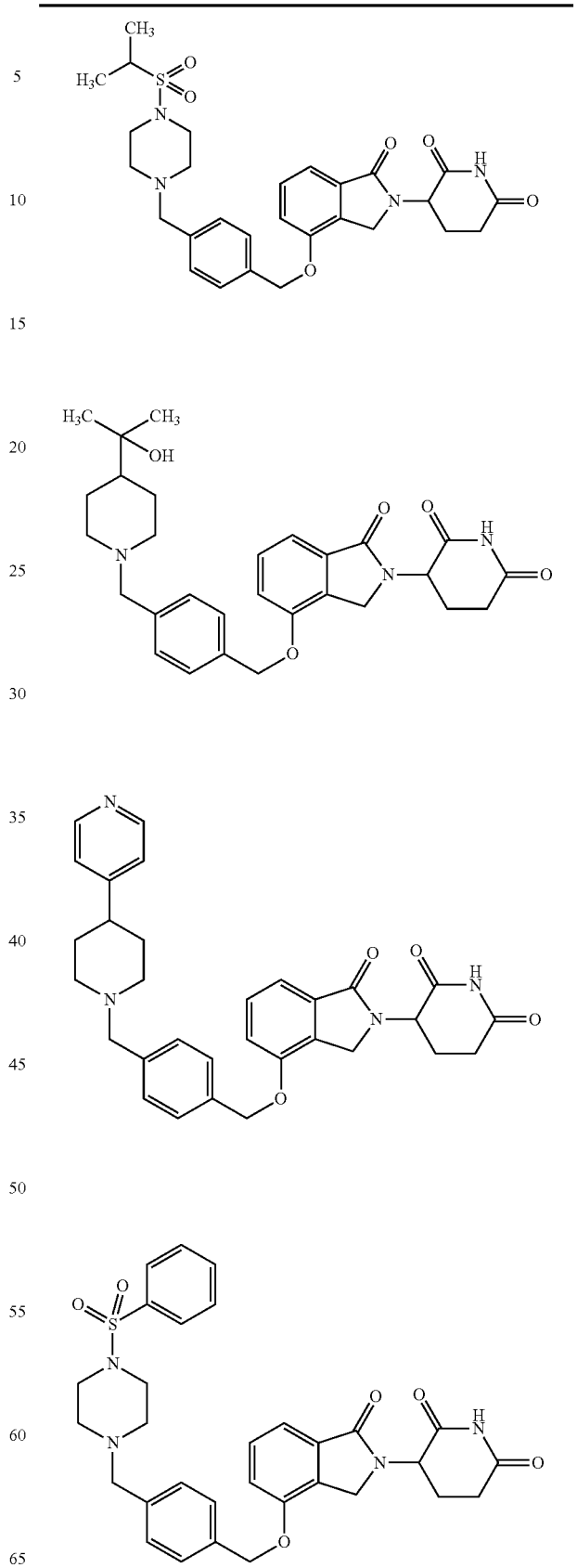

TABLE Z-continued
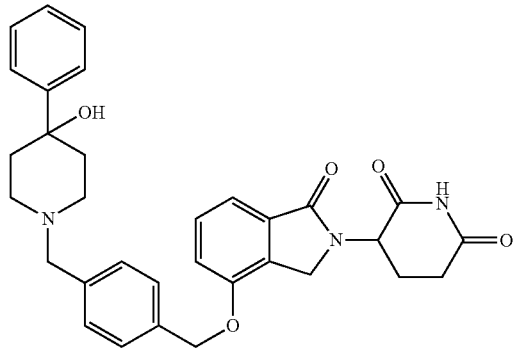 [SMILES: O=C1CCC(N2Cc3c(OCc4ccc(CN5CCC(O)(c6ccccc6)CC5)cc4)cccc3C2=O)C(=O)N1]
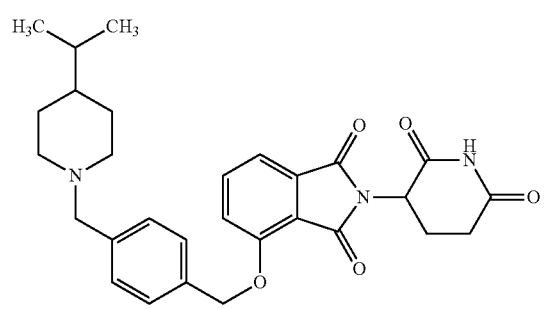 [SMILES: CC(C)C1CCN(Cc2ccc(COc3cccc4c3C(=O)N(C3CCC(=O)NC3=O)C4=O)cc2)CC1]
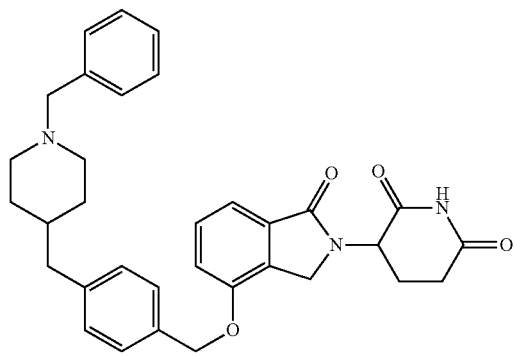
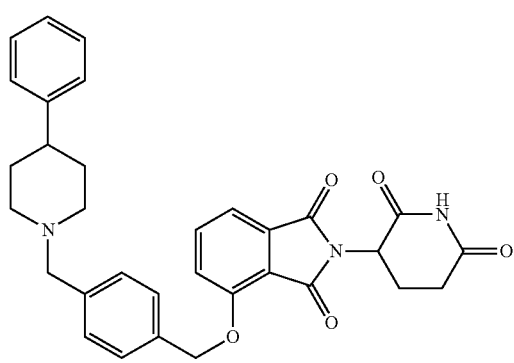 [SMILES: O=C1CCC(N2C(=O)c3cccc(OCc4ccc(CN5CCC(c6ccccc6)CC5)cc4)c3C2=O)C(=O)N1]
TABLE Z-continued
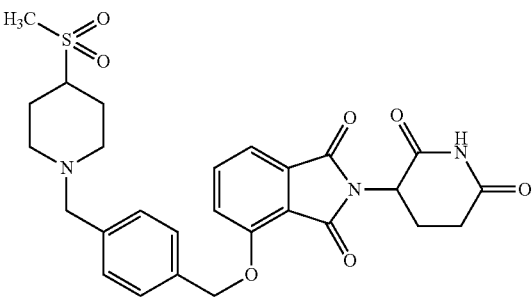 [SMILES: CS(=O)(=O)C1CCN(Cc2ccc(COc3cccc4c3C(=O)N(C3CCC(=O)NC3=O)C4=O)cc2)CC1]
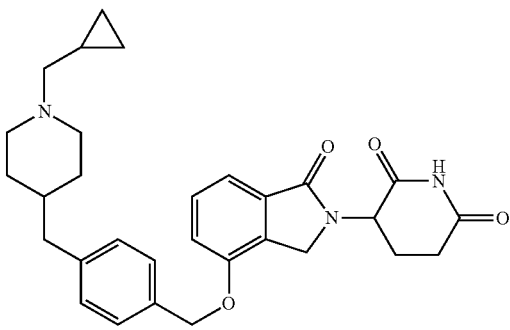 [SMILES: O=C1CCC(N2Cc3c(OCc4ccc(CC5CCN(CC6CC6)CC5)cc4)cccc3C2=O)C(=O)N1]
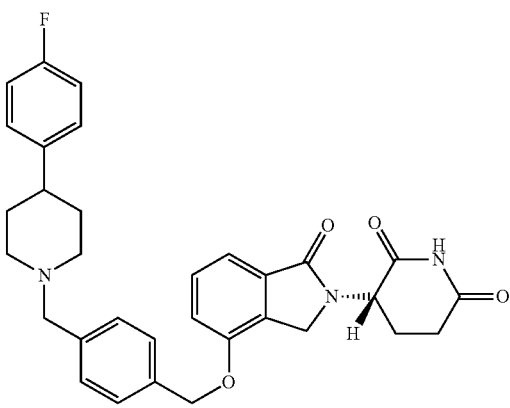
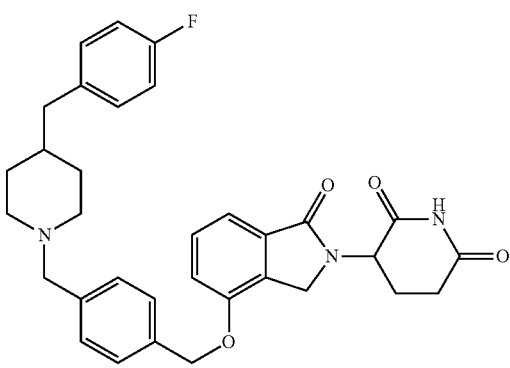 [SMILES: O=C1CCC(N2Cc3c(OCc4ccc(CN5CCC(Cc6ccc(F)cc6)CC5)cc4)cccc3C2=O)C(=O)N1]

TABLE Z-continued
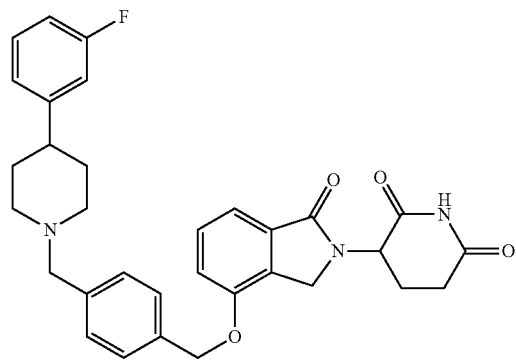 [SMILES: O=C1CCC(N2Cc3c(OCc4ccc(CN5CCC(c6cccc(F)c6)CC5)cc4)cccc3C2=O)C(=O)N1]
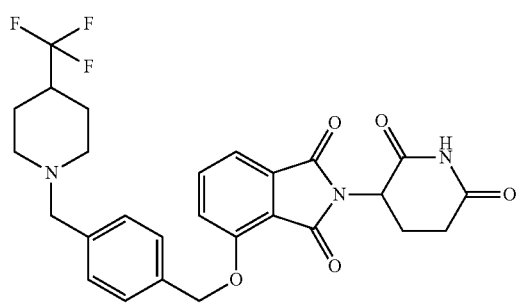 [SMILES: O=C1CCC(N2C(=O)c3cccc(OCc4ccc(CN5CCC(C(F)(F)F)CC5)cc4)c3C2=O)C(=O)N1]
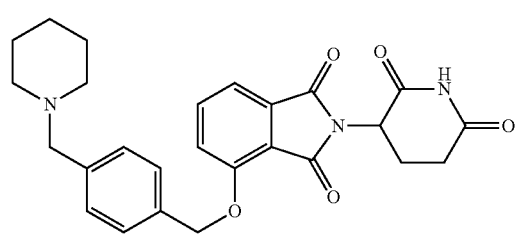 [SMILES: O=C1CCC(N2C(=O)c3cccc(OCc4ccc(CN5CCCCC5)cc4)c3C2=O)C(=O)N1]
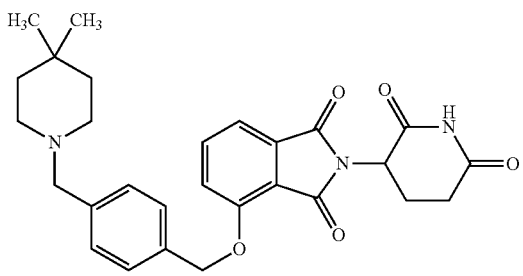 [SMILES: CC1(C)CCN(Cc2ccc(COc3cccc4c3C(=O)N(C3CCC(=O)NC3=O)C4=O)cc2)CC1]
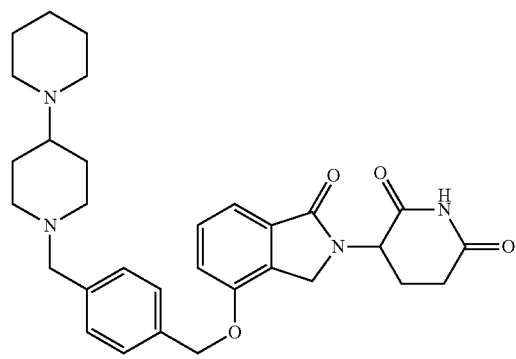 [SMILES: O=C1CCC(N2Cc3c(OCc4ccc(CN5CCC(N6CCCCC6)CC5)cc4)cccc3C2=O)C(=O)N1]
TABLE Z-continued
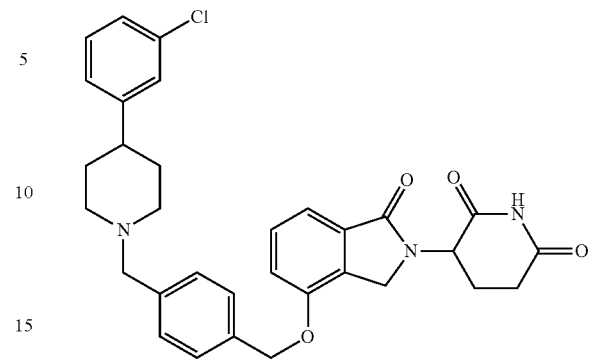
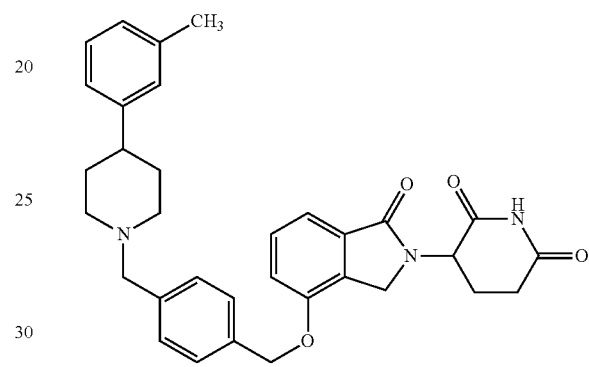
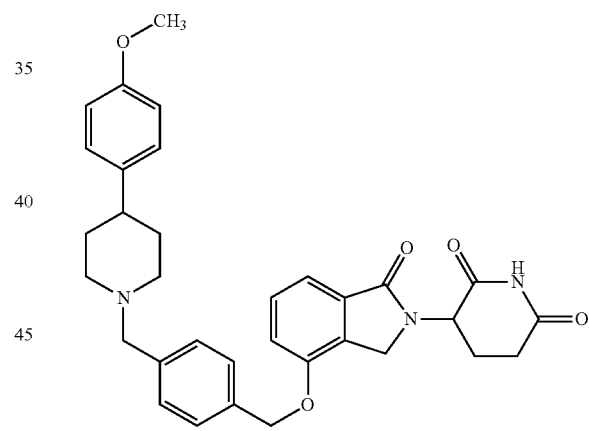
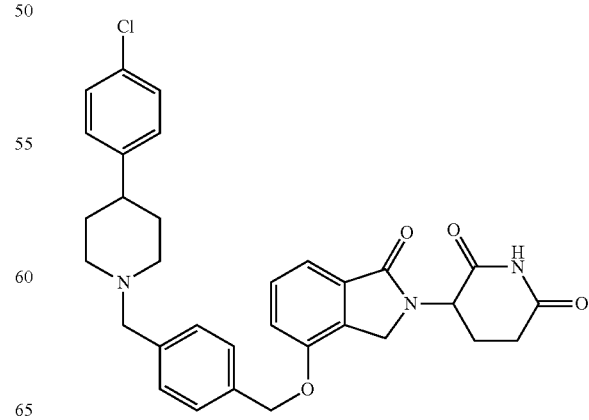

TABLE Z-continued
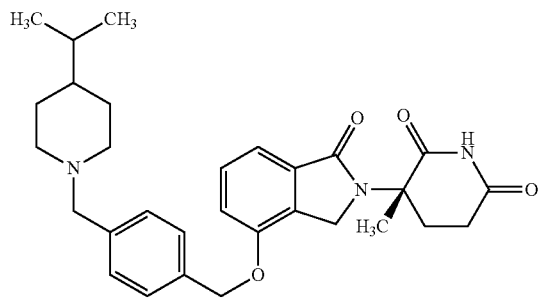 [SMILES: CC(C)C1CCN(Cc2ccc(COc3cccc4c3CN([C@@]3(C)CCC(=O)NC3=O)C4=O)cc2)CC1]
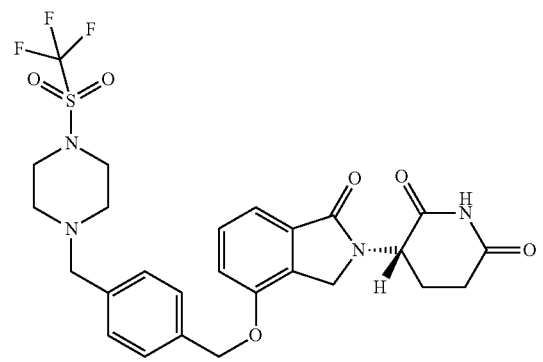
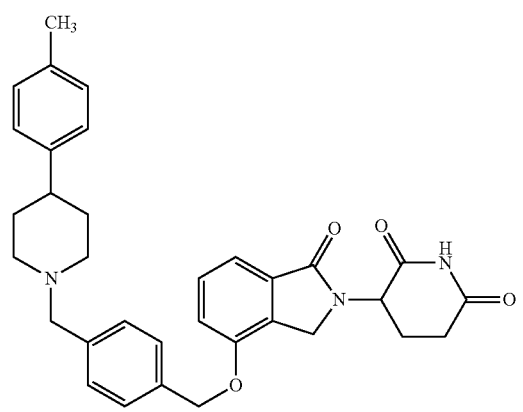 [SMILES: Cc1ccc(C2CCN(Cc3ccc(COc4cccc5c4CN(C4CCC(=O)NC4=O)C5=O)cc3)CC2)cc1]
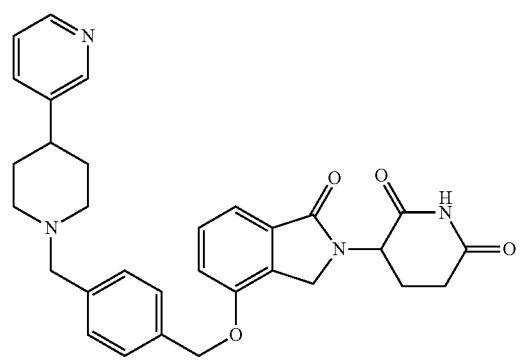 [SMILES: O=C1CCC(N2Cc3c(OCc4ccc(CN5CCC(c6cccnc6)CC5)cc4)cccc3C2=O)C(=O)N1]
TABLE Z-continued
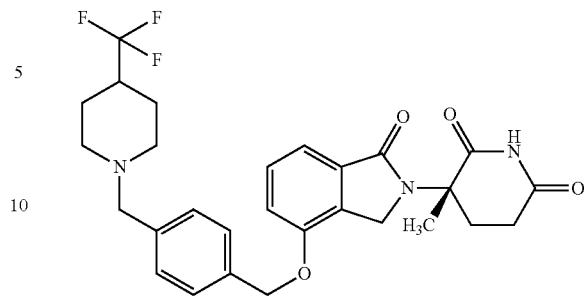
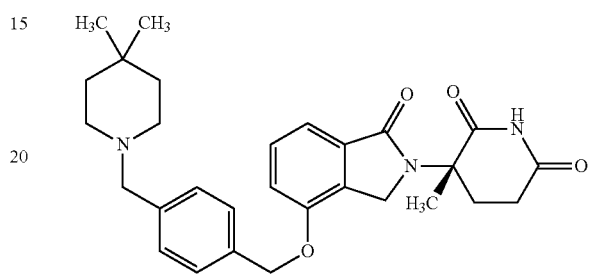
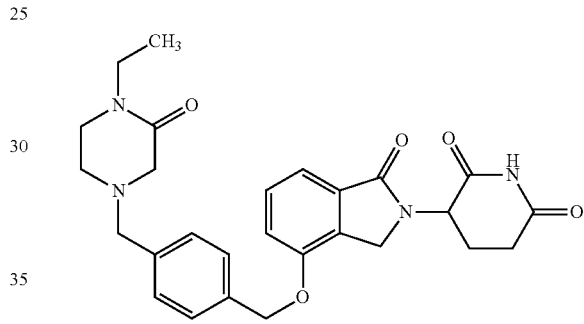
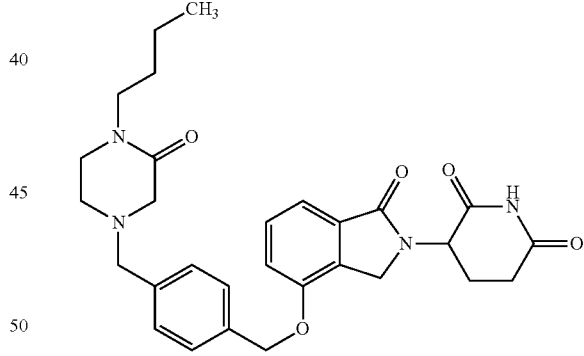
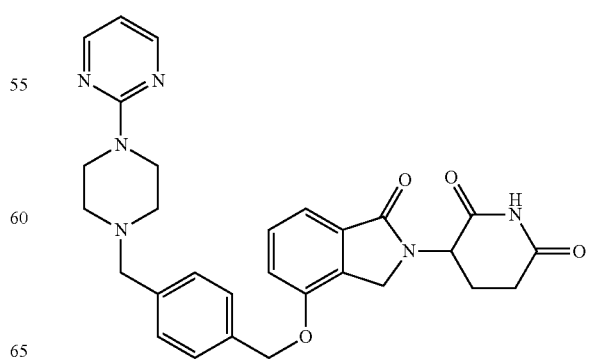

US 10,034,872 B2
245
TABLE Z-continued
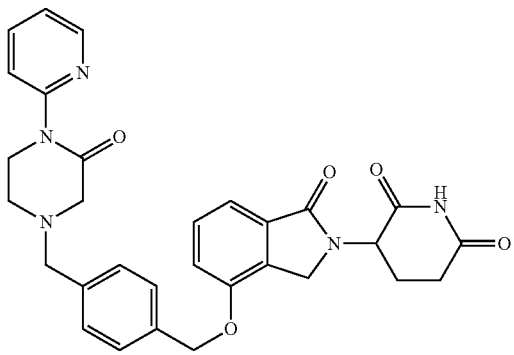 [SMILES: O=C1CCC(N2Cc3c(OCc4ccc(CN5CCN(c6ccccn6)C(=O)C5)cc4)cccc3C2=O)C(=O)N1]
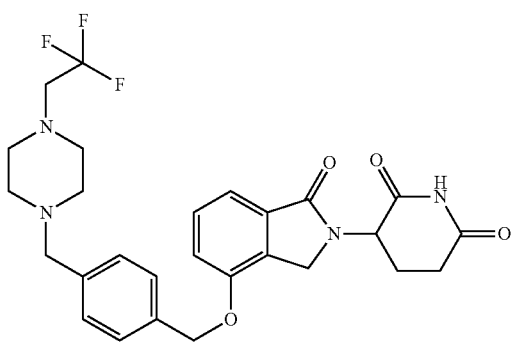 [SMILES: O=C1CCC(N2Cc3c(OCc4ccc(CN5CCN(CC(F)(F)F)CC5)cc4)cccc3C2=O)C(=O)N1]
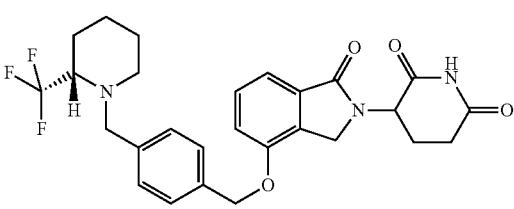
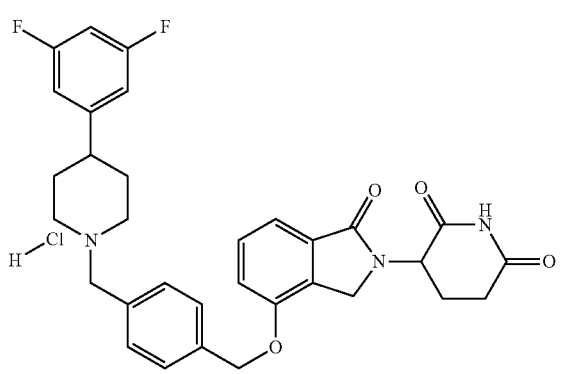
246
TABLE Z-continued
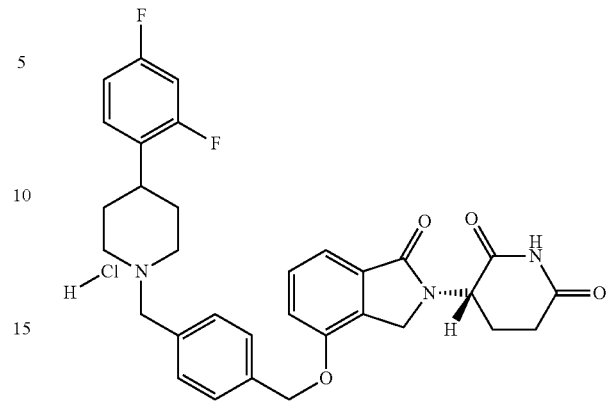
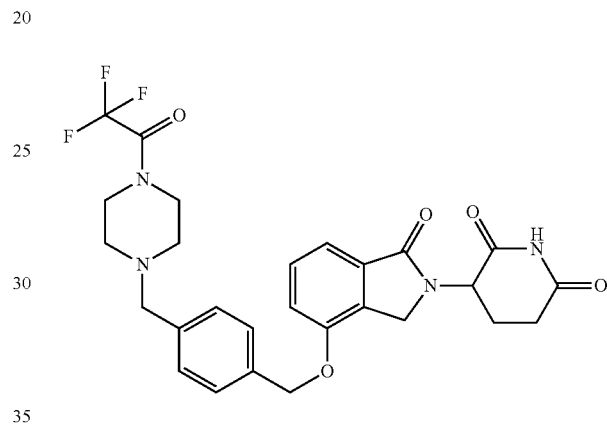
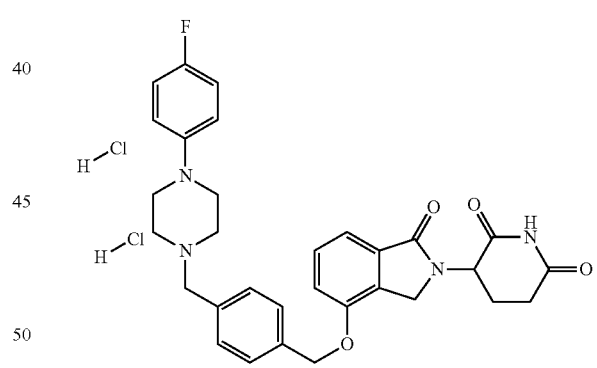
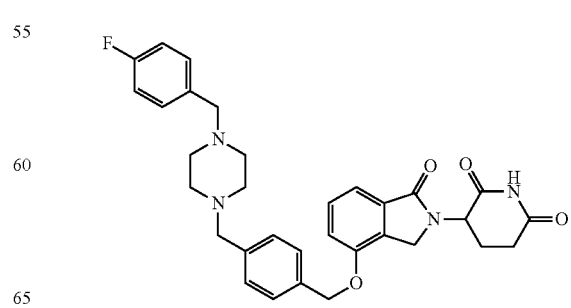

TABLE Z-continued
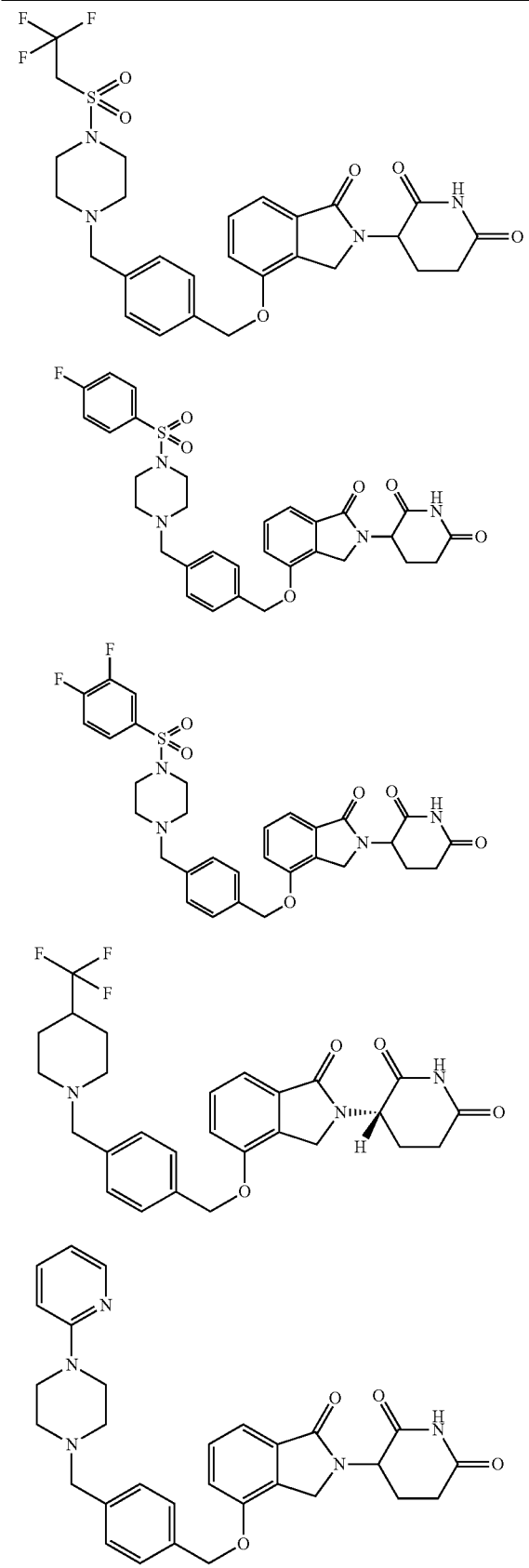
TABLE Z-continued
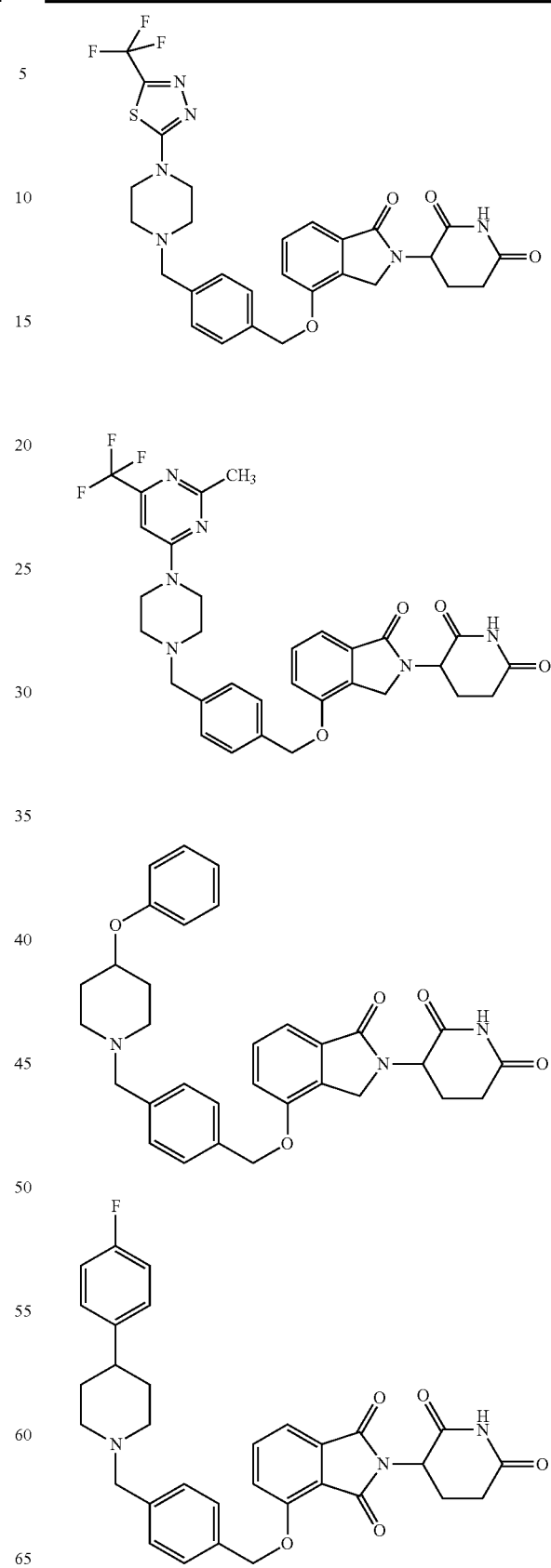

TABLE Z-continued
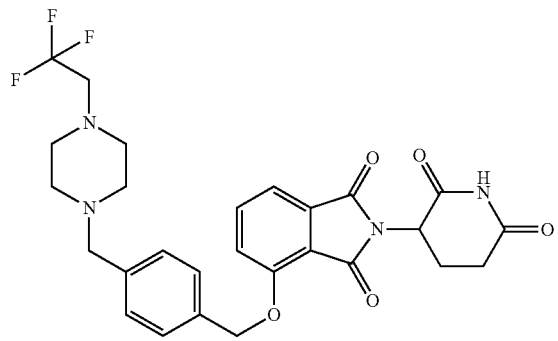 [SMILES: O=C1CCC(N2C(=O)c3cccc(OCc4ccc(CN5CCN(CC(F)(F)F)CC5)cc4)c3C2=O)C(=O)N1]
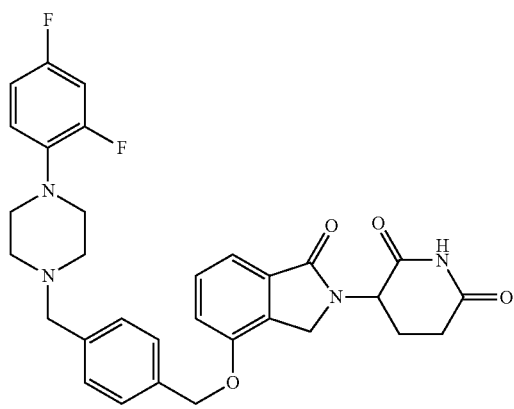 [SMILES: O=C1CCC(N2Cc3c(OCc4ccc(CN5CCN(c6ccc(F)cc6F)CC5)cc4)cccc3C2=O)C(=O)N1]
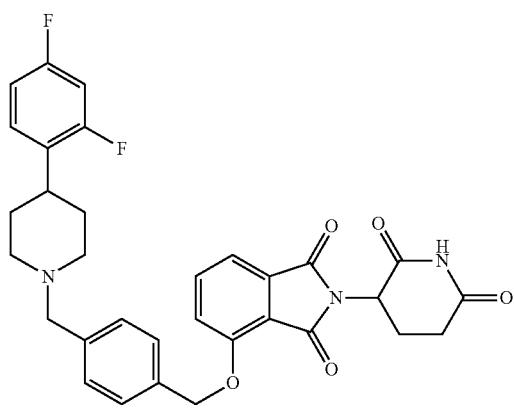 [SMILES: O=C1CCC(N2C(=O)c3cccc(OCc4ccc(CN5CCC(c6ccc(F)cc6F)CC5)cc4)c3C2=O)C(=O)N1]
TABLE Z-continued
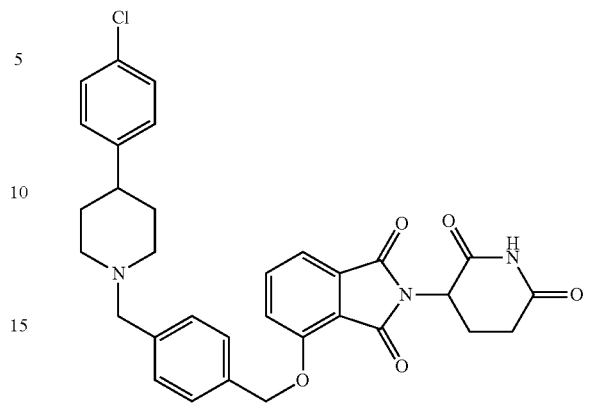
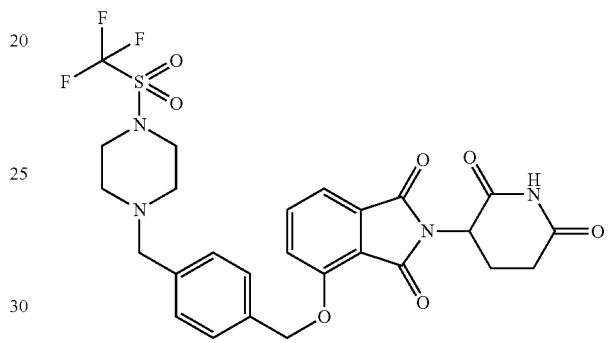
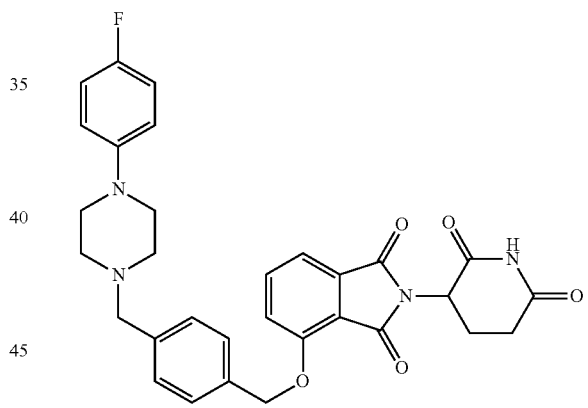
or a pharmaceutically acceptable salt, solvate or stereoisomer thereof.
In another embodiment, representative compounds are those listed in Table AA, below:
TABLE AA
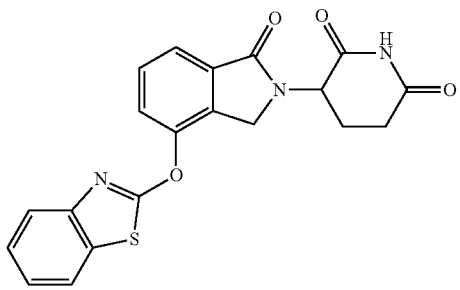 [SMILES: O=C1CCC(N2Cc3c(Oc4nc5ccccc5s4)cccc3C2=O)C(=O)N1]

TABLE AA-continued
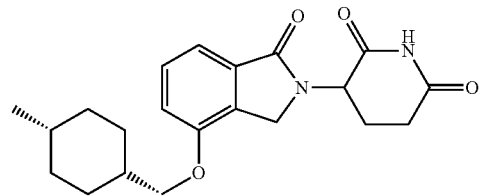
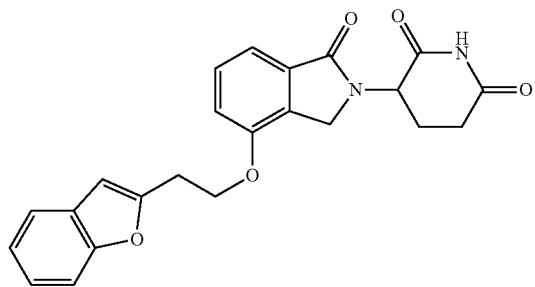 [SMILES: O=C1CCC(N2Cc3c(OCCc4cc5ccccc5o4)cccc3C2=O)C(=O)N1]
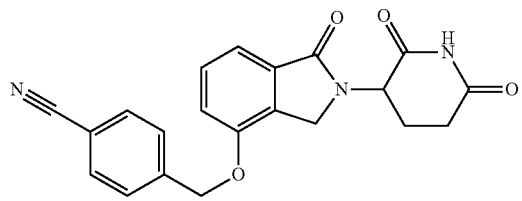 [SMILES: N#Cc1ccc(COc2cccc3c2CN(C2CCC(=O)NC2=O)C3=O)cc1]
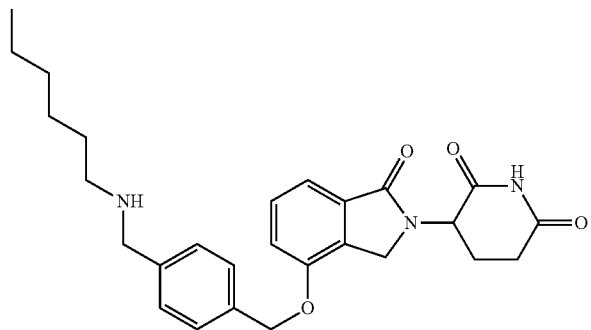 [SMILES: CCCCCCNCc1ccc(COc2cccc3c2CN(C2CCC(=O)NC2=O)C3=O)cc1]
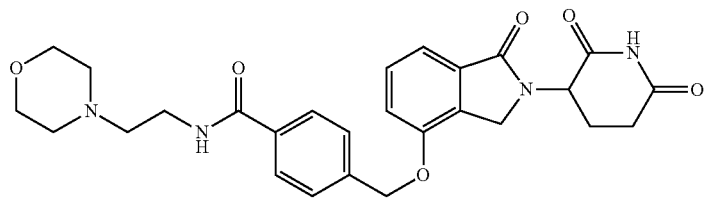 [SMILES: O=C1CCC(N2Cc3c(OCc4ccc(C(=O)NCCN5CCOCC5)cc4)cccc3C2=O)C(=O)N1]
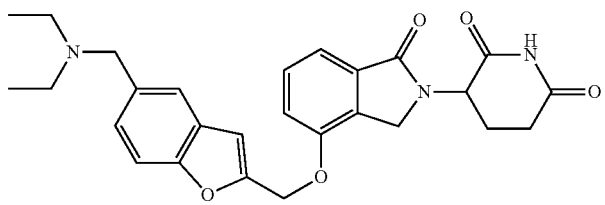 [SMILES: CCN(CC)Cc1ccc2oc(COc3cccc4c3CN(C3CCC(=O)NC3=O)C4=O)cc2c1]

US 10,034,872 B2
TABLE AA-continued
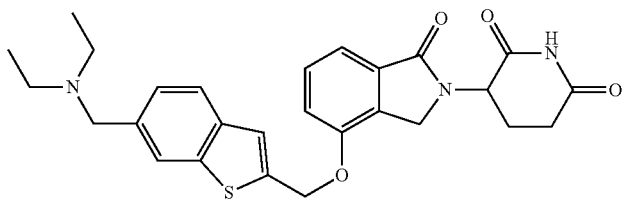 [SMILES: CCN(CC)Cc1ccc2cc(COc3cccc4c3CN(C3CCC(=O)NC3=O)C4=O)sc2c1]
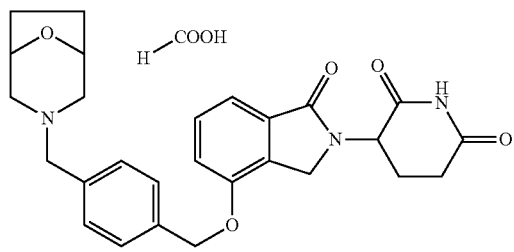
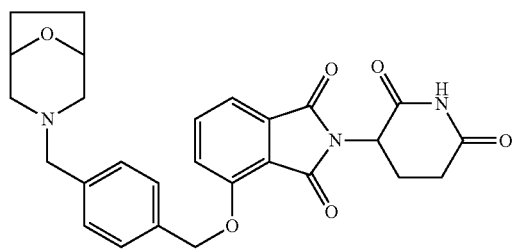 [SMILES: O=C1CCC(N2C(=O)c3cccc(OCc4ccc(CN5CC6CCC(C5)O6)cc4)c3C2=O)C(=O)N1]
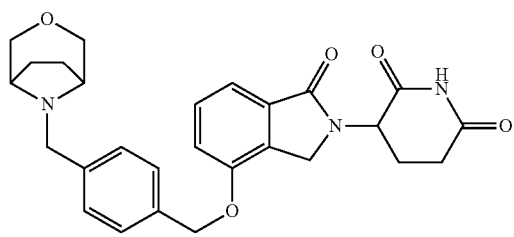 [SMILES: O=C1CCC(N2Cc3c(OCc4ccc(CN5C6CCC5COC6)cc4)cccc3C2=O)C(=O)N1]
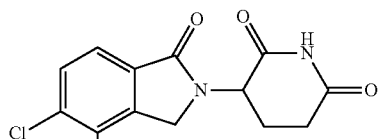
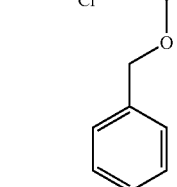
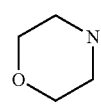
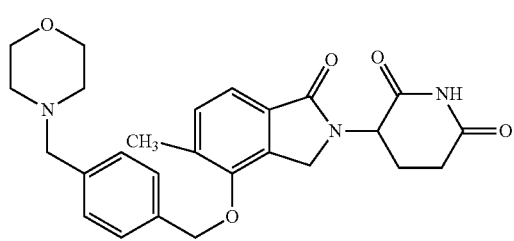 [SMILES: Cc1ccc2c(c1OCc1ccc(CN3CCOCC3)cc1)CN(C1CCC(=O)NC1=O)C2=O]

TABLE AA-continued
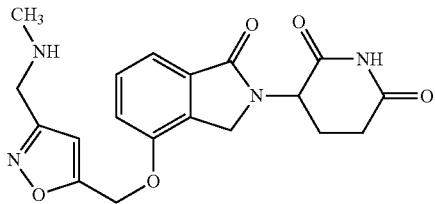 [SMILES: CNCc1cc(COc2cccc3c2CN(C2CCC(=O)NC2=O)C3=O)on1]
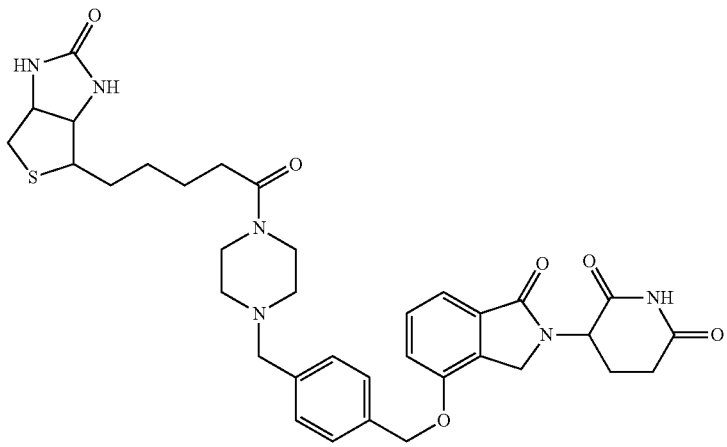 [SMILES: O=C1CCC(N2Cc3c(OCc4ccc(CN5CCN(C(=O)CCCCC6SCC7NC(=O)NC76)CC5)cc4)cccc3C2=O)C(=O)N1]
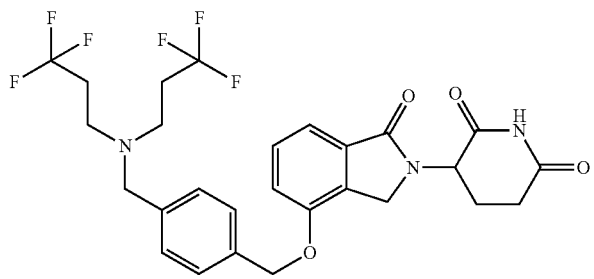 [SMILES: O=C1CCC(N2Cc3c(OCc4ccc(CN(CCC(F)(F)F)CCC(F)(F)F)cc4)cccc3C2=O)C(=O)N1]
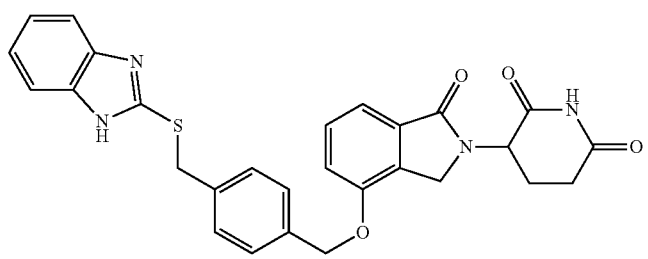 [SMILES: O=C1CCC(N2Cc3c(OCc4ccc(CSc5nc6ccccc6[nH]5)cc4)cccc3C2=O)C(=O)N1]
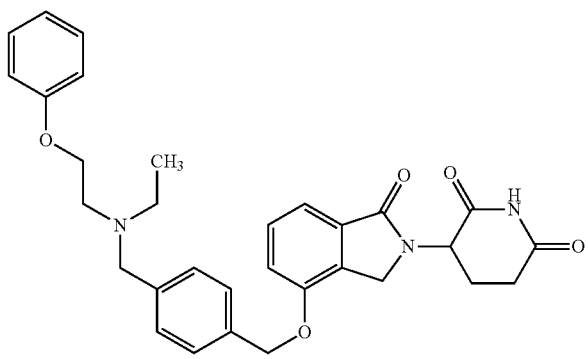 [SMILES: CCN(CCOc1ccccc1)Cc1ccc(COc2cccc3c2CN(C2CCC(=O)NC2=O)C3=O)cc1]

TABLE AA-continued

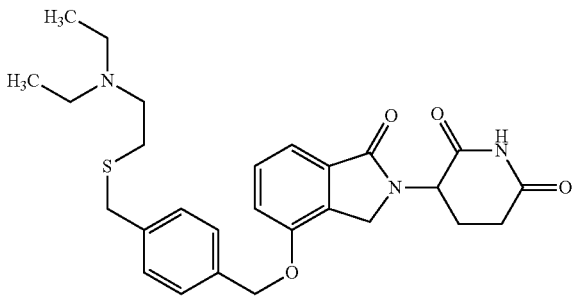 [SMILES: CCN(CC)CCSCc1ccc(COc2cccc3c2CN(C2CCC(=O)NC2=O)C3=O)cc1]

or a pharmaceutically acceptable salt, solvate or stereoisomer thereof.

In one embodiment, the immunomodulatory compound is:

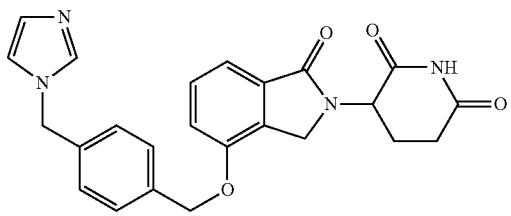 [SMILES: O=C1CCC(N2Cc3c(OCc4ccc(Cn5ccnc5)cc4)cccc3C2=O)C(=O)N1]

or a pharmaceutically acceptable salt, solvate, prodrug, or stereoisomer thereof.

In one embodiment, the immunomodulatory compound is:

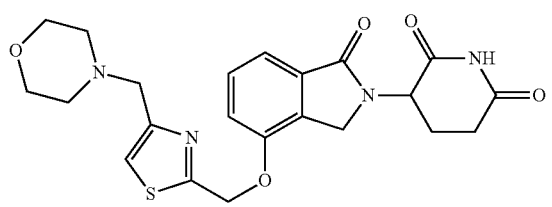 [SMILES: O=C1CCC(N2Cc3c(OCc4nc(CN5CCOCC5)cs4)cccc3C2=O)C(=O)N1]

or a pharmaceutically acceptable salt, solvate, prodrug, or stereoisomer thereof.

In one embodiment, the immunomodulatory compound is:

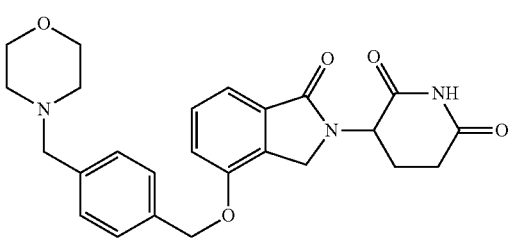 [SMILES: O=C1CCC(N2Cc3c(OCc4ccc(CN5CCOCC5)cc4)cccc3C2=O)C(=O)N1]

or a pharmaceutically acceptable salt, solvate, prodrug, or stereoisomer thereof.

The most preferred immunomodulatory compounds of the invention are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635,517, incorporated herein by reference). The compounds are available from Celgene Corporation, Warren, N.J. 4-(Amino)-2-(2,6-dioxo(3-piperidyl))-isoindoline-1,3-dione (pomalidomide) has the following chemical structure:

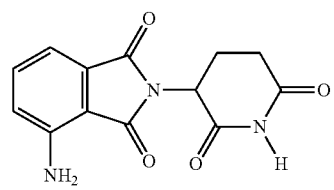 [SMILES: Nc1cccc2c1C(=O)N(C1CCC(=O)NC1=O)C2=O]

The compound 3-(4-amino-1-oxo-1,3-dihydro-isoindol-2-yl)-piperidine-2,6-dione (lenalidomide) has the following chemical structure:

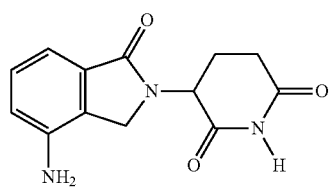 [SMILES: Nc1cccc2c1CN(C1CCC(=O)NC1=O)C2=O]

Compounds of the invention can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of immunomodulatory compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the invention that comprise —NO, —$NO_2$, —ONO, or —$ONO_2$ moieties. Prodrugs can typically be prepared using well-known methods, such as those described in 1 *Burger's Medicinal Chemistry and Drug Discovery,* 172-178, 949-982 (Manfred E. Wolff ed., 5th ed. 1995), and *Design of Prodrugs* (H. Bundgaard ed., Elsevier, New York 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

Various immunomodulatory compounds of the invention contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular immunomodulatory compounds of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. A stereomerically pure compound according to the invention comprises greater than about 80% by weight of one stereoisomer of the compound, more preferably greater than about 90% by weight of one stereoisomer of the compound, even more preferably greater than about 95% by weight of one stereoisomer of the compound, and most preferably greater than about 97% by weight of one stereoisomer of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.,* 20: 393 (1982); Lijinsky et. al., *J. Nat. Cancer Inst.,* 69: 1127 (1982); Mangold et. al., *Mutation Res.* 308: 33 (1994); Gordon et. al., *Drug Metab. Dispos.,* 15: 589 (1987); Zello et. al., *Metabolism,* 43: 487 (1994); Gately et. al., *J. Nucl. Med.,* 27: 388 (1986); Wade D, *Chem. Biol. Interact.* 117: 191 (1999).

Without being limited by any particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. As a result, these drugs often require the administration of multiple or high daily doses.

Isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of C—H bond cleavage during metabolism.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2 Combination Therapy

Antibodies that can be used in combination with the immunomodulatory compounds include monoclonal and polyclonal antibodies. Examples of antibodies include, but are not limited to, trastuzumab (Herceptin®), bevacizumab (Avastin™), pertuzumab (Omnitarg™), edrecolomab (Panorex®), and G250. The immunomodulatory compounds can also be combined with, or used in combination with, anti-TNF-α antibodies.

The antibody is preferably an anti-CS1 antibody, and, more preferably, a humanized monoclonal anti-CS1 antibody. In a particular embodiment, the anti-CS1 antibody is elotuzumab.

The antibody is also preferably an anti-CD20 antibody, such as obinutuzumab (Gazyva®), rituximab (e.g., Rituxan®), ibritumomab tiuxetan (Zevalin®), tositumomab (Bexxar®), ofatumumab (Arzerra®), AME-133v (ocaratuzumab), ocrelizumab, TRU-015, or IMMU-106 (veltuzumab).

The antibody is also preferably an anti-PD-L1 antibody, such as lambrolizumab (MK-3475), BMS-936559, atezolizumab (MPDL3280A), pidilizumab (CT-011), pembrolizumab (Keytruda®), Medi7436, nivolumab (OPDIVO®; BMS-936558), MDX-1106, or ONO-4538.

The antibody may also be an anti-KIR antibody such as IPH2101; an anti-CD40 antibody such as SGN-40 (dacetuzumab), HCD122 (lucatumumab); an anti-IGF1-R antibody such as CP751,871 (figitumumab); an anti-DKK-1 antibody such as BHQ880; an anti-FGFR3 antibody such as PRO-001; an anti-CD56 antibody such as IMGN901 (lorvotuzumab); an anti-RANKL antibody such as denosumab; an anti-IL-6 antibody such as siltuximab; an anti-CD138 antibody such as BT062 (indatuximab), or an anti-CD38 antibody suh as daratum umab.

The immunomodulatory compounds and antibodies can be administered in further combination with other pharmacologically active compounds ("second active agents") in methods and compositions of the invention. It is believed that certain combinations work synergistically in the treatment of particular types of cancer and certain diseases and conditions associated with, or characterized by, undesired angiogenesis. Immunomodulatory compounds can also work to alleviate adverse effects associated with certain second active agents, and some second active agents can be used to alleviate adverse effects associated with immunomodulatory compounds.

One or more second active ingredients or agents can be used in the methods and compositions of the invention together with an immunomodulatory compound and an antibody. Second active agents can be large molecules (e.g., proteins) or small molecules (e.g., synthetic inorganic, organometallic, or organic molecules).

Examples of large molecule active agents include, but are not limited to, hematopoietic growth factors and cytokines. Typical large molecule active agents are biological molecules, such as naturally occurring or artificially made proteins. Proteins that are particularly useful in this invention include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions of the invention include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

This invention encompasses the use of native, naturally occurring, and recombinant proteins. The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits of the invention. See, e.g., Emens, L. A., et al., *Curr. Opinion Mol. Ther.* 3(1):77-84 (2001). Other vaccines include anti-infection vaccines such as Prevnar.

In one embodiment of the invention, the large molecule active agent reduces, eliminates, or prevents an adverse effect associated with the administration of an immunomodulatory compound. Depending on the particular immunomodulatory compound and the disease or disorder begin treated, adverse effects can include, but are not limited to, drowsiness and somnolence, dizziness and orthostatic hypotension, neutropenia, infections that result from neutropenia, increased HIV-viral load, bradycardia, Stevens-Johnson Syndrome and toxic epidermal necrolysis, and seizures (e.g., grand mal convulsions). A specific adverse effect is neutropenia.

Second active agents that are small molecules can also be used to alleviate adverse effects associated with the administration of an immunomodulatory compound. However, like some large molecules, many are believed to be capable of providing a synergistic effect when administered with (e.g., before, after or simultaneously) an immunomodulatory compound. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin;

amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, oblimersen (Genasense®), remicade, docetaxel, celecoxib, melphalan, dexamethasone (Decadron®), steroids, gemcitabine, cisplatinum, temozolomide, etoposide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

Further specific second active agents include, but are not limited to, proteasome inhibitors such as ixazomib and marizomib, immunomodulators such as cyclophosphamide, checkpoint inhibitors such as PD-L1 inhibitors, and epigenetic modifiers such as azacitidine.

4.3 Methods of Treatments and Prevention

Methods of this invention encompass methods of treating, preventing and/or managing multiple myeloma. As used herein, unless otherwise specified, the term "treating" refers to the administration of an immunomodulatory compound described herein and an antibody, and, optionally, other additional active agent after the onset of symptoms of multiple myeloma. As used herein, unless otherwise specified, the term "preventing" refers to the administration prior to the onset of symptoms, particularly to patients at risk of multiple myeloma. The term "prevention" includes the inhibition of a symptom of multiple myeloma. Patients with familial history of multiple myeloma are preferred candidates for preventive regimens. As used herein and unless otherwise indicated, the term "managing" encompasses preventing the recurrence of multiple myeloma in a patient who had suffered from it, and/or lengthening the time a patient who had suffered from multiple myeloma remains in remission.

This invention encompasses methods of treating patients who have been previously treated for multiple myeloma, but are non-responsive to standard therapies, as well as those who have not previously been treated. The invention also encompasses methods of treating patients regardless of patient's age, although multiple myeloma is more common in certain age groups. The invention further encompasses methods of treating patients who have undergone surgery in an attempt to treat the disease or condition at issue, as well as those who have not. Because patients with multiple myeloma have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with multiple myeloma.

Methods encompassed by this invention comprise administering one or more immunomodulatory compounds described herein, or a pharmaceutically acceptable salt, solvate, hydrate, stereoisomer, clathrate, or prodrug thereof, in combination with one or more antibodies to a patient (e.g., a human) suffering, or likely to suffer, from multiple myeloma.

In one embodiment of the invention, an immunomodulatory compound of the invention can be administered orally and in single or divided daily doses in an amount of from about 0.10 to about 150 mg/day. In a particular embodiment, 4-(amino)-2-(2,6-dioxo(3-piperidyl))-isoindoline-1,3-dione (pomalidomide) may be administered in an amount of from about 0.1 to about 5 mg per day. In a preferred embodiment, 3-(4-amino-1-oxo-1,3-dihydro-isoindol-2-yl-piperidine-2,6-dione (lenalidomide) may be administered in an amount of from about 1 to 50 mg per day, or more preferably from about 5 to about 25 mg per day.

In a specific embodiment, 4-(amino)-2-(2,6-dioxo(3-piperidyl))-isoindoline-1,3-dione (pomalidomide) may be administered daily and continuously at an initial dose of 0.1 to 5 mg/day with dose escalation (every week) by 1 to 10 mg/day to a maximum dose of 50 mg/day for as long as therapy is tolerated. In a particular embodiment, pomalidomide can be administered in an amount of about 1, 2, 3, 4 or 5 mg per day to patients with relapsed multiple myeloma. In another specific embodiment, 3-(4-amino-1-oxo-1,3-dihydro-isoindol-2-yl)-piperidine-2,6-dione (lenalidomide) may be administered initially in an amount of 5 mg/day and the dose can be escalated every week to 10, 15, 20, 25, 30, 35, 40, 45 and 50 mg/day. The escalating dosing regimen can be used to overcome adverse effects. In a particular embodiment, lenalidomide can be administered in an amount of about 2.5 mg, 5 mg, 10 mg, 15 mg, 20 mg or 25 mg per day to patients with multiple myeloma.

In one embodiment, an antibody can be administered intravenously or subcutaneously, in an amount of from about 1 to about 1000 mg weekly or every other week. In a specific embodiment, an anti-CS1 antibody (e.g., elotuzumab) is administered intravenously in an amount of about 10 mg/kg weekly or every other week.

4.3.1 Combination Therapy with a Second Active Agent

Specific methods of the invention comprise administering an immunomodulatory compound, or a pharmaceutically acceptable salt, solvate, hydrate, stereoisomer, clathrate, or prodrug thereof, and an antibody (e.g., elotuzumab) further in combination with one or more second active agents, and/or in combination with radiation therapy, blood transfusions, or surgery. Specific methods of the invention comprise administering an immunomodulatory compound, or a pharmaceutically acceptable salt, solvate, hydrate, stereoisomer, clathrate, or prodrug thereof, and an antibody (e.g., elotuzumab) further in combination with one or more second active agents, or in combination with radiation therapy, blood transfusions, or surgery. Specific methods of the invention comprise administering an immunomodulatory compound, or a pharmaceutically acceptable salt, solvate, hydrate, stereoisomer, clathrate, or prodrug thereof, and an antibody (e.g., elotuzumab) further in combination with one or more second active agents, and in combination with radiation therapy, blood transfusions, or surgery. Examples of immunomodulatory compounds of the invention are disclosed herein (see, e.g., section 4.1). Examples of second active agents are also disclosed herein (see, e.g., section 4.2).

Administration of the immunomodulatory compounds, the antibodies, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for an immunomodulatory compound is orally. A preferred route of administration for an antibody (e.g., elotuzumab) is intravenous infusion. Preferred routes of administration for the second active agents or ingredients of the invention are known to those of ordinary skill in the art. See, e.g., Physicians' Desk Reference, 1755-1760 ($56^{th}$ ed., 2002).

The second active agent can be administered orally, intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of immunomodulatory compounds of the invention and any optional additional active agents concurrently administered to the patient. In a particular embodiment, the second active agent is oblimersen (Genasense®), GM-CSF, G-CSF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, ixazomib, marizomib, cyclophosphamide, Prevnar, an PD-L1 inhibitor, azacitidine, or a combination thereof.

In a particular embodiment, GM-CSF, G-CSF or EPO is administered subcutaneously during about five days in a four or six week cycle in an amount of from about 1 to about 750 mg/m$^2$/day, preferably in an amount of from about 25 to about 500 mg/m$^2$/day, more preferably in an amount of from about 50 to about 250 mg/m$^2$/day, and most preferably in an amount of from about 50 to about 200 mg/m$^2$/day. In a certain embodiment, GM-CSF may be administered in an amount of from about 60 to about 500 mcg/m$^2$ intravenously over 2 hours, or from about 5 to about 12 mcg/m$^2$/day subcutaneously. In a specific embodiment, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In a certain embodiment, EPO may be administered subcutaneously in an amount of 10,000 Unit 3 times per week.

In one embodiment, the second active agents that can be administered to patients with various types or stages of multiple myeloma in combination with an immunomodulatory compound and an antibody include, but are not limited to, dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, ixazomib, marizomib, Prevnar, an PD-L1 inhibitor, azacitidine, or a combination thereof.

In another embodiment, the second active agents that can be administered to patients with relapsed or refractory multiple myeloma in combination with an immunomodulatory compound and an antibody is doxorubicin (Doxil®), vincristine and/or dexamethasone (Decadron®).

In a specific embodiment, lenalidomide is administered in combination with elotuzumab and dexamethasone to patients with multiple myeloma.

This invention also encompasses a method of increasing the dosage of an anti-cancer drug or agent that can be safely and effectively administered to a patient, which comprises administering to a patient (e.g., a human) an immunomodulatory compound, or a pharmaceutically acceptable derivative, salt, solvate, clathrate, hydrate, or prodrug thereof, in combination with an antibody. Patients that can benefit by this method are those likely to suffer from an adverse effect associated with anti-cancer drugs for treating multiple myeloma. The administration of an immunomodulatory compound in combination with an antibody alleviates or reduces adverse effects which are of such severity that it would otherwise limit the amount of anti-cancer drug.

In one embodiment, an immunomodulatory compound can be administered orally and daily in an amount of from about 0.1 to about 150 mg, and preferably from about 1 to about 50 mg, more preferably from about 2 to about 25 mg prior to, during, or after the occurrence of the adverse effect associated with the administration of an anti-cancer drug to a patient. In a particular embodiment, an immunomodulatory compound of the invention is administered further in combination with specific agents such as heparin, aspirin, coumadin, or G-CSF to avoid adverse effects that are associated with anti-cancer drugs such as but not limited to neutropenia or thrombocytopenia.

In one embodiment, an immunomodulatory compound can be administered to patients with multiple myeloma further in combination with additional active ingredients including but not limited to anti-cancer drugs, anti-inflammatories, antihistamines, antibiotics, and steroids.

In another embodiment, this invention encompasses a method of treating, preventing and/or managing multiple myeloma, which comprises administering an immunomodulatory compound, or a pharmaceutically acceptable salt, solvate, hydrate, stereoisomer, clathrate, or prodrug thereof, in combination with an antibody, further in conjunction with (e.g. before, during, or after) conventional therapy including, but not limited to, surgery, immunotherapy, biological therapy, radiation therapy, or other non-drug based therapy presently used to treat, prevent or manage cancer. Such therapies also include cell therapy such as CAR T-cell immunotherapy. The combined use of the immunomodulatory compound, antibody and conventional therapy may provide a unique treatment regimen that is unexpectedly effective in certain patients. Without being limited by theory, it is believed that immunomodulatory compounds and/or antibodies may provide additive or synergistic effects when given concurrently with conventional therapy.

As discussed elsewhere herein, the invention encompasses a method of reducing, treating and/or preventing adverse or undesired effects associated with conventional therapy including, but not limited to, surgery, chemotherapy, radiation therapy, hormonal therapy, biological therapy and immunotherapy. One or more immunomodulatory compounds in combination with one or more antibodies, and, optionally, additional active ingredient can be administered to a patient prior to, during, or after the occurrence of the adverse effect associated with conventional therapy.

In one embodiment, an immunomodulatory compound can be administered in an amount of from about 0.1 to about 150 mg, and preferably from about 1 to about 50 mg, more preferably from about 2 to about 25 mg orally and daily, prior to, during, or after the use of conventional therapy.

4.3.2 Use with Transplantation Therapy

The invention encompasses a method of treating, preventing and/or managing cancer, which comprises administering the immunomodulatory compound, or a pharmaceutically acceptable salt, solvate, hydrate, stereoisomer, clathrate, or prodrug thereof, and an antibody in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of the immunomodulatory compound, antibody and transplantation therapy provides a unique and unexpected synergism. In particular, an immunomodulatory compound exhibits immunomodulatory activity that may provide additive or synergistic effects when given concurrently with transplantation therapy in patients with cancer.

This invention encompasses a method of treating, preventing and/or managing multiple myeloma which comprises administering to a patient (e.g., a human) an immunomodulatory compound, or a pharmaceutically acceptable salt, solvate, hydrate, stereoisomer, clathrate, or prodrug thereof in combination with an antibody, before, during, or after the transplantation of umbilical cord blood, placental blood, peripheral blood stem cell, hematopoietic stem cell preparation or bone marrow. Examples of stem cells suitable for use in the methods of the invention are disclosed in U.S.

Pat. No. 7,498,171 by R. Hariri et al., the entirety of which is incorporated herein by reference.

In one embodiment of this method, an immunomodulatory compound is administered in combination with an antibody to patients with multiple myeloma before, during, or after the transplantation of autologous peripheral blood progenitor cell.

In another embodiment, an immunomodulatory compound is administered in combination with an antibody to patients with relapsing multiple myeloma after the stem cell transplantation.

In another embodiment, an immunomodulatory compound, an antibody and prednisone are administered as maintenance therapy to patients with multiple myeloma following the transplantation of autologous stem cell.

In another embodiment, an immunomodulatory compound, an antibody and dexamethasone are administered as salvage therapy for low risk post transplantation to patients with multiple myeloma.

In another embodiment, an immunomodulatory compound, an antibody and dexamethasone are administered as maintenance therapy to patients with multiple myeloma following the transplantation of autologous bone marrow.

In another embodiment, an immunomodulatory compound and an antibody are administered following the administration of high dose of melphalan and the transplantation of autologous stem cell to patients with chemotherapy responsive multiple myeloma.

In another embodiment, an immunomodulatory compound, an antibody and PEG INTRO-A are administered to patients with multiple myeloma following the transplantation of autologous CD34-selected peripheral stem cell.

In another embodiment, an immunomodulatory compound and an antibody are administered with post transplant consolidation chemotherapy to patients with newly diagnosed multiple myeloma to evaluate anti-angiogenesis.

In another embodiment, an immunomodulatory compound, an antibody and dexamethasone are administered as maintenance therapy after DCEP consolidation, following the treatment with high dose of melphalan and the transplantation of peripheral blood stem cell to 65 years of age or older patients with multiple myeloma.

In a preferred embodiment, an immunomodulatory compound (e.g., lenalidomide) and an anti-CS1 antibody (e.g., elotuzumab) are administered to patients with minimal residual disease after autologous stem cell transplantation. In a more particular embodiment, the patient has received treatment with an immunomodulatory compound (e.g., lenalidomide), a proteasome inhibitor (e.g., bortezomib or carfilzomib), or both, as induction therapy for newly diagnosed multiple myeloma. In another preferred embodiment, an immunomodulatory compound (e.g., lenalidomide) is administered in combination with an anti-CS1 antibody (e.g., elotuzumab) and dexamethasone.

4.3.3 Cycling Therapy

In certain embodiments, the prophylactic or therapeutic agents of the invention are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment of the invention, an immunomodulatory compound is administered daily in a single or divided doses in a four to six week cycle with a rest period of about a week or two weeks. The invention further allows the frequency, number, and length of dosing cycles to be increased. Thus, another specific embodiment of the invention encompasses the administration of an immunomodulatory compound of the invention for more cycles than are typical when it is administered alone. In yet another specific embodiment of the invention, an immunomodulatory compound of the invention is administered for a greater number of cycles that would typically cause dose-limiting toxicity in a patient to whom a second active ingredient is not also being administered.

In one embodiment, an immunomodulatory compound described herein is administered daily and continuously for three or four weeks at a dose of from about 0.1 to about 150 mg/day followed by a break of one or two weeks. In a particular embodiment, pomalidomide is administered in an amount of about 1, 2, 3, 4 and 5 mg/day for three to four weeks, followed by one week or two weeks of rest in a four or six week cycle. In another particular embodiment, lenalidomide is administered in an amount of about 2.5, 5, 10, 15, 20 or 25 mg/day, preferably in an amount of about 10 mg/day or 25 mg/day for three to four weeks, followed by one week or two weeks of rest in a four or six week cycle.

In one embodiment of the invention, an immunomodulatory compound and a second active ingredient are administered orally, with administration of an immunomodulatory compound of the invention occurring 30 to 60 minutes prior to a second active ingredient, during a cycle of four to six weeks. In another embodiment of the invention, the combination of an immunomodulatory compound and a second active ingredient is administered by intravenous infusion over about 90 minutes every cycle. In a specific embodiment, one cycle comprises the administration of from about 5 to about 25 mg/day of lenalidomide and from about 50 to about 200 mg/m$^2$/day of a second active ingredient daily for three to four weeks and then one or two weeks of rest. In another specific embodiment, each cycle comprises the administration of from about 1 to about 10 mg/day of pomalidomide and from about 50 to about 200 mg/m$^2$/day of a second active ingredient for 3 to 4 weeks followed by one or two weeks of rest. Typically, the number of cycles during which the combinatorial treatment is administered to a patient will be from about one to about 24 cycles, more typically from about two to about 16 cycles, and even more typically from about four to about three cycles.

Antibodies in the methods of the present invention can also be administered cyclically to patients with multiple myeloma. An anti-CS1 antibody (e.g., elotuzumab) is preferably administered weekly or every other week. In a specific embodiment, the anti-CS1 antibody is administered on days 1, 8, 15 and 22 in the first two 28-day cycles, and then on days 1 and 15 in the following 28-day cycles.

4.4 Pharmaceutical Compositions and Dosage Forms

Pharmaceutical compositions can be used in the preparation of individual, single unit dosage forms. Pharmaceutical compositions and dosage forms of the invention comprise an immunomodulatory compound of the invention, or a pharmaceutically acceptable salt, solvate, hydrate, stereoisomer, clathrate, or prodrug thereof. Pharmaceutical compositions and dosage forms of the invention can further comprise one or more excipients.

Pharmaceutical compositions and dosage forms of the invention can also comprise one or more antibodies, and, optionally, additional active ingredients. Consequently, pharmaceutical compositions and dosage forms of the invention comprise the active ingredients disclosed herein (e.g., an immunomodulatory compound and an antibody).

Examples of optional second, or additional, active ingredients are disclosed herein (see, e.g., section 5.2).

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise an immunomodulatory compound or a pharmaceutically acceptable salt, solvate, hydrate, stereoisomer, clathrate, or prodrug thereof in an amount of from about 0.10 to about 150 mg. Typical dosage forms comprise an immunomodulatory compound or a pharmaceutically acceptable salt, solvate, hydrate, stereoisomer, clathrate, or prodrug thereof in an amount of about 0.1, 1, 2, 2.5, 3, 4, 5, 7.5, 10, 12.5, 15, 17.5, 20, 25, 50, 100, 150 or 200 mg. In a particular embodiment, a preferred dosage form comprises 4-(amino)-2-(2,6-dioxo (3-piperidyl))-isoindoline-1,3-dione (pomalidomide) in an amount of about 1, 2, 3, 4, 5, 10, 25 or 50 mg. In a specific embodiment, a preferred dosage form comprises 3-(4-amino-1-oxo-1,3-dihydro-isoindol-2-yl)-piperidine-2,6-dione (lenalidomide) in an amount of about 2.5, 5, 10, 15, 20, 25 or 50 mg. In a specific embodiment, a preferred dosage form comprises 3-(4-amino-1-oxo-1,3-dihydro-isoindol-2-yl)-piperidine-2,6-dione (lenalidomide) in an amount of about 2.5 mg. In a specific embodiment, a preferred dosage form comprises 3-(4-amino-1-oxo-1,3-dihydro-isoindol-2-yl)-piperidine-2,6-dione (lenalidomide) in an amount of about 5 mg. In a specific embodiment, a preferred dosage form comprises 3-(4-amino-1-oxo-1,3-dihydro-isoindol-2-yl)-piperidine-2,6-dione (lenalidomide) in an amount of about 10 mg. In a specific embodiment, a preferred dosage form comprises 3-(4-amino-1-oxo-1,3-dihydro-isoindol-2-yl)-piperidine-2,6-dione (lenalidomide) in an amount of about 15 mg. In a specific embodiment, a preferred dosage form comprises 3-(4-amino-1-oxo-1,3-dihydro-isoindol-2-yl)-piperidine-2,6-dione (lenalidomide) in an amount of about 20 mg. In a specific embodiment, a preferred dosage form comprises 3-(4-amino-1-oxo-1,3-dihydro-isoindol-2-yl)-piperidine-2,6-dione (lenalidomide) in an amount of about 25 mg. In a specific embodiment, a preferred dosage form comprises 3-(4-amino-1-oxo-1,3-dihydro-isoindol-2-yl)-piperidine-2,6-dione (lenalidomide) in an amount of about 50 mg. In a specific embodiment, a preferred dosage form comprises 4-(amino)-2-(2,6-dioxo(3-piperidyl))-isoindoline-1,3-dione (pomalidomide) in an amount of about 1 mg. In a specific embodiment, a preferred dosage form comprises 4-(amino)-2-(2,6-dioxo(3-piperidyl))-isoindoline-1,3-dione (pomalidomide) in an amount of about 2 mg. In a specific embodiment, a preferred dosage form comprises 4-(amino)-2-(2,6-dioxo(3-piperidyl))-isoindoline-1, 3-dione (pomalidomide) in an amount of about 3 mg. In a specific embodiment, a preferred dosage form comprises 4-(amino)-2-(2,6-dioxo(3-piperidyl))-isoindoline-1,3-dione (pomalidomide) in an amount of about 4 mg.

Typical dosage forms comprise the antibody in an amount of 1 to about 1000 mg, from about 5 to about 500 mg, from about 10 to about 350 mg, or from about 50 to about 200 mg. In a specific embodiment, elotuzumab is in a 10 mg/kg IV solution. Of course, the specific amount of the antibody or second, additional anticancer drug will depend on the specific agent used, the type of cancer being treated or managed, and the amount(s) of an immunomodulatory compound and any optional additional active agents concurrently administered to the patient.

4.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an immunomodulatory compound described herein, anhydrous lactose, microcrystalline cellulose, polyvinylpyrrolidone, stearic acid, colloidal anhydrous silica, and gelatin. In a specific embodiment, the solid oral dosage form is a capsule comprising an immunomodulatory compound, lactose anhydrous, microcrystalline cellulose, croscarmellose sodium and magnesium stearate.

4.4.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of an immunomodulatory compound of the invention and its derivatives. See, e.g., U.S. Pat. No. 5,134,127, which is incorporated herein by reference.

4.4.4 Topical and Mucosal Dosage Forms

Topical and mucosal dosage forms of the invention include, but are not limited to, sprays, aerosols, solutions, emulsions, suspensions, eye drops or other ophthalmic preparations, or other forms known to one of skill in the art. See, e.g., *Remington's Pharmaceutical Sciences*, $16^{th}$ and $18^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, $16^{th}$ and $18^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.4.5 Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of an immunomodulatory compound, or a pharmaceutically acceptable salt, solvate, hydrate, stereoisomer, prodrug, or clathrate thereof. Kits encompassed by this invention can further comprise an antibody (e.g., elotuzumab) for administration in with the immunomodulatory compound. The kits can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see, e.g., section 4.2).

Kits of the invention can further comprise devices that are used to administer the active ingredients. Examples of such devices include, but are not limited to, syringes, drip bags, patches, and inhalers.

Kits of the invention can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain embodiments of the invention are illustrated by the following non-limiting examples.

5.1 Cycling Therapy in Patients

In a specific embodiment, an immunomodulatory compound, e.g., lenalidomide, is cyclically administered to patients with multiple myeloma. Cycling therapy involves the administration of a first agent for a period of time, followed by a rest for a period of time and repeating this sequential administration. Cycling therapy can reduce the development of resistance to one or more of the therapies, avoid or reduce the side effects of one of the therapies, and/or improves the efficacy of the treatment.

In a specific embodiment, prophylactic or therapeutic agents are administered in a cycle of about 4 to 6 weeks, about once or twice every day. One cycle can comprise the administration of a therapeutic on prophylactic agent for three to four weeks and at least a week or two weeks of rest. The number of cycles administered is from about one to about 24 cycles, more typically from about two to about 16 cycles, and more typically from about four to about eight cycles.

For example, in a cycle of four weeks, on day 1, the administration of 10 mg/day of 3-(4-amino-1-oxo-1,3-dihydro-isoindol-2-yl)-piperidine-2,6-dione is started. On day 22, the administration of the compound is stopped for a week of rest. On day 29, the administration of 10 mg/day 3-(4-amino-1-oxo-1,3-dihydro-isoindol-2-yl)-piperidine-2, 6-dione is resumed.

An anti-CS1 antibody, e.g., elotuzumab, can also be cyclically administered to patients with multiple myeloma. For example, in a cycle of four weeks, elotuzumab is administered intravenously in 10 mg/kg IV solution on days 1, 8, 15 and 22, but not on the other days in the four week cycle. After the initial two cycles, elotuzumab is administered intravenously in 10 mg/kg IV solution on days 1 and 15, but not on the other days in the four week cycle.

5.2 Clinical Studies in Patients

Clinical studies of patients who have received stem cell transplantation for treating multiple myeloma is conducted to assess the ability of lenalidomide in combination with elotuzumab to treat multiple myeloma.

5.2.1. MRD (+) Study (CC-5013-MM-029)

MRD(+) (MRD positive) is defined as having $10^{-5}$ cells or greater as determined by Sequenta.

Patients eighteen years of age or older can participate in this study after signing informed consent. The patients must have newly diagnosed multiple myeloma with symptomatic multiple myeloma and have undergone induction lenalidomide in combination with bortezomib/carfilzomib and dexamethasone (triplet) or bortezomib/carfilzomib in combination with dexamethasone (doublet) therapy and, subsequently, stem cell transplantation. Prior to induction the following criteria must have been met:
  i. All 3 criteria MM diagnostic criteria and at least one of the CRAB criteria must be met prior to induction
  ii. Monoclonal plasma cells in the bone marrow ≥10% and/or presence of a biopsy-proven plasmacytoma
  iii. Monoclonal protein in the serum and/or urine
  iv. Myeloma-related organ dysfunction (at least one of the following*):
    a) [C] Calcium elevation in the blood (Serum Calcemia≥upper limit of normal [ULN])
    b) [R] Renal insufficiency (serum creatinine >2 mg/dL)
    c) [A] Anemia (hemoglobin <10 g/dL or 2 g<laboratory normal)
    d) [B] Lytic bone lesions or osteoporosis.

Patients must have minimum residue disease (MRD) determination by Sequenta, LDH, cytogenetics, B2M and serum albumin (ISS stage) from their initial diagnosis at screening. No prior anti-myeloma chemotherapy except for induction regimen prior to autologous stem cell transplantation. Complete response (CR), very good partial response (VGPR), partial response (PR), or stable disease (SD) must be documented according to International Myeloma Working Group (IMWG) criteria prior to randomization.

Prior to the autologous stem cell transplantation, the patients must have received in induction a proteasome inhibitor- or lenalidomide-based therapy. At 100 days after the stem cell transplantation, the patients who achieve at least stable disease are randomized to lenalidomide plus elotuzumab cohort and lenalidomide plus placebo cohort. The stratification at randomization is based on cytogenetics (high risk vs standard risk), types of induction therapy prior to stem cell transplantation (doublet vs triplet regimen), and minimization. In the lenalidomide plus elotuzumab cohort, lenalidomide is administered orally in an amount of 10 mg per day on days 1-21 of 28-day cycles. Elotuzumab is administered as a 10 mg/kg IV solution weekly on days 1, 8, 15, 22 in 28-day cycles (cycles 1 & 2); and on days 1 & 15 in 28-day cycles (cycle 3 and onward). In both cohorts the treatments continue until progressive disease (PD) or unacceptable toxicity.

Prior to the lenalidomide- or proteasome inhibitor-based induction therapy, the MRD status is evaluated by bone marrow aspirate (BMA) and Sequenta. Baseline evaluation of cytogenetics is also conducted. The MRD status is also monitored at randomization (BMA), every 12 months (BMA), every 2 cycles (BMA), and at discontinuation (peripheral blood). Once MRD (−) status is obtained, the status is confirmed with BMA.

The primary endpoint of the study is progression-free survival (PFS). The second endpoints for all patient subjects include the following: progression-free survival 2 (PFS2); overall survival (OS); overall response rate (ORR); duration of response (DoR); MRD(−) conversion rate; time from randomization to MRD(−) conversion; safety; duration of MRD(−) status; MRD levels over time (Exploratory); correlation of MRD status change with outcomes (PFS, OS) (Exploratory); and quality of life (QoL). The second end points for patient subjects achieving MRD(−) conversion include the following: time to MRD(+) recurrence (Exploratory); and time from MRD(+) recurrence to IMWG-defined progression (Exploratory). An interim analysis will be performed to assess MRD(−) conversion rates.

5.2.2. MRD (−) Study (Phase II)

MRD(−) (MRD negative) is defined as having $10^{-4}$ cells or fewer as determined by Sequenta. Prior to the autologous stem cell transplantation, the patients must have received in induction a proteasome inhibitor- or lenalidomide-based therapy. At 100 days after the stem cell transplantation, the patients who achieve at least stable disease are randomized to lenalidomide plus elotuzumab cohort and lenalidomide plus placebo cohort. The stratification at randomization is based on cytogenetics (high risk vs standard risk), and types of induction therapy prior to stem cell transplantation (doublet vs triplet regimen). In the lenalidomide plus elotuzumab cohort, lenalidomide is administered orally in an amount of 10 mg per day on days 1-21 of 28-day cycles. Elotuzumab is administered as a 10 mg/kg IV solution weekly on days 1, 8, 15, 22 in 28-day cycles (cycles 1 & 2); and on days 1 & 15 in 28-day cycles (cycle 3 and onward). In both cohorts the treatments continue until progressive disease (PD) or unacceptable toxicity.

Prior to the lenalidomide- or proteasome inhibitor-based induction therapy, the MRD status is evaluated by bone marrow aspirate (BMA) and Sequenta. Baseline evaluation of cytogenetics is also conducted. The MRD status is also monitored at randomization (BMA), every 12 months (BMA), every 2 cycles (BMA), and at discontinuation (peripheral blood). Once MRD (+) status is obtained, the status is confirmed with peripheral blood.

The primary endpoint of the study is progression-free survival (PFS) Rate at 24 months. The second endpoints for all patient subjects include the following: PFS; PFS2; PFS at interim analysis; OS; OS at interim analysis; ORR; DoR; rate of loss of MRD(−); comparison of High Risk patients vs. Standard Risk patients for loss of MRD(−) status; MRD(+) conversion at 12 and 18 months; time from MRD (+) conversion to IMWG-defined progression; time to MRD (+) conversion; duration of MRD(−) status; MRD levels over time (Exploratory); correlation of MRD status change with outcomes (PFS, OS) (Exploratory); QoL; and safety.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating multiple myeloma in a patient having multiple myeloma and having received stem cell transplantation, which comprises:
   a. determining the minimal residual disease (MRD) status of the patient following the stem cell transplantation, wherein the patient has received induction therapy with a compound having the formula:

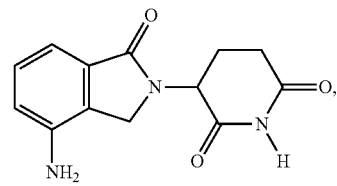 [SMILES: Nc1cccc2c1CN(C1CCC(=O)NC1=O)C2=O]

or a pharmaceutically acceptable salt, solvate or stereoisomer thereof before receiving the stem cell transplantation; and
   b. wherein if the patient is MRD positive, administering to the patient about 1 to about 50 mg per day of the compound
   or a pharmaceutically acceptable salt, solvate or stereoisomer thereof, in combination with a therapeutically effective amount of an anti-CS1 antibody.

2. The method of claim 1, wherein the patient has received induction therapy with a combination of the compound and a proteasome inhibitor prior to the stem cell transplantation.

3. The method of claim 1, wherein the multiple myeloma is relapsed, refractory, or relapsed and refractory multiple myeloma.

4. The method of claim 1, wherein the method comprises cyclic administration of the compound.

5. The method of claim 4, wherein the compound is administered for 21 days followed by seven days of rest in a 28 day cycle.

6. The method of claim 1, wherein the compound is administered in an amount of about 2.5 mg, 5 mg, 10 mg, 15 mg, 20 mg or 25 mg per day.

7. The method of claim 6, wherein the compound is administered in an amount of about 25 mg per day.

8. The method of claim 6, wherein the compound is administered in an amount of about 10 mg per day.

9. The method of claim 6, wherein the compound is administered in an amount of about 5 mg per day.

10. The method of claim 6, wherein the compound is administered in a capsule in an amount of about 25 mg.

11. The method of claim 1, wherein the compound is administered orally.

12. The method of claim 11, wherein the compound is administered in the form of a capsule or tablet.

13. The method of claim 12, wherein the capsule comprises the compound, lactose anhydrous, microcrystalline cellulose, croscarmellose sodium and magnesium stearate.

14. The method of claim 1, wherein the compound is administered in a capsule in an amount of 2.5 mg, 5 mg, 10 mg, 15 mg, 20 mg or 25 mg.

15. The method of claim 14, wherein the compound is administered in a capsule in an amount of about 10 mg.

16. The method of claim 14, wherein the compound is administered in a capsule in an amount of about 5 mg.

17. The method of claim 14, wherein the compound is administered in a capsule in an amount of about 2.5 mg.

18. The method of claim 1, wherein the anti-CS1 antibody is a monoclonal antibody.

19. The method of claim 18, wherein the anti-CS1 antibody is elotuzumab.

20. The method of claim 18, wherein the antibody is administered intravenously in an amount of from about 1 to about 1000 mg weekly or every other week.

21. The method of claim 18, wherein the antibody is administered in an amount of about 10 mg/kg.

22. The method of claim 18, wherein the antibody is administered weekly or every other week in a 28 day cycle.

23. The method of claim 18, wherein the antibody is administered on days 1, 8, 15 and 22 in a 28 day cycle.

24. The method of claim 18, wherein the antibody is administered on days 1 and 15 in a 28 day cycle.

25. The method of claim 1, wherein the compound is

[Chemical structure]

and is not a pharmaceutically acceptable salt, solvate or stereoisomer thereof.

26. The method of claim 1, wherein the compound is a pharmaceutically acceptable salt of

[Chemical structure]

27. The method of claim 1, wherein the compound is a pharmaceutically acceptable solvate of

[Chemical structure]

28. The method of claim 2, wherein the proteasome inhibitor is bortezomib or carfilzomib.

29. The method of claim 28, wherein the patient has received induction therapy with lenalidomide in combination with bortezomib or carfilzomib.

30. The method of claim 28, wherein the patient has received induction therapy with lenalidomide in combination with bortezomib or carfilzomib, and dexamethasone.

31. The method of claim 1, wherein the stem cell transplantation is autologous stem cell transplantation.

32. The method of claim 1, wherein the stem cell transplantation is hematopoietic stem cell transplantation.

33. The method of claim 1, wherein the stem cell transplantation is peripheral blood stem cell transplantation.

34. The method of claim 22, wherein the patient is further administered with dexamethasone.

35. The method of claim 34, wherein the dexamethasone is administered daily or on weeks when the anti-CS1 antibody is not administered in the cycle.

* * * * *